United States Patent
Davila

(10) Patent No.: US 11,976,121 B2
(45) Date of Patent: *May 7, 2024

(54) CD123-BINDING CHIMERIC ANTIGEN RECEPTORS

(71) Applicant: H. Lee Moffitt Cancer Center and Research Institute, Inc., Tampa, FL (US)

(72) Inventor: Marco L. Davila, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 905 days.

This patent is subject to a terminal disclaimer.

(21) Appl. No.: 16/632,086

(22) PCT Filed: Jul. 18, 2018

(86) PCT No.: PCT/US2018/042686
§ 371 (c)(1),
(2) Date: Jan. 17, 2020

(87) PCT Pub. No.: WO2019/018525
PCT Pub. Date: Jan. 24, 2019

(65) Prior Publication Data
US 2020/0165348 A1 May 28, 2020

Related U.S. Application Data

(60) Provisional application No. 62/592,102, filed on Nov. 29, 2017, provisional application No. 62/534,960, filed on Jul. 20, 2017.

(51) Int. Cl.
| | | |
|---|---|---|
| C07K 16/28 | (2006.01) | |
| A61K 35/17 | (2015.01) | |
| A61P 35/00 | (2006.01) | |
| C07K 14/435 | (2006.01) | |
| C12N 5/078 | (2010.01) | |

(52) U.S. Cl.
CPC .......... C07K 16/2866 (2013.01); A61K 35/17 (2013.01); C12N 5/0634 (2013.01); C07K 2317/24 (2013.01); C07K 2317/565 (2013.01); C07K 2317/622 (2013.01); C07K 2319/02 (2013.01); C07K 2319/30 (2013.01); C07K 2319/33 (2013.01)

(58) Field of Classification Search
CPC ............ C07K 16/2866; C07K 2317/24; C07K 2317/565; C07K 2317/622; C07K 2319/02; C07K 2319/30; C07K 2319/33; C07K 2319/03; C07K 14/435; A61K 35/17; A61K 39/001119; A61K 2039/5156; A61K 2039/5158; C12N 5/0634

See application file for complete search history.

(56) References Cited

U.S. PATENT DOCUMENTS

| | | | |
|---|---|---|---|
| 11,525,004 B2 * | 12/2022 | Davila | C07K 16/2866 |
| 2009/0324604 A1 | 12/2009 | Liu et al. | |
| 2011/0318339 A1 | 12/2011 | Smider et al. | |
| 2016/0068601 A1 | 3/2016 | Brogdon et al. | |
| 2021/0024608 A1 * | 1/2021 | Davila | A61K 39/0011 |
| 2023/0121135 A1 * | 4/2023 | Davila | A61K 39/464411 424/134.1 |

FOREIGN PATENT DOCUMENTS

| | | | | |
|---|---|---|---|---|
| AU | 2016305075 A1 * | 3/2018 | ............. | A61K 35/17 |
| DE | 102011054413 A1 * | 4/2013 | ......... | C07K 16/4241 |
| WO | WO-2015038884 A2 * | 3/2015 | ............. | C07K 16/40 |
| WO | WO-2016210293 A1 * | 12/2016 | ............. | A61K 35/17 |
| WO | 2017035430 A2 | 3/2017 | | |
| WO | WO-2018228406 A1 * | 12/2018 | ........... | A61K 39/395 |

OTHER PUBLICATIONS

Pech M. et al, Differences between germ-line and rearranged immunoglobulin V-kappa coding sequences suggest a localized mutation mechanism, Nature 291, 668-670, Published Jun. 1981 (Year: 1981).*
Page A. et al, Exploiting B Cell Transfer for Cancer Therapy: Engineered B Cells to Eradicate Tumors, Int. J. Mol. Sci. 2021, 22, 9991 (Year: 2021).*
Al Qaraghuli M. et al, Antibody-protein binding and conformational changes: identifying allosteric signaling pathways to engineer a better effector response, Scientific Reports, 10:13696, 2020 (Year: 2020).*
Munoz et al., Interleukin-3 receptor α chain (CD123) is widely expresssed in hematologic malignancies, Haematologica, 86:1261-1269, 2001.
Thokala et al., Redirecting Specificity of T cells Using the Sleeping Beauty System to Express Chimeric Antigen Receptors by Mix-and-Matching of VL and VH Domains Targeting CD123+ Tumors, PLoS One, vol. 11(8), p. 1-23, 2016.
International Search Report issued for application PCT/US2018/042686, mailed Nov. 9, 2018.

* cited by examiner

Primary Examiner — Ilia I Ouspenski
(74) Attorney, Agent, or Firm — Thomas | Horstemeyer, LLP

(57) ABSTRACT

Disclosed are compositions and methods for targeted treatment of CD123-expressing cancers. In particular, chimeric antigen receptor (CAR) polypeptides are disclosed that can be used with adoptive cell transfer to target and kill CD123-expressing cancers. Also disclosed are immune effector cells, such as T cells or Natural Killer (NK) cells, that are engineered to express these CARs. Therefore, also disclosed are methods of providing an anti-tumor immunity in a subject with a CD123-expressing cancer that involves adoptive transfer of the disclosed immune effector cells engineered to express the disclosed CARs.

18 Claims, 12 Drawing Sheets
Specification includes a Sequence Listing.

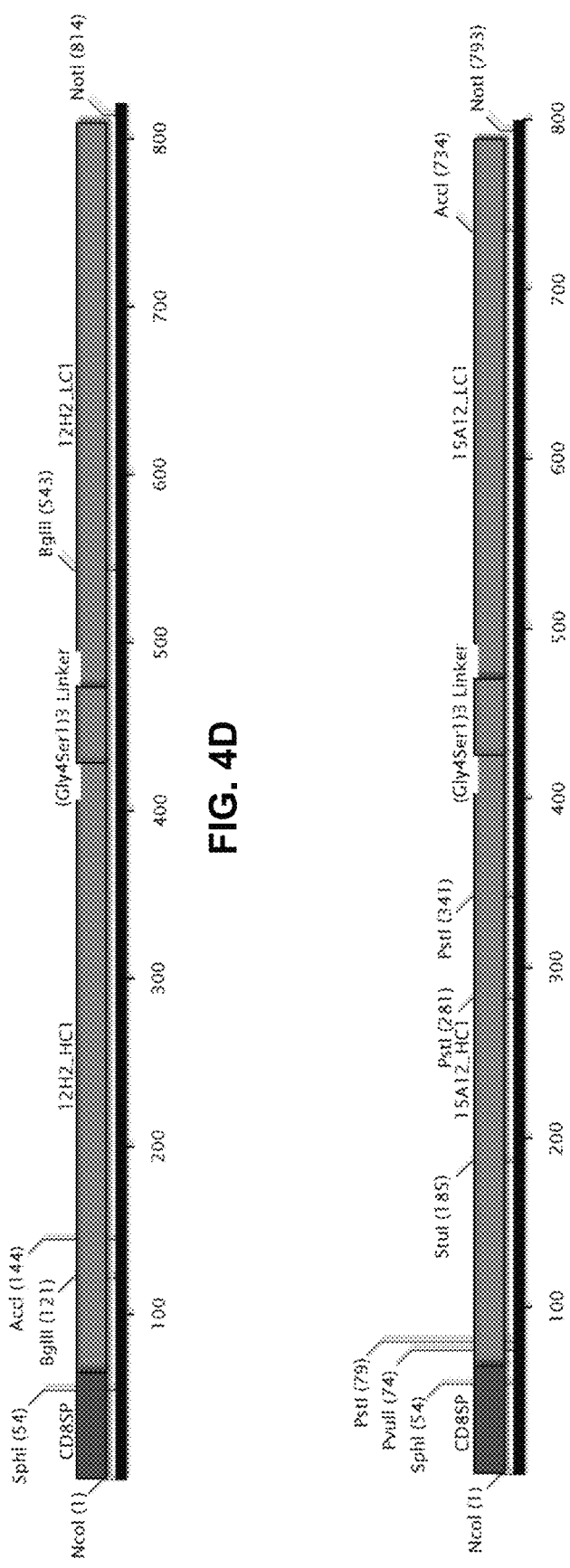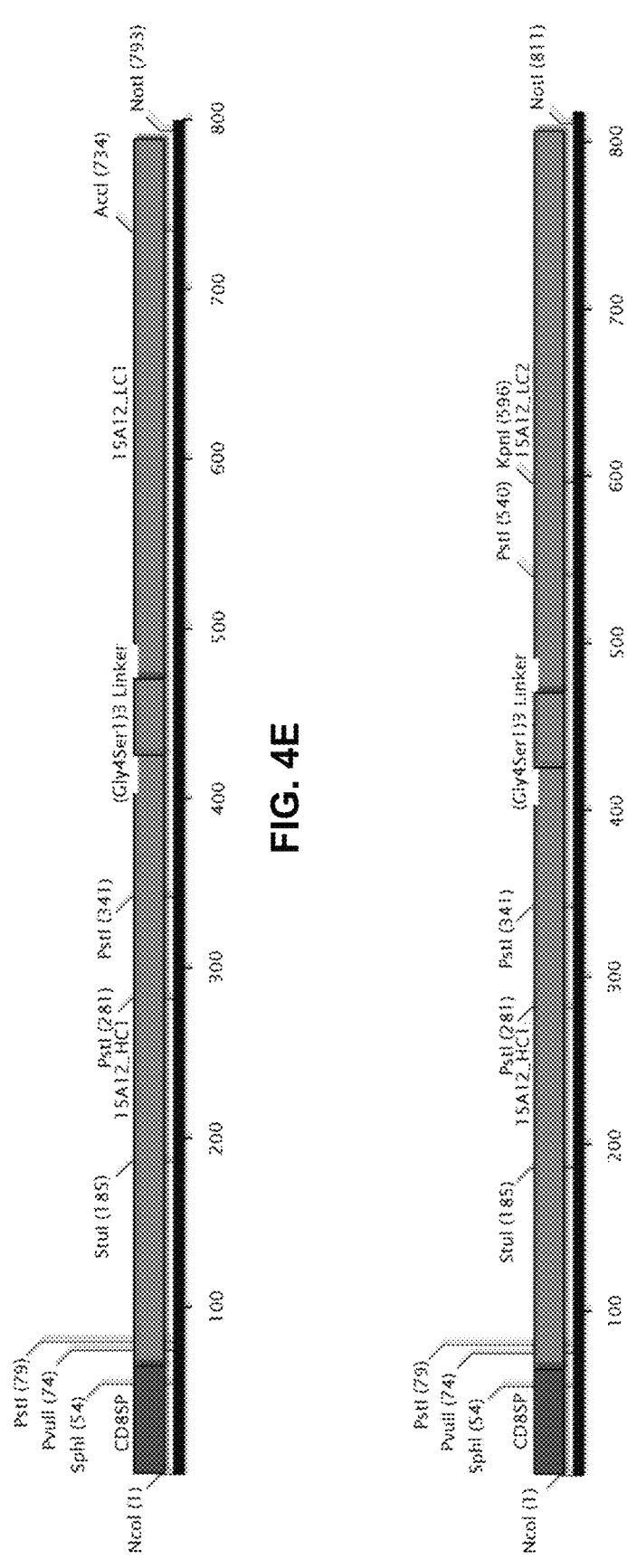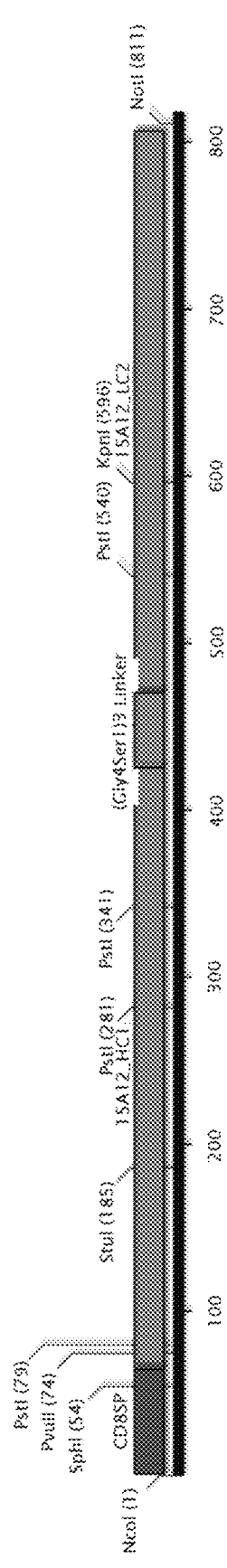
FIG. 4D
FIG. 4E
FIG. 4F

US 11,976,121 B2

CD123-BINDING CHIMERIC ANTIGEN RECEPTORS

CROSS-REFERENCE TO RELATED APPLICATIONS

This application is a National Stage of International Application No. PCT/US2018/042686, filed Jul. 18, 2018, which claims benefit of U.S. Provisional Application No. 62/534,960, filed Jul. 20, 2017, and Application Ser. No. 62/592,102, filed Nov. 29, 2017, which are hereby incorporated herein by reference in their entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Chimeric antigen receptor (CAR) polypeptides are disclosed that can be used with adoptive cell transfer to target and kill CD123-expressing cancers. The disclosed CAR polypeptides contain in an ectodomain an anti-CD123 binding agent that can bind CD123-expressing cancer cells. Also disclosed is an immune effector cell genetically modified to express the disclosed CAR polypeptide.

The anti-CD123 binding agent is in some embodiments an antibody fragment that specifically binds CD123. For example, the antigen binding domain can be a Fab or a single-chain variable fragment (scFv) of an antibody that specifically binds CD123. The anti-CD123 binding agent is in some embodiments an aptamer that specifically binds CD123. For example, the anti-CD123 binding agent can be a peptide aptamer selected from a random sequence pool based on its ability to bind CD123. The anti-CD123 binding agent can also be a natural ligand of CD123, or a variant and/or fragment thereof capable of binding CD123.

In some embodiments, the anti-CD123 scFv is derived from hybridoma 3F5, 4E10, 12H5, 15A12, 17E7, 12H11, or combinations thereof. In some embodiments, the anti-CD123 scFv can comprise a variable heavy ($V_H$) domain having CDR1, CDR2 and CDR3 sequences and a variable light ($V_L$) domain having CDR1, CDR2 and CDR3 sequences.

For example, in some embodiments, the CDR1 sequence of the $V_H$ domain comprises the amino acid sequence GYTFTDYN (SEQ ID NO:1), CDR2 sequence of the $V_H$ domain comprises the amino acid sequence INPNNGGT (SEQ ID NO:2), CDR3 sequence of the $V_H$ domain comprises the amino acid sequence ARKGYGGNYDYFDY (SEQ ID NO:3), CDR1 sequence of the $V_L$ comprises the amino acid sequence QSIGTS (SEQ ID NO:4), CDR2 sequence of the $V_L$ domain comprises the amino acid sequence YASx (SEQ ID NO:5), and CDR3 sequence of the $V_L$ domain comprises the amino acid sequence QQSNSWPYT (SEQ ID NO:6).

In some embodiments, the CDR1 sequence of the $V_H$ domain comprises the amino acid sequence GFNIKDTY (SEQ ID NO:7) or GFSLSTYGMG (SEQ ID NO:8), the CDR2 sequence of the $V_H$ domain comprises the amino acid sequence IDPANGNT (SEQ ID NO:9) or IYWDDDK (SEQ ID NO:10), the CDR3 sequence of the $V_H$ domain comprises the amino acid sequence ALYYYGGSLDY (SEQ ID NO:11) or AQSLIYDGYYGFAY (SEQ ID NO:12), the CDR1 sequence of the $V_L$ comprises the amino acid sequence QSLLYSGNQKNY (SEQ ID NO:13), the CDR2 sequence of the $V_L$ domain comprises the amino acid sequence WASx (SEQ ID NO:14), and the CDR3 sequence of the $V_L$ domain comprises the amino acid sequence QQYYSYPRT (SEQ ID NO:15).

In some embodiments, the CDR1 sequence of the $V_H$ domain comprises the amino acid sequence GYTFTYYG (SEQ ID NO:16), the CDR2 sequence of the $V_H$ domain comprises the amino acid sequence INTYSGVP (SEQ ID NO:17), the CDR3 sequence of the $V_H$ domain comprises the amino acid sequence ARWIYYSDLYGMDY (SEQ ID NO:18), the CDR1 sequence of the $V_L$ comprises the amino acid sequence QSIVHSNGDTY (SEQ ID NO:19), the CDR2 sequence of the $V_L$ domain comprises the amino acid sequence KVSx (SEQ ID NO:20), and the CDR3 sequence of the $V_L$ domain comprises the amino acid sequence FQGSHVPWT (SEQ ID NO:21).

In some embodiments, the CDR1 sequence of the $V_H$ domain comprises the amino acid sequence GYTFSSYW (SEQ ID NO:22) or GYTLTTYL (SEQ ID NO:23), the CDR2 sequence of the $V_H$ domain comprises the amino acid sequence INPSSGYT (SEQ ID NO:24) or INPNSGSS (SEQ ID NO:25), the CDR3 sequence of the $V_H$ domain comprises the amino acid sequence ARDGNYDHWYFDV (SEQ ID NO:26) or AIRHYGGSLFDY (SEQ ID NO:27), the CDR1 sequence of the $V_L$ comprises the amino acid sequence QDINSY (SEQ ID NO:28) or QSLLNSRTRKNY (SEQ ID NO:29), the CDR2 sequence of the $V_L$ domain comprises the amino acid sequence WASx (SEQ ID NO:14), or RANx (SEQ ID NO:30), and the CDR3 sequence of the $V_L$ domain comprises the amino acid sequence LQYDELLT (SEQ ID NO:31) or EQSYNLFT (SEQ ID NO:32).

In some embodiments, the some embodiments, the CDR1 sequence of the $V_H$ domain comprises the amino acid sequence GYTFTDYN (SEQ ID NO:1), GFNIKDTY (SEQ ID NO:7), GFSLSTYGMG (SEQ ID NO:8), GYTFTYYG (SEQ ID NO:16), GYTFSSYW (SEQ ID NO:22), or GYTLTTYL (SEQ ID NO:23); the CDR2 sequence of the $V_H$ domain comprises the amino acid sequence INPNNGGT (SEQ ID NO:2), IDPANGNT (SEQ ID NO:9), IYWDDDK (SEQ ID NO:10), INTYSGVP (SEQ ID NO:17), INPSSGYT (SEQ ID NO:24), or INPNSGSS (SEQ ID NO:25); the CDR3 sequence of the $V_H$ domain comprises the amino acid sequence ARKGYGGNYDYFDY (SEQ ID NO:3), ALYYYGGSLDY (SEQ ID NO:11), AQSLIYDGYYGFAY (SEQ ID NO:12), ARWIYYSD-LYGMDY (SEQ ID NO:18), ARDGNYDHWYFDV (SEQ ID NO:26), or AIRHYGGSLFDY (SEQ ID NO:27); the CDR1 sequence of the $V_L$ comprises the amino acid sequence QSIGTS (SEQ ID NO:4), QSLLYSGNQKNY (SEQ ID NO:13), QSIVHSNGDTY (SEQ ID NO:19), QDINSY (SEQ ID NO:28), or QSLLNSRTRKNY (SEQ ID NO:29); the CDR2 sequence of the $V_L$ domain comprises the amino acid sequence YASx (SEQ ID NO:5), WASx (SEQ ID NO:14), KVSx (SEQ ID NO:20), or RANx (SEQ ID NO:30); the CDR3 sequence of the $V_L$ domain comprises the amino acid sequence QQSNSWPYT (SEQ ID NO:6), QQYYSYPRT (SEQ ID NO:15), FQGSHVPWT (SEQ ID NO:21), LQYDELLT (SEQ ID NO:31), or EQSYNLFT (SEQ ID NO:32); or any combination thereof.

The heavy and light chains are preferably separated by a linker. Suitable linkers for scFv antibodies are known in the art. In some embodiments, the linker comprises the amino acid sequence GGGGSGGGGSGGGGS (SEQ ID NO:60).

Therefore, in some embodiments, the anti-CD123 scFv $V_H$ domain comprises the amino acid sequence:

```
                                     (SEQ ID NO: 33, 3F5HC1)
EVQLQQSGPELVKPGSSVKISCKASGYTFTDYNMDWVKQSHGKSLEWIGTI

NPNNGGTSYNQKFKGKATLTVDKSSSTAYMELRSLTSEDSAVYYCARKGYG

GNYDYFDYWGQGTTLTVSS, (SEQ ID NO: 34, 12H1HC1)
EVQLQQSGAELVKPGASVKLSCTASGFNIKDTYMHWVKQRPEQGLEWIGRI

DPANGNTIYASKFQGKATITADTSSNTAYMQLSSLTSGDTAVYYCALYYYG

GSLDYWGQGTTLTVSS, (SEQ ID NO: 35, 12H1HC2)
QVTLKESGPGILQPSQTLSLTCSFSGFSLSTYGMGVSWIRQPSGKGLEWLA

HIYWDDDKRYNPSLKSRLTISKDTSNNQVFLKITSVDTADTATYYCAQSLI

YDGYYGFAYWGQGTLVTVSA, (SEQ ID NO: 36, 12H2HC1)
QIQLVQSGPELKKPGETVKISCKASGYTFTYYGMNWVKQAPGKGLEWMGWI

NTYSGVPTYADDFKGRFAFSLETSVSTAYLQINNLKNEDTATYFCARWIYY

SDLYGMDYWGQGTSVTVSS, (SEQ ID NO: 37, 15A12HC1)
QVQLQQSGAELAKPGASVKMSCKASGYTFSSYWMHWLKQRPGQGLEWIGYI

NPSSGYTNYNQKFKDKATLTADKSSSTAYMQLSSLTSEDSAVYYCARDGNY

DHWYFDVWGTGTTVTVSS,
or
                                     (SEQ ID NO: 38, 15A12HC2)
QVQLQQPGAELVRPGASVKMSCKASGYTLTTYLMDWVKQRLGQGFEWIGNI

NPNSGSSNYNEKFKGKAKLTVDKSSSTAYMQLSSLTSEDSAVYYCAIRHYG

GSLFDYWGQGTTLTVSS.
```

In some embodiments, the anti-CD123 scFv $V_L$ domain comprises the amino acid sequence:

```
                                     (SEQ ID NO: 39, 3F5LC1)
DILLTQSPAILSVSPGERVSFSCRASQSIGTSIHWYQQRTNGSPRLLIKYA

SESISGIPSRFSGSGSGTDFTLSINSVESEDIADYYCQQSNSWPYTFGGGT

KLEIK,
                                     (SEQ ID NO: 40, 12H1LC1)
DIVMSQSPSSLAVSVGERVTMSCKSSQSLLYSGNQKNYLAWYQQKPGQSPK

LLIYWASTRESGVPDRFTGSGSGTDFTLTISSVKAEDLAVYYCQQYYSYPR

TFGGGTKLEIK,
                                     (SEQ ID NO: 41, 12H2LC)
DVLMTQSPLSLPVSLGDQASISCRSSQSIVHSNGDTYLEWYLQKPGQSPKL

LIYKVSNRFSGVPDRFSGSGSGTDFTLKISRVEAEDLGVYHCFQGSHVPWT

FGGGTKLEIK, (SEQ ID NO: 42, 15A12LC1)
DIKMTQSPSSMYASLGERVTITCKASQDINSYLSWFQQKPGKSPKTLIYRA

NRLVDGVPSRFSGSGSGQDYSLTISSLEYEDMGIYYCLQYDELLTFGAGTK

LELK,
or
                                     (SEQ ID NO: 43, 15A12LC2)
DIVMSQSPSSLAVSAGERVTMSCRSSQSLLNSRTRKNYLAWYQQKPGQSPK

LLIYWASTRESGVPDRFSGSGSGTDFTLTISSVQAEDLAVYYCEQSYNLFT

FGSGTKLEIK.
```

In some embodiments, the anti-CD123 scFv comprises an amino acid sequence:

```
                                     (SEQ ID NO: 44 3F5HC1_LC)
EVQLQQSGPELVKPGSSVKISCKASGYTFTDYNMDWVKQSHGKSLEWIGTI

NPNNGGTSYNQKFKGKATLTVDKSSSTAYMELRSLTSEDSAVYYCARKGYG

GNYDYFDYWGQGTTLTVSSGGGGSGGGGSGGGGSDILLTQSPAILSVSPGE

RVSFSCRASQSIGTSIHWYQQRTNGSPRLLIKYASESISGIPSRFSGSGSG

TDFTLSINSVESEDIADYYCQQSNSWPYTFGGGTKLEIK.
```

In some embodiments, the anti-CD123 scFv comprises an amino acid sequence:

```
                                     (SEQ ID NO: 45, 12H1HC1_LC1)
EVQLQQSGAELVKPGASVKLSCTASGFNIKDTYMHWVKQRPEQGLEWIGRI

DPANGNTIYASKFQGKATITADTSSNTAYMQLSSLTSGDTAVYYCALYYYG

GSLDYWGQGTTLTVSSGGGGSGGGGSGGGGSDIVMSQSPSSLAVSVGERVT

MSCKSSQSLLYSGNQKNYLAWYQQKPGQSPKLLIYWASTRESGVPDRFTGS

GSGTDFTLTISSVKAEDLAVYYCQQYYSYPRTFGGGTKLEIK.
```

In some embodiments, the anti-CD123 scFv comprises an amino acid sequence:

```
                                     (SEQ ID NO: 46, 12H1HC2_LC1)
QVTLKESGPGILQPSQTLSLTCSFSGFSLSTYGMGVSWIRQPSGKGLEWLA

HIYWDDDKRYNPSLKSRLTISKDTSNNQVFLKITSVDTADTATYYCAQSLI

YDGYYGFAYWGQGTLVTVSAGGGGSGGGGSGGGGSDIVMSQSPSSLAVSVG

ERVTMSCKSSQSLLYSGNQKNYLAWYQQKPGQSPKLLIYWASTRESGVPDR

FTGSGSGTDFTLTISSVKAEDLAVYYCQQYYSYPRTFGGGTKLEIK.
```

In some embodiments, the anti-CD123 scFv comprises an amino acid sequence:

```
                                     (SEQ ID NO: 47, 12H2HC1_LC1)
QIQLVQSGPELKKPGETVKISCKASGYTFTYYGMNVVVKQAPGKGLEVVMG

WINTYSGVPTYADDFKGRFAFSLETSVSTAYLQINNLKNEDTATYFCARWI

YYSDLYGMDYWGQGTSVTVSSGGGGSGGGGSGGGGSDVLMTQSPLSLPVSL

GDQASISCRSSQSIVHSNGDTYLEVVYLQKPGQSPKLLIYKVSNRFSGVPD

RFSGSGSGTDFTLKISRVEAEDLGVYHCFQGSHVPWTFGGGTKLEIK.
```

In some embodiments, the anti-CD123 scFv comprises an amino acid sequence:

(SEQ ID NO: 48, 15A12HC1_LC1)
QVQLQQSGAELAKPGASVKMSCKASGYTFSSYWMHWLKQRPGQGLEWIGYI
NPSSGYTNYNQKFKDKATLTADKSSSTAYMQLSSLTSEDSAVYYCARDGNY
DHWYFDVWGTGTTVTVSSGGGGSGGGGSGGGGSDIKMTQSPSSMYASLGER
VTITCKASQDINSYLSWFQQKPGKSPKTLIYRANRLVDGVPSRFSGSGSGQ
DYSLTISSLEYEDMGIYYCLQYDELLTFGAGTKLELK.

In some embodiments, the anti-CD123 scFv comprises an amino acid sequence:

(SEQ ID NO: 49, 15A12HC1_LC2)
QVQLQQSGAELAKPGASVKMSCKASGYTFSSYWMHWLKQRPGQGLEWIGYI
NPSSGYTNYNQKFKDKATLTADKSSSTAYMQLSSLTSEDSAVYYCARDGNY
DHWYFDVWGTGTTVTVSSGGGGSGGGGSGGGGSDIVMSQSPSSLAVSAGER
VTMSCRSSQSLLNSRTRKNYLAWYQQKPGQSPKLLIYWASTRESGVPDRFS
GSGSGTDFTLTISSVQAEDLAVYYCEQSYNLFTFGSGTKLEIK.

In some embodiments, the anti-CD123 scFv comprises an amino acid sequence:

(SEQ ID NO: 50, 15A12HC2_LC1)
QVQLQQPGAELVRPGASVKMSCKASGYTLTTYLMDWVKQRLGQGFEWIGNI
NPNSGSSNYNEKFKGKAKLTVDKSSSTAYMQLSSLTSEDSAVYYCAIRHYG
GSLFDYWGQGTTLTVSSGGGGSGGGGSGGGGSDIKMTQSPSSMYASLGERV
TITCKASQDINSYLSWFQQKPGKSPKTLIYRANRLVDGVPSRFSGSGSGQD
YSLTISSLEYEDMGIYYCLQYDELLTFGAGTKLELK.

In some embodiments, the anti-CD123 scFv comprises an amino acid sequence:

(SEQ ID NO: 51, 15A12HC2_LC2)
QVQLQQPGAELVRPGASVKMSCKASGYTLTTYLMDWVKQRLGQGFEWIGNI
NPNSGSSNYNEKFKGKAKLTVDKSSSTAYMQLSSLTSEDSAVYYCAIRHYG
GSLFDYWGQGTTLTVSSGGGGSGGGGSGGGGSDIVMSQSPSSLAVSAGERV
TMSCRSSQSLLNSRTRKNYLAWYQQKPGQSPKLLIYWASTRESGVPDRFSG
SGSGTDFTLTISSVQAEDLAVYYCEQSYNLFTFGSGTKLEIK.

In some embodiments, the anti-CD123 scFv is encoded by the nucleic acid sequence:

(SEQ ID NO: 52, 3F5HC1_LC)
CCATGGCCCTCCCGGTAACGGCTCTGCTGCTTCCACTCGCACTGCTCTTGC
ATGCTGCCAGACCAGAGGTCCAGCTGCAACAGTCTGGACCTGAGCTGGTGA
AGCCTGGGTCTTCAGTGAAGATATCCTGCAAAGCTTCTGGATACACATTCA
CTGACTACAACATGGACTGGGTGAAGCAGAGTCATGGAAAGAGCCTTGAGT
GGATTGGAACTATTAATCCTAACAATGGTGGTACTAGCTACAACCAGAAGT
TCAAGGGCAAGGCCACATTGACTGTAGACAAGTCCTCCAGCACAGCCTACA
TGGAGCTCCGCAGCCTGACATCTGAAGACTCTGCAGTCTATTACTGTGCAA
GAAAGGGCTATGGTGGTAACTACGACTACTTTGACTACTGGGGCCAAGGCA
CCACTCTCACAGTCTCCTCAGGTGGAGGTGGATCAGGTGGAGGTGGATCTG

GTGGAGGTGGATCTGACATCTTGCTGACTCAGTCTCCAGCCATCCTGTCTG
TGAGTCCAGGAGAAAGAGTCAGTTTCTCCTGCAGGGCCAGTCAGAGCATTG
GCACAAGCATACACTGGTATCAGCAAAGAACAAATGGTTCTCCAAGGCTTC
TCATAAAGTATGCTTCTGAGTCTATCTCTGGGTTCCCTTCCAGGTTTAGTG
GCAGTGGATCAGGGACAGATTTTACTCTTAGCATCAACAGTGTGGAGTCTG
AAGATATTGCAGATTATTACTGTCAACAAAGTAATAGCTGGCCGTACACGT
TCGGAGGGGGGACCAAGCTGGAAATAAAACGGGCGGCCGCA.

In some embodiments, the anti-CD123 scFv is encoded by the nucleic acid sequence:

(SEQ ID NO: 53, 12H1HC1_LC1)
ATGGCCCTCCCGGTAACGGCTCTGCTGCTTCCACTCGCACTGCTCTTGCAT
GCTGCCAGACCAGAGGTTCAGCTGCAGCAGTCTGGGGCAGAGCTTGTGAAG
CCAGGGGCCTCAGTCAAGTTGTCCTGCACAGCTTCTGGCTTCAACATTAAA
GACACCTATATGCACTGGGTGAAGCAGAGGCCTGAACAGGGCCTGGAGTGG
ATTGGAAGGATTGATCCTGCGAATGGTAATACTATATATGCCTCAAAGTTC
CAGGGCAAGGCCACTATAACAGCAGACACATCATCCAACACAGCCTACATG
CAGCTCAGCAGCCTGACATCTGGGGACACTGCCGTCTATTACTGTGCTCTT
TATTACTATGGTGGTAGCCTTGACTACTGGGGCCAAGGCACCACTCTCACA
GTCTCCTCAGGTGGAGGTGGATCAGGTGGAGGTGGATCTGGTGGAGGTGGA
TCTGACATTGTGATGTCACAGTCTCCATCCTCCCTAGCTGTGTCAGTTGGA
GAGAGGGTTACTATGAGCTGCAAGTCCAGTCAGAGCCTTTTATATAGTGGC
AATCAAAAGAACTACTTGGCCTGGTACCAGCAGAAACCAGGGCAGTCTCCT
AAACTGCTGATTTACTGGGCATCCACTAGGGAATCTGGGGTCCCTGATCGC
TTCACAGGCAGTGGATCTGGGACAGATTTCACTCTCACCATCAGCAGTGTG
AAGGCTGAAGACCTGGCAGTTTATTACTGTCAGCAATATATAGCTATCCT
CGGACGTTCGGTGGAGGCACCAAGCTGGAAATCAAACGG.

In some embodiments, the anti-CD123 scFv is encoded by the nucleic acid sequence:

(SEQ ID NO: 54, 12H1HC1_LC2)
ATGGCCCTCCCGGTAACGGCTCTGCTGCTTCCACTCGCACTGCTCTTGCAT
GCTGCCAGACCACAGGTTACTCTGAAAGAGTCTGGCCCTGGGATATTGCAG
CCCTCCCAGACCCTCAGTCTGACTTGTTCTTTCTCTGGGTTTTCACTGAGC
ACTTATGGTATGGGTGTGAGCTGGATTCGTCAGCCTTCAGGAAAGGGTCTG
GAGTGGCTGGCACACATTTACTGGGATGATGACAAGCGCTATAACCCATCC
CTGAAGAGCCGGCTCACAATCTCCAAGGATACCTCCAACAACCAGGTATTC
CTCAAGATCACCAGTGTGGACACTGCAGATACTGCCACATACTACTGTGCT
CAAAGCCTGATCTATGATGGTTACTACGGGTTTGCCTACTGGGGCCAAGGG
ACTCTGGTCACTGTCTCTGCAGGTGGAGGTGGATCAGGTGGAGGTGGATCT
GGTGGAGGTGGATCTGACATTGTGATGTCACAGTCTCCATCCTCCCTAGCT
GTGTCAGTTGGAGAGAGGGTTACTATGAGCTGCAAGTCCAGTCAGAGCCTT

-continued
TTATATAGTGGCAATCAAAAGAACTACTTGGCCTGGTACCAGCAGAAACCA

GGGCAGTCTCCTAAACTGCTGATTTACTGGGCATCCACTAGGGAATCTGGG

GTCCCTGATCGCTTCACAGGCAGTGGATCTGGGACAGATTTCACTCTCACC

ATCAGCAGTGTGAAGGCTGAAGACCTGGCAGTTTATTACTGTCAGCAATAT

TATAGCTATCCTCGGACGTTCGGTGGAGGCACCAAGCTGGAAATCAAACG

G.

In some embodiments, the an i-CD123 scFv is encoded by the nucleic acid sequence:

(SEQ ID NO: 55, 12H2HC1_LC1)
ATGGCCCTCCCGGTAACGGCTCTGCTGCTTCCACTCGCACTGCTCTTGCAT

GCTGCCAGACCACAGATCCAGTTGGTGCAATCTGGACCTGAGCTGAAGAAG

CCTGGAGAGACAGTCAAGATCTCCTGCAAGGCTTCTGGGTATACCTTCACA

TACTATGGAATGAACTGGGTGAAGCAGGCTCCAGGAAAGGGTTTAGAGTGG

ATGGGCTGGATAAACACCTACTCTGGAGTGCCAACATATGCTGATGACTTC

AAGGGACGGTTTGCCTTCTCTTTGGAAACCTCTGTCAGCACTGCCTATTTG

CAGATCAACAACCTCAAAAATGAGGACACGGCTACATATTTTTGTGCAAGA

TGGATCTACTATAGTGACCTCTATGGTATGGACTACTGGGGTCAAGGAACC

TCAGTCACCGTCTCCTCAGGTGGAGGTGGATCAGGTGGAGGTGGATCTGGT

GGAGGTGGATCTGATGTTTTGATGACCCAAAGTCCACTCTCCCTGCCTGTC

AGTCTTGGAGATCAAGCCTCCATCTCTTGTAGATCTAGTCAGAGTATTGTA

CATAGTAATGGAGACACGTATTTAGAATGGTATTTGCAGAAACCAGGCCAG

TCTCCAAAGCTCCTGATCTACAAAGTTTCTAACCGATTTTCTGGGGTCCCA

GACAGGTTCAGTGGCAGTGGATCAGGGACAGATTTCACACTCAAGATCAGC

AGAGTGGAGGCTGAGGATCTGGGAGTTTATCACTGCTTTCAAGGTTCACAT

GTTCCGTGGACGTTCGGTGGAGGCACCAAGCTGGAAATCAAACG.

In some embodiments, the anti-CD123 scFv is encoded by the nucleic acid sequence:

(SEQ ID NO: 56, 15A12HC1_LC1)
ATGGCCCTCCCGGTAACGGCTCTGCTGCTTCCACTCGCACTGCTCTTGCAT

GCTGCCAGACCACAGGTCCAGCTGCAGCAGTCTGGGGCTGAACTGGCAAAA

CCTGGGGCCTCAGTGAAGATGTCCTGCAAGGCTTCTGGCTACACCTTTTCT

AGCTACTGGATGCACTGGCTAAAACAGAGGCCTGGACAGGGTCTGGAGTGG

ATTGGATACATTAATCCTAGCAGTGGTTATACTAACTACAATCAGAAGTTC

AAGGACAAGGCCACATTGACTGCAGACAAATCCTCCAGCACAGCCTACATG

CAACTGAGCAGCCTGACATCTGAGGACTCTGCAGTCTATTACTGTGCAAGA

GATGGTAACTATGACCACTGGTACTTCGATGTCTGGGGCACAGGGACCACG

GTCACCGTCTCCTCAGGTGGAGGTGGATCAGGTGGAGGTGGATCTGGTGGA

GGTGGATCTGACATCAAGATGACCCAGTCTCCATCTTCCATGTATGCATCT

CTAGGAGAGAGTCACTATCACTTGCAAGGCGAGTCAGGACATTAATAGC

TATTTAAGCTGGTTCCAGCAGAAACCAGGGAAATCTCCTAAGACCCTGATC

TATCGTGCAAACAGATTGGTAGATGGGGTCCCATCAAGGTTCAGTGGCAGT

-continued
GGATCTGGGCAAGATTATTCTCTCACCATCAGCAGCCTGGAGTATGAAGAT

ATGGGAATTTATTATTGTCTACAGTATGATGAGTTGCTCACGTTCGGTGCT

GGGACCAAGCTGGAGCTGAAACGG.

In some embodiments, the anti-CD123 scFv is encoded by the nucleic acid sequence:

(SEQ ID NO: 57, 15A12HC1_LC2)
ATGGCCCTCCCGGTAACGGCTCTGCTGCTTCCACTCGCACTGCTCTTGCAT

GCTGCCAGACCACAGGTCCAGCTGCAGCAGTCTGGGGCTGAACTGGCAAAA

CCTGGGGCCTCAGTGAAGATGTCCTGCAAGGCTTCTGGCTACACCTTTTCT

AGCTACTGGATGCACTGGCTAAAACAGAGGCCTGGACAGGGTCTGGAGTGG

ATTGGATACATTAATCCTAGCAGTGGTTATACTAACTACAATCAGAAGTTC

AAGGACAAGGCCACATTGACTGCAGACAAATCCTCCAGCACAGCCTACATG

CAACTGAGCAGCCTGACATCTGAGGACTCTGCAGTCTATTACTGTGCAAGA

GATGGTAACTATGACCACTGGTACTTCGATGTCTGGGGCACAGGGACCACG

GTCACCGTCTCCTCAGGTGGAGGTGGATCAGGTGGAGGTGGATCTGGTGGA

GGTGGATCTGACATTGTGATGTCACAGTCTCCATCCTCCCTGGCTGTGTCA

GCAGGAGAGAGGGTCACTATGAGCTGCAGATCCAGTCAGAGTCTGCTCAAC

AGTAGAACCCGAAAGAACTACTTGGCTTGGTACCAGCAGAAACCAGGGCAG

TCTCCTAAGCTGCTGATCTACTGGGCATCCACTAGGGAATCTGGGGTCCCT

GATCGCTTCTCAGGCAGTGGATCTGGGACAGATTTCACTCTCACCATCAGC

AGTGTGCAGGCTGAAGACCTGGCAGTTTATTACTGCGAGCAATCTTATAAT

CTATTCACGTTCGGCTCGGGGACAAAGTTGGAAATAAAACGG.

In some embodiments, the anti-CD123 scFv is encoded by the nucleic acid sequence:

(SEQ ID NO: 58, 15A12HC2_LC1)
ATGGCCCTCCCGGTAACGGCTCTGCTGCTTCCACTCGCACTGCTCTTGCAT

GCTGCCAGACCACAGGTTCAACTGCAGCAGCCTGGGGCTGAGCTGGTGAGG

CCTGGGGCTTCAGTGAAGATGTCCTGCAAGGCTTCTGGCTACACCCTCACC

ACCTACTTGATGGACTGGGTAAAACAGAGGCTTGGACAAGGCTTTGAGTGG

ATTGGAAATATTAATCCTAATAGTGGTAGTAGTAACTACAATGAGAAGTTC

AAGGGCAAGGCCAAGCTGACTGTAGACAAATCCTCCAGCACAGCCTACATG

CAACTCAGCAGCCTGACATCTGAGGACTCTGCGGTCTATTACTGTGCAATA

CGGCACTATGGTGGTAGTCTTTTGACTACTGGGGCCAAGGCACCACTCTC

ACAGTCCCTCAGGTGGAGGTGGATCAGGTGGAGGTGGATCTGGTGGAGGT

GGATCTGACATCAAGATGACCCAGTCTCCATCTTCCATGTATGCATCTCTA

GGAGAGAGAGTCACTATCACTTGCAAGGCGAGTCAGGACATTAATAGCTAT

TTAAGCTGGTTCCAGCAGAAACCAGGGAAATCTCCTAAGACCCTGATCTAT

CGTGCAAACAGATTGGTAGATGGGGTCCCATCAAGGTTCAGTGGCAGTGGA

TCTGGGCAAGATTATTCTCTCACCATCAGCAGCCTGGAGTATGAAGATATG

-continued

```
GGAATTTATTATTGTCTACAGTATGATGAGTTGCTCACGTTCGGTGCTGGG

ACCAAGCTGGAGCTGAAACGG.
```

In some embodiments, the anti-CD123 scFv is encoded by the nucleic acid sequence:

```
                                (SEQ ID NO: 59, 15A12HC2_LC2)
ATGGCCCTCCCGGTAACGGCTCTGCTGCTTCCACTCGCACTGCTCTTGCAT

GCTGCCAGACCACAGGTTCAACTGCAGCAGCCTGGGGCTGAGCTGGTGAGG

CCTGGGGCTTCAGTGAAGATGTCCTGCAAGGCTTCTGGCTACACCCTCACC

ACCTACTTGATGGACTGGGTAAAACAGAGGCTTGGACAAGGCTTTGAGTGG

ATTGGAAATATTAATCCTAATAGTGGTAGTAGTAACTACAATGAGAAGTTC

AAGGGCAAGGCCAAGCTGACTGTAGACAAATCCTCCAGCACAGCCTACATG

CAACTCAGCAGCCTGACATCTGAGGACTCTGCGGTCTATTACTGTGCAATA

CGGCACTATGGTGGTAGTCTCTTTGACTACTGGGCCAAGGCACCACTCTC

ACAGTCTCCTCAGGTGGAGGTGGATCAGGTGGAGGTGGATCTGGTGGAGGT

GGATCTGACATTGTGATGTCACAGTCTCCATCCTCCCTGGCTGTGTCAGCA

GGAGAGAGGGTCACTATGAGCTGCAGATCCAGTCAGAGTCTGCTCAACAGT

AGAACCCGAAAGAACTACTTGGCTTGGTACCAGCAGAAACCAGGGCAGTCT

CCTAAGCTGCTGATCTACTGGGCATCCACTAGGGAATCTGGGGTCCCTGAT

CGCTTCTCAGGCAGTGGATCTGGGACAGATTTCACTCTCACCATCAGCAGT

GTGCAGGCTGAAGACCTGGCAGTTTATTACTGCGAGCAATCTTATAATCTA

TTCACGTTCGGCTCGGGGACAAAGTTGGAAATAAAACGG.
```

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the intracellular signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1BB that enhance signaling.

Also disclosed is dual CAR T cell containing the disclosed CD123-specific CAR, and at least one other CAR with a different ligand binding target. In these embodiments, one CAR can include only the CD3ζ domain and the other CAR can include only the co-stimulatory domain(s). In these embodiments, dual CAR T cell activation would require co-expression of both targets on the target cell.

Therefore, in some embodiments, the disclosed CD123-specific CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective targets. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1BB, or a combination thereof, but does not contain a CD3 zeta (CD3ζ) signaling domain (SD).

The disclosed dual CAR T cell can contain the disclosed CD123-specific CAR and at least one other CAR with a different ligand binding target, such as CD123, TIM3, or CLEC12A. CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). These additional CARs can therefore contain an antibody that binds the second target, such as CD33, TIM3, or CLEC12A.

In some embodiments, the intracellular signaling domain is a CD3 zeta (CD3ζ) signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1BB that enhance signaling.

In some embodiments, the disclosed CARs comprises a costimulatory signaling region comprising a mutated form of the cytoplasmic domain of CD28 with altered phosphorylation at Y206 and/or Y218. In some embodiments, the disclosed CAR comprises an attenuating mutation at Y206, which will reduce the activity of the CAR. In some embodiments, the disclosed CAR comprises an attenuating mutation at Y218, which will reduce expression of the CAR. Any amino acid residue, such as alanine or phenylalanine, can be substituted for the tyrosine to achieve attenuation. In some embodiments, the tyrosine at Y206 and/or Y218 is substituted with a phosphomimetic residue. In some embodiments, the disclosed CAR substitution of Y206 with a phosphomimetic residue, which will increase the activity of the CAR. In some embodiments, the disclosed CAR comprises substitution of Y218 with a phosphomimetic residue, which will increase expression of the CAR. For example, the phosphomimetic residue can be phosphotyrosine. In some embodiments, a CAR may contain a combination of phosphomimetic amino acids and substitution(s) with non-phosphorylatable amino acids in different residues of the same CAR. For instance, a CAR may contain an alanine or phenylalanine substitution in Y209 and/or Y191 PLUS a phosphomimetic substitution in Y206 and/or Y218.

In some embodiments, the disclosed CARs comprises one or more 41BB domains with mutations that enhance binding to specific TRAF proteins, such as TRAF1, TRAF2, TRAF3, TRAF4, TRAF5, TRAF6, or any combination thereof. In some cases, the 41BB mutation enhances TRAF1- and/or TRAF2-dependent proliferation and survival of the T-cell, e.g. through NF-kB. In some cases, the 41BB mutation enhances TRAF3-dependent antitumor efficacy, e.g. through IRF7/INFβ. In some cases, the cytoplasmic domain of 41BB comprises the amino acid sequence KRGRKKLLY-IFKQPFMRPVQTT<u>QEED</u>GCSCRFP<u>EEEE</u>GGCEL (SEQ ID NO:X), where the regions of this domain responsible for TRAF binding are underlined. Therefore, the disclosed CARs can comprise cytoplasmic domain(s) of 41BB having at least one mutation in these underligned sequences that enhance TRAF-binding and/or enhance NFκB signaling.

Also as disclosed herein, TRAF proteins can in some cases enhance CAR T cell function independent of NFκB and 41BB. For example, TRAF proteins can in some cases enhance CD28 co-stimulation in T cells. Therefore, also disclosed herein are immune effector cells co-expressing CARs with one or more TRAF proteins, such as TRAF1, TRAF2, TRAF3, TRAF4, TRAF5, TRAF6, or any combination thereof. In some cases, the CAR is any CAR that targets a tumor antigen. For example, first-generation CARs typically had the intracellular domain from the CD3ζ chain, while second-generation CARs added intracellular signaling domains from various costimulatory protein receptors (e.g., CD28, 41BB, ICOS) to the endodomain of the CAR to provide additional signals to the T cell. In some cases, the CAR is the disclosed CAR with enhanced 41BB activation.

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell. In some embodiments, the cell exhibits an anti-tumor immunity when the antigen binding domain of the CAR binds to CD123.

In some embodiments, the cell further comprises a second CAR polypeptide comprising a second antigen binding domain, wherein the cell exhibits an anti-tumor immunity when both the antigen binding domain of the first CAR binds to CD123 and the antigen binding domain of the second CAR binds to its antigen. In these embodiments, each of the first and second CAR polypeptides can have incomplete endodomains. In some embodiments, the second CAR polypeptide binds to CD33, CLEC12A, CD99, or NKG2D ligands.

In some embodiments, the cell further comprises a molecular suicide switch system to remove the transferred cell population. For example, the nucleic acid encoding the CAR polypeptide can be part of an expression cassette that also includes an accessory gene. For example, in some embodiments, the accessory gene is a truncated EGFR gene (EGFRt). An EGFRt may be used as a non-immunogenic selection tool (e.g., immunomagnetic selection using biotinylated cetuximab in combination with anti-biotin microbeads for enrichment of T cells that have been lentivirally transduced with EGFRt-containing constructs), tracking marker (e.g., flow cytometric analysis for tracking T cell engraftment), or a suicide gene (e.g., via Cetuximab/Erbitux® mediated antibody dependent cellular cytotoxicity (ADCC) pathways). An example of a truncated EGFR (EGFRt) gene that may be used in accordance with the embodiments described herein is described in International Application No. PCT/US2010/055329, the subject matter of which is hereby incorporated by reference as if fully set forth herein. In other embodiments, the accessory gene is a truncated CD19 gene (CD19t). In other embodiments, the accessory gene is an inducible caspase 9 gene.

Also disclosed is a method of providing an anti-tumor immunity in a subject with a CD123-expressing cancer that involves administering to the subject an effective amount of an immune effector cell genetically modified with a disclosed CD123-specific CAR. In some cases, the cancer can be any CD123-expressing malignancy. In some cases, the cancer comprises Acute Myeloid Leukemia (AML), blastic plasmocytoid dendritic cell neoplasm, hairy cell leukemia, and Acute Lymphoblastic Leukemia.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A to 4H are CD123 CAR diagrams for 3F5HC1_LC (FIG. 4A), 12H1HC1_LC1 (FIG. 4B), 12H1HC1_LC2 (FIG. 4C), 12H2HC1_LC1 (FIG. 4D), 15A12HC1_LC1 (FIG. 4E), 15A12HC1_LC2 (FIG. 4F), 15A12HC2_LC1 (FIG. 4G), and 15A12HC2_LC2 (FIG. 4H).

DETAILED DESCRIPTION

Figure 1:
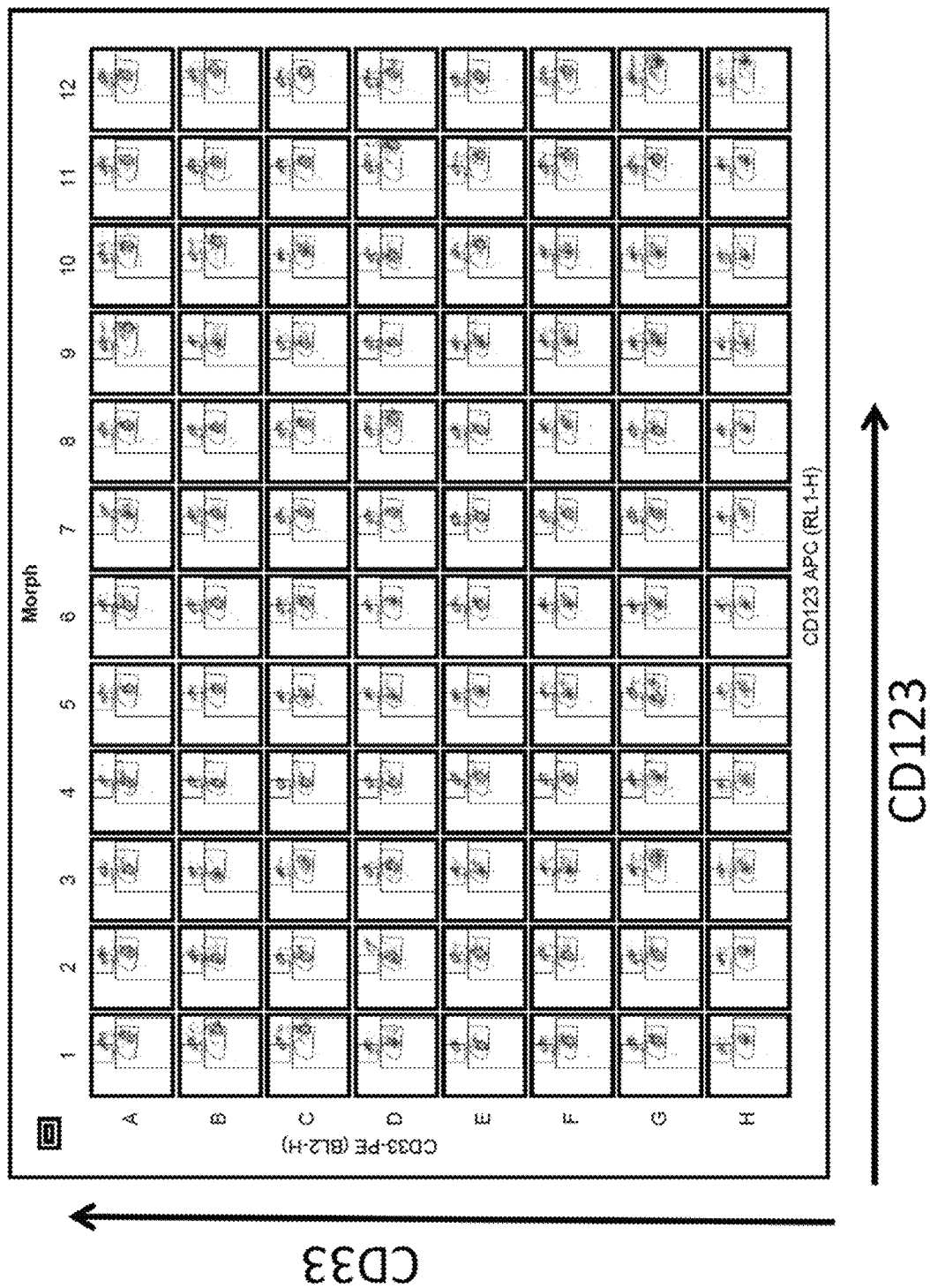
FIG. 1 shows results of primary screen for anti-CD123 antibodies, which was performed by incubating CD123+ cells with antibodies produced from hybridomas from CD123-immunized mice.

Disclosed herein are chimeric antigen receptors (CAR) that can specifically recognize tumor-associated antigens (TAA) on CD123-expressing cancers. Also disclosed are immune effector cells, such as T cells or Natural Killer (NK) cells, that are engineered to express these CARs. Therefore, also disclosed are methods for providing an anti-tumor immunity in a subject with CD123-expressing cancers that involves adoptive transfer of the disclosed immune effector cells engineered to express the disclosed CD123-specific CARs.

CD123-Specific Chimeric Antigen Receptors (CAR)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a CD123-specific chimeric antigen receptor (CAR) that can be that can be expressed in immune effector cells to enhance antitumor activity against CD123-specific CARs.

The disclosed CAR is generally made up of three domains: an ectodomain, a transmembrane domain, and an endodomain. The ectodomain comprises the CD123-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP-CD123-HG-TM-CSR-SD; or

SP-CD123-HG-TM-SD-CSR;

wherein "SP" represents an optional signal peptide,
wherein "CD123" represents a CD123-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain, sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIα), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CD123 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of CD123-binding region, co-stimulatory signaling regions, and intracellular signaling domain that can occur in the disclosed CARs.

TABLE 1

| First Generation CARs | |
|---|---|
| ScFv | Signal Domain |
| CD123 | CD8 |
| CD123 | CD3ζ |
| CD123 | CD3δ |
| CD123 | CD3γ |
| CD123 | CD3ε |
| CD123 | FcγRI-γ |
| CD123 | FcγRIII-γ |
| CD123 | FcεRIβ |
| CD123 | FcεRIγ |
| CD123 | DAP10 |
| CD123 | DAP12 |

TABLE 1-continued

First Generation CARs

| ScFv | Signal Domain |
|---|---|
| CD123 | CD32 |
| CD123 | CD79a |

TABLE 2

Second Generation CARs

| ScFv | Co-stimulatory Signal | Signal Domain |
|---|---|---|
| CD123 | CD28 | CD8 |
| CD123 | CD28 | CD3ζ |
| CD123 | CD28 | CD3δ |
| CD123 | CD28 | CD3γ |
| CD123 | CD28 | CD3ε |
| CD123 | CD28 | FcγRI-γ |
| CD123 | CD28 | FcγRIII-γ |
| CD123 | CD28 | FcεRIβ |
| CD123 | CD28 | FcεRIγ |
| CD123 | CD28 | DAP10 |
| CD123 | CD28 | DAP12 |
| CD123 | CD28 | CD32 |
| CD123 | CD28 | CD79a |
| CD123 | CD28 | CD79b |
| CD123 | CD8 | CD8 |
| CD123 | CD8 | CD3ζ |
| CD123 | CD8 | CD3δ |
| CD123 | CD8 | CD3γ |
| CD123 | CD8 | CD3ε |
| CD123 | CD8 | FcγRI-γ |
| CD123 | CD8 | FcγRIII-γ |
| CD123 | CD8 | FcεRIβ |
| CD123 | CD8 | FcεRIγ |
| CD123 | CD8 | DAP10 |
| CD123 | CD8 | DAP12 |
| CD123 | CD8 | CD32 |
| CD123 | CD8 | CD79a |
| CD123 | CD8 | CD79b |
| CD123 | CD4 | CD8 |
| CD123 | CD4 | CD3ζ |
| CD123 | CD4 | CD3δ |
| CD123 | CD4 | CD3γ |
| CD123 | CD4 | CD3ε |
| CD123 | CD4 | FcγRI-γ |
| CD123 | CD4 | FcγRIII-γ |
| CD123 | CD4 | FcεRIβ |
| CD123 | CD4 | FcεRIγ |
| CD123 | CD4 | DAP10 |
| CD123 | CD4 | DAP12 |
| CD123 | CD4 | CD32 |
| CD123 | CD4 | CD79a |
| CD123 | CD4 | CD79b |
| CD123 | b2c | CD8 |
| CD123 | b2c | CD3ζ |
| CD123 | b2c | CD3δ |
| CD123 | b2c | CD3γ |
| CD123 | b2c | CD3ε |
| CD123 | b2c | FcγRI-γ |
| CD123 | b2c | FcγRIII-γ |
| CD123 | b2c | FcεRIβ |
| CD123 | b2c | FcεRIγ |
| CD123 | b2c | DAP10 |
| CD123 | b2c | DAP12 |
| CD123 | b2c | CD32 |
| CD123 | b2c | CD79a |
| CD123 | b2c | CD79b |
| CD123 | CD137/41BB | CD8 |
| CD123 | CD137/41BB | CD3ζ |
| CD123 | CD137/41BB | CD3δ |
| CD123 | CD137/41BB | CD3γ |
| CD123 | CD137/41BB | CD3ε |
| CD123 | CD137/41BB | FcγRI-γ |
| CD123 | CD137/41BB | FcγRIII-γ |
| CD123 | CD137/41BB | FcεRIβ |
| CD123 | CD137/41BB | FcεRIγ |
| CD123 | CD137/41BB | DAP10 |
| CD123 | CD137/41BB | DAP12 |
| CD123 | CD137/41BB | CD32 |
| CD123 | CD137/41BB | CD79a |
| CD123 | CD137/41BB | CD79b |
| CD123 | ICOS | CD8 |
| CD123 | ICOS | CD3ζ |
| CD123 | ICOS | CD3δ |
| CD123 | ICOS | CD3γ |
| CD123 | ICOS | CD3ε |
| CD123 | ICOS | FcγRI-γ |
| CD123 | ICOS | FcγRIII-γ |
| CD123 | ICOS | FcεRIβ |
| CD123 | ICOS | FcεRIγ |
| CD123 | ICOS | DAP10 |
| CD123 | ICOS | DAP12 |
| CD123 | ICOS | CD32 |
| CD123 | ICOS | CD79a |
| CD123 | ICOS | CD79b |
| CD123 | CD27 | CD8 |
| CD123 | CD27 | CD3ζ |
| CD123 | CD27 | CD3δ |
| CD123 | CD27 | CD3γ |
| CD123 | CD27 | CD3ε |
| CD123 | CD27 | FcγRI-γ |
| CD123 | CD27 | FcγRIII-γ |
| CD123 | CD27 | FcεRIβ |
| CD123 | CD27 | FcεRIγ |
| CD123 | CD27 | DAP10 |
| CD123 | CD27 | DAP12 |
| CD123 | CD27 | CD32 |
| CD123 | CD27 | CD79a |
| CD123 | CD27 | CD79b |
| CD123 | CD28δ | CD8 |
| CD123 | CD28δ | CD3ζ |
| CD123 | CD28δ | CD3δ |
| CD123 | CD28δ | CD3γ |
| CD123 | CD28δ | CD3ε |
| CD123 | CD28δ | FcγRI-γ |
| CD123 | CD28δ | FcγRIII-γ |
| CD123 | CD28δ | FcεRIβ |
| CD123 | CD28δ | FcεRIγ |
| CD123 | CD28δ | DAP10 |
| CD123 | CD28δ | DAP12 |
| CD123 | CD28δ | CD32 |
| CD123 | CD28δ | CD79a |
| CD123 | CD28δ | CD79b |
| CD123 | CD80 | CD8 |
| CD123 | CD80 | CD3ζ |
| CD123 | CD80 | CD3δ |
| CD123 | CD80 | CD3γ |
| CD123 | CD80 | CD3ε |
| CD123 | CD80 | FcγRI-γ |
| CD123 | CD80 | FcγRIII-γ |
| CD123 | CD80 | FcεRIβ |
| CD123 | CD80 | FcεRIγ |
| CD123 | CD80 | DAP10 |
| CD123 | CD80 | DAP12 |
| CD123 | CD80 | CD32 |
| CD123 | CD80 | CD79a |
| CD123 | CD80 | CD79b |
| CD123 | CD86 | CD8 |
| CD123 | CD86 | CD3ζ |
| CD123 | CD86 | CD3δ |
| CD123 | CD86 | CD3γ |
| CD123 | CD86 | CD3ε |
| CD123 | CD86 | FcγRI-γ |
| CD123 | CD86 | FcγRIII-γ |
| CD123 | CD86 | FcεRIβ |
| CD123 | CD86 | FcεRIγ |
| CD123 | CD86 | DAP10 |
| CD123 | CD86 | DAP12 |
| CD123 | CD86 | CD32 |

TABLE 2-continued

Second Generation CARs

| ScFv | Co-stimulatory Signal | Signal Domain |
|---|---|---|
| CD123 | CD86 | CD79a |
| CD123 | CD86 | CD79b |
| CD123 | OX40 | CD8 |
| CD123 | OX40 | CD3ζ |
| CD123 | OX40 | CD3δ |
| CD123 | OX40 | CD3γ |
| CD123 | OX40 | CD3ε |
| CD123 | OX40 | FcγRI-γ |
| CD123 | OX40 | FcγRIII-γ |
| CD123 | OX40 | FcεRIβ |
| CD123 | OX40 | FcεRIγ |
| CD123 | OX40 | DAP10 |
| CD123 | OX40 | DAP12 |
| CD123 | OX40 | CD32 |
| CD123 | OX40 | CD79a |
| CD123 | OX40 | CD79b |
| CD123 | DAP10 | CD8 |
| CD123 | DAP10 | CD3ζ |
| CD123 | DAP10 | CD3δ |
| CD123 | DAP10 | CD3γ |
| CD123 | DAP10 | CD3ε |
| CD123 | DAP10 | FcγRI-γ |
| CD123 | DAP10 | FcγRIII-γ |
| CD123 | DAP10 | FcεRIβ |
| CD123 | DAP10 | FcεRIγ |
| CD123 | DAP10 | DAP10 |
| CD123 | DAP10 | DAP12 |
| CD123 | DAP10 | CD32 |
| CD123 | DAP10 | CD79a |
| CD123 | DAP10 | CD79b |
| CD123 | DAP12 | CD8 |
| CD123 | DAP12 | CD3ζ |
| CD123 | DAP12 | CD3δ |
| CD123 | DAP12 | CD3γ |
| CD123 | DAP12 | CD3ε |
| CD123 | DAP12 | FcγRI-γ |
| CD123 | DAP12 | FcγRIII-γ |
| CD123 | DAP12 | FcεRIβ |
| CD123 | DAP12 | FcεRIγ |
| CD123 | DAP12 | DAP10 |
| CD123 | DAP12 | DAP12 |
| CD123 | DAP12 | CD32 |
| CD123 | DAP12 | CD79a |
| CD123 | DAP12 | CD79b |
| CD123 | MyD88 | CD8 |
| CD123 | MyD88 | CD3ζ |
| CD123 | MyD88 | CD3δ |
| CD123 | MyD88 | CD3γ |
| CD123 | MyD88 | CD3ε |
| CD123 | MyD88 | FcγRI-γ |
| CD123 | MyD88 | FcγRIII-γ |
| CD123 | MyD88 | FcεRIβ |
| CD123 | MyD88 | FcεRIγ |
| CD123 | MyD88 | DAP10 |
| CD123 | MyD88 | DAP12 |
| CD123 | MyD88 | CD32 |
| CD123 | MyD88 | CD79a |
| CD123 | MyD88 | CD79b |
| CD123 | CD7 | CD8 |
| CD123 | CD7 | CD3ζ |
| CD123 | CD7 | CD3δ |
| CD123 | CD7 | CD3γ |
| CD123 | CD7 | CD3ε |
| CD123 | CD7 | FcγRI-γ |
| CD123 | CD7 | FcγRIII-γ |
| CD123 | CD7 | FcεRIβ |
| CD123 | CD7 | FcεRIγ |
| CD123 | CD7 | DAP10 |
| CD123 | CD7 | DAP12 |
| CD123 | CD7 | CD32 |
| CD123 | CD7 | CD79a |
| CD123 | CD7 | CD79b |
| CD123 | BTNL3 | CD8 |
| CD123 | BTNL3 | CD3ζ |
| CD123 | BTNL3 | CD3δ |
| CD123 | BTNL3 | CD3γ |
| CD123 | BTNL3 | CD3ε |
| CD123 | BTNL3 | FcγRI-γ |
| CD123 | BTNL3 | FcγRIII-γ |
| CD123 | BTNL3 | FcεRIβ |
| CD123 | BTNL3 | FcεRIγ |
| CD123 | BTNL3 | DAP10 |
| CD123 | BTNL3 | DAP12 |
| CD123 | BTNL3 | CD32 |
| CD123 | BTNL3 | CD79a |
| CD123 | BTNL3 | CD79b |
| CD123 | NKG2D | CD8 |
| CD123 | NKG2D | CD3ζ |
| CD123 | NKG2D | CD3δ |
| CD123 | NKG2D | CD3γ |
| CD123 | NKG2D | CD3ε |
| CD123 | NKG2D | FcγRI-γ |
| CD123 | NKG2D | FcγRIII-γ |
| CD123 | NKG2D | FcεRIβ |
| CD123 | NKG2D | FcεRIγ |
| CD123 | NKG2D | DAP10 |
| CD123 | NKG2D | DAP12 |
| CD123 | NKG2D | CD32 |
| CD123 | NKG2D | CD79a |
| CD123 | NKG2D | CD79b |

TABLE 3

Third Generation CARs

| ScFv | Co-stimulatory Signal | Co-stimulatory Signal | Signal Domain |
|---|---|---|---|
| CD123 | CD28 | CD28 | CD8 |
| CD123 | CD28 | CD28 | CD3ζ |
| CD123 | CD28 | CD28 | CD3δ |
| CD123 | CD28 | CD28 | CD3γ |
| CD123 | CD28 | CD28 | CD3ε |
| CD123 | CD28 | CD28 | FcγRI-γ |
| CD123 | CD28 | CD28 | FcγRIII-γ |
| CD123 | CD28 | CD28 | FcεRIβ |
| CD123 | CD28 | CD28 | FcεRIγ |
| CD123 | CD28 | CD28 | DAP10 |
| CD123 | CD28 | CD28 | DAP12 |
| CD123 | CD28 | CD28 | CD32 |
| CD123 | CD28 | CD28 | CD79a |
| CD123 | CD28 | CD28 | CD79b |
| CD123 | CD28 | CD8 | CD8 |
| CD123 | CD28 | CD8 | CD3ζ |
| CD123 | CD28 | CD8 | CD3δ |
| CD123 | CD28 | CD8 | CD3γ |
| CD123 | CD28 | CD8 | CD3ε |
| CD123 | CD28 | CD8 | FcγRI-γ |
| CD123 | CD28 | CD8 | FcγRIII-γ |
| CD123 | CD28 | CD8 | FcεRIβ |
| CD123 | CD28 | CD8 | FcεRIγ |
| CD123 | CD28 | CD8 | DAP10 |
| CD123 | CD28 | CD8 | DAP12 |
| CD123 | CD28 | CD8 | CD32 |
| CD123 | CD28 | CD8 | CD79a |
| CD123 | CD28 | CD8 | CD79b |
| CD123 | CD28 | CD4 | CD8 |
| CD123 | CD28 | CD4 | CD3ζ |
| CD123 | CD28 | CD4 | CD3δ |
| CD123 | CD28 | CD4 | CD3γ |
| CD123 | CD28 | CD4 | CD3ε |
| CD123 | CD28 | CD4 | FcγRI-γ |
| CD123 | CD28 | CD4 | FcγRIII-γ |
| CD123 | CD28 | CD4 | FcεRIβ |
| CD123 | CD28 | CD4 | FcεRIγ |
| CD123 | CD28 | CD4 | DAP10 |
| CD123 | CD28 | CD4 | DAP12 |

TABLE 3-continued

Third Generation CARs

| ScFv | Co-stimulatory Signal | Co-stimulatory Signal | Signal Domain |
|---|---|---|---|
| CD123 | CD28 | CD4 | CD32 |
| CD123 | CD28 | CD4 | CD79a |
| CD123 | CD28 | CD4 | CD79b |
| CD123 | CD28 | b2c | CD8 |
| CD123 | CD28 | b2c | CD3ζ |
| CD123 | CD28 | b2c | CD3δ |
| CD123 | CD28 | b2c | CD3γ |
| CD123 | CD28 | b2c | CD3ε |
| CD123 | CD28 | b2c | FcγRI-γ |
| CD123 | CD28 | b2c | FcγRIII-γ |
| CD123 | CD28 | b2c | FcεRIβ |
| CD123 | CD28 | b2c | FcεRIγ |
| CD123 | CD28 | b2c | DAP10 |
| CD123 | CD28 | b2c | DAP12 |
| CD123 | CD28 | b2c | CD32 |
| CD123 | CD28 | b2c | CD79a |
| CD123 | CD28 | b2c | CD79b |
| CD123 | CD28 | CD137/41BB | CD8 |
| CD123 | CD28 | CD137/41BB | CD3ζ |
| CD123 | CD28 | CD137/41BB | CD3δ |
| CD123 | CD28 | CD137/41BB | CD3γ |
| CD123 | CD28 | CD137/41BB | CD3ε |
| CD123 | CD28 | CD137/41BB | FcγRI-γ |
| CD123 | CD28 | CD137/41BB | FcγRIII-γ |
| CD123 | CD28 | CD137/41BB | FcεRIβ |
| CD123 | CD28 | CD137/41BB | FcεRIγ |
| CD123 | CD28 | CD137/41BB | DAP10 |
| CD123 | CD28 | CD137/41BB | DAP12 |
| CD123 | CD28 | CD137/41BB | CD32 |
| CD123 | CD28 | CD137/41BB | CD79a |
| CD123 | CD28 | CD137/41BB | CD79b |
| CD123 | CD28 | ICOS | CD8 |
| CD123 | CD28 | ICOS | CD3ζ |
| CD123 | CD28 | ICOS | CD3δ |
| CD123 | CD28 | ICOS | CD3γ |
| CD123 | CD28 | ICOS | CD3ε |
| CD123 | CD28 | ICOS | FcγRI-γ |
| CD123 | CD28 | ICOS | FcγRIII-γ |
| CD123 | CD28 | ICOS | FcεRIβ |
| CD123 | CD28 | ICOS | FcεRIγ |
| CD123 | CD28 | ICOS | DAP10 |
| CD123 | CD28 | ICOS | DAP12 |
| CD123 | CD28 | ICOS | CD32 |
| CD123 | CD28 | ICOS | CD79a |
| CD123 | CD28 | ICOS | CD79b |
| CD123 | CD28 | CD27 | CD8 |
| CD123 | CD28 | CD27 | CD3ζ |
| CD123 | CD28 | CD27 | CD3δ |
| CD123 | CD28 | CD27 | CD3γ |
| CD123 | CD28 | CD27 | CD3ε |
| CD123 | CD28 | CD27 | FcγRI-γ |
| CD123 | CD28 | CD27 | FcγRIII-γ |
| CD123 | CD28 | CD27 | FcεRIβ |
| CD123 | CD28 | CD27 | FcεRIγ |
| CD123 | CD28 | CD27 | DAP10 |
| CD123 | CD28 | CD27 | DAP12 |
| CD123 | CD28 | CD27 | CD32 |
| CD123 | CD28 | CD27 | CD79a |
| CD123 | CD28 | CD27 | CD79b |
| CD123 | CD28 | CD28δ | CD8 |
| CD123 | CD28 | CD28δ | CD3ζ |
| CD123 | CD28 | CD28δ | CD3δ |
| CD123 | CD28 | CD28δ | CD3γ |
| CD123 | CD28 | CD28δ | CD3ε |
| CD123 | CD28 | CD28δ | FcγRI-γ |
| CD123 | CD28 | CD28δ | FcγRIII-γ |
| CD123 | CD28 | CD28δ | FcεRIβ |
| CD123 | CD28 | CD28δ | FcεRIγ |
| CD123 | CD28 | CD28δ | DAP10 |
| CD123 | CD28 | CD28δ | DAP12 |
| CD123 | CD28 | CD28δ | CD32 |
| CD123 | CD28 | CD28δ | CD79a |
| CD123 | CD28 | CD28δ | CD79b |
| CD123 | CD28 | CD80 | CD8 |
| CD123 | CD28 | CD80 | CD3ζ |
| CD123 | CD28 | CD80 | CD3δ |
| CD123 | CD28 | CD80 | CD3γ |
| CD123 | CD28 | CD80 | CD3ε |
| CD123 | CD28 | CD80 | FcγRI-γ |
| CD123 | CD28 | CD80 | FcγRIII-γ |
| CD123 | CD28 | CD80 | FcεRIβ |
| CD123 | CD28 | CD80 | FcεRIγ |
| CD123 | CD28 | CD80 | DAP10 |
| CD123 | CD28 | CD80 | DAP12 |
| CD123 | CD28 | CD80 | CD32 |
| CD123 | CD28 | CD80 | CD79a |
| CD123 | CD28 | CD80 | CD79b |
| CD123 | CD28 | CD86 | CD8 |
| CD123 | CD28 | CD86 | CD3ζ |
| CD123 | CD28 | CD86 | CD3δ |
| CD123 | CD28 | CD86 | CD3γ |
| CD123 | CD28 | CD86 | CD3ε |
| CD123 | CD28 | CD86 | FcγRI-γ |
| CD123 | CD28 | CD86 | FcγRIII-γ |
| CD123 | CD28 | CD86 | FcεRIβ |
| CD123 | CD28 | CD86 | FcεRIγ |
| CD123 | CD28 | CD86 | DAP10 |
| CD123 | CD28 | CD86 | DAP12 |
| CD123 | CD28 | CD86 | CD32 |
| CD123 | CD28 | CD86 | CD79a |
| CD123 | CD28 | CD86 | CD79b |
| CD123 | CD28 | OX40 | CD8 |
| CD123 | CD28 | OX40 | CD3ζ |
| CD123 | CD28 | OX40 | CD3δ |
| CD123 | CD28 | OX40 | CD3γ |
| CD123 | CD28 | OX40 | CD3ε |
| CD123 | CD28 | OX40 | FcγRI-γ |
| CD123 | CD28 | OX40 | FcγRIII-γ |
| CD123 | CD28 | OX40 | FcεRIβ |
| CD123 | CD28 | OX40 | FcεRIγ |
| CD123 | CD28 | OX40 | DAP10 |
| CD123 | CD28 | OX40 | DAP12 |
| CD123 | CD28 | OX40 | CD32 |
| CD123 | CD28 | OX40 | CD79a |
| CD123 | CD28 | OX40 | CD79b |
| CD123 | CD28 | DAP10 | CD8 |
| CD123 | CD28 | DAP10 | CD3ζ |
| CD123 | CD28 | DAP10 | CD3δ |
| CD123 | CD28 | DAP10 | CD3γ |
| CD123 | CD28 | DAP10 | CD3ε |
| CD123 | CD28 | DAP10 | FcγRI-γ |
| CD123 | CD28 | DAP10 | FcγRIII-γ |
| CD123 | CD28 | DAP10 | FcεRIβ |
| CD123 | CD28 | DAP10 | FcεRIγ |
| CD123 | CD28 | DAP10 | DAP10 |
| CD123 | CD28 | DAP10 | DAP12 |
| CD123 | CD28 | DAP10 | CD32 |
| CD123 | CD28 | DAP10 | CD79a |
| CD123 | CD28 | DAP10 | CD79b |
| CD123 | CD28 | DAP12 | CD8 |
| CD123 | CD28 | DAP12 | CD3ζ |
| CD123 | CD28 | DAP12 | CD3δ |
| CD123 | CD28 | DAP12 | CD3γ |
| CD123 | CD28 | DAP12 | CD3ε |
| CD123 | CD28 | DAP12 | FcγRI-γ |
| CD123 | CD28 | DAP12 | FcγRIII-γ |
| CD123 | CD28 | DAP12 | FcεRIβ |
| CD123 | CD28 | DAP12 | FcεRIγ |
| CD123 | CD28 | DAP12 | DAP10 |
| CD123 | CD28 | DAP12 | DAP12 |
| CD123 | CD28 | DAP12 | CD32 |
| CD123 | CD28 | DAP12 | CD79a |
| CD123 | CD28 | DAP12 | CD79b |
| CD123 | CD28 | MyD88 | CD8 |
| CD123 | CD28 | MyD88 | CD3ζ |
| CD123 | CD28 | MyD88 | CD3δ |
| CD123 | CD28 | MyD88 | CD3γ |
| CD123 | CD28 | MyD88 | CD3ε |
| CD123 | CD28 | MyD88 | FcγRI-γ |
| CD123 | CD28 | MyD88 | FcγRIII-γ |

TABLE 3-continued

Third Generation CARs

| ScFv | Co-stimulatory Signal | Co-stimulatory Signal | Signal Domain |
|---|---|---|---|
| CD123 | CD28 | MyD88 | FcεRIβ |
| CD123 | CD28 | MyD88 | FcεRIγ |
| CD123 | CD28 | MyD88 | DAP10 |
| CD123 | CD28 | MyD88 | DAP12 |
| CD123 | CD28 | MyD88 | CD32 |
| CD123 | CD28 | MyD88 | CD79a |
| CD123 | CD28 | MyD88 | CD79b |
| CD123 | CD28 | CD7 | CD8 |
| CD123 | CD28 | CD7 | CD3ζ |
| CD123 | CD28 | CD7 | CD3δ |
| CD123 | CD28 | CD7 | CD3γ |
| CD123 | CD28 | CD7 | CD3ε |
| CD123 | CD28 | CD7 | FcγRI-γ |
| CD123 | CD28 | CD7 | FcγRIII-γ |
| CD123 | CD28 | CD7 | FcεRIβ |
| CD123 | CD28 | CD7 | FcεRIγ |
| CD123 | CD28 | CD7 | DAP10 |
| CD123 | CD28 | CD7 | DAP12 |
| CD123 | CD28 | CD7 | CD32 |
| CD123 | CD28 | CD7 | CD79a |
| CD123 | CD28 | CD7 | CD79b |
| CD123 | CD28 | BTNL3 | CD8 |
| CD123 | CD28 | BTNL3 | CD3ζ |
| CD123 | CD28 | BTNL3 | CD3δ |
| CD123 | CD28 | BTNL3 | CD3γ |
| CD123 | CD28 | BTNL3 | CD3ε |
| CD123 | CD28 | BTNL3 | FcγRI-γ |
| CD123 | CD28 | BTNL3 | FcγRIII-γ |
| CD123 | CD28 | BTNL3 | FcεRIβ |
| CD123 | CD28 | BTNL3 | FcεRIγ |
| CD123 | CD28 | BTNL3 | DAP10 |
| CD123 | CD28 | BTNL3 | DAP12 |
| CD123 | CD28 | BTNL3 | CD32 |
| CD123 | CD28 | BTNL3 | CD79a |
| CD123 | CD28 | BTNL3 | CD79b |
| CD123 | CD28 | NKG2D | CD8 |
| CD123 | CD28 | NKG2D | CD3ζ |
| CD123 | CD28 | NKG2D | CD3δ |
| CD123 | CD28 | NKG2D | CD3γ |
| CD123 | CD28 | NKG2D | CD3ε |
| CD123 | CD28 | NKG2D | FcγRI-γ |
| CD123 | CD28 | NKG2D | FcγRIII-γ |
| CD123 | CD28 | NKG2D | FcεRIβ |
| CD123 | CD28 | NKG2D | FcεRIγ |
| CD123 | CD28 | NKG2D | DAP10 |
| CD123 | CD28 | NKG2D | DAP12 |
| CD123 | CD28 | NKG2D | CD32 |
| CD123 | CD28 | NKG2D | CD79a |
| CD123 | CD28 | NKG2D | CD79b |
| CD123 | CD8 | CD28 | CD8 |
| CD123 | CD8 | CD28 | CD3ζ |
| CD123 | CD8 | CD28 | CD3δ |
| CD123 | CD8 | CD28 | CD3γ |
| CD123 | CD8 | CD28 | CD3ε |
| CD123 | CD8 | CD28 | FcγRI-γ |
| CD123 | CD8 | CD28 | FcγRIII-γ |
| CD123 | CD8 | CD28 | FcεRIβ |
| CD123 | CD8 | CD28 | FcεRIγ |
| CD123 | CD8 | CD28 | DAP10 |
| CD123 | CD8 | CD28 | DAP12 |
| CD123 | CD8 | CD28 | CD32 |
| CD123 | CD8 | CD28 | CD79a |
| CD123 | CD8 | CD28 | CD79b |
| CD123 | CD8 | CD8 | CD8 |
| CD123 | CD8 | CD8 | CD3ζ |
| CD123 | CD8 | CD8 | CD3δ |
| CD123 | CD8 | CD8 | CD3γ |
| CD123 | CD8 | CD8 | CD3ε |
| CD123 | CD8 | CD8 | FcγRI-γ |
| CD123 | CD8 | CD8 | FcγRIII-γ |
| CD123 | CD8 | CD8 | FcεRIβ |
| CD123 | CD8 | CD8 | FcεRIγ |
| CD123 | CD8 | CD8 | DAP10 |
| CD123 | CD8 | CD8 | DAP12 |
| CD123 | CD8 | CD8 | CD32 |
| CD123 | CD8 | CD8 | CD79a |
| CD123 | CD8 | CD8 | CD79b |
| CD123 | CD8 | CD4 | CD8 |
| CD123 | CD8 | CD4 | CD3ζ |
| CD123 | CD8 | CD4 | CD3δ |
| CD123 | CD8 | CD4 | CD3γ |
| CD123 | CD8 | CD4 | CD3ε |
| CD123 | CD8 | CD4 | FcγRI-γ |
| CD123 | CD8 | CD4 | FcγRIII-γ |
| CD123 | CD8 | CD4 | FcεRIβ |
| CD123 | CD8 | CD4 | FcεRIγ |
| CD123 | CD8 | CD4 | DAP10 |
| CD123 | CD8 | CD4 | DAP12 |
| CD123 | CD8 | CD4 | CD32 |
| CD123 | CD8 | CD4 | CD79a |
| CD123 | CD8 | CD4 | CD79b |
| CD123 | CD8 | b2c | CD8 |
| CD123 | CD8 | b2c | CD3ζ |
| CD123 | CD8 | b2c | CD3δ |
| CD123 | CD8 | b2c | CD3γ |
| CD123 | CD8 | b2c | CD3ε |
| CD123 | CD8 | b2c | FcγRI-γ |
| CD123 | CD8 | b2c | FcγRIII-γ |
| CD123 | CD8 | b2c | FcεRIβ |
| CD123 | CD8 | b2c | FcεRIγ |
| CD123 | CD8 | b2c | DAP10 |
| CD123 | CD8 | b2c | DAP12 |
| CD123 | CD8 | b2c | CD32 |
| CD123 | CD8 | b2c | CD79a |
| CD123 | CD8 | b2c | CD79b |
| CD123 | CD8 | CD137/41BB | CD8 |
| CD123 | CD8 | CD137/41BB | CD3ζ |
| CD123 | CD8 | CD137/41BB | CD3δ |
| CD123 | CD8 | CD137/41BB | CD3γ |
| CD123 | CD8 | CD137/41BB | CD3ε |
| CD123 | CD8 | CD137/41BB | FcγRI-γ |
| CD123 | CD8 | CD137/41BB | FcγRIII-γ |
| CD123 | CD8 | CD137/41BB | FcεRIβ |
| CD123 | CD8 | CD137/41BB | FcεRIγ |
| CD123 | CD8 | CD137/41BB | DAP10 |
| CD123 | CD8 | CD137/41BB | DAP12 |
| CD123 | CD8 | CD137/41BB | CD32 |
| CD123 | CD8 | CD137/41BB | CD79a |
| CD123 | CD8 | CD137/41BB | CD79b |
| CD123 | CD8 | ICOS | CD8 |
| CD123 | CD8 | ICOS | CD3ζ |
| CD123 | CD8 | ICOS | CD3δ |
| CD123 | CD8 | ICOS | CD3γ |
| CD123 | CD8 | ICOS | CD3ε |
| CD123 | CD8 | ICOS | FcγRI-γ |
| CD123 | CD8 | ICOS | FcγRIII-γ |
| CD123 | CD8 | ICOS | FcεRIβ |
| CD123 | CD8 | ICOS | FcεRIγ |
| CD123 | CD8 | ICOS | DAP10 |
| CD123 | CD8 | ICOS | DAP12 |
| CD123 | CD8 | ICOS | CD32 |
| CD123 | CD8 | ICOS | CD79a |
| CD123 | CD8 | ICOS | CD79b |
| CD123 | CD8 | CD27 | CD8 |
| CD123 | CD8 | CD27 | CD3ζ |
| CD123 | CD8 | CD27 | CD3δ |
| CD123 | CD8 | CD27 | CD3γ |
| CD123 | CD8 | CD27 | CD3ε |
| CD123 | CD8 | CD27 | FcγRI-γ |
| CD123 | CD8 | CD27 | FcγRIII-γ |
| CD123 | CD8 | CD27 | FcεRIβ |
| CD123 | CD8 | CD27 | FcεRIγ |
| CD123 | CD8 | CD27 | DAP10 |
| CD123 | CD8 | CD27 | DAP12 |
| CD123 | CD8 | CD27 | CD32 |
| CD123 | CD8 | CD27 | CD79a |
| CD123 | CD8 | CD27 | CD79b |
| CD123 | CD8 | CD28δ | CD8 |
| CD123 | CD8 | CD28δ | CD3ζ |
| CD123 | CD8 | CD28δ | CD3δ |

TABLE 3-continued

| Third Generation CARs | | | |
|---|---|---|---|
| ScFv | Co-stimulatory Signal | Co-stimulatory Signal | Signal Domain |
| CD123 | CD8 | CD28δ | CD3γ |
| CD123 | CD8 | CD28δ | CD3ε |
| CD123 | CD8 | CD28δ | FcγRI-γ |
| CD123 | CD8 | CD28δ | FcγRIII-γ |
| CD123 | CD8 | CD28δ | FcεRIβ |
| CD123 | CD8 | CD28δ | FcεRIγ |
| CD123 | CD8 | CD28δ | DAP10 |
| CD123 | CD8 | CD28δ | DAP12 |
| CD123 | CD8 | CD28δ | CD32 |
| CD123 | CD8 | CD28δ | CD79a |
| CD123 | CD8 | CD28δ | CD79b |
| CD123 | CD8 | CD80 | CD8 |
| CD123 | CD8 | CD80 | CD3ζ |
| CD123 | CD8 | CD80 | CD3δ |
| CD123 | CD8 | CD80 | CD3γ |
| CD123 | CD8 | CD80 | CD3ε |
| CD123 | CD8 | CD80 | FcγRI-γ |
| CD123 | CD8 | CD80 | FcγRIII-γ |
| CD123 | CD8 | CD80 | FcεRIβ |
| CD123 | CD8 | CD80 | FcεRIγ |
| CD123 | CD8 | CD80 | DAP10 |
| CD123 | CD8 | CD80 | DAP12 |
| CD123 | CD8 | CD80 | CD32 |
| CD123 | CD8 | CD80 | CD79a |
| CD123 | CD8 | CD80 | CD79b |
| CD123 | CD8 | CD86 | CD8 |
| CD123 | CD8 | CD86 | CD3ζ |
| CD123 | CD8 | CD86 | CD3δ |
| CD123 | CD8 | CD86 | CD3γ |
| CD123 | CD8 | CD86 | CD3ε |
| CD123 | CD8 | CD86 | FcγRI-γ |
| CD123 | CD8 | CD86 | FcγRIII-γ |
| CD123 | CD8 | CD86 | FcεRIβ |
| CD123 | CD8 | CD86 | FcεRIγ |
| CD123 | CD8 | CD86 | DAP10 |
| CD123 | CD8 | CD86 | DAP12 |
| CD123 | CD8 | CD86 | CD32 |
| CD123 | CD8 | CD86 | CD79a |
| CD123 | CD8 | CD86 | CD79b |
| CD123 | CD8 | OX40 | CD8 |
| CD123 | CD8 | OX40 | CD3ζ |
| CD123 | CD8 | OX40 | CD3δ |
| CD123 | CD8 | OX40 | CD3γ |
| CD123 | CD8 | OX40 | CD3ε |
| CD123 | CD8 | OX40 | FcγRI-γ |
| CD123 | CD8 | OX40 | FcγRIII-γ |
| CD123 | CD8 | OX40 | FcεRIβ |
| CD123 | CD8 | OX40 | FcεRIγ |
| CD123 | CD8 | OX40 | DAP10 |
| CD123 | CD8 | OX40 | DAP12 |
| CD123 | CD8 | OX40 | CD32 |
| CD123 | CD8 | OX40 | CD79a |
| CD123 | CD8 | OX40 | CD79b |
| CD123 | CD8 | DAP10 | CD8 |
| CD123 | CD8 | DAP10 | CD3ζ |
| CD123 | CD8 | DAP10 | CD3δ |
| CD123 | CD8 | DAP10 | CD3γ |
| CD123 | CD8 | DAP10 | CD3ε |
| CD123 | CD8 | DAP10 | FcγRI-γ |
| CD123 | CD8 | DAP10 | FcγRIII-γ |
| CD123 | CD8 | DAP10 | FcεRIβ |
| CD123 | CD8 | DAP10 | FcεRIγ |
| CD123 | CD8 | DAP10 | DAP10 |
| CD123 | CD8 | DAP10 | DAP12 |
| CD123 | CD8 | DAP10 | CD32 |
| CD123 | CD8 | DAP10 | CD79a |
| CD123 | CD8 | DAP10 | CD79b |
| CD123 | CD8 | DAP12 | CD8 |
| CD123 | CD8 | DAP12 | CD3ζ |
| CD123 | CD8 | DAP12 | CD3δ |
| CD123 | CD8 | DAP12 | CD3γ |
| CD123 | CD8 | DAP12 | CD3ε |
| CD123 | CD8 | DAP12 | FcγRI-γ |
| CD123 | CD8 | DAP12 | FcγRIII-γ |
| CD123 | CD8 | DAP12 | FcεRIβ |
| CD123 | CD8 | DAP12 | FcεRIγ |
| CD123 | CD8 | DAP12 | DAP10 |
| CD123 | CD8 | DAP12 | DAP12 |
| CD123 | CD8 | DAP12 | CD32 |
| CD123 | CD8 | DAP12 | CD79a |
| CD123 | CD8 | DAP12 | CD79b |
| CD123 | CD8 | MyD88 | CD8 |
| CD123 | CD8 | MyD88 | CD3ζ |
| CD123 | CD8 | MyD88 | CD3δ |
| CD123 | CD8 | MyD88 | CD3γ |
| CD123 | CD8 | MyD88 | CD3ε |
| CD123 | CD8 | MyD88 | FcγRI-γ |
| CD123 | CD8 | MyD88 | FcγRIII-γ |
| CD123 | CD8 | MyD88 | FcεRIβ |
| CD123 | CD8 | MyD88 | FcεRIγ |
| CD123 | CD8 | MyD88 | DAP10 |
| CD123 | CD8 | MyD88 | DAP12 |
| CD123 | CD8 | MyD88 | CD32 |
| CD123 | CD8 | MyD88 | CD79a |
| CD123 | CD8 | MyD88 | CD79b |
| CD123 | CD8 | CD7 | CD8 |
| CD123 | CD8 | CD7 | CD3ζ |
| CD123 | CD8 | CD7 | CD3δ |
| CD123 | CD8 | CD7 | CD3γ |
| CD123 | CD8 | CD7 | CD3ε |
| CD123 | CD8 | CD7 | FcγRI-γ |
| CD123 | CD8 | CD7 | FcγRIII-γ |
| CD123 | CD8 | CD7 | FcεRIβ |
| CD123 | CD8 | CD7 | FcεRIγ |
| CD123 | CD8 | CD7 | DAP10 |
| CD123 | CD8 | CD7 | DAP12 |
| CD123 | CD8 | CD7 | CD32 |
| CD123 | CD8 | CD7 | CD79a |
| CD123 | CD8 | CD7 | CD79b |
| CD123 | CD8 | BTNL3 | CD8 |
| CD123 | CD8 | BTNL3 | CD3ζ |
| CD123 | CD8 | BTNL3 | CD3δ |
| CD123 | CD8 | BTNL3 | CD3γ |
| CD123 | CD8 | BTNL3 | CD3ε |
| CD123 | CD8 | BTNL3 | FcγRI-γ |
| CD123 | CD8 | BTNL3 | FcγRIII-γ |
| CD123 | CD8 | BTNL3 | FcεRIβ |
| CD123 | CD8 | BTNL3 | FcεRIγ |
| CD123 | CD8 | BTNL3 | DAP10 |
| CD123 | CD8 | BTNL3 | DAP12 |
| CD123 | CD8 | BTNL3 | CD32 |
| CD123 | CD8 | BTNL3 | CD79a |
| CD123 | CD8 | BTNL3 | CD79b |
| CD123 | CD8 | NKG2D | CD8 |
| CD123 | CD8 | NKG2D | CD3ζ |
| CD123 | CD8 | NKG2D | CD3δ |
| CD123 | CD8 | NKG2D | CD3γ |
| CD123 | CD8 | NKG2D | CD3ε |
| CD123 | CD8 | NKG2D | FcγRI-γ |
| CD123 | CD8 | NKG2D | FcγRIII-γ |
| CD123 | CD8 | NKG2D | FcεRIβ |
| CD123 | CD8 | NKG2D | FcεRIγ |
| CD123 | CD8 | NKG2D | DAP10 |
| CD123 | CD8 | NKG2D | DAP12 |
| CD123 | CD8 | NKG2D | CD32 |
| CD123 | CD8 | NKG2D | CD79a |
| CD123 | CD8 | NKG2D | CD79b |
| CD123 | CD4 | CD28 | CD8 |
| CD123 | CD4 | CD28 | CD3ζ |
| CD123 | CD4 | CD28 | CD3δ |
| CD123 | CD4 | CD28 | CD3γ |
| CD123 | CD4 | CD28 | CD3ε |
| CD123 | CD4 | CD28 | FcγRI-γ |
| CD123 | CD4 | CD28 | FcγRIII-γ |
| CD123 | CD4 | CD28 | FcεRIβ |
| CD123 | CD4 | CD28 | FcεRIγ |
| CD123 | CD4 | CD28 | DAP10 |
| CD123 | CD4 | CD28 | DAP12 |
| CD123 | CD4 | CD28 | CD32 |
| CD123 | CD4 | CD28 | CD79a |

TABLE 3-continued

Third Generation CARs

| ScFv | Co-stimulatory Signal | Co-stimulatory Signal | Signal Domain |
|---|---|---|---|
| CD123 | CD4 | CD28 | CD79b |
| CD123 | CD4 | CD8 | CD8 |
| CD123 | CD4 | CD8 | CD3ζ |
| CD123 | CD4 | CD8 | CD3δ |
| CD123 | CD4 | CD8 | CD3γ |
| CD123 | CD4 | CD8 | CD3ε |
| CD123 | CD4 | CD8 | FcγRI-γ |
| CD123 | CD4 | CD8 | FcγRIII-γ |
| CD123 | CD4 | CD8 | FcεRIβ |
| CD123 | CD4 | CD8 | FcεRIγ |
| CD123 | CD4 | CD8 | DAP10 |
| CD123 | CD4 | CD8 | DAP12 |
| CD123 | CD4 | CD8 | CD32 |
| CD123 | CD4 | CD8 | CD79a |
| CD123 | CD4 | CD8 | CD79b |
| CD123 | CD4 | CD4 | CD8 |
| CD123 | CD4 | CD4 | CD3ζ |
| CD123 | CD4 | CD4 | CD3δ |
| CD123 | CD4 | CD4 | CD3γ |
| CD123 | CD4 | CD4 | CD3ε |
| CD123 | CD4 | CD4 | FcγRI-γ |
| CD123 | CD4 | CD4 | FcγRIII-γ |
| CD123 | CD4 | CD4 | FcεRIβ |
| CD123 | CD4 | CD4 | FcεRIγ |
| CD123 | CD4 | CD4 | DAP10 |
| CD123 | CD4 | CD4 | DAP12 |
| CD123 | CD4 | CD4 | CD32 |
| CD123 | CD4 | CD4 | CD79a |
| CD123 | CD4 | CD4 | CD79b |
| CD123 | CD4 | b2c | CD8 |
| CD123 | CD4 | b2c | CD3ζ |
| CD123 | CD4 | b2c | CD3δ |
| CD123 | CD4 | b2c | CD3γ |
| CD123 | CD4 | b2c | CD3ε |
| CD123 | CD4 | b2c | FcγRI-γ |
| CD123 | CD4 | b2c | FcγRIII-γ |
| CD123 | CD4 | b2c | FcεRIβ |
| CD123 | CD4 | b2c | FcεRIγ |
| CD123 | CD4 | b2c | DAP10 |
| CD123 | CD4 | b2c | DAP12 |
| CD123 | CD4 | b2c | CD32 |
| CD123 | CD4 | b2c | CD79a |
| CD123 | CD4 | b2c | CD79b |
| CD123 | CD4 | CD137/41BB | CD8 |
| CD123 | CD4 | CD137/41BB | CD3ζ |
| CD123 | CD4 | CD137/41BB | CD3δ |
| CD123 | CD4 | CD137/41BB | CD3γ |
| CD123 | CD4 | CD137/41BB | CD3ε |
| CD123 | CD4 | CD137/41BB | FcγRI-γ |
| CD123 | CD4 | CD137/41BB | FcγRIII-γ |
| CD123 | CD4 | CD137/41BB | FcεRIβ |
| CD123 | CD4 | CD137/41BB | FcεRIγ |
| CD123 | CD4 | CD137/41BB | DAP10 |
| CD123 | CD4 | CD137/41BB | DAP12 |
| CD123 | CD4 | CD137/41BB | CD32 |
| CD123 | CD4 | CD137/41BB | CD79a |
| CD123 | CD4 | CD137/41BB | CD79b |
| CD123 | CD4 | ICOS | CD8 |
| CD123 | CD4 | ICOS | CD3ζ |
| CD123 | CD4 | ICOS | CD3δ |
| CD123 | CD4 | ICOS | CD3γ |
| CD123 | CD4 | ICOS | CD3ε |
| CD123 | CD4 | ICOS | FcγRI-γ |
| CD123 | CD4 | ICOS | FcγRIII-γ |
| CD123 | CD4 | ICOS | FcεRIβ |
| CD123 | CD4 | ICOS | FcεRIγ |
| CD123 | CD4 | ICOS | DAP10 |
| CD123 | CD4 | ICOS | DAP12 |
| CD123 | CD4 | ICOS | CD32 |
| CD123 | CD4 | ICOS | CD79a |
| CD123 | CD4 | ICOS | CD79b |
| CD123 | CD4 | CD27 | CD8 |
| CD123 | CD4 | CD27 | CD3ζ |
| CD123 | CD4 | CD27 | CD3δ |
| CD123 | CD4 | CD27 | CD3γ |
| CD123 | CD4 | CD27 | CD3ε |
| CD123 | CD4 | CD27 | FcγRI-γ |
| CD123 | CD4 | CD27 | FcγRIII-γ |
| CD123 | CD4 | CD27 | FcεRIβ |
| CD123 | CD4 | CD27 | FcεRIγ |
| CD123 | CD4 | CD27 | DAP10 |
| CD123 | CD4 | CD27 | DAP12 |
| CD123 | CD4 | CD27 | CD32 |
| CD123 | CD4 | CD27 | CD79a |
| CD123 | CD4 | CD27 | CD79b |
| CD123 | CD4 | CD28δ | CD8 |
| CD123 | CD4 | CD28δ | CD3ζ |
| CD123 | CD4 | CD28δ | CD3δ |
| CD123 | CD4 | CD28δ | CD3γ |
| CD123 | CD4 | CD28δ | CD3ε |
| CD123 | CD4 | CD28δ | FcγRI-γ |
| CD123 | CD4 | CD28δ | FcγRIII-γ |
| CD123 | CD4 | CD28δ | FcεRIβ |
| CD123 | CD4 | CD28δ | FcεRIγ |
| CD123 | CD4 | CD28δ | DAP10 |
| CD123 | CD4 | CD28δ | DAP12 |
| CD123 | CD4 | CD28δ | CD32 |
| CD123 | CD4 | CD28δ | CD79a |
| CD123 | CD4 | CD28δ | CD79b |
| CD123 | CD4 | CD80 | CD8 |
| CD123 | CD4 | CD80 | CD3ζ |
| CD123 | CD4 | CD80 | CD3δ |
| CD123 | CD4 | CD80 | CD3γ |
| CD123 | CD4 | CD80 | CD3ε |
| CD123 | CD4 | CD80 | FcγRI-γ |
| CD123 | CD4 | CD80 | FcγRIII-γ |
| CD123 | CD4 | CD80 | FcεRIβ |
| CD123 | CD4 | CD80 | FcεRIγ |
| CD123 | CD4 | CD80 | DAP10 |
| CD123 | CD4 | CD80 | DAP12 |
| CD123 | CD4 | CD80 | CD32 |
| CD123 | CD4 | CD80 | CD79a |
| CD123 | CD4 | CD80 | CD79b |
| CD123 | CD4 | CD86 | CD8 |
| CD123 | CD4 | CD86 | CD3ζ |
| CD123 | CD4 | CD86 | CD3δ |
| CD123 | CD4 | CD86 | CD3γ |
| CD123 | CD4 | CD86 | CD3ε |
| CD123 | CD4 | CD86 | FcγRI-γ |
| CD123 | CD4 | CD86 | FcγRIII-γ |
| CD123 | CD4 | CD86 | FcεRIβ |
| CD123 | CD4 | CD86 | FcεRIγ |
| CD123 | CD4 | CD86 | DAP10 |
| CD123 | CD4 | CD86 | DAP12 |
| CD123 | CD4 | CD86 | CD32 |
| CD123 | CD4 | CD86 | CD79a |
| CD123 | CD4 | CD86 | CD79b |
| CD123 | CD4 | OX40 | CD8 |
| CD123 | CD4 | OX40 | CD3ζ |
| CD123 | CD4 | OX40 | CD3δ |
| CD123 | CD4 | OX40 | CD3γ |
| CD123 | CD4 | OX40 | CD3ε |
| CD123 | CD4 | OX40 | FcγRI-γ |
| CD123 | CD4 | OX40 | FcγRIII-γ |
| CD123 | CD4 | OX40 | FcεRIβ |
| CD123 | CD4 | OX40 | FcεRIγ |
| CD123 | CD4 | OX40 | DAP10 |
| CD123 | CD4 | OX40 | DAP12 |
| CD123 | CD4 | OX40 | CD32 |
| CD123 | CD4 | OX40 | CD79a |
| CD123 | CD4 | OX40 | CD79b |
| CD123 | CD4 | DAP10 | CD8 |
| CD123 | CD4 | DAP10 | CD3ζ |
| CD123 | CD4 | DAP10 | CD3δ |
| CD123 | CD4 | DAP10 | CD3γ |
| CD123 | CD4 | DAP10 | CD3ε |
| CD123 | CD4 | DAP10 | FcγRI-γ |
| CD123 | CD4 | DAP10 | FcγRIII-γ |
| CD123 | CD4 | DAP10 | FcεRIβ |
| CD123 | CD4 | DAP10 | FcεRIγ |

TABLE 3-continued

Third Generation CARs

| ScFv | Co-stimulatory Signal | Co-stimulatory Signal | Signal Domain |
|---|---|---|---|
| CD123 | CD4 | DAP10 | DAP10 |
| CD123 | CD4 | DAP10 | DAP12 |
| CD123 | CD4 | DAP10 | CD32 |
| CD123 | CD4 | DAP10 | CD79a |
| CD123 | CD4 | DAP10 | CD79b |
| CD123 | CD4 | DAP12 | CD8 |
| CD123 | CD4 | DAP12 | CD3ζ |
| CD123 | CD4 | DAP12 | CD3δ |
| CD123 | CD4 | DAP12 | CD3γ |
| CD123 | CD4 | DAP12 | CD3ε |
| CD123 | CD4 | DAP12 | FcγRI-γ |
| CD123 | CD4 | DAP12 | FcγRIII-γ |
| CD123 | CD4 | DAP12 | FcεRIβ |
| CD123 | CD4 | DAP12 | FcεRIγ |
| CD123 | CD4 | DAP12 | DAP10 |
| CD123 | CD4 | DAP12 | DAP12 |
| CD123 | CD4 | DAP12 | CD32 |
| CD123 | CD4 | DAP12 | CD79a |
| CD123 | CD4 | DAP12 | CD79b |
| CD123 | CD4 | MyD88 | CD8 |
| CD123 | CD4 | MyD88 | CD3ζ |
| CD123 | CD4 | MyD88 | CD3δ |
| CD123 | CD4 | MyD88 | CD3γ |
| CD123 | CD4 | MyD88 | CD3ε |
| CD123 | CD4 | MyD88 | FcγRI-γ |
| CD123 | CD4 | MyD88 | FcγRIII-γ |
| CD123 | CD4 | MyD88 | FcεRIβ |
| CD123 | CD4 | MyD88 | FcεRIγ |
| CD123 | CD4 | MyD88 | DAP10 |
| CD123 | CD4 | MyD88 | DAP12 |
| CD123 | CD4 | MyD88 | CD32 |
| CD123 | CD4 | MyD88 | CD79a |
| CD123 | CD4 | MyD88 | CD79b |
| CD123 | CD4 | CD7 | CD8 |
| CD123 | CD4 | CD7 | CD3ζ |
| CD123 | CD4 | CD7 | CD3δ |
| CD123 | CD4 | CD7 | CD3γ |
| CD123 | CD4 | CD7 | CD3ε |
| CD123 | CD4 | CD7 | FcγRI-γ |
| CD123 | CD4 | CD7 | FcγRIII-γ |
| CD123 | CD4 | CD7 | FcεRIβ |
| CD123 | CD4 | CD7 | FcεRIγ |
| CD123 | CD4 | CD7 | DAP10 |
| CD123 | CD4 | CD7 | DAP12 |
| CD123 | CD4 | CD7 | CD32 |
| CD123 | CD4 | CD7 | CD79a |
| CD123 | CD4 | CD7 | CD79b |
| CD123 | CD4 | BTNL3 | CD8 |
| CD123 | CD4 | BTNL3 | CD3ζ |
| CD123 | CD4 | BTNL3 | CD3δ |
| CD123 | CD4 | BTNL3 | CD3γ |
| CD123 | CD4 | BTNL3 | CD3ε |
| CD123 | CD4 | BTNL3 | FcγRI-γ |
| CD123 | CD4 | BTNL3 | FcγRIII-γ |
| CD123 | CD4 | BTNL3 | FcεRIβ |
| CD123 | CD4 | BTNL3 | FcεRIγ |
| CD123 | CD4 | BTNL3 | DAP10 |
| CD123 | CD4 | BTNL3 | DAP12 |
| CD123 | CD4 | BTNL3 | CD32 |
| CD123 | CD4 | BTNL3 | CD79a |
| CD123 | CD4 | BTNL3 | CD79b |
| CD123 | CD4 | NKG2D | CD8 |
| CD123 | CD4 | NKG2D | CD3ζ |
| CD123 | CD4 | NKG2D | CD3δ |
| CD123 | CD4 | NKG2D | CD3γ |
| CD123 | CD4 | NKG2D | CD3ε |
| CD123 | CD4 | NKG2D | FcγRI-γ |
| CD123 | CD4 | NKG2D | FcγRIII-γ |
| CD123 | CD4 | NKG2D | FcεRIβ |
| CD123 | CD4 | NKG2D | FcεRIγ |
| CD123 | CD4 | NKG2D | DAP10 |
| CD123 | CD4 | NKG2D | DAP12 |
| CD123 | CD4 | NKG2D | CD32 |
| CD123 | CD4 | NKG2D | CD79a |
| CD123 | CD4 | NKG2D | CD79b |
| CD123 | b2c | CD28 | CD8 |
| CD123 | b2c | CD28 | CD3ζ |
| CD123 | b2c | CD28 | CD3δ |
| CD123 | b2c | CD28 | CD3γ |
| CD123 | b2c | CD28 | CD3ε |
| CD123 | b2c | CD28 | FcγRI-γ |
| CD123 | b2c | CD28 | FcγRIII-γ |
| CD123 | b2c | CD28 | FcεRIβ |
| CD123 | b2c | CD28 | FcεRIγ |
| CD123 | b2c | CD28 | DAP10 |
| CD123 | b2c | CD28 | DAP12 |
| CD123 | b2c | CD28 | CD32 |
| CD123 | b2c | CD28 | CD79a |
| CD123 | b2c | CD28 | CD79b |
| CD123 | b2c | CD8 | CD8 |
| CD123 | b2c | CD8 | CD3ζ |
| CD123 | b2c | CD8 | CD3δ |
| CD123 | b2c | CD8 | CD3γ |
| CD123 | b2c | CD8 | CD3ε |
| CD123 | b2c | CD8 | FcγRI-γ |
| CD123 | b2c | CD8 | FcγRIII-γ |
| CD123 | b2c | CD8 | FcεRIβ |
| CD123 | b2c | CD8 | FcεRIγ |
| CD123 | b2c | CD8 | DAP10 |
| CD123 | b2c | CD8 | DAP12 |
| CD123 | b2c | CD8 | CD32 |
| CD123 | b2c | CD8 | CD79a |
| CD123 | b2c | CD8 | CD79b |
| CD123 | b2c | CD4 | CD8 |
| CD123 | b2c | CD4 | CD3ζ |
| CD123 | b2c | CD4 | CD3δ |
| CD123 | b2c | CD4 | CD3γ |
| CD123 | b2c | CD4 | CD3ε |
| CD123 | b2c | CD4 | FcγRI-γ |
| CD123 | b2c | CD4 | FcγRIII-γ |
| CD123 | b2c | CD4 | FcεRIβ |
| CD123 | b2c | CD4 | FcεRIγ |
| CD123 | b2c | CD4 | DAP10 |
| CD123 | b2c | CD4 | DAP12 |
| CD123 | b2c | CD4 | CD32 |
| CD123 | b2c | CD4 | CD79a |
| CD123 | b2c | CD4 | CD79b |
| CD123 | b2c | b2c | CD8 |
| CD123 | b2c | b2c | CD3ζ |
| CD123 | b2c | b2c | CD3δ |
| CD123 | b2c | b2c | CD3γ |
| CD123 | b2c | b2c | CD3ε |
| CD123 | b2c | b2c | FcγRI-γ |
| CD123 | b2c | b2c | FcγRIII-γ |
| CD123 | b2c | b2c | FcεRIβ |
| CD123 | b2c | b2c | FcεRIγ |
| CD123 | b2c | b2c | DAP10 |
| CD123 | b2c | b2c | DAP12 |
| CD123 | b2c | b2c | CD32 |
| CD123 | b2c | b2c | CD79a |
| CD123 | b2c | b2c | CD79b |
| CD123 | b2c | CD137/41BB | CD8 |
| CD123 | b2c | CD137/41BB | CD3ζ |
| CD123 | b2c | CD137/41BB | CD3δ |
| CD123 | b2c | CD137/41BB | CD3γ |
| CD123 | b2c | CD137/41BB | CD3ε |
| CD123 | b2c | CD137/41BB | FcγRI-γ |
| CD123 | b2c | CD137/41BB | FcγRIII-γ |
| CD123 | b2c | CD137/41BB | FcεRIβ |
| CD123 | b2c | CD137/41BB | FcεRIγ |
| CD123 | b2c | CD137/41BB | DAP10 |
| CD123 | b2c | CD137/41BB | DAP12 |
| CD123 | b2c | CD137/41BB | CD32 |
| CD123 | b2c | CD137/41BB | CD79a |
| CD123 | b2c | CD137/41BB | CD79b |
| CD123 | b2c | ICOS | CD8 |
| CD123 | b2c | ICOS | CD3ζ |
| CD123 | b2c | ICOS | CD3δ |
| CD123 | b2c | ICOS | CD3γ |
| CD123 | b2c | ICOS | CD3ε |

TABLE 3-continued

Third Generation CARs

| ScFv | Co-stimulatory Signal | Co-stimulatory Signal | Signal Domain |
|---|---|---|---|
| CD123 | b2c | ICOS | FcγRI-γ |
| CD123 | b2c | ICOS | FcγRIII-γ |
| CD123 | b2c | ICOS | FcεRIβ |
| CD123 | b2c | ICOS | FcεRIγ |
| CD123 | b2c | ICOS | DAP10 |
| CD123 | b2c | ICOS | DAP12 |
| CD123 | b2c | ICOS | CD32 |
| CD123 | b2c | ICOS | CD79a |
| CD123 | b2c | ICOS | CD79b |
| CD123 | b2c | CD27 | CD8 |
| CD123 | b2c | CD27 | CD3ζ |
| CD123 | b2c | CD27 | CD3δ |
| CD123 | b2c | CD27 | CD3γ |
| CD123 | b2c | CD27 | CD3ε |
| CD123 | b2c | CD27 | FcγRI-γ |
| CD123 | b2c | CD27 | FcγRIII-γ |
| CD123 | b2c | CD27 | FcεRIβ |
| CD123 | b2c | CD27 | FcεRIγ |
| CD123 | b2c | CD27 | DAP10 |
| CD123 | b2c | CD27 | DAP12 |
| CD123 | b2c | CD27 | CD32 |
| CD123 | b2c | CD27 | CD79a |
| CD123 | b2c | CD27 | CD79b |
| CD123 | b2c | CD28δ | CD8 |
| CD123 | b2c | CD28δ | CD3ζ |
| CD123 | b2c | CD28δ | CD3δ |
| CD123 | b2c | CD28δ | CD3γ |
| CD123 | b2c | CD28δ | CD3ε |
| CD123 | b2c | CD28δ | FcγRI-γ |
| CD123 | b2c | CD28δ | FcγRIII-γ |
| CD123 | b2c | CD28δ | FcεRIβ |
| CD123 | b2c | CD28δ | FcεRIγ |
| CD123 | b2c | CD28δ | DAP10 |
| CD123 | b2c | CD28δ | DAP12 |
| CD123 | b2c | CD28δ | CD32 |
| CD123 | b2c | CD28δ | CD79a |
| CD123 | b2c | CD28δ | CD79b |
| CD123 | b2c | CD80 | CD8 |
| CD123 | b2c | CD80 | CD3ζ |
| CD123 | b2c | CD80 | CD3δ |
| CD123 | b2c | CD80 | CD3γ |
| CD123 | b2c | CD80 | CD3ε |
| CD123 | b2c | CD80 | FcγRI-γ |
| CD123 | b2c | CD80 | FcγRIII-γ |
| CD123 | b2c | CD80 | FcεRIβ |
| CD123 | b2c | CD80 | FcεRIγ |
| CD123 | b2c | CD80 | DAP10 |
| CD123 | b2c | CD80 | DAP12 |
| CD123 | b2c | CD80 | CD32 |
| CD123 | b2c | CD80 | CD79a |
| CD123 | b2c | CD80 | CD79b |
| CD123 | b2c | CD86 | CD8 |
| CD123 | b2c | CD86 | CD3ζ |
| CD123 | b2c | CD86 | CD3δ |
| CD123 | b2c | CD86 | CD3γ |
| CD123 | b2c | CD86 | CD3ε |
| CD123 | b2c | CD86 | FcγRI-γ |
| CD123 | b2c | CD86 | FcγRIII-γ |
| CD123 | b2c | CD86 | FcεRIβ |
| CD123 | b2c | CD86 | FcεRIγ |
| CD123 | b2c | CD86 | DAP10 |
| CD123 | b2c | CD86 | DAP12 |
| CD123 | b2c | CD86 | CD32 |
| CD123 | b2c | CD86 | CD79a |
| CD123 | b2c | CD86 | CD79b |
| CD123 | b2c | OX40 | CD8 |
| CD123 | b2c | OX40 | CD3ζ |
| CD123 | b2c | OX40 | CD3δ |
| CD123 | b2c | OX40 | CD3γ |
| CD123 | b2c | OX40 | CD3ε |
| CD123 | b2c | OX40 | FcγRI-γ |
| CD123 | b2c | OX40 | FcγRIII-γ |
| CD123 | b2c | OX40 | FcεRIβ |
| CD123 | b2c | OX40 | FcεRIγ |
| CD123 | b2c | OX40 | DAP10 |
| CD123 | b2c | OX40 | DAP12 |
| CD123 | b2c | OX40 | CD32 |
| CD123 | b2c | OX40 | CD79a |
| CD123 | b2c | OX40 | CD79b |
| CD123 | b2c | DAP10 | CD8 |
| CD123 | b2c | DAP10 | CD3ζ |
| CD123 | b2c | DAP10 | CD3δ |
| CD123 | b2c | DAP10 | CD3γ |
| CD123 | b2c | DAP10 | CD3ε |
| CD123 | b2c | DAP10 | FcγRI-γ |
| CD123 | b2c | DAP10 | FcγRIII-γ |
| CD123 | b2c | DAP10 | FcεRIβ |
| CD123 | b2c | DAP10 | FcεRIγ |
| CD123 | b2c | DAP10 | DAP10 |
| CD123 | b2c | DAP10 | DAP12 |
| CD123 | b2c | DAP10 | CD32 |
| CD123 | b2c | DAP10 | CD79a |
| CD123 | b2c | DAP10 | CD79b |
| CD123 | b2c | DAP12 | CD8 |
| CD123 | b2c | DAP12 | CD3ζ |
| CD123 | b2c | DAP12 | CD3δ |
| CD123 | b2c | DAP12 | CD3γ |
| CD123 | b2c | DAP12 | CD3ε |
| CD123 | b2c | DAP12 | FcγRI-γ |
| CD123 | b2c | DAP12 | FcγRIII-γ |
| CD123 | b2c | DAP12 | FcεRIβ |
| CD123 | b2c | DAP12 | FcεRIγ |
| CD123 | b2c | DAP12 | DAP10 |
| CD123 | b2c | DAP12 | DAP12 |
| CD123 | b2c | DAP12 | CD32 |
| CD123 | b2c | DAP12 | CD79a |
| CD123 | b2c | DAP12 | CD79b |
| CD123 | b2c | MyD88 | CD8 |
| CD123 | b2c | MyD88 | CD3ζ |
| CD123 | b2c | MyD88 | CD3δ |
| CD123 | b2c | MyD88 | CD3γ |
| CD123 | b2c | MyD88 | CD3ε |
| CD123 | b2c | MyD88 | FcγRI-γ |
| CD123 | b2c | MyD88 | FcγRIII-γ |
| CD123 | b2c | MyD88 | FcεRIβ |
| CD123 | b2c | MyD88 | FcεRIγ |
| CD123 | b2c | MyD88 | DAP10 |
| CD123 | b2c | MyD88 | DAP12 |
| CD123 | b2c | MyD88 | CD32 |
| CD123 | b2c | MyD88 | CD79a |
| CD123 | b2c | MyD88 | CD79b |
| CD123 | b2c | CD7 | CD8 |
| CD123 | b2c | CD7 | CD3ζ |
| CD123 | b2c | CD7 | CD3δ |
| CD123 | b2c | CD7 | CD3γ |
| CD123 | b2c | CD7 | CD3ε |
| CD123 | b2c | CD7 | FcγRI-γ |
| CD123 | b2c | CD7 | FcγRIII-γ |
| CD123 | b2c | CD7 | FcεRIβ |
| CD123 | b2c | CD7 | FcεRIγ |
| CD123 | b2c | CD7 | DAP10 |
| CD123 | b2c | CD7 | DAP12 |
| CD123 | b2c | CD7 | CD32 |
| CD123 | b2c | CD7 | CD79a |
| CD123 | b2c | CD7 | CD79b |
| CD123 | b2c | BTNL3 | CD8 |
| CD123 | b2c | BTNL3 | CD3ζ |
| CD123 | b2c | BTNL3 | CD3δ |
| CD123 | b2c | BTNL3 | CD3γ |
| CD123 | b2c | BTNL3 | CD3ε |
| CD123 | b2c | BTNL3 | FcγRI-γ |
| CD123 | b2c | BTNL3 | FcγRIII-γ |
| CD123 | b2c | BTNL3 | FcεRIβ |
| CD123 | b2c | BTNL3 | FcεRIγ |
| CD123 | b2c | BTNL3 | DAP10 |
| CD123 | b2c | BTNL3 | DAP12 |
| CD123 | b2c | BTNL3 | CD32 |
| CD123 | b2c | BTNL3 | CD79a |
| CD123 | b2c | BTNL3 | CD79b |
| CD123 | b2c | NKG2D | CD8 |

TABLE 3-continued

Third Generation CARs

| ScFv | Co-stimulatory Signal | Co-stimulatory Signal | Signal Domain |
|---|---|---|---|
| CD123 | b2c | NKG2D | CD3ζ |
| CD123 | b2c | NKG2D | CD3δ |
| CD123 | b2c | NKG2D | CD3γ |
| CD123 | b2c | NKG2D | CD3ε |
| CD123 | b2c | NKG2D | FcγRI-γ |
| CD123 | b2c | NKG2D | FcγRIII-γ |
| CD123 | b2c | NKG2D | FcεRIβ |
| CD123 | b2c | NKG2D | FcεRIγ |
| CD123 | b2c | NKG2D | DAP10 |
| CD123 | b2c | NKG2D | DAP12 |
| CD123 | b2c | NKG2D | CD32 |
| CD123 | b2c | NKG2D | CD79a |
| CD123 | b2c | NKG2D | CD79b |
| CD123 | CD137/41BB | CD28 | CD8 |
| CD123 | CD137/41BB | CD28 | CD3ζ |
| CD123 | CD137/41BB | CD28 | CD3δ |
| CD123 | CD137/41BB | CD28 | CD3γ |
| CD123 | CD137/41BB | CD28 | CD3ε |
| CD123 | CD137/41BB | CD28 | FcγRI-γ |
| CD123 | CD137/41BB | CD28 | FcγRIII-γ |
| CD123 | CD137/41BB | CD28 | FcεRIβ |
| CD123 | CD137/41BB | CD28 | FcεRIγ |
| CD123 | CD137/41BB | CD28 | DAP10 |
| CD123 | CD137/41BB | CD28 | DAP12 |
| CD123 | CD137/41BB | CD28 | CD32 |
| CD123 | CD137/41BB | CD28 | CD79a |
| CD123 | CD137/41BB | CD28 | CD79b |
| CD123 | CD137/41BB | CD8 | CD8 |
| CD123 | CD137/41BB | CD8 | CD3ζ |
| CD123 | CD137/41BB | CD8 | CD3δ |
| CD123 | CD137/41BB | CD8 | CD3γ |
| CD123 | CD137/41BB | CD8 | CD3ε |
| CD123 | CD137/41BB | CD8 | FcγRI-γ |
| CD123 | CD137/41BB | CD8 | FcγRIII-γ |
| CD123 | CD137/41BB | CD8 | FcεRIβ |
| CD123 | CD137/41BB | CD8 | FcεRIγ |
| CD123 | CD137/41BB | CD8 | DAP10 |
| CD123 | CD137/41BB | CD8 | DAP12 |
| CD123 | CD137/41BB | CD8 | CD32 |
| CD123 | CD137/41BB | CD8 | CD79a |
| CD123 | CD137/41BB | CD8 | CD79b |
| CD123 | CD137/41BB | CD4 | CD8 |
| CD123 | CD137/41BB | CD4 | CD3ζ |
| CD123 | CD137/41BB | CD4 | CD3δ |
| CD123 | CD137/41BB | CD4 | CD3γ |
| CD123 | CD137/41BB | CD4 | CD3ε |
| CD123 | CD137/41BB | CD4 | FcγRI-γ |
| CD123 | CD137/41BB | CD4 | FcγRIII-γ |
| CD123 | CD137/41BB | CD4 | FcεRIβ |
| CD123 | CD137/41BB | CD4 | FcεRIγ |
| CD123 | CD137/41BB | CD4 | DAP10 |
| CD123 | CD137/41BB | CD4 | DAP12 |
| CD123 | CD137/41BB | CD4 | CD32 |
| CD123 | CD137/41BB | CD4 | CD79a |
| CD123 | CD137/41BB | CD4 | CD79b |
| CD123 | CD137/41BB | b2c | CD8 |
| CD123 | CD137/41BB | b2c | CD3ζ |
| CD123 | CD137/41BB | b2c | CD3δ |
| CD123 | CD137/41BB | b2c | CD3γ |
| CD123 | CD137/41BB | b2c | CD3ε |
| CD123 | CD137/41BB | b2c | FcγRI-γ |
| CD123 | CD137/41BB | b2c | FcγRIII-γ |
| CD123 | CD137/41BB | b2c | FcεRIβ |
| CD123 | CD137/41BB | b2c | FcεRIγ |
| CD123 | CD137/41BB | b2c | DAP10 |
| CD123 | CD137/41BB | b2c | DAP12 |
| CD123 | CD137/41BB | b2c | CD32 |
| CD123 | CD137/41BB | b2c | CD79a |
| CD123 | CD137/41BB | b2c | CD79b |
| CD123 | CD137/41BB | CD137/41BB | CD8 |
| CD123 | CD137/41BB | CD137/41BB | CD3ζ |
| CD123 | CD137/41BB | CD137/41BB | CD3δ |
| CD123 | CD137/41BB | CD137/41BB | CD3γ |
| CD123 | CD137/41BB | CD137/41BB | CD3ε |
| CD123 | CD137/41BB | CD137/41BB | FcγRI-γ |
| CD123 | CD137/41BB | CD137/41BB | FcγRIII-γ |
| CD123 | CD137/41BB | CD137/41BB | FcεRIβ |
| CD123 | CD137/41BB | CD137/41BB | FcεRIγ |
| CD123 | CD137/41BB | CD137/41BB | DAP10 |
| CD123 | CD137/41BB | CD137/41BB | DAP12 |
| CD123 | CD137/41BB | CD137/41BB | CD32 |
| CD123 | CD137/41BB | CD137/41BB | CD79a |
| CD123 | CD137/41BB | CD137/41BB | CD79b |
| CD123 | CD137/41BB | ICOS | CD8 |
| CD123 | CD137/41BB | ICOS | CD3ζ |
| CD123 | CD137/41BB | ICOS | CD3δ |
| CD123 | CD137/41BB | ICOS | CD3γ |
| CD123 | CD137/41BB | ICOS | CD3ε |
| CD123 | CD137/41BB | ICOS | FcγRI-γ |
| CD123 | CD137/41BB | ICOS | FcγRIII-γ |
| CD123 | CD137/41BB | ICOS | FcεRIβ |
| CD123 | CD137/41BB | ICOS | FcεRIγ |
| CD123 | CD137/41BB | ICOS | DAP10 |
| CD123 | CD137/41BB | ICOS | DAP12 |
| CD123 | CD137/41BB | ICOS | CD32 |
| CD123 | CD137/41BB | ICOS | CD79a |
| CD123 | CD137/41BB | ICOS | CD79b |
| CD123 | CD137/41BB | CD27 | CD8 |
| CD123 | CD137/41BB | CD27 | CD3ζ |
| CD123 | CD137/41BB | CD27 | CD3δ |
| CD123 | CD137/41BB | CD27 | CD3γ |
| CD123 | CD137/41BB | CD27 | CD3ε |
| CD123 | CD137/41BB | CD27 | FcγRI-γ |
| CD123 | CD137/41BB | CD27 | FcγRIII-γ |
| CD123 | CD137/41BB | CD27 | FcεRIβ |
| CD123 | CD137/41BB | CD27 | FcεRIγ |
| CD123 | CD137/41BB | CD27 | DAP10 |
| CD123 | CD137/41BB | CD27 | DAP12 |
| CD123 | CD137/41BB | CD27 | CD32 |
| CD123 | CD137/41BB | CD27 | CD79a |
| CD123 | CD137/41BB | CD27 | CD79b |
| CD123 | CD137/41BB | CD28δ | CD8 |
| CD123 | CD137/41BB | CD28δ | CD3ζ |
| CD123 | CD137/41BB | CD28δ | CD3δ |
| CD123 | CD137/41BB | CD28δ | CD3γ |
| CD123 | CD137/41BB | CD28δ | CD3ε |
| CD123 | CD137/41BB | CD28δ | FcγRI-γ |
| CD123 | CD137/41BB | CD28δ | FcγRIII-γ |
| CD123 | CD137/41BB | CD28δ | FcεRIβ |
| CD123 | CD137/41BB | CD28δ | FcεRIγ |
| CD123 | CD137/41BB | CD28δ | DAP10 |
| CD123 | CD137/41BB | CD28δ | DAP12 |
| CD123 | CD137/41BB | CD28δ | CD32 |
| CD123 | CD137/41BB | CD28δ | CD79a |
| CD123 | CD137/41BB | CD28δ | CD79b |
| CD123 | CD137/41BB | CD80 | CD8 |
| CD123 | CD137/41BB | CD80 | CD3ζ |
| CD123 | CD137/41BB | CD80 | CD3δ |
| CD123 | CD137/41BB | CD80 | CD3γ |
| CD123 | CD137/41BB | CD80 | CD3ε |
| CD123 | CD137/41BB | CD80 | FcγRI-γ |
| CD123 | CD137/41BB | CD80 | FcγRIII-γ |
| CD123 | CD137/41BB | CD80 | FcεRIβ |
| CD123 | CD137/41BB | CD80 | FcεRIγ |
| CD123 | CD137/41BB | CD80 | DAP10 |
| CD123 | CD137/41BB | CD80 | DAP12 |
| CD123 | CD137/41BB | CD80 | CD32 |
| CD123 | CD137/41BB | CD80 | CD79a |
| CD123 | CD137/41BB | CD80 | CD79b |
| CD123 | CD137/41BB | CD86 | CD8 |
| CD123 | CD137/41BB | CD86 | CD3ζ |
| CD123 | CD137/41BB | CD86 | CD3δ |
| CD123 | CD137/41BB | CD86 | CD3γ |
| CD123 | CD137/41BB | CD86 | CD3ε |
| CD123 | CD137/41BB | CD86 | FcγRI-γ |
| CD123 | CD137/41BB | CD86 | FcγRIII-γ |
| CD123 | CD137/41BB | CD86 | FcεRIβ |
| CD123 | CD137/41BB | CD86 | FcεRIγ |
| CD123 | CD137/41BB | CD86 | DAP10 |
| CD123 | CD137/41BB | CD86 | DAP12 |

TABLE 3-continued

Third Generation CARs

| ScFv | Co-stimulatory Signal | Co-stimulatory Signal | Signal Domain |
|---|---|---|---|
| CD123 | CD137/41BB | CD86 | CD32 |
| CD123 | CD137/41BB | CD86 | CD79a |
| CD123 | CD137/41BB | CD86 | CD79b |
| CD123 | CD137/41BB | OX40 | CD8 |
| CD123 | CD137/41BB | OX40 | CD3ζ |
| CD123 | CD137/41BB | OX40 | CD3δ |
| CD123 | CD137/41BB | OX40 | CD3γ |
| CD123 | CD137/41BB | OX40 | CD3ε |
| CD123 | CD137/41BB | OX40 | FcγRI-γ |
| CD123 | CD137/41BB | OX40 | FcγRIII-γ |
| CD123 | CD137/41BB | OX40 | FcεRIβ |
| CD123 | CD137/41BB | OX40 | FcεRIγ |
| CD123 | CD137/41BB | OX40 | DAP10 |
| CD123 | CD137/41BB | OX40 | DAP12 |
| CD123 | CD137/41BB | OX40 | CD32 |
| CD123 | CD137/41BB | OX40 | CD79a |
| CD123 | CD137/41BB | OX40 | CD79b |
| CD123 | CD137/41BB | DAP10 | CD8 |
| CD123 | CD137/41BB | DAP10 | CD3ζ |
| CD123 | CD137/41BB | DAP10 | CD3δ |
| CD123 | CD137/41BB | DAP10 | CD3γ |
| CD123 | CD137/41BB | DAP10 | CD3ε |
| CD123 | CD137/41BB | DAP10 | FcγRI-γ |
| CD123 | CD137/41BB | DAP10 | FcγRIII-γ |
| CD123 | CD137/41BB | DAP10 | FcεRIβ |
| CD123 | CD137/41BB | DAP10 | FcεRIγ |
| CD123 | CD137/41BB | DAP10 | DAP10 |
| CD123 | CD137/41BB | DAP10 | DAP12 |
| CD123 | CD137/41BB | DAP10 | CD32 |
| CD123 | CD137/41BB | DAP10 | CD79a |
| CD123 | CD137/41BB | DAP10 | CD79b |
| CD123 | CD137/41BB | DAP12 | CD8 |
| CD123 | CD137/41BB | DAP12 | CD3ζ |
| CD123 | CD137/41BB | DAP12 | CD3δ |
| CD123 | CD137/41BB | DAP12 | CD3γ |
| CD123 | CD137/41BB | DAP12 | CD3ε |
| CD123 | CD137/41BB | DAP12 | FcγRI-γ |
| CD123 | CD137/41BB | DAP12 | FcγRIII-γ |
| CD123 | CD137/41BB | DAP12 | FcεRIβ |
| CD123 | CD137/41BB | DAP12 | FcεRIγ |
| CD123 | CD137/41BB | DAP12 | DAP10 |
| CD123 | CD137/41BB | DAP12 | DAP12 |
| CD123 | CD137/41BB | DAP12 | CD32 |
| CD123 | CD137/41BB | DAP12 | CD79a |
| CD123 | CD137/41BB | DAP12 | CD79b |
| CD123 | CD137/41BB | MyD88 | CD8 |
| CD123 | CD137/41BB | MyD88 | CD3ζ |
| CD123 | CD137/41BB | MyD88 | CD3δ |
| CD123 | CD137/41BB | MyD88 | CD3γ |
| CD123 | CD137/41BB | MyD88 | CD3ε |
| CD123 | CD137/41BB | MyD88 | FcγRI-γ |
| CD123 | CD137/41BB | MyD88 | FcγRIII-γ |
| CD123 | CD137/41BB | MyD88 | FcεRIβ |
| CD123 | CD137/41BB | MyD88 | FcεRIγ |
| CD123 | CD137/41BB | MyD88 | DAP10 |
| CD123 | CD137/41BB | MyD88 | DAP12 |
| CD123 | CD137/41BB | MyD88 | CD32 |
| CD123 | CD137/41BB | MyD88 | CD79a |
| CD123 | CD137/41BB | MyD88 | CD79b |
| CD123 | CD137/41BB | CD7 | CD8 |
| CD123 | CD137/41BB | CD7 | CD3ζ |
| CD123 | CD137/41BB | CD7 | CD3δ |
| CD123 | CD137/41BB | CD7 | CD3γ |
| CD123 | CD137/41BB | CD7 | CD3ε |
| CD123 | CD137/41BB | CD7 | FcγRI-γ |
| CD123 | CD137/41BB | CD7 | FcγRIII-γ |
| CD123 | CD137/41BB | CD7 | FcεRIβ |
| CD123 | CD137/41BB | CD7 | FcεRIγ |
| CD123 | CD137/41BB | CD7 | DAP10 |
| CD123 | CD137/41BB | CD7 | DAP12 |
| CD123 | CD137/41BB | CD7 | CD32 |
| CD123 | CD137/41BB | CD7 | CD79a |
| CD123 | CD137/41BB | CD7 | CD79b |
| CD123 | CD137/41BB | BTNL3 | CD8 |
| CD123 | CD137/41BB | BTNL3 | CD3ζ |
| CD123 | CD137/41BB | BTNL3 | CD3δ |
| CD123 | CD137/41BB | BTNL3 | CD3γ |
| CD123 | CD137/41BB | BTNL3 | CD3ε |
| CD123 | CD137/41BB | BTNL3 | FcγRI-γ |
| CD123 | CD137/41BB | BTNL3 | FcγRIII-γ |
| CD123 | CD137/41BB | BTNL3 | FcεRIβ |
| CD123 | CD137/41BB | BTNL3 | FcεRIγ |
| CD123 | CD137/41BB | BTNL3 | DAP10 |
| CD123 | CD137/41BB | BTNL3 | DAP12 |
| CD123 | CD137/41BB | BTNL3 | CD32 |
| CD123 | CD137/41BB | BTNL3 | CD79a |
| CD123 | CD137/41BB | BTNL3 | CD79b |
| CD123 | CD137/41BB | NKG2D | CD8 |
| CD123 | CD137/41BB | NKG2D | CD3ζ |
| CD123 | CD137/41BB | NKG2D | CD3δ |
| CD123 | CD137/41BB | NKG2D | CD3γ |
| CD123 | CD137/41BB | NKG2D | CD3ε |
| CD123 | CD137/41BB | NKG2D | FcγRI-γ |
| CD123 | CD137/41BB | NKG2D | FcγRIII-γ |
| CD123 | CD137/41BB | NKG2D | FcεRIβ |
| CD123 | CD137/41BB | NKG2D | FcεRIγ |
| CD123 | CD137/41BB | NKG2D | DAP10 |
| CD123 | CD137/41BB | NKG2D | DAP12 |
| CD123 | CD137/41BB | NKG2D | CD32 |
| CD123 | CD137/41BB | NKG2D | CD79a |
| CD123 | CD137/41BB | NKG2D | CD79b |
| CD123 | ICOS | CD28 | CD8 |
| CD123 | ICOS | CD28 | CD3ζ |
| CD123 | ICOS | CD28 | CD3δ |
| CD123 | ICOS | CD28 | CD3γ |
| CD123 | ICOS | CD28 | CD3ε |
| CD123 | ICOS | CD28 | FcγRI-γ |
| CD123 | ICOS | CD28 | FcγRIII-γ |
| CD123 | ICOS | CD28 | FcεRIβ |
| CD123 | ICOS | CD28 | FcεRIγ |
| CD123 | ICOS | CD28 | DAP10 |
| CD123 | ICOS | CD28 | DAP12 |
| CD123 | ICOS | CD28 | CD32 |
| CD123 | ICOS | CD28 | CD79a |
| CD123 | ICOS | CD28 | CD79b |
| CD123 | ICOS | CD8 | CD8 |
| CD123 | ICOS | CD8 | CD3ζ |
| CD123 | ICOS | CD8 | CD3δ |
| CD123 | ICOS | CD8 | CD3γ |
| CD123 | ICOS | CD8 | CD3ε |
| CD123 | ICOS | CD8 | FcγRI-γ |
| CD123 | ICOS | CD8 | FcγRIII-γ |
| CD123 | ICOS | CD8 | FcεRIβ |
| CD123 | ICOS | CD8 | FcεRIγ |
| CD123 | ICOS | CD8 | DAP10 |
| CD123 | ICOS | CD8 | DAP12 |
| CD123 | ICOS | CD8 | CD32 |
| CD123 | ICOS | CD8 | CD79a |
| CD123 | ICOS | CD8 | CD79b |
| CD123 | ICOS | CD4 | CD8 |
| CD123 | ICOS | CD4 | CD3ζ |
| CD123 | ICOS | CD4 | CD3δ |
| CD123 | ICOS | CD4 | CD3γ |
| CD123 | ICOS | CD4 | CD3ε |
| CD123 | ICOS | CD4 | FcγRI-γ |
| CD123 | ICOS | CD4 | FcγRIII-γ |
| CD123 | ICOS | CD4 | FcεRIβ |
| CD123 | ICOS | CD4 | FcεRIγ |
| CD123 | ICOS | CD4 | DAP10 |
| CD123 | ICOS | CD4 | DAP12 |
| CD123 | ICOS | CD4 | CD32 |
| CD123 | ICOS | CD4 | CD79a |
| CD123 | ICOS | CD4 | CD79b |
| CD123 | ICOS | b2c | CD8 |
| CD123 | ICOS | b2c | CD3ζ |
| CD123 | ICOS | b2c | CD3δ |
| CD123 | ICOS | b2c | CD3γ |
| CD123 | ICOS | b2c | CD3ε |
| CD123 | ICOS | b2c | FcγRI-γ |
| CD123 | ICOS | b2c | FcγRIII-γ |

TABLE 3-continued

Third Generation CARs

| ScFv | Co-stimulatory Signal | Co-stimulatory Signal | Signal Domain |
|---|---|---|---|
| CD123 | ICOS | b2c | FcεRIβ |
| CD123 | ICOS | b2c | FcεRIγ |
| CD123 | ICOS | b2c | DAP10 |
| CD123 | ICOS | b2c | DAP12 |
| CD123 | ICOS | b2c | CD32 |
| CD123 | ICOS | b2c | CD79a |
| CD123 | ICOS | b2c | CD79b |
| CD123 | ICOS | CD137/41BB | CD8 |
| CD123 | ICOS | CD137/41BB | CD3ζ |
| CD123 | ICOS | CD137/41BB | CD3δ |
| CD123 | ICOS | CD137/41BB | CD3γ |
| CD123 | ICOS | CD137/41BB | CD3ε |
| CD123 | ICOS | CD137/41BB | FcγRI-γ |
| CD123 | ICOS | CD137/41BB | FcγRIII-γ |
| CD123 | ICOS | CD137/41BB | FcεRIβ |
| CD123 | ICOS | CD137/41BB | FcεRIγ |
| CD123 | ICOS | CD137/41BB | DAP10 |
| CD123 | ICOS | CD137/41BB | DAP12 |
| CD123 | ICOS | CD137/41BB | CD32 |
| CD123 | ICOS | CD137/41BB | CD79a |
| CD123 | ICOS | CD137/41BB | CD79b |
| CD123 | ICOS | ICOS | CD8 |
| CD123 | ICOS | ICOS | CD3ζ |
| CD123 | ICOS | ICOS | CD3δ |
| CD123 | ICOS | ICOS | CD3γ |
| CD123 | ICOS | ICOS | CD3ε |
| CD123 | ICOS | ICOS | FcγRI-γ |
| CD123 | ICOS | ICOS | FcγRIII-γ |
| CD123 | ICOS | ICOS | FcεRIβ |
| CD123 | ICOS | ICOS | FcεRIγ |
| CD123 | ICOS | ICOS | DAP10 |
| CD123 | ICOS | ICOS | DAP12 |
| CD123 | ICOS | ICOS | CD32 |
| CD123 | ICOS | ICOS | CD79a |
| CD123 | ICOS | ICOS | CD79b |
| CD123 | ICOS | CD27 | CD8 |
| CD123 | ICOS | CD27 | CD3ζ |
| CD123 | ICOS | CD27 | CD3δ |
| CD123 | ICOS | CD27 | CD3γ |
| CD123 | ICOS | CD27 | CD3ε |
| CD123 | ICOS | CD27 | FcγRI-γ |
| CD123 | ICOS | CD27 | FcγRIII-γ |
| CD123 | ICOS | CD27 | FcεRIβ |
| CD123 | ICOS | CD27 | FcεRIγ |
| CD123 | ICOS | CD27 | DAP10 |
| CD123 | ICOS | CD27 | DAP12 |
| CD123 | ICOS | CD27 | CD32 |
| CD123 | ICOS | CD27 | CD79a |
| CD123 | ICOS | CD27 | CD79b |
| CD123 | ICOS | CD28δ | CD8 |
| CD123 | ICOS | CD28δ | CD3ζ |
| CD123 | ICOS | CD28δ | CD3δ |
| CD123 | ICOS | CD28δ | CD3γ |
| CD123 | ICOS | CD28δ | CD3ε |
| CD123 | ICOS | CD28δ | FcγRI-γ |
| CD123 | ICOS | CD28δ | FcγRIII-γ |
| CD123 | ICOS | CD28δ | FcεRIβ |
| CD123 | ICOS | CD28δ | FcεRIγ |
| CD123 | ICOS | CD28δ | DAP10 |
| CD123 | ICOS | CD28δ | DAP12 |
| CD123 | ICOS | CD28δ | CD32 |
| CD123 | ICOS | CD28δ | CD79a |
| CD123 | ICOS | CD28δ | CD79b |
| CD123 | ICOS | CD80 | CD8 |
| CD123 | ICOS | CD80 | CD3ζ |
| CD123 | ICOS | CD80 | CD3δ |
| CD123 | ICOS | CD80 | CD3γ |
| CD123 | ICOS | CD80 | CD3ε |
| CD123 | ICOS | CD80 | FcγRI-γ |
| CD123 | ICOS | CD80 | FcγRIII-γ |
| CD123 | ICOS | CD80 | FcεRIβ |
| CD123 | ICOS | CD80 | FcεRIγ |
| CD123 | ICOS | CD80 | DAP10 |
| CD123 | ICOS | CD80 | DAP12 |
| CD123 | ICOS | CD80 | CD32 |
| CD123 | ICOS | CD80 | CD79a |
| CD123 | ICOS | CD80 | CD79b |
| CD123 | ICOS | CD86 | CD8 |
| CD123 | ICOS | CD86 | CD3ζ |
| CD123 | ICOS | CD86 | CD3δ |
| CD123 | ICOS | CD86 | CD3γ |
| CD123 | ICOS | CD86 | CD3ε |
| CD123 | ICOS | CD86 | FcγRI-γ |
| CD123 | ICOS | CD86 | FcγRIII-γ |
| CD123 | ICOS | CD86 | FcεRIβ |
| CD123 | ICOS | CD86 | FcεRIγ |
| CD123 | ICOS | CD86 | DAP10 |
| CD123 | ICOS | CD86 | DAP12 |
| CD123 | ICOS | CD86 | CD32 |
| CD123 | ICOS | CD86 | CD79a |
| CD123 | ICOS | CD86 | CD79b |
| CD123 | ICOS | OX40 | CD8 |
| CD123 | ICOS | OX40 | CD3ζ |
| CD123 | ICOS | OX40 | CD3δ |
| CD123 | ICOS | OX40 | CD3γ |
| CD123 | ICOS | OX40 | CD3ε |
| CD123 | ICOS | OX40 | FcγRI-γ |
| CD123 | ICOS | OX40 | FcγRIII-γ |
| CD123 | ICOS | OX40 | FcεRIβ |
| CD123 | ICOS | OX40 | FcεRIγ |
| CD123 | ICOS | OX40 | DAP10 |
| CD123 | ICOS | OX40 | DAP12 |
| CD123 | ICOS | OX40 | CD32 |
| CD123 | ICOS | OX40 | CD79a |
| CD123 | ICOS | OX40 | CD79b |
| CD123 | ICOS | DAP10 | CD8 |
| CD123 | ICOS | DAP10 | CD3ζ |
| CD123 | ICOS | DAP10 | CD3δ |
| CD123 | ICOS | DAP10 | CD3γ |
| CD123 | ICOS | DAP10 | CD3ε |
| CD123 | ICOS | DAP10 | FcγRI-γ |
| CD123 | ICOS | DAP10 | FcγRIII-γ |
| CD123 | ICOS | DAP10 | FcεRIβ |
| CD123 | ICOS | DAP10 | FcεRIγ |
| CD123 | ICOS | DAP10 | DAP10 |
| CD123 | ICOS | DAP10 | DAP12 |
| CD123 | ICOS | DAP10 | CD32 |
| CD123 | ICOS | DAP10 | CD79a |
| CD123 | ICOS | DAP10 | CD79b |
| CD123 | ICOS | DAP12 | CD8 |
| CD123 | ICOS | DAP12 | CD3ζ |
| CD123 | ICOS | DAP12 | CD3δ |
| CD123 | ICOS | DAP12 | CD3γ |
| CD123 | ICOS | DAP12 | CD3ε |
| CD123 | ICOS | DAP12 | FcγRI-γ |
| CD123 | ICOS | DAP12 | FcγRIII-γ |
| CD123 | ICOS | DAP12 | FcεRIβ |
| CD123 | ICOS | DAP12 | FcεRIγ |
| CD123 | ICOS | DAP12 | DAP10 |
| CD123 | ICOS | DAP12 | DAP12 |
| CD123 | ICOS | DAP12 | CD32 |
| CD123 | ICOS | DAP12 | CD79a |
| CD123 | ICOS | DAP12 | CD79b |
| CD123 | ICOS | MyD88 | CD8 |
| CD123 | ICOS | MyD88 | CD3ζ |
| CD123 | ICOS | MyD88 | CD3δ |
| CD123 | ICOS | MyD88 | CD3γ |
| CD123 | ICOS | MyD88 | CD3ε |
| CD123 | ICOS | MyD88 | FcγRI-γ |
| CD123 | ICOS | MyD88 | FcγRIII-γ |
| CD123 | ICOS | MyD88 | FcεRIβ |
| CD123 | ICOS | MyD88 | FcεRIγ |
| CD123 | ICOS | MyD88 | DAP10 |
| CD123 | ICOS | MyD88 | DAP12 |
| CD123 | ICOS | MyD88 | CD32 |
| CD123 | ICOS | MyD88 | CD79a |
| CD123 | ICOS | MyD88 | CD79b |
| CD123 | ICOS | CD7 | CD8 |
| CD123 | ICOS | CD7 | CD3ζ |
| CD123 | ICOS | CD7 | CD3δ |

TABLE 3-continued

Third Generation CARs

| ScFv | Co-stimulatory Signal | Co-stimulatory Signal | Signal Domain |
|---|---|---|---|
| CD123 | ICOS | CD7 | CD3γ |
| CD123 | ICOS | CD7 | CD3ε |
| CD123 | ICOS | CD7 | FcγRI-γ |
| CD123 | ICOS | CD7 | FcγRIII-γ |
| CD123 | ICOS | CD7 | FcεRIβ |
| CD123 | ICOS | CD7 | FcεRIγ |
| CD123 | ICOS | CD7 | DAP10 |
| CD123 | ICOS | CD7 | DAP12 |
| CD123 | ICOS | CD7 | CD32 |
| CD123 | ICOS | CD7 | CD79a |
| CD123 | ICOS | CD7 | CD79b |
| CD123 | ICOS | BTNL3 | CD8 |
| CD123 | ICOS | BTNL3 | CD3ζ |
| CD123 | ICOS | BTNL3 | CD3δ |
| CD123 | ICOS | BTNL3 | CD3γ |
| CD123 | ICOS | BTNL3 | CD3ε |
| CD123 | ICOS | BTNL3 | FcγRI-γ |
| CD123 | ICOS | BTNL3 | FcγRIII-γ |
| CD123 | ICOS | BTNL3 | FcεRIβ |
| CD123 | ICOS | BTNL3 | FcεRIγ |
| CD123 | ICOS | BTNL3 | DAP10 |
| CD123 | ICOS | BTNL3 | DAP12 |
| CD123 | ICOS | BTNL3 | CD32 |
| CD123 | ICOS | BTNL3 | CD79a |
| CD123 | ICOS | BTNL3 | CD79b |
| CD123 | ICOS | NKG2D | CD8 |
| CD123 | ICOS | NKG2D | CD3ζ |
| CD123 | ICOS | NKG2D | CD3δ |
| CD123 | ICOS | NKG2D | CD3γ |
| CD123 | ICOS | NKG2D | CD3ε |
| CD123 | ICOS | NKG2D | FcγRI-γ |
| CD123 | ICOS | NKG2D | FcγRIII-γ |
| CD123 | ICOS | NKG2D | FcεRIβ |
| CD123 | ICOS | NKG2D | FcεRIγ |
| CD123 | ICOS | NKG2D | DAP10 |
| CD123 | ICOS | NKG2D | DAP12 |
| CD123 | ICOS | NKG2D | CD32 |
| CD123 | ICOS | NKG2D | CD79a |
| CD123 | ICOS | NKG2D | CD79b |
| CD123 | CD27 | CD28 | CD8 |
| CD123 | CD27 | CD28 | CD3ζ |
| CD123 | CD27 | CD28 | CD3δ |
| CD123 | CD27 | CD28 | CD3γ |
| CD123 | CD27 | CD28 | CD3ε |
| CD123 | CD27 | CD28 | FcγRI-γ |
| CD123 | CD27 | CD28 | FcγRIII-γ |
| CD123 | CD27 | CD28 | FcεRIβ |
| CD123 | CD27 | CD28 | FcεRIγ |
| CD123 | CD27 | CD28 | DAP10 |
| CD123 | CD27 | CD28 | DAP12 |
| CD123 | CD27 | CD28 | CD32 |
| CD123 | CD27 | CD28 | CD79a |
| CD123 | CD27 | CD28 | CD79b |
| CD123 | CD27 | CD8 | CD8 |
| CD123 | CD27 | CD8 | CD3ζ |
| CD123 | CD27 | CD8 | CD3δ |
| CD123 | CD27 | CD8 | CD3γ |
| CD123 | CD27 | CD8 | CD3ε |
| CD123 | CD27 | CD8 | FcγRI-γ |
| CD123 | CD27 | CD8 | FcγRIII-γ |
| CD123 | CD27 | CD8 | FcεRIβ |
| CD123 | CD27 | CD8 | FcεRIγ |
| CD123 | CD27 | CD8 | DAP10 |
| CD123 | CD27 | CD8 | DAP12 |
| CD123 | CD27 | CD8 | CD32 |
| CD123 | CD27 | CD8 | CD79a |
| CD123 | CD27 | CD8 | CD79b |
| CD123 | CD27 | CD4 | CD8 |
| CD123 | CD27 | CD4 | CD3ζ |
| CD123 | CD27 | CD4 | CD3δ |
| CD123 | CD27 | CD4 | CD3γ |
| CD123 | CD27 | CD4 | CD3ε |
| CD123 | CD27 | CD4 | FcγRI-γ |
| CD123 | CD27 | CD4 | FcγRIII-γ |
| CD123 | CD27 | CD4 | FcεRIβ |
| CD123 | CD27 | CD4 | FcεRIγ |
| CD123 | CD27 | CD4 | DAP10 |
| CD123 | CD27 | CD4 | DAP12 |
| CD123 | CD27 | CD4 | CD32 |
| CD123 | CD27 | CD4 | CD79a |
| CD123 | CD27 | CD4 | CD79b |
| CD123 | CD27 | b2c | CD8 |
| CD123 | CD27 | b2c | CD3ζ |
| CD123 | CD27 | b2c | CD3δ |
| CD123 | CD27 | b2c | CD3γ |
| CD123 | CD27 | b2c | CD3ε |
| CD123 | CD27 | b2c | FcγRI-γ |
| CD123 | CD27 | b2c | FcγRIII-γ |
| CD123 | CD27 | b2c | FcεRIβ |
| CD123 | CD27 | b2c | FcεRIγ |
| CD123 | CD27 | b2c | DAP10 |
| CD123 | CD27 | b2c | DAP12 |
| CD123 | CD27 | b2c | CD32 |
| CD123 | CD27 | b2c | CD79a |
| CD123 | CD27 | b2c | CD79b |
| CD123 | CD27 | CD137/41BB | CD8 |
| CD123 | CD27 | CD137/41BB | CD3ζ |
| CD123 | CD27 | CD137/41BB | CD3δ |
| CD123 | CD27 | CD137/41BB | CD3γ |
| CD123 | CD27 | CD137/41BB | CD3ε |
| CD123 | CD27 | CD137/41BB | FcγRI-γ |
| CD123 | CD27 | CD137/41BB | FcγRIII-γ |
| CD123 | CD27 | CD137/41BB | FcεRIβ |
| CD123 | CD27 | CD137/41BB | FcεRIγ |
| CD123 | CD27 | CD137/41BB | DAP10 |
| CD123 | CD27 | CD137/41BB | DAP12 |
| CD123 | CD27 | CD137/41BB | CD32 |
| CD123 | CD27 | CD137/41BB | CD79a |
| CD123 | CD27 | CD137/41BB | CD79b |
| CD123 | CD27 | ICOS | CD8 |
| CD123 | CD27 | ICOS | CD3ζ |
| CD123 | CD27 | ICOS | CD3δ |
| CD123 | CD27 | ICOS | CD3γ |
| CD123 | CD27 | ICOS | CD3ε |
| CD123 | CD27 | ICOS | FcγRI-γ |
| CD123 | CD27 | ICOS | FcγRIII-γ |
| CD123 | CD27 | ICOS | FcεRIβ |
| CD123 | CD27 | ICOS | FcεRIγ |
| CD123 | CD27 | ICOS | DAP10 |
| CD123 | CD27 | ICOS | DAP12 |
| CD123 | CD27 | ICOS | CD32 |
| CD123 | CD27 | ICOS | CD79a |
| CD123 | CD27 | ICOS | CD79b |
| CD123 | CD27 | CD27 | CD8 |
| CD123 | CD27 | CD27 | CD3ζ |
| CD123 | CD27 | CD27 | CD3δ |
| CD123 | CD27 | CD27 | CD3γ |
| CD123 | CD27 | CD27 | CD3ε |
| CD123 | CD27 | CD27 | FcγRI-γ |
| CD123 | CD27 | CD27 | FcγRIII-γ |
| CD123 | CD27 | CD27 | FcεRIβ |
| CD123 | CD27 | CD27 | FcεRIγ |
| CD123 | CD27 | CD27 | DAP10 |
| CD123 | CD27 | CD27 | DAP12 |
| CD123 | CD27 | CD27 | CD32 |
| CD123 | CD27 | CD27 | CD79a |
| CD123 | CD27 | CD27 | CD79b |
| CD123 | CD27 | CD28δ | CD8 |
| CD123 | CD27 | CD28δ | CD3ζ |
| CD123 | CD27 | CD28δ | CD3δ |
| CD123 | CD27 | CD28δ | CD3γ |
| CD123 | CD27 | CD28δ | CD3ε |
| CD123 | CD27 | CD28δ | FcγRI-γ |
| CD123 | CD27 | CD28δ | FcγRIII-γ |
| CD123 | CD27 | CD28δ | FcεRIβ |
| CD123 | CD27 | CD28δ | FcεRIγ |
| CD123 | CD27 | CD28δ | DAP10 |
| CD123 | CD27 | CD28δ | DAP12 |
| CD123 | CD27 | CD28δ | CD32 |
| CD123 | CD27 | CD28δ | CD79a |

TABLE 3-continued

Third Generation CARs

| ScFv | Co-stimulatory Signal | Co-stimulatory Signal | Signal Domain |
|---|---|---|---|
| CD123 | CD27 | CD28δ | CD79b |
| CD123 | CD27 | CD80 | CD8 |
| CD123 | CD27 | CD80 | CD3ζ |
| CD123 | CD27 | CD80 | CD3δ |
| CD123 | CD27 | CD80 | CD3γ |
| CD123 | CD27 | CD80 | CD3ε |
| CD123 | CD27 | CD80 | FcγRI-γ |
| CD123 | CD27 | CD80 | FcγRIII-γ |
| CD123 | CD27 | CD80 | FcεRIβ |
| CD123 | CD27 | CD80 | FcεRIγ |
| CD123 | CD27 | CD80 | DAP10 |
| CD123 | CD27 | CD80 | DAP12 |
| CD123 | CD27 | CD80 | CD32 |
| CD123 | CD27 | CD80 | CD79a |
| CD123 | CD27 | CD80 | CD79b |
| CD123 | CD27 | CD86 | CD8 |
| CD123 | CD27 | CD86 | CD3ζ |
| CD123 | CD27 | CD86 | CD3δ |
| CD123 | CD27 | CD86 | CD3γ |
| CD123 | CD27 | CD86 | CD3ε |
| CD123 | CD27 | CD86 | FcγRI-γ |
| CD123 | CD27 | CD86 | FcγRIII-γ |
| CD123 | CD27 | CD86 | FcεRIβ |
| CD123 | CD27 | CD86 | FcεRIγ |
| CD123 | CD27 | CD86 | DAP10 |
| CD123 | CD27 | CD86 | DAP12 |
| CD123 | CD27 | CD86 | CD32 |
| CD123 | CD27 | CD86 | CD79a |
| CD123 | CD27 | CD86 | CD79b |
| CD123 | CD27 | OX40 | CD8 |
| CD123 | CD27 | OX40 | CD3ζ |
| CD123 | CD27 | OX40 | CD3δ |
| CD123 | CD27 | OX40 | CD3γ |
| CD123 | CD27 | OX40 | CD3ε |
| CD123 | CD27 | OX40 | FcγRI-γ |
| CD123 | CD27 | OX40 | FcγRIII-γ |
| CD123 | CD27 | OX40 | FcεRIβ |
| CD123 | CD27 | OX40 | FcεRIγ |
| CD123 | CD27 | OX40 | DAP10 |
| CD123 | CD27 | OX40 | DAP12 |
| CD123 | CD27 | OX40 | CD32 |
| CD123 | CD27 | OX40 | CD79a |
| CD123 | CD27 | OX40 | CD79b |
| CD123 | CD27 | DAP10 | CD8 |
| CD123 | CD27 | DAP10 | CD3ζ |
| CD123 | CD27 | DAP10 | CD3δ |
| CD123 | CD27 | DAP10 | CD3γ |
| CD123 | CD27 | DAP10 | CD3ε |
| CD123 | CD27 | DAP10 | FcγRI-γ |
| CD123 | CD27 | DAP10 | FcγRIII-γ |
| CD123 | CD27 | DAP10 | FcεRIβ |
| CD123 | CD27 | DAP10 | FcεRIγ |
| CD123 | CD27 | DAP10 | DAP10 |
| CD123 | CD27 | DAP10 | DAP12 |
| CD123 | CD27 | DAP10 | CD32 |
| CD123 | CD27 | DAP10 | CD79a |
| CD123 | CD27 | DAP10 | CD79b |
| CD123 | CD27 | DAP12 | CD8 |
| CD123 | CD27 | DAP12 | CD3ζ |
| CD123 | CD27 | DAP12 | CD3δ |
| CD123 | CD27 | DAP12 | CD3γ |
| CD123 | CD27 | DAP12 | CD3ε |
| CD123 | CD27 | DAP12 | FcγRI-γ |
| CD123 | CD27 | DAP12 | FcγRIII-γ |
| CD123 | CD27 | DAP12 | FcεRIβ |
| CD123 | CD27 | DAP12 | FcεRIγ |
| CD123 | CD27 | DAP12 | DAP10 |
| CD123 | CD27 | DAP12 | DAP12 |
| CD123 | CD27 | DAP12 | CD32 |
| CD123 | CD27 | DAP12 | CD79a |
| CD123 | CD27 | DAP12 | CD79b |
| CD123 | CD27 | MyD88 | CD8 |
| CD123 | CD27 | MyD88 | CD3ζ |
| CD123 | CD27 | MyD88 | CD3δ |
| CD123 | CD27 | MyD88 | CD3γ |
| CD123 | CD27 | MyD88 | CD3ε |
| CD123 | CD27 | MyD88 | FcγRI-γ |
| CD123 | CD27 | MyD88 | FcγRIII-γ |
| CD123 | CD27 | MyD88 | FcεRIβ |
| CD123 | CD27 | MyD88 | FcεRIγ |
| CD123 | CD27 | MyD88 | DAP10 |
| CD123 | CD27 | MyD88 | DAP12 |
| CD123 | CD27 | MyD88 | CD32 |
| CD123 | CD27 | MyD88 | CD79a |
| CD123 | CD27 | MyD88 | CD79b |
| CD123 | CD27 | CD7 | CD8 |
| CD123 | CD27 | CD7 | CD3ζ |
| CD123 | CD27 | CD7 | CD3δ |
| CD123 | CD27 | CD7 | CD3γ |
| CD123 | CD27 | CD7 | CD3ε |
| CD123 | CD27 | CD7 | FcγRI-γ |
| CD123 | CD27 | CD7 | FcγRIII-γ |
| CD123 | CD27 | CD7 | FcεRIβ |
| CD123 | CD27 | CD7 | FcεRIγ |
| CD123 | CD27 | CD7 | DAP10 |
| CD123 | CD27 | CD7 | DAP12 |
| CD123 | CD27 | CD7 | CD32 |
| CD123 | CD27 | CD7 | CD79a |
| CD123 | CD27 | CD7 | CD79b |
| CD123 | CD27 | BTNL3 | CD8 |
| CD123 | CD27 | BTNL3 | CD3ζ |
| CD123 | CD27 | BTNL3 | CD3δ |
| CD123 | CD27 | BTNL3 | CD3γ |
| CD123 | CD27 | BTNL3 | CD3ε |
| CD123 | CD27 | BTNL3 | FcγRI-γ |
| CD123 | CD27 | BTNL3 | FcγRIII-γ |
| CD123 | CD27 | BTNL3 | FcεRIβ |
| CD123 | CD27 | BTNL3 | FcεRIγ |
| CD123 | CD27 | BTNL3 | DAP10 |
| CD123 | CD27 | BTNL3 | DAP12 |
| CD123 | CD27 | BTNL3 | CD32 |
| CD123 | CD27 | BTNL3 | CD79a |
| CD123 | CD27 | BTNL3 | CD79b |
| CD123 | CD27 | NKG2D | CD8 |
| CD123 | CD27 | NKG2D | CD3ζ |
| CD123 | CD27 | NKG2D | CD3δ |
| CD123 | CD27 | NKG2D | CD3γ |
| CD123 | CD27 | NKG2D | CD3ε |
| CD123 | CD27 | NKG2D | FcγRI-γ |
| CD123 | CD27 | NKG2D | FcγRIII-γ |
| CD123 | CD27 | NKG2D | FcεRIβ |
| CD123 | CD27 | NKG2D | FcεRIγ |
| CD123 | CD27 | NKG2D | DAP10 |
| CD123 | CD27 | NKG2D | DAP12 |
| CD123 | CD27 | NKG2D | CD32 |
| CD123 | CD27 | NKG2D | CD79a |
| CD123 | CD27 | NKG2D | CD79b |
| CD123 | CD28δ | CD28 | CD8 |
| CD123 | CD28δ | CD28 | CD3ζ |
| CD123 | CD28δ | CD28 | CD3δ |
| CD123 | CD28δ | CD28 | CD3γ |
| CD123 | CD28δ | CD28 | CD3ε |
| CD123 | CD28δ | CD28 | FcγRI-γ |
| CD123 | CD28δ | CD28 | FcγRIII-γ |
| CD123 | CD28δ | CD28 | FcεRIβ |
| CD123 | CD28δ | CD28 | FcεRIγ |
| CD123 | CD28δ | CD28 | DAP10 |
| CD123 | CD28δ | CD28 | DAP12 |
| CD123 | CD28δ | CD28 | CD32 |
| CD123 | CD28δ | CD28 | CD79a |
| CD123 | CD28δ | CD28 | CD79b |
| CD123 | CD28δ | CD8 | CD8 |
| CD123 | CD28δ | CD8 | CD3ζ |
| CD123 | CD28δ | CD8 | CD3δ |
| CD123 | CD28δ | CD8 | CD3γ |
| CD123 | CD28δ | CD8 | CD3ε |
| CD123 | CD28δ | CD8 | FcγRI-γ |
| CD123 | CD28δ | CD8 | FcγRIII-γ |
| CD123 | CD28δ | CD8 | FcεRIβ |
| CD123 | CD28δ | CD8 | FcεRIγ |

TABLE 3-continued

Third Generation CARs

| ScFv | Co-stimulatory Signal | Co-stimulatory Signal | Signal Domain |
|---|---|---|---|
| CD123 | CD28δ | CD8 | DAP10 |
| CD123 | CD28δ | CD8 | DAP12 |
| CD123 | CD28δ | CD8 | CD32 |
| CD123 | CD28δ | CD8 | CD79a |
| CD123 | CD28δ | CD8 | CD79b |
| CD123 | CD28δ | CD4 | CD8 |
| CD123 | CD28δ | CD4 | CD3ζ |
| CD123 | CD28δ | CD4 | CD3δ |
| CD123 | CD28δ | CD4 | CD3γ |
| CD123 | CD28δ | CD4 | CD3ε |
| CD123 | CD28δ | CD4 | FcγRI-γ |
| CD123 | CD28δ | CD4 | FcγRIII-γ |
| CD123 | CD28δ | CD4 | FcεRIβ |
| CD123 | CD28δ | CD4 | FcεRIγ |
| CD123 | CD28δ | CD4 | DAP10 |
| CD123 | CD28δ | CD4 | DAP12 |
| CD123 | CD28δ | CD4 | CD32 |
| CD123 | CD28δ | CD4 | CD79a |
| CD123 | CD28δ | CD4 | CD79b |
| CD123 | CD28δ | b2c | CD8 |
| CD123 | CD28δ | b2c | CD3ζ |
| CD123 | CD28δ | b2c | CD3δ |
| CD123 | CD28δ | b2c | CD3γ |
| CD123 | CD28δ | b2c | CD3ε |
| CD123 | CD28δ | b2c | FcγRI-γ |
| CD123 | CD28δ | b2c | FcγRIII-γ |
| CD123 | CD28δ | b2c | FcεRIβ |
| CD123 | CD28δ | b2c | FcεRIγ |
| CD123 | CD28δ | b2c | DAP10 |
| CD123 | CD28δ | b2c | DAP12 |
| CD123 | CD28δ | b2c | CD32 |
| CD123 | CD28δ | b2c | CD79a |
| CD123 | CD28δ | b2c | CD79b |
| CD123 | CD28δ | CD137/41BB | CD8 |
| CD123 | CD28δ | CD137/41BB | CD3ζ |
| CD123 | CD28δ | CD137/41BB | CD3δ |
| CD123 | CD28δ | CD137/41BB | CD3γ |
| CD123 | CD28δ | CD137/41BB | CD3ε |
| CD123 | CD28δ | CD137/41BB | FcγRI-γ |
| CD123 | CD28δ | CD137/41BB | FcγRIII-γ |
| CD123 | CD28δ | CD137/41BB | FcεRIβ |
| CD123 | CD28δ | CD137/41BB | FcεRIγ |
| CD123 | CD28δ | CD137/41BB | DAP10 |
| CD123 | CD28δ | CD137/41BB | DAP12 |
| CD123 | CD28δ | CD137/41BB | CD32 |
| CD123 | CD28δ | CD137/41BB | CD79a |
| CD123 | CD28δ | CD137/41BB | CD79b |
| CD123 | CD28δ | ICOS | CD8 |
| CD123 | CD28δ | ICOS | CD3ζ |
| CD123 | CD28δ | ICOS | CD3δ |
| CD123 | CD28δ | ICOS | CD3γ |
| CD123 | CD28δ | ICOS | CD3ε |
| CD123 | CD28δ | ICOS | FcγRI-γ |
| CD123 | CD28δ | ICOS | FcγRIII-γ |
| CD123 | CD28δ | ICOS | FcεRIβ |
| CD123 | CD28δ | ICOS | FcεRIγ |
| CD123 | CD28δ | ICOS | DAP10 |
| CD123 | CD28δ | ICOS | DAP12 |
| CD123 | CD28δ | ICOS | CD32 |
| CD123 | CD28δ | ICOS | CD79a |
| CD123 | CD28δ | ICOS | CD79b |
| CD123 | CD28δ | CD27 | CD8 |
| CD123 | CD28δ | CD27 | CD3ζ |
| CD123 | CD28δ | CD27 | CD3δ |
| CD123 | CD28δ | CD27 | CD3γ |
| CD123 | CD28δ | CD27 | CD3ε |
| CD123 | CD28δ | CD27 | FcγRI-γ |
| CD123 | CD28δ | CD27 | FcγRIII-γ |
| CD123 | CD28δ | CD27 | FcεRIβ |
| CD123 | CD28δ | CD27 | FcεRIγ |
| CD123 | CD28δ | CD27 | DAP10 |
| CD123 | CD28δ | CD27 | DAP12 |
| CD123 | CD28δ | CD27 | CD32 |
| CD123 | CD28δ | CD27 | CD79a |
| CD123 | CD28δ | CD27 | CD79b |
| CD123 | CD28δ | CD28δ | CD8 |
| CD123 | CD28δ | CD28δ | CD3ζ |
| CD123 | CD28δ | CD28δ | CD3δ |
| CD123 | CD28δ | CD28δ | CD3γ |
| CD123 | CD28δ | CD28δ | CD3ε |
| CD123 | CD28δ | CD28δ | FcγRI-γ |
| CD123 | CD28δ | CD28δ | FcγRIII-γ |
| CD123 | CD28δ | CD28δ | FcεRIβ |
| CD123 | CD28δ | CD28δ | FcεRIγ |
| CD123 | CD28δ | CD28δ | DAP10 |
| CD123 | CD28δ | CD28δ | DAP12 |
| CD123 | CD28δ | CD28δ | CD32 |
| CD123 | CD28δ | CD28δ | CD79a |
| CD123 | CD28δ | CD28δ | CD79b |
| CD123 | CD28δ | CD80 | CD8 |
| CD123 | CD28δ | CD80 | CD3ζ |
| CD123 | CD28δ | CD80 | CD3δ |
| CD123 | CD28δ | CD80 | CD3γ |
| CD123 | CD28δ | CD80 | CD3ε |
| CD123 | CD28δ | CD80 | FcγRI-γ |
| CD123 | CD28δ | CD80 | FcγRIII-γ |
| CD123 | CD28δ | CD80 | FcεRIβ |
| CD123 | CD28δ | CD80 | FcεRIγ |
| CD123 | CD28δ | CD80 | DAP10 |
| CD123 | CD28δ | CD80 | DAP12 |
| CD123 | CD28δ | CD80 | CD32 |
| CD123 | CD28δ | CD80 | CD79a |
| CD123 | CD28δ | CD80 | CD79b |
| CD123 | CD28δ | CD86 | CD8 |
| CD123 | CD28δ | CD86 | CD3ζ |
| CD123 | CD28δ | CD86 | CD3δ |
| CD123 | CD28δ | CD86 | CD3γ |
| CD123 | CD28δ | CD86 | CD3ε |
| CD123 | CD28δ | CD86 | FcγRI-γ |
| CD123 | CD28δ | CD86 | FcγRIII-γ |
| CD123 | CD28δ | CD86 | FcεRIβ |
| CD123 | CD28δ | CD86 | FcεRIγ |
| CD123 | CD28δ | CD86 | DAP10 |
| CD123 | CD28δ | CD86 | DAP12 |
| CD123 | CD28δ | CD86 | CD32 |
| CD123 | CD28δ | CD86 | CD79a |
| CD123 | CD28δ | CD86 | CD79b |
| CD123 | CD28δ | OX40 | CD8 |
| CD123 | CD28δ | OX40 | CD3ζ |
| CD123 | CD28δ | OX40 | CD3δ |
| CD123 | CD28δ | OX40 | CD3γ |
| CD123 | CD28δ | OX40 | CD3ε |
| CD123 | CD28δ | OX40 | FcγRI-γ |
| CD123 | CD28δ | OX40 | FcγRIII-γ |
| CD123 | CD28δ | OX40 | FcεRIβ |
| CD123 | CD28δ | OX40 | FcεRIγ |
| CD123 | CD28δ | OX40 | DAP10 |
| CD123 | CD28δ | OX40 | DAP12 |
| CD123 | CD28δ | OX40 | CD32 |
| CD123 | CD28δ | OX40 | CD79a |
| CD123 | CD28δ | OX40 | CD79b |
| CD123 | CD28δ | DAP10 | CD8 |
| CD123 | CD28δ | DAP10 | CD3ζ |
| CD123 | CD28δ | DAP10 | CD3δ |
| CD123 | CD28δ | DAP10 | CD3γ |
| CD123 | CD28δ | DAP10 | CD3ε |
| CD123 | CD28δ | DAP10 | FcγRI-γ |
| CD123 | CD28δ | DAP10 | FcγRIII-γ |
| CD123 | CD28δ | DAP10 | FcεRIβ |
| CD123 | CD28δ | DAP10 | FcεRIγ |
| CD123 | CD28δ | DAP10 | DAP10 |
| CD123 | CD28δ | DAP10 | DAP12 |
| CD123 | CD28δ | DAP10 | CD32 |
| CD123 | CD28δ | DAP10 | CD79a |
| CD123 | CD28δ | DAP10 | CD79b |
| CD123 | CD28δ | DAP12 | CD8 |
| CD123 | CD28δ | DAP12 | CD3ζ |
| CD123 | CD28δ | DAP12 | CD3δ |
| CD123 | CD28δ | DAP12 | CD3γ |
| CD123 | CD28δ | DAP12 | CD3ε |

TABLE 3-continued

Third Generation CARs

| ScFv | Co-stimulatory Signal | Co-stimulatory Signal | Signal Domain |
|---|---|---|---|
| CD123 | CD28δ | DAP12 | FcγRI-γ |
| CD123 | CD28δ | DAP12 | FcγRIII-γ |
| CD123 | CD28δ | DAP12 | FcεRIβ |
| CD123 | CD28δ | DAP12 | FcεRIγ |
| CD123 | CD28δ | DAP12 | DAP10 |
| CD123 | CD28δ | DAP12 | DAP12 |
| CD123 | CD28δ | DAP12 | CD32 |
| CD123 | CD28δ | DAP12 | CD79a |
| CD123 | CD28δ | DAP12 | CD79b |
| CD123 | CD28δ | MyD88 | CD8 |
| CD123 | CD28δ | MyD88 | CD3ζ |
| CD123 | CD28δ | MyD88 | CD3δ |
| CD123 | CD28δ | MyD88 | CD3γ |
| CD123 | CD28δ | MyD88 | CD3ε |
| CD123 | CD28δ | MyD88 | FcγRI-γ |
| CD123 | CD28δ | MyD88 | FcγRIII-γ |
| CD123 | CD28δ | MyD88 | FcεRIβ |
| CD123 | CD28δ | MyD88 | FcεRIγ |
| CD123 | CD28δ | MyD88 | DAP10 |
| CD123 | CD28δ | MyD88 | DAP12 |
| CD123 | CD28δ | MyD88 | CD32 |
| CD123 | CD28δ | MyD88 | CD79a |
| CD123 | CD28δ | MyD88 | CD79b |
| CD123 | CD28δ | CD7 | CD8 |
| CD123 | CD28δ | CD7 | CD3ζ |
| CD123 | CD28δ | CD7 | CD3δ |
| CD123 | CD28δ | CD7 | CD3γ |
| CD123 | CD28δ | CD7 | CD3ε |
| CD123 | CD28δ | CD7 | FcγRI-γ |
| CD123 | CD28δ | CD7 | FcγRIII-γ |
| CD123 | CD28δ | CD7 | FcεRIβ |
| CD123 | CD28δ | CD7 | FcεRIγ |
| CD123 | CD28δ | CD7 | DAP10 |
| CD123 | CD28δ | CD7 | DAP12 |
| CD123 | CD28δ | CD7 | CD32 |
| CD123 | CD28δ | CD7 | CD79a |
| CD123 | CD28δ | CD7 | CD79b |
| CD123 | CD28δ | BTNL3 | CD8 |
| CD123 | CD28δ | BTNL3 | CD3ζ |
| CD123 | CD28δ | BTNL3 | CD3δ |
| CD123 | CD28δ | BTNL3 | CD3γ |
| CD123 | CD28δ | BTNL3 | CD3ε |
| CD123 | CD28δ | BTNL3 | FcγRI-γ |
| CD123 | CD28δ | BTNL3 | FcγRIII-γ |
| CD123 | CD28δ | BTNL3 | FcεRIβ |
| CD123 | CD28δ | BTNL3 | FcεRIγ |
| CD123 | CD28δ | BTNL3 | DAP10 |
| CD123 | CD28δ | BTNL3 | DAP12 |
| CD123 | CD28δ | BTNL3 | CD32 |
| CD123 | CD28δ | BTNL3 | CD79a |
| CD123 | CD28δ | BTNL3 | CD79b |
| CD123 | CD28δ | NKG2D | CD8 |
| CD123 | CD28δ | NKG2D | CD3ζ |
| CD123 | CD28δ | NKG2D | CD3δ |
| CD123 | CD28δ | NKG2D | CD3γ |
| CD123 | CD28δ | NKG2D | CD3ε |
| CD123 | CD28δ | NKG2D | FcγRI-γ |
| CD123 | CD28δ | NKG2D | FcγRIII-γ |
| CD123 | CD28δ | NKG2D | FcεRIβ |
| CD123 | CD28δ | NKG2D | FcεRIγ |
| CD123 | CD28δ | NKG2D | DAP10 |
| CD123 | CD28δ | NKG2D | DAP12 |
| CD123 | CD28δ | NKG2D | CD32 |
| CD123 | CD28δ | NKG2D | CD79a |
| CD123 | CD28δ | NKG2D | CD79b |
| CD123 | CD80 | CD28 | CD8 |
| CD123 | CD80 | CD28 | CD3ζ |
| CD123 | CD80 | CD28 | CD3δ |
| CD123 | CD80 | CD28 | CD3γ |
| CD123 | CD80 | CD28 | CD3ε |
| CD123 | CD80 | CD28 | FcγRI-γ |
| CD123 | CD80 | CD28 | FcγRIII-γ |
| CD123 | CD80 | CD28 | FcεRIβ |
| CD123 | CD80 | CD28 | FcεRIγ |
| CD123 | CD80 | CD28 | DAP10 |
| CD123 | CD80 | CD28 | DAP12 |
| CD123 | CD80 | CD28 | CD32 |
| CD123 | CD80 | CD28 | CD79a |
| CD123 | CD80 | CD28 | CD79b |
| CD123 | CD80 | CD8 | CD8 |
| CD123 | CD80 | CD8 | CD3ζ |
| CD123 | CD80 | CD8 | CD3δ |
| CD123 | CD80 | CD8 | CD3γ |
| CD123 | CD80 | CD8 | CD3ε |
| CD123 | CD80 | CD8 | FcγRI-γ |
| CD123 | CD80 | CD8 | FcγRIII-γ |
| CD123 | CD80 | CD8 | FcεRIβ |
| CD123 | CD80 | CD8 | FcεRIγ |
| CD123 | CD80 | CD8 | DAP10 |
| CD123 | CD80 | CD8 | DAP12 |
| CD123 | CD80 | CD8 | CD32 |
| CD123 | CD80 | CD8 | CD79a |
| CD123 | CD80 | CD8 | CD79b |
| CD123 | CD80 | CD4 | CD8 |
| CD123 | CD80 | CD4 | CD3ζ |
| CD123 | CD80 | CD4 | CD3δ |
| CD123 | CD80 | CD4 | CD3γ |
| CD123 | CD80 | CD4 | CD3ε |
| CD123 | CD80 | CD4 | FcγRI-γ |
| CD123 | CD80 | CD4 | FcγRIII-γ |
| CD123 | CD80 | CD4 | FcεRIβ |
| CD123 | CD80 | CD4 | FcεRIγ |
| CD123 | CD80 | CD4 | DAP10 |
| CD123 | CD80 | CD4 | DAP12 |
| CD123 | CD80 | CD4 | CD32 |
| CD123 | CD80 | CD4 | CD79a |
| CD123 | CD80 | CD4 | CD79b |
| CD123 | CD80 | b2c | CD8 |
| CD123 | CD80 | b2c | CD3ζ |
| CD123 | CD80 | b2c | CD3δ |
| CD123 | CD80 | b2c | CD3γ |
| CD123 | CD80 | b2c | CD3ε |
| CD123 | CD80 | b2c | FcγRI-γ |
| CD123 | CD80 | b2c | FcγRIII-γ |
| CD123 | CD80 | b2c | FcεRIβ |
| CD123 | CD80 | b2c | FcεRIγ |
| CD123 | CD80 | b2c | DAP10 |
| CD123 | CD80 | b2c | DAP12 |
| CD123 | CD80 | b2c | CD32 |
| CD123 | CD80 | b2c | CD79a |
| CD123 | CD80 | b2c | CD79b |
| CD123 | CD80 | CD137/41BB | CD8 |
| CD123 | CD80 | CD137/41BB | CD3ζ |
| CD123 | CD80 | CD137/41BB | CD3δ |
| CD123 | CD80 | CD137/41BB | CD3γ |
| CD123 | CD80 | CD137/41BB | CD3ε |
| CD123 | CD80 | CD137/41BB | FcγRI-γ |
| CD123 | CD80 | CD137/41BB | FcγRIII-γ |
| CD123 | CD80 | CD137/41BB | FcεRIβ |
| CD123 | CD80 | CD137/41BB | FcεRIγ |
| CD123 | CD80 | CD137/41BB | DAP10 |
| CD123 | CD80 | CD137/41BB | DAP12 |
| CD123 | CD80 | CD137/41BB | CD32 |
| CD123 | CD80 | CD137/41BB | CD79a |
| CD123 | CD80 | CD137/41BB | CD79b |
| CD123 | CD80 | ICOS | CD8 |
| CD123 | CD80 | ICOS | CD3ζ |
| CD123 | CD80 | ICOS | CD3δ |
| CD123 | CD80 | ICOS | CD3γ |
| CD123 | CD80 | ICOS | CD3ε |
| CD123 | CD80 | ICOS | FcγRI-γ |
| CD123 | CD80 | ICOS | FcγRIII-γ |
| CD123 | CD80 | ICOS | FcεRIβ |
| CD123 | CD80 | ICOS | FcεRIγ |
| CD123 | CD80 | ICOS | DAP10 |
| CD123 | CD80 | ICOS | DAP12 |
| CD123 | CD80 | ICOS | CD32 |
| CD123 | CD80 | ICOS | CD79a |
| CD123 | CD80 | ICOS | CD79b |
| CD123 | CD80 | CD27 | CD8 |

TABLE 3-continued

Third Generation CARs

| ScFv | Co-stimulatory Signal | Co-stimulatory Signal | Signal Domain |
|---|---|---|---|
| CD123 | CD80 | CD27 | CD3ζ |
| CD123 | CD80 | CD27 | CD3δ |
| CD123 | CD80 | CD27 | CD3γ |
| CD123 | CD80 | CD27 | CD3ε |
| CD123 | CD80 | CD27 | FcγRI-γ |
| CD123 | CD80 | CD27 | FcγRIII-γ |
| CD123 | CD80 | CD27 | FcεRIβ |
| CD123 | CD80 | CD27 | FcεRIγ |
| CD123 | CD80 | CD27 | DAP10 |
| CD123 | CD80 | CD27 | DAP12 |
| CD123 | CD80 | CD27 | CD32 |
| CD123 | CD80 | CD27 | CD79a |
| CD123 | CD80 | CD27 | CD79b |
| CD123 | CD80 | CD28δ | CD8 |
| CD123 | CD80 | CD28δ | CD3ζ |
| CD123 | CD80 | CD28δ | CD3δ |
| CD123 | CD80 | CD28δ | CD3γ |
| CD123 | CD80 | CD28δ | CD3ε |
| CD123 | CD80 | CD28δ | FcγRI-γ |
| CD123 | CD80 | CD28δ | FcγRIII-γ |
| CD123 | CD80 | CD28δ | FcεRIβ |
| CD123 | CD80 | CD28δ | FcεRIγ |
| CD123 | CD80 | CD28δ | DAP10 |
| CD123 | CD80 | CD28δ | DAP12 |
| CD123 | CD80 | CD28δ | CD32 |
| CD123 | CD80 | CD28δ | CD79a |
| CD123 | CD80 | CD28δ | CD79b |
| CD123 | CD80 | CD80 | CD8 |
| CD123 | CD80 | CD80 | CD3ζ |
| CD123 | CD80 | CD80 | CD3δ |
| CD123 | CD80 | CD80 | CD3γ |
| CD123 | CD80 | CD80 | CD3ε |
| CD123 | CD80 | CD80 | FcγRI-γ |
| CD123 | CD80 | CD80 | FcγRIII-γ |
| CD123 | CD80 | CD80 | FcεRIβ |
| CD123 | CD80 | CD80 | FcεRIγ |
| CD123 | CD80 | CD80 | DAP10 |
| CD123 | CD80 | CD80 | DAP12 |
| CD123 | CD80 | CD80 | CD32 |
| CD123 | CD80 | CD80 | CD79a |
| CD123 | CD80 | CD80 | CD79b |
| CD123 | CD80 | CD86 | CD8 |
| CD123 | CD80 | CD86 | CD3ζ |
| CD123 | CD80 | CD86 | CD3δ |
| CD123 | CD80 | CD86 | CD3γ |
| CD123 | CD80 | CD86 | CD3ε |
| CD123 | CD80 | CD86 | FcγRI-γ |
| CD123 | CD80 | CD86 | FcγRIII-γ |
| CD123 | CD80 | CD86 | FcεRIβ |
| CD123 | CD80 | CD86 | FcεRIγ |
| CD123 | CD80 | CD86 | DAP10 |
| CD123 | CD80 | CD86 | DAP12 |
| CD123 | CD80 | CD86 | CD32 |
| CD123 | CD80 | CD86 | CD79a |
| CD123 | CD80 | CD86 | CD79b |
| CD123 | CD80 | OX40 | CD8 |
| CD123 | CD80 | OX40 | CD3ζ |
| CD123 | CD80 | OX40 | CD3δ |
| CD123 | CD80 | OX40 | CD3γ |
| CD123 | CD80 | OX40 | CD3ε |
| CD123 | CD80 | OX40 | FcγRI-γ |
| CD123 | CD80 | OX40 | FcγRIII-γ |
| CD123 | CD80 | OX40 | FcεRIβ |
| CD123 | CD80 | OX40 | FcεRIγ |
| CD123 | CD80 | OX40 | DAP10 |
| CD123 | CD80 | OX40 | DAP12 |
| CD123 | CD80 | OX40 | CD32 |
| CD123 | CD80 | OX40 | CD79a |
| CD123 | CD80 | OX40 | CD79b |
| CD123 | CD80 | DAP10 | CD8 |
| CD123 | CD80 | DAP10 | CD3ζ |
| CD123 | CD80 | DAP10 | CD3δ |
| CD123 | CD80 | DAP10 | CD3γ |
| CD123 | CD80 | DAP10 | CD3ε |
| CD123 | CD80 | DAP10 | FcγRI-γ |
| CD123 | CD80 | DAP10 | FcγRIII-γ |
| CD123 | CD80 | DAP10 | FcεRIβ |
| CD123 | CD80 | DAP10 | FcεRIγ |
| CD123 | CD80 | DAP10 | DAP10 |
| CD123 | CD80 | DAP10 | DAP12 |
| CD123 | CD80 | DAP10 | CD32 |
| CD123 | CD80 | DAP10 | CD79a |
| CD123 | CD80 | DAP10 | CD79b |
| CD123 | CD80 | DAP12 | CD8 |
| CD123 | CD80 | DAP12 | CD3ζ |
| CD123 | CD80 | DAP12 | CD3δ |
| CD123 | CD80 | DAP12 | CD3γ |
| CD123 | CD80 | DAP12 | CD3ε |
| CD123 | CD80 | DAP12 | FcγRI-γ |
| CD123 | CD80 | DAP12 | FcγRIII-γ |
| CD123 | CD80 | DAP12 | FcεRIβ |
| CD123 | CD80 | DAP12 | FcεRIγ |
| CD123 | CD80 | DAP12 | DAP10 |
| CD123 | CD80 | DAP12 | DAP12 |
| CD123 | CD80 | DAP12 | CD32 |
| CD123 | CD80 | DAP12 | CD79a |
| CD123 | CD80 | DAP12 | CD79b |
| CD123 | CD80 | MyD88 | CD8 |
| CD123 | CD80 | MyD88 | CD3ζ |
| CD123 | CD80 | MyD88 | CD3δ |
| CD123 | CD80 | MyD88 | CD3γ |
| CD123 | CD80 | MyD88 | CD3ε |
| CD123 | CD80 | MyD88 | FcγRI-γ |
| CD123 | CD80 | MyD88 | FcγRIII-γ |
| CD123 | CD80 | MyD88 | FcεRIβ |
| CD123 | CD80 | MyD88 | FcεRIγ |
| CD123 | CD80 | MyD88 | DAP10 |
| CD123 | CD80 | MyD88 | DAP12 |
| CD123 | CD80 | MyD88 | CD32 |
| CD123 | CD80 | MyD88 | CD79a |
| CD123 | CD80 | MyD88 | CD79b |
| CD123 | CD80 | CD7 | CD8 |
| CD123 | CD80 | CD7 | CD3ζ |
| CD123 | CD80 | CD7 | CD3δ |
| CD123 | CD80 | CD7 | CD3γ |
| CD123 | CD80 | CD7 | CD3ε |
| CD123 | CD80 | CD7 | FcγRI-γ |
| CD123 | CD80 | CD7 | FcγRIII-γ |
| CD123 | CD80 | CD7 | FcεRIβ |
| CD123 | CD80 | CD7 | FcεRIγ |
| CD123 | CD80 | CD7 | DAP10 |
| CD123 | CD80 | CD7 | DAP12 |
| CD123 | CD80 | CD7 | CD32 |
| CD123 | CD80 | CD7 | CD79a |
| CD123 | CD80 | CD7 | CD79b |
| CD123 | CD80 | BTNL3 | CD8 |
| CD123 | CD80 | BTNL3 | CD3ζ |
| CD123 | CD80 | BTNL3 | CD3δ |
| CD123 | CD80 | BTNL3 | CD3γ |
| CD123 | CD80 | BTNL3 | CD3ε |
| CD123 | CD80 | BTNL3 | FcγRI-γ |
| CD123 | CD80 | BTNL3 | FcγRIII-γ |
| CD123 | CD80 | BTNL3 | FcεRIβ |
| CD123 | CD80 | BTNL3 | FcεRIγ |
| CD123 | CD80 | BTNL3 | DAP10 |
| CD123 | CD80 | BTNL3 | DAP12 |
| CD123 | CD80 | BTNL3 | CD32 |
| CD123 | CD80 | BTNL3 | CD79a |
| CD123 | CD80 | BTNL3 | CD79b |
| CD123 | CD80 | NKG2D | CD8 |
| CD123 | CD80 | NKG2D | CD3ζ |
| CD123 | CD80 | NKG2D | CD3δ |
| CD123 | CD80 | NKG2D | CD3γ |
| CD123 | CD80 | NKG2D | CD3ε |
| CD123 | CD80 | NKG2D | FcγRI-γ |
| CD123 | CD80 | NKG2D | FcγRIII-γ |
| CD123 | CD80 | NKG2D | FcεRIβ |
| CD123 | CD80 | NKG2D | FcεRIγ |
| CD123 | CD80 | NKG2D | DAP10 |
| CD123 | CD80 | NKG2D | DAP12 |

TABLE 3-continued

Third Generation CARs

| ScFv | Co-stimulatory Signal | Co-stimulatory Signal | Signal Domain |
|---|---|---|---|
| CD123 | CD80 | NKG2D | CD32 |
| CD123 | CD80 | NKG2D | CD79a |
| CD123 | CD80 | NKG2D | CD79b |
| CD123 | CD86 | CD28 | CD8 |
| CD123 | CD86 | CD28 | CD3ζ |
| CD123 | CD86 | CD28 | CD3δ |
| CD123 | CD86 | CD28 | CD3γ |
| CD123 | CD86 | CD28 | CD3ε |
| CD123 | CD86 | CD28 | FcγRI-γ |
| CD123 | CD86 | CD28 | FcγRIII-γ |
| CD123 | CD86 | CD28 | FcεRIβ |
| CD123 | CD86 | CD28 | FcεRIγ |
| CD123 | CD86 | CD28 | DAP10 |
| CD123 | CD86 | CD28 | DAP12 |
| CD123 | CD86 | CD28 | CD32 |
| CD123 | CD86 | CD28 | CD79a |
| CD123 | CD86 | CD28 | CD79b |
| CD123 | CD86 | CD8 | CD8 |
| CD123 | CD86 | CD8 | CD3ζ |
| CD123 | CD86 | CD8 | CD3δ |
| CD123 | CD86 | CD8 | CD3γ |
| CD123 | CD86 | CD8 | CD3ε |
| CD123 | CD86 | CD8 | FcγRI-γ |
| CD123 | CD86 | CD8 | FcγRIII-γ |
| CD123 | CD86 | CD8 | FcεRIβ |
| CD123 | CD86 | CD8 | FcεRIγ |
| CD123 | CD86 | CD8 | DAP10 |
| CD123 | CD86 | CD8 | DAP12 |
| CD123 | CD86 | CD8 | CD32 |
| CD123 | CD86 | CD8 | CD79a |
| CD123 | CD86 | CD8 | CD79b |
| CD123 | CD86 | CD4 | CD8 |
| CD123 | CD86 | CD4 | CD3ζ |
| CD123 | CD86 | CD4 | CD3δ |
| CD123 | CD86 | CD4 | CD3γ |
| CD123 | CD86 | CD4 | CD3ε |
| CD123 | CD86 | CD4 | FcγRI-γ |
| CD123 | CD86 | CD4 | FcγRIII-γ |
| CD123 | CD86 | CD4 | FcεRIβ |
| CD123 | CD86 | CD4 | FcεRIγ |
| CD123 | CD86 | CD4 | DAP10 |
| CD123 | CD86 | CD4 | DAP12 |
| CD123 | CD86 | CD4 | CD32 |
| CD123 | CD86 | CD4 | CD79a |
| CD123 | CD86 | CD4 | CD79b |
| CD123 | CD86 | b2c | CD8 |
| CD123 | CD86 | b2c | CD3ζ |
| CD123 | CD86 | b2c | CD3δ |
| CD123 | CD86 | b2c | CD3γ |
| CD123 | CD86 | b2c | CD3ε |
| CD123 | CD86 | b2c | FcγRI-γ |
| CD123 | CD86 | b2c | FcγRIII-γ |
| CD123 | CD86 | b2c | FcεRIβ |
| CD123 | CD86 | b2c | FcεRIγ |
| CD123 | CD86 | b2c | DAP10 |
| CD123 | CD86 | b2c | DAP12 |
| CD123 | CD86 | b2c | CD32 |
| CD123 | CD86 | b2c | CD79a |
| CD123 | CD86 | b2c | CD79b |
| CD123 | CD86 | CD137/41BB | CD8 |
| CD123 | CD86 | CD137/41BB | CD3ζ |
| CD123 | CD86 | CD137/41BB | CD3δ |
| CD123 | CD86 | CD137/41BB | CD3γ |
| CD123 | CD86 | CD137/41BB | CD3ε |
| CD123 | CD86 | CD137/41BB | FcγRI-γ |
| CD123 | CD86 | CD137/41BB | FcγRIII-γ |
| CD123 | CD86 | CD137/41BB | FcεRIβ |
| CD123 | CD86 | CD137/41BB | FcεRIγ |
| CD123 | CD86 | CD137/41BB | DAP10 |
| CD123 | CD86 | CD137/41BB | DAP12 |
| CD123 | CD86 | CD137/41BB | CD32 |
| CD123 | CD86 | CD137/41BB | CD79a |
| CD123 | CD86 | CD137/41BB | CD79b |
| CD123 | CD86 | ICOS | CD8 |
| CD123 | CD86 | ICOS | CD3ζ |
| CD123 | CD86 | ICOS | CD3δ |
| CD123 | CD86 | ICOS | CD3γ |
| CD123 | CD86 | ICOS | CD3ε |
| CD123 | CD86 | ICOS | FcγRI-γ |
| CD123 | CD86 | ICOS | FcγRIII-γ |
| CD123 | CD86 | ICOS | FcεRIβ |
| CD123 | CD86 | ICOS | FcεRIγ |
| CD123 | CD86 | ICOS | DAP10 |
| CD123 | CD86 | ICOS | DAP12 |
| CD123 | CD86 | ICOS | CD32 |
| CD123 | CD86 | ICOS | CD79a |
| CD123 | CD86 | ICOS | CD79b |
| CD123 | CD86 | CD27 | CD8 |
| CD123 | CD86 | CD27 | CD3ζ |
| CD123 | CD86 | CD27 | CD3δ |
| CD123 | CD86 | CD27 | CD3γ |
| CD123 | CD86 | CD27 | CD3ε |
| CD123 | CD86 | CD27 | FcγRI-γ |
| CD123 | CD86 | CD27 | FcγRIII-γ |
| CD123 | CD86 | CD27 | FcεRIβ |
| CD123 | CD86 | CD27 | FcεRIγ |
| CD123 | CD86 | CD27 | DAP10 |
| CD123 | CD86 | CD27 | DAP12 |
| CD123 | CD86 | CD27 | CD32 |
| CD123 | CD86 | CD27 | CD79a |
| CD123 | CD86 | CD27 | CD79b |
| CD123 | CD86 | CD28δ | CD8 |
| CD123 | CD86 | CD28δ | CD3ζ |
| CD123 | CD86 | CD28δ | CD3δ |
| CD123 | CD86 | CD28δ | CD3γ |
| CD123 | CD86 | CD28δ | CD3ε |
| CD123 | CD86 | CD28δ | FcγRI-γ |
| CD123 | CD86 | CD28δ | FcγRIII-γ |
| CD123 | CD86 | CD28δ | FcεRIβ |
| CD123 | CD86 | CD28δ | FcεRIγ |
| CD123 | CD86 | CD28δ | DAP10 |
| CD123 | CD86 | CD28δ | DAP12 |
| CD123 | CD86 | CD28δ | CD32 |
| CD123 | CD86 | CD28δ | CD79a |
| CD123 | CD86 | CD28δ | CD79b |
| CD123 | CD86 | CD80 | CD8 |
| CD123 | CD86 | CD80 | CD3ζ |
| CD123 | CD86 | CD80 | CD3δ |
| CD123 | CD86 | CD80 | CD3γ |
| CD123 | CD86 | CD80 | CD3ε |
| CD123 | CD86 | CD80 | FcγRI-γ |
| CD123 | CD86 | CD80 | FcγRIII-γ |
| CD123 | CD86 | CD80 | FcεRIβ |
| CD123 | CD86 | CD80 | FcεRIγ |
| CD123 | CD86 | CD80 | DAP10 |
| CD123 | CD86 | CD80 | DAP12 |
| CD123 | CD86 | CD80 | CD32 |
| CD123 | CD86 | CD80 | CD79a |
| CD123 | CD86 | CD80 | CD79b |
| CD123 | CD86 | CD86 | CD8 |
| CD123 | CD86 | CD86 | CD3ζ |
| CD123 | CD86 | CD86 | CD3δ |
| CD123 | CD86 | CD86 | CD3γ |
| CD123 | CD86 | CD86 | CD3ε |
| CD123 | CD86 | CD86 | FcγRI-γ |
| CD123 | CD86 | CD86 | FcγRIII-γ |
| CD123 | CD86 | CD86 | FcεRIβ |
| CD123 | CD86 | CD86 | FcεRIγ |
| CD123 | CD86 | CD86 | DAP10 |
| CD123 | CD86 | CD86 | DAP12 |
| CD123 | CD86 | CD86 | CD32 |
| CD123 | CD86 | CD86 | CD79a |
| CD123 | CD86 | CD86 | CD79b |
| CD123 | CD86 | OX40 | CD8 |
| CD123 | CD86 | OX40 | CD3ζ |
| CD123 | CD86 | OX40 | CD3δ |
| CD123 | CD86 | OX40 | CD3γ |
| CD123 | CD86 | OX40 | CD3ε |
| CD123 | CD86 | OX40 | FcγRI-γ |
| CD123 | CD86 | OX40 | FcγRIII-γ |

TABLE 3-continued

Third Generation CARs

| ScFv | Co-stimulatory Signal | Co-stimulatory Signal | Signal Domain |
|---|---|---|---|
| CD123 | CD86 | OX40 | FcεRIβ |
| CD123 | CD86 | OX40 | FcεRIγ |
| CD123 | CD86 | OX40 | DAP10 |
| CD123 | CD86 | OX40 | DAP12 |
| CD123 | CD86 | OX40 | CD32 |
| CD123 | CD86 | OX40 | CD79a |
| CD123 | CD86 | OX40 | CD79b |
| CD123 | CD86 | DAP10 | CD8 |
| CD123 | CD86 | DAP10 | CD3ζ |
| CD123 | CD86 | DAP10 | CD3δ |
| CD123 | CD86 | DAP10 | CD3γ |
| CD123 | CD86 | DAP10 | CD3ε |
| CD123 | CD86 | DAP10 | FcγRI-γ |
| CD123 | CD86 | DAP10 | FcγRIII-γ |
| CD123 | CD86 | DAP10 | FcεRIβ |
| CD123 | CD86 | DAP10 | FcεRIγ |
| CD123 | CD86 | DAP10 | DAP10 |
| CD123 | CD86 | DAP10 | DAP12 |
| CD123 | CD86 | DAP10 | CD32 |
| CD123 | CD86 | DAP10 | CD79a |
| CD123 | CD86 | DAP10 | CD79b |
| CD123 | CD86 | DAP12 | CD8 |
| CD123 | CD86 | DAP12 | CD3ζ |
| CD123 | CD86 | DAP12 | CD3δ |
| CD123 | CD86 | DAP12 | CD3γ |
| CD123 | CD86 | DAP12 | CD3ε |
| CD123 | CD86 | DAP12 | FcγRI-γ |
| CD123 | CD86 | DAP12 | FcγRIII-γ |
| CD123 | CD86 | DAP12 | FcεRIβ |
| CD123 | CD86 | DAP12 | FcεRIγ |
| CD123 | CD86 | DAP12 | DAP10 |
| CD123 | CD86 | DAP12 | DAP12 |
| CD123 | CD86 | DAP12 | CD32 |
| CD123 | CD86 | DAP12 | CD79a |
| CD123 | CD86 | DAP12 | CD79b |
| CD123 | CD86 | MyD88 | CD8 |
| CD123 | CD86 | MyD88 | CD3ζ |
| CD123 | CD86 | MyD88 | CD3δ |
| CD123 | CD86 | MyD88 | CD3γ |
| CD123 | CD86 | MyD88 | CD3ε |
| CD123 | CD86 | MyD88 | FcγRI-γ |
| CD123 | CD86 | MyD88 | FcγRIII-γ |
| CD123 | CD86 | MyD88 | FcεRIβ |
| CD123 | CD86 | MyD88 | FcεRIγ |
| CD123 | CD86 | MyD88 | DAP10 |
| CD123 | CD86 | MyD88 | DAP12 |
| CD123 | CD86 | MyD88 | CD32 |
| CD123 | CD86 | MyD88 | CD79a |
| CD123 | CD86 | MyD88 | CD79b |
| CD123 | CD86 | CD7 | CD8 |
| CD123 | CD86 | CD7 | CD3ζ |
| CD123 | CD86 | CD7 | CD3δ |
| CD123 | CD86 | CD7 | CD3γ |
| CD123 | CD86 | CD7 | CD3ε |
| CD123 | CD86 | CD7 | FcγRI-γ |
| CD123 | CD86 | CD7 | FcγRIII-γ |
| CD123 | CD86 | CD7 | FcεRIβ |
| CD123 | CD86 | CD7 | FcεRIγ |
| CD123 | CD86 | CD7 | DAP10 |
| CD123 | CD86 | CD7 | DAP12 |
| CD123 | CD86 | CD7 | CD32 |
| CD123 | CD86 | CD7 | CD79a |
| CD123 | CD86 | CD7 | CD79b |
| CD123 | CD86 | BTNL3 | CD8 |
| CD123 | CD86 | BTNL3 | CD3ζ |
| CD123 | CD86 | BTNL3 | CD3δ |
| CD123 | CD86 | BTNL3 | CD3γ |
| CD123 | CD86 | BTNL3 | CD3ε |
| CD123 | CD86 | BTNL3 | FcγRI-γ |
| CD123 | CD86 | BTNL3 | FcγRIII-γ |
| CD123 | CD86 | BTNL3 | FcεRIβ |
| CD123 | CD86 | BTNL3 | FcεRIγ |
| CD123 | CD86 | BTNL3 | DAP10 |
| CD123 | CD86 | BTNL3 | DAP12 |
| CD123 | CD86 | BTNL3 | CD32 |
| CD123 | CD86 | BTNL3 | CD79a |
| CD123 | CD86 | BTNL3 | CD79b |
| CD123 | CD86 | NKG2D | CD8 |
| CD123 | CD86 | NKG2D | CD3ζ |
| CD123 | CD86 | NKG2D | CD3δ |
| CD123 | CD86 | NKG2D | CD3γ |
| CD123 | CD86 | NKG2D | CD3ε |
| CD123 | CD86 | NKG2D | FcγRI-γ |
| CD123 | CD86 | NKG2D | FcγRIII-γ |
| CD123 | CD86 | NKG2D | FcεRIβ |
| CD123 | CD86 | NKG2D | FcεRIγ |
| CD123 | CD86 | NKG2D | DAP10 |
| CD123 | CD86 | NKG2D | DAP12 |
| CD123 | CD86 | NKG2D | CD32 |
| CD123 | CD86 | NKG2D | CD79a |
| CD123 | CD86 | NKG2D | CD79b |
| CD123 | OX40 | CD28 | CD8 |
| CD123 | OX40 | CD28 | CD3ζ |
| CD123 | OX40 | CD28 | CD3δ |
| CD123 | OX40 | CD28 | CD3γ |
| CD123 | OX40 | CD28 | CD3ε |
| CD123 | OX40 | CD28 | FcγRI-γ |
| CD123 | OX40 | CD28 | FcγRIII-γ |
| CD123 | OX40 | CD28 | FcεRIβ |
| CD123 | OX40 | CD28 | FcεRIγ |
| CD123 | OX40 | CD28 | DAP10 |
| CD123 | OX40 | CD28 | DAP12 |
| CD123 | OX40 | CD28 | CD32 |
| CD123 | OX40 | CD28 | CD79a |
| CD123 | OX40 | CD28 | CD79b |
| CD123 | OX40 | CD8 | CD8 |
| CD123 | OX40 | CD8 | CD3ζ |
| CD123 | OX40 | CD8 | CD3δ |
| CD123 | OX40 | CD8 | CD3γ |
| CD123 | OX40 | CD8 | CD3ε |
| CD123 | OX40 | CD8 | FcγRI-γ |
| CD123 | OX40 | CD8 | FcγRIII-γ |
| CD123 | OX40 | CD8 | FcεRIβ |
| CD123 | OX40 | CD8 | FcεRIγ |
| CD123 | OX40 | CD8 | DAP10 |
| CD123 | OX40 | CD8 | DAP12 |
| CD123 | OX40 | CD8 | CD32 |
| CD123 | OX40 | CD8 | CD79a |
| CD123 | OX40 | CD8 | CD79b |
| CD123 | OX40 | CD4 | CD8 |
| CD123 | OX40 | CD4 | CD3ζ |
| CD123 | OX40 | CD4 | CD3δ |
| CD123 | OX40 | CD4 | CD3γ |
| CD123 | OX40 | CD4 | CD3ε |
| CD123 | OX40 | CD4 | FcγRI-γ |
| CD123 | OX40 | CD4 | FcγRIII-γ |
| CD123 | OX40 | CD4 | FcεRIβ |
| CD123 | OX40 | CD4 | FcεRIγ |
| CD123 | OX40 | CD4 | DAP10 |
| CD123 | OX40 | CD4 | DAP12 |
| CD123 | OX40 | CD4 | CD32 |
| CD123 | OX40 | CD4 | CD79a |
| CD123 | OX40 | CD4 | CD79b |
| CD123 | OX40 | b2c | CD8 |
| CD123 | OX40 | b2c | CD3ζ |
| CD123 | OX40 | b2c | CD3δ |
| CD123 | OX40 | b2c | CD3γ |
| CD123 | OX40 | b2c | CD3ε |
| CD123 | OX40 | b2c | FcγRI-γ |
| CD123 | OX40 | b2c | FcγRIII-γ |
| CD123 | OX40 | b2c | FcεRIβ |
| CD123 | OX40 | b2c | FcεRIγ |
| CD123 | OX40 | b2c | DAP10 |
| CD123 | OX40 | b2c | DAP12 |
| CD123 | OX40 | b2c | CD32 |
| CD123 | OX40 | b2c | CD79a |
| CD123 | OX40 | b2c | CD79b |
| CD123 | OX40 | CD137/41BB | CD8 |
| CD123 | OX40 | CD137/41BB | CD3ζ |
| CD123 | OX40 | CD137/41BB | CD3δ |

TABLE 3-continued

Third Generation CARs

| ScFv | Co-stimulatory Signal | Co-stimulatory Signal | Signal Domain |
|---|---|---|---|
| CD123 | OX40 | CD137/41BB | CD3γ |
| CD123 | OX40 | CD137/41BB | CD3ε |
| CD123 | OX40 | CD137/41BB | FcγRI-γ |
| CD123 | OX40 | CD137/41BB | FcγRIII-γ |
| CD123 | OX40 | CD137/41BB | FcεRIβ |
| CD123 | OX40 | CD137/41BB | FcεRIγ |
| CD123 | OX40 | CD137/41BB | DAP10 |
| CD123 | OX40 | CD137/41BB | DAP12 |
| CD123 | OX40 | CD137/41BB | CD32 |
| CD123 | OX40 | CD137/41BB | CD79a |
| CD123 | OX40 | CD137/41BB | CD79b |
| CD123 | OX40 | ICOS | CD8 |
| CD123 | OX40 | ICOS | CD3ζ |
| CD123 | OX40 | ICOS | CD3δ |
| CD123 | OX40 | ICOS | CD3γ |
| CD123 | OX40 | ICOS | CD3ε |
| CD123 | OX40 | ICOS | FcγRI-γ |
| CD123 | OX40 | ICOS | FcγRIII-γ |
| CD123 | OX40 | ICOS | FcεRIβ |
| CD123 | OX40 | ICOS | FcεRIγ |
| CD123 | OX40 | ICOS | DAP10 |
| CD123 | OX40 | ICOS | DAP12 |
| CD123 | OX40 | ICOS | CD32 |
| CD123 | OX40 | ICOS | CD79a |
| CD123 | OX40 | ICOS | CD79b |
| CD123 | OX40 | CD27 | CD8 |
| CD123 | OX40 | CD27 | CD3ζ |
| CD123 | OX40 | CD27 | CD3δ |
| CD123 | OX40 | CD27 | CD3γ |
| CD123 | OX40 | CD27 | CD3ε |
| CD123 | OX40 | CD27 | FcγRI-γ |
| CD123 | OX40 | CD27 | FcγRIII-γ |
| CD123 | OX40 | CD27 | FcεRIβ |
| CD123 | OX40 | CD27 | FcεRIγ |
| CD123 | OX40 | CD27 | DAP10 |
| CD123 | OX40 | CD27 | DAP12 |
| CD123 | OX40 | CD27 | CD32 |
| CD123 | OX40 | CD27 | CD79a |
| CD123 | OX40 | CD27 | CD79b |
| CD123 | OX40 | CD28δ | CD8 |
| CD123 | OX40 | CD28δ | CD3ζ |
| CD123 | OX40 | CD28δ | CD3δ |
| CD123 | OX40 | CD28δ | CD3γ |
| CD123 | OX40 | CD28δ | CD3ε |
| CD123 | OX40 | CD28δ | FcγRI-γ |
| CD123 | OX40 | CD28δ | FcγRIII-γ |
| CD123 | OX40 | CD28δ | FcεRIβ |
| CD123 | OX40 | CD28δ | FcεRIγ |
| CD123 | OX40 | CD28δ | DAP10 |
| CD123 | OX40 | CD28δ | DAP12 |
| CD123 | OX40 | CD28δ | CD32 |
| CD123 | OX40 | CD28δ | CD79a |
| CD123 | OX40 | CD28δ | CD79b |
| CD123 | OX40 | CD80 | CD8 |
| CD123 | OX40 | CD80 | CD3ζ |
| CD123 | OX40 | CD80 | CD3δ |
| CD123 | OX40 | CD80 | CD3γ |
| CD123 | OX40 | CD80 | CD3ε |
| CD123 | OX40 | CD80 | FcγRI-γ |
| CD123 | OX40 | CD80 | FcγRIII-γ |
| CD123 | OX40 | CD80 | FcεRIβ |
| CD123 | OX40 | CD80 | FcεRIγ |
| CD123 | OX40 | CD80 | DAP10 |
| CD123 | OX40 | CD80 | DAP12 |
| CD123 | OX40 | CD80 | CD32 |
| CD123 | OX40 | CD80 | CD79a |
| CD123 | OX40 | CD80 | CD79b |
| CD123 | OX40 | CD86 | CD8 |
| CD123 | OX40 | CD86 | CD3ζ |
| CD123 | OX40 | CD86 | CD3δ |
| CD123 | OX40 | CD86 | CD3γ |
| CD123 | OX40 | CD86 | CD3ε |
| CD123 | OX40 | CD86 | FcγRI-γ |
| CD123 | OX40 | CD86 | FcγRIII-γ |
| CD123 | OX40 | CD86 | FcεRIβ |
| CD123 | OX40 | CD86 | FcεRIγ |
| CD123 | OX40 | CD86 | DAP10 |
| CD123 | OX40 | CD86 | DAP12 |
| CD123 | OX40 | CD86 | CD32 |
| CD123 | OX40 | CD86 | CD79a |
| CD123 | OX40 | CD86 | CD79b |
| CD123 | OX40 | OX40 | CD8 |
| CD123 | OX40 | OX40 | CD3ζ |
| CD123 | OX40 | OX40 | CD3δ |
| CD123 | OX40 | OX40 | CD3γ |
| CD123 | OX40 | OX40 | CD3ε |
| CD123 | OX40 | OX40 | FcγRI-γ |
| CD123 | OX40 | OX40 | FcγRIII-γ |
| CD123 | OX40 | OX40 | FcεRIβ |
| CD123 | OX40 | OX40 | FcεRIγ |
| CD123 | OX40 | OX40 | DAP10 |
| CD123 | OX40 | OX40 | DAP12 |
| CD123 | OX40 | OX40 | CD32 |
| CD123 | OX40 | OX40 | CD79a |
| CD123 | OX40 | OX40 | CD79b |
| CD123 | OX40 | DAP10 | CD8 |
| CD123 | OX40 | DAP10 | CD3ζ |
| CD123 | OX40 | DAP10 | CD3δ |
| CD123 | OX40 | DAP10 | CD3γ |
| CD123 | OX40 | DAP10 | CD3ε |
| CD123 | OX40 | DAP10 | FcγRI-γ |
| CD123 | OX40 | DAP10 | FcγRIII-γ |
| CD123 | OX40 | DAP10 | FcεRIβ |
| CD123 | OX40 | DAP10 | FcεRIγ |
| CD123 | OX40 | DAP10 | DAP10 |
| CD123 | OX40 | DAP10 | DAP12 |
| CD123 | OX40 | DAP10 | CD32 |
| CD123 | OX40 | DAP10 | CD79a |
| CD123 | OX40 | DAP10 | CD79b |
| CD123 | OX40 | DAP12 | CD8 |
| CD123 | OX40 | DAP12 | CD3ζ |
| CD123 | OX40 | DAP12 | CD3δ |
| CD123 | OX40 | DAP12 | CD3γ |
| CD123 | OX40 | DAP12 | CD3ε |
| CD123 | OX40 | DAP12 | FcγRI-γ |
| CD123 | OX40 | DAP12 | FcγRIII-γ |
| CD123 | OX40 | DAP12 | FcεRIβ |
| CD123 | OX40 | DAP12 | FcεRIγ |
| CD123 | OX40 | DAP12 | DAP10 |
| CD123 | OX40 | DAP12 | DAP12 |
| CD123 | OX40 | DAP12 | CD32 |
| CD123 | OX40 | DAP12 | CD79a |
| CD123 | OX40 | DAP12 | CD79b |
| CD123 | OX40 | MyD88 | CD8 |
| CD123 | OX40 | MyD88 | CD3ζ |
| CD123 | OX40 | MyD88 | CD3δ |
| CD123 | OX40 | MyD88 | CD3γ |
| CD123 | OX40 | MyD88 | CD3ε |
| CD123 | OX40 | MyD88 | FcγRI-γ |
| CD123 | OX40 | MyD88 | FcγRIII-γ |
| CD123 | OX40 | MyD88 | FcεRIβ |
| CD123 | OX40 | MyD88 | FcεRIγ |
| CD123 | OX40 | MyD88 | DAP10 |
| CD123 | OX40 | MyD88 | DAP12 |
| CD123 | OX40 | MyD88 | CD32 |
| CD123 | OX40 | MyD88 | CD79a |
| CD123 | OX40 | MyD88 | CD79b |
| CD123 | OX40 | CD7 | CD8 |
| CD123 | OX40 | CD7 | CD3ζ |
| CD123 | OX40 | CD7 | CD3δ |
| CD123 | OX40 | CD7 | CD3γ |
| CD123 | OX40 | CD7 | CD3ε |
| CD123 | OX40 | CD7 | FcγRI-γ |
| CD123 | OX40 | CD7 | FcγRIII-γ |
| CD123 | OX40 | CD7 | FcεRIβ |
| CD123 | OX40 | CD7 | FcεRIγ |
| CD123 | OX40 | CD7 | DAP10 |
| CD123 | OX40 | CD7 | DAP12 |
| CD123 | OX40 | CD7 | CD32 |
| CD123 | OX40 | CD7 | CD79a |

TABLE 3-continued

Third Generation CARs

| ScFv | Co-stimulatory Signal | Co-stimulatory Signal | Signal Domain |
|---|---|---|---|
| CD123 | OX40 | CD7 | CD79b |
| CD123 | OX40 | BTNL3 | CD8 |
| CD123 | OX40 | BTNL3 | CD3ζ |
| CD123 | OX40 | BTNL3 | CD3δ |
| CD123 | OX40 | BTNL3 | CD3γ |
| CD123 | OX40 | BTNL3 | CD3ε |
| CD123 | OX40 | BTNL3 | FcγRI-γ |
| CD123 | OX40 | BTNL3 | FcγRIII-γ |
| CD123 | OX40 | BTNL3 | FcεRIβ |
| CD123 | OX40 | BTNL3 | FcεRIγ |
| CD123 | OX40 | BTNL3 | DAP10 |
| CD123 | OX40 | BTNL3 | DAP12 |
| CD123 | OX40 | BTNL3 | CD32 |
| CD123 | OX40 | BTNL3 | CD79a |
| CD123 | OX40 | BTNL3 | CD79b |
| CD123 | OX40 | NKG2D | CD8 |
| CD123 | OX40 | NKG2D | CD3ζ |
| CD123 | OX40 | NKG2D | CD3δ |
| CD123 | OX40 | NKG2D | CD3γ |
| CD123 | OX40 | NKG2D | CD3ε |
| CD123 | OX40 | NKG2D | FcγRI-γ |
| CD123 | OX40 | NKG2D | FcγRIII-γ |
| CD123 | OX40 | NKG2D | FcεRIβ |
| CD123 | OX40 | NKG2D | FcεRIγ |
| CD123 | OX40 | NKG2D | DAP10 |
| CD123 | OX40 | NKG2D | DAP12 |
| CD123 | OX40 | NKG2D | CD32 |
| CD123 | OX40 | NKG2D | CD79a |
| CD123 | OX40 | NKG2D | CD79b |
| CD123 | DAP10 | CD28 | CD8 |
| CD123 | DAP10 | CD28 | CD3ζ |
| CD123 | DAP10 | CD28 | CD3δ |
| CD123 | DAP10 | CD28 | CD3γ |
| CD123 | DAP10 | CD28 | CD3ε |
| CD123 | DAP10 | CD28 | FcγRI-γ |
| CD123 | DAP10 | CD28 | FcγRIII-γ |
| CD123 | DAP10 | CD28 | FcεRIβ |
| CD123 | DAP10 | CD28 | FcεRIγ |
| CD123 | DAP10 | CD28 | DAP10 |
| CD123 | DAP10 | CD28 | DAP12 |
| CD123 | DAP10 | CD28 | CD32 |
| CD123 | DAP10 | CD28 | CD79a |
| CD123 | DAP10 | CD28 | CD79b |
| CD123 | DAP10 | CD8 | CD8 |
| CD123 | DAP10 | CD8 | CD3ζ |
| CD123 | DAP10 | CD8 | CD3δ |
| CD123 | DAP10 | CD8 | CD3γ |
| CD123 | DAP10 | CD8 | CD3ε |
| CD123 | DAP10 | CD8 | FcγRI-γ |
| CD123 | DAP10 | CD8 | FcγRIII-γ |
| CD123 | DAP10 | CD8 | FcεRIβ |
| CD123 | DAP10 | CD8 | FcεRIγ |
| CD123 | DAP10 | CD8 | DAP10 |
| CD123 | DAP10 | CD8 | DAP12 |
| CD123 | DAP10 | CD8 | CD32 |
| CD123 | DAP10 | CD8 | CD79a |
| CD123 | DAP10 | CD8 | CD79b |
| CD123 | DAP10 | CD4 | CD8 |
| CD123 | DAP10 | CD4 | CD3ζ |
| CD123 | DAP10 | CD4 | CD3δ |
| CD123 | DAP10 | CD4 | CD3γ |
| CD123 | DAP10 | CD4 | CD3ε |
| CD123 | DAP10 | CD4 | FcγRI-γ |
| CD123 | DAP10 | CD4 | FcγRIII-γ |
| CD123 | DAP10 | CD4 | FcεRIβ |
| CD123 | DAP10 | CD4 | FcεRIγ |
| CD123 | DAP10 | CD4 | DAP10 |
| CD123 | DAP10 | CD4 | DAP12 |
| CD123 | DAP10 | CD4 | CD32 |
| CD123 | DAP10 | CD4 | CD79a |
| CD123 | DAP10 | CD4 | CD79b |
| CD123 | DAP10 | b2c | CD8 |
| CD123 | DAP10 | b2c | CD3ζ |
| CD123 | DAP10 | b2c | CD3δ |
| CD123 | DAP10 | b2c | CD3γ |
| CD123 | DAP10 | b2c | CD3ε |
| CD123 | DAP10 | b2c | FcγRI-γ |
| CD123 | DAP10 | b2c | FcγRIII-γ |
| CD123 | DAP10 | b2c | FcεRIβ |
| CD123 | DAP10 | b2c | FcεRIγ |
| CD123 | DAP10 | b2c | DAP10 |
| CD123 | DAP10 | b2c | DAP12 |
| CD123 | DAP10 | b2c | CD32 |
| CD123 | DAP10 | b2c | CD79a |
| CD123 | DAP10 | b2c | CD79b |
| CD123 | DAP10 | CD137/41BB | CD8 |
| CD123 | DAP10 | CD137/41BB | CD3ζ |
| CD123 | DAP10 | CD137/41BB | CD3δ |
| CD123 | DAP10 | CD137/41BB | CD3γ |
| CD123 | DAP10 | CD137/41BB | CD3ε |
| CD123 | DAP10 | CD137/41BB | FcγRI-γ |
| CD123 | DAP10 | CD137/41BB | FcγRIII-γ |
| CD123 | DAP10 | CD137/41BB | FcεRIβ |
| CD123 | DAP10 | CD137/41BB | FcεRIγ |
| CD123 | DAP10 | CD137/41BB | DAP10 |
| CD123 | DAP10 | CD137/41BB | DAP12 |
| CD123 | DAP10 | CD137/41BB | CD32 |
| CD123 | DAP10 | CD137/41BB | CD79a |
| CD123 | DAP10 | CD137/41BB | CD79b |
| CD123 | DAP10 | ICOS | CD8 |
| CD123 | DAP10 | ICOS | CD3ζ |
| CD123 | DAP10 | ICOS | CD3δ |
| CD123 | DAP10 | ICOS | CD3γ |
| CD123 | DAP10 | ICOS | CD3ε |
| CD123 | DAP10 | ICOS | FcγRI-γ |
| CD123 | DAP10 | ICOS | FcγRIII-γ |
| CD123 | DAP10 | ICOS | FcεRIβ |
| CD123 | DAP10 | ICOS | FcεRIγ |
| CD123 | DAP10 | ICOS | DAP10 |
| CD123 | DAP10 | ICOS | DAP12 |
| CD123 | DAP10 | ICOS | CD32 |
| CD123 | DAP10 | ICOS | CD79a |
| CD123 | DAP10 | ICOS | CD79b |
| CD123 | DAP10 | CD27 | CD8 |
| CD123 | DAP10 | CD27 | CD3ζ |
| CD123 | DAP10 | CD27 | CD3δ |
| CD123 | DAP10 | CD27 | CD3γ |
| CD123 | DAP10 | CD27 | CD3ε |
| CD123 | DAP10 | CD27 | FcγRI-γ |
| CD123 | DAP10 | CD27 | FcγRIII-γ |
| CD123 | DAP10 | CD27 | FcεRIβ |
| CD123 | DAP10 | CD27 | FcεRIγ |
| CD123 | DAP10 | CD27 | DAP10 |
| CD123 | DAP10 | CD27 | DAP12 |
| CD123 | DAP10 | CD27 | CD32 |
| CD123 | DAP10 | CD27 | CD79a |
| CD123 | DAP10 | CD27 | CD79b |
| CD123 | DAP10 | CD28δ | CD8 |
| CD123 | DAP10 | CD28δ | CD3ζ |
| CD123 | DAP10 | CD28δ | CD3δ |
| CD123 | DAP10 | CD28δ | CD3γ |
| CD123 | DAP10 | CD28δ | CD3ε |
| CD123 | DAP10 | CD28δ | FcγRI-γ |
| CD123 | DAP10 | CD28δ | FcγRIII-γ |
| CD123 | DAP10 | CD28δ | FcεRIβ |
| CD123 | DAP10 | CD28δ | FcεRIγ |
| CD123 | DAP10 | CD28δ | DAP10 |
| CD123 | DAP10 | CD28δ | DAP12 |
| CD123 | DAP10 | CD28δ | CD32 |
| CD123 | DAP10 | CD28δ | CD79a |
| CD123 | DAP10 | CD28δ | CD79b |
| CD123 | DAP10 | CD80 | CD8 |
| CD123 | DAP10 | CD80 | CD3ζ |
| CD123 | DAP10 | CD80 | CD3δ |
| CD123 | DAP10 | CD80 | CD3γ |
| CD123 | DAP10 | CD80 | CD3ε |
| CD123 | DAP10 | CD80 | FcγRI-γ |
| CD123 | DAP10 | CD80 | FcγRIII-γ |
| CD123 | DAP10 | CD80 | FcεRIβ |
| CD123 | DAP10 | CD80 | FcεRIγ |

TABLE 3-continued

Third Generation CARs

| ScFv | Co-stimulatory Signal | Co-stimulatory Signal | Signal Domain |
|---|---|---|---|
| CD123 | DAP10 | CD80 | DAP10 |
| CD123 | DAP10 | CD80 | DAP12 |
| CD123 | DAP10 | CD80 | CD32 |
| CD123 | DAP10 | CD80 | CD79a |
| CD123 | DAP10 | CD80 | CD79b |
| CD123 | DAP10 | CD86 | CD8 |
| CD123 | DAP10 | CD86 | CD3ζ |
| CD123 | DAP10 | CD86 | CD3δ |
| CD123 | DAP10 | CD86 | CD3γ |
| CD123 | DAP10 | CD86 | CD3ε |
| CD123 | DAP10 | CD86 | FcγRI-γ |
| CD123 | DAP10 | CD86 | FcγRIII-γ |
| CD123 | DAP10 | CD86 | FcεRIβ |
| CD123 | DAP10 | CD86 | FcεRIγ |
| CD123 | DAP10 | CD86 | DAP10 |
| CD123 | DAP10 | CD86 | DAP12 |
| CD123 | DAP10 | CD86 | CD32 |
| CD123 | DAP10 | CD86 | CD79a |
| CD123 | DAP10 | CD86 | CD79b |
| CD123 | DAP10 | OX40 | CD8 |
| CD123 | DAP10 | OX40 | CD3ζ |
| CD123 | DAP10 | OX40 | CD3δ |
| CD123 | DAP10 | OX40 | CD3γ |
| CD123 | DAP10 | OX40 | CD3ε |
| CD123 | DAP10 | OX40 | FcγRI-γ |
| CD123 | DAP10 | OX40 | FcγRIII-γ |
| CD123 | DAP10 | OX40 | FcεRIβ |
| CD123 | DAP10 | OX40 | FcεRIγ |
| CD123 | DAP10 | OX40 | DAP10 |
| CD123 | DAP10 | OX40 | DAP12 |
| CD123 | DAP10 | OX40 | CD32 |
| CD123 | DAP10 | OX40 | CD79a |
| CD123 | DAP10 | OX40 | CD79b |
| CD123 | DAP10 | DAP10 | CD8 |
| CD123 | DAP10 | DAP10 | CD3ζ |
| CD123 | DAP10 | DAP10 | CD3δ |
| CD123 | DAP10 | DAP10 | CD3γ |
| CD123 | DAP10 | DAP10 | CD3ε |
| CD123 | DAP10 | DAP10 | FcγRI-γ |
| CD123 | DAP10 | DAP10 | FcγRIII-γ |
| CD123 | DAP10 | DAP10 | FcεRIβ |
| CD123 | DAP10 | DAP10 | FcεRIγ |
| CD123 | DAP10 | DAP10 | DAP10 |
| CD123 | DAP10 | DAP10 | DAP12 |
| CD123 | DAP10 | DAP10 | CD32 |
| CD123 | DAP10 | DAP10 | CD79a |
| CD123 | DAP10 | DAP10 | CD79b |
| CD123 | DAP10 | DAP12 | CD8 |
| CD123 | DAP10 | DAP12 | CD3ζ |
| CD123 | DAP10 | DAP12 | CD3δ |
| CD123 | DAP10 | DAP12 | CD3γ |
| CD123 | DAP10 | DAP12 | CD3ε |
| CD123 | DAP10 | DAP12 | FcγRI-γ |
| CD123 | DAP10 | DAP12 | FcγRIII-γ |
| CD123 | DAP10 | DAP12 | FcεRIβ |
| CD123 | DAP10 | DAP12 | FcεRIγ |
| CD123 | DAP10 | DAP12 | DAP10 |
| CD123 | DAP10 | DAP12 | DAP12 |
| CD123 | DAP10 | DAP12 | CD32 |
| CD123 | DAP10 | DAP12 | CD79a |
| CD123 | DAP10 | DAP12 | CD79b |
| CD123 | DAP10 | MyD88 | CD8 |
| CD123 | DAP10 | MyD88 | CD3ζ |
| CD123 | DAP10 | MyD88 | CD3δ |
| CD123 | DAP10 | MyD88 | CD3γ |
| CD123 | DAP10 | MyD88 | CD3ε |
| CD123 | DAP10 | MyD88 | FcγRI-γ |
| CD123 | DAP10 | MyD88 | FcγRIII-γ |
| CD123 | DAP10 | MyD88 | FcεRIβ |
| CD123 | DAP10 | MyD88 | FcεRIγ |
| CD123 | DAP10 | MyD88 | DAP10 |
| CD123 | DAP10 | MyD88 | DAP12 |
| CD123 | DAP10 | MyD88 | CD32 |
| CD123 | DAP10 | MyD88 | CD79a |
| CD123 | DAP10 | MyD88 | CD79b |
| CD123 | DAP10 | CD7 | CD8 |
| CD123 | DAP10 | CD7 | CD3ζ |
| CD123 | DAP10 | CD7 | CD3δ |
| CD123 | DAP10 | CD7 | CD3γ |
| CD123 | DAP10 | CD7 | CD3ε |
| CD123 | DAP10 | CD7 | FcγRI-γ |
| CD123 | DAP10 | CD7 | FcγRIII-γ |
| CD123 | DAP10 | CD7 | FcεRIβ |
| CD123 | DAP10 | CD7 | FcεRIγ |
| CD123 | DAP10 | CD7 | DAP10 |
| CD123 | DAP10 | CD7 | DAP12 |
| CD123 | DAP10 | CD7 | CD32 |
| CD123 | DAP10 | CD7 | CD79a |
| CD123 | DAP10 | CD7 | CD79b |
| CD123 | DAP10 | BTNL3 | CD8 |
| CD123 | DAP10 | BTNL3 | CD3ζ |
| CD123 | DAP10 | BTNL3 | CD3δ |
| CD123 | DAP10 | BTNL3 | CD3γ |
| CD123 | DAP10 | BTNL3 | CD3ε |
| CD123 | DAP10 | BTNL3 | FcγRI-γ |
| CD123 | DAP10 | BTNL3 | FcγRIII-γ |
| CD123 | DAP10 | BTNL3 | FcεRIβ |
| CD123 | DAP10 | BTNL3 | FcεRIγ |
| CD123 | DAP10 | BTNL3 | DAP10 |
| CD123 | DAP10 | BTNL3 | DAP12 |
| CD123 | DAP10 | BTNL3 | CD32 |
| CD123 | DAP10 | BTNL3 | CD79a |
| CD123 | DAP10 | BTNL3 | CD79b |
| CD123 | DAP10 | NKG2D | CD8 |
| CD123 | DAP10 | NKG2D | CD3ζ |
| CD123 | DAP10 | NKG2D | CD3δ |
| CD123 | DAP10 | NKG2D | CD3γ |
| CD123 | DAP10 | NKG2D | CD3ε |
| CD123 | DAP10 | NKG2D | FcγRI-γ |
| CD123 | DAP10 | NKG2D | FcγRIII-γ |
| CD123 | DAP10 | NKG2D | FcεRIβ |
| CD123 | DAP10 | NKG2D | FcεRIγ |
| CD123 | DAP10 | NKG2D | DAP10 |
| CD123 | DAP10 | NKG2D | DAP12 |
| CD123 | DAP10 | NKG2D | CD32 |
| CD123 | DAP10 | NKG2D | CD79a |
| CD123 | DAP10 | NKG2D | CD79b |
| CD123 | DAP12 | CD28 | CD8 |
| CD123 | DAP12 | CD28 | CD3ζ |
| CD123 | DAP12 | CD28 | CD3δ |
| CD123 | DAP12 | CD28 | CD3γ |
| CD123 | DAP12 | CD28 | CD3ε |
| CD123 | DAP12 | CD28 | FcγRI-γ |
| CD123 | DAP12 | CD28 | FcγRIII-γ |
| CD123 | DAP12 | CD28 | FcεRIβ |
| CD123 | DAP12 | CD28 | FcεRIγ |
| CD123 | DAP12 | CD28 | DAP10 |
| CD123 | DAP12 | CD28 | DAP12 |
| CD123 | DAP12 | CD28 | CD32 |
| CD123 | DAP12 | CD28 | CD79a |
| CD123 | DAP12 | CD28 | CD79b |
| CD123 | DAP12 | CD8 | CD8 |
| CD123 | DAP12 | CD8 | CD3ζ |
| CD123 | DAP12 | CD8 | CD3δ |
| CD123 | DAP12 | CD8 | CD3γ |
| CD123 | DAP12 | CD8 | CD3ε |
| CD123 | DAP12 | CD8 | FcγRI-γ |
| CD123 | DAP12 | CD8 | FcγRIII-γ |
| CD123 | DAP12 | CD8 | FcεRIβ |
| CD123 | DAP12 | CD8 | FcεRIγ |
| CD123 | DAP12 | CD8 | DAP10 |
| CD123 | DAP12 | CD8 | DAP12 |
| CD123 | DAP12 | CD8 | CD32 |
| CD123 | DAP12 | CD8 | CD79a |
| CD123 | DAP12 | CD8 | CD79b |
| CD123 | DAP12 | CD4 | CD8 |
| CD123 | DAP12 | CD4 | CD3ζ |
| CD123 | DAP12 | CD4 | CD3δ |
| CD123 | DAP12 | CD4 | CD3γ |
| CD123 | DAP12 | CD4 | CD3ε |

TABLE 3-continued

Third Generation CARs

| ScFv | Co-stimulatory Signal | Co-stimulatory Signal | Signal Domain |
|---|---|---|---|
| CD123 | DAP12 | CD4 | FcγRI-γ |
| CD123 | DAP12 | CD4 | FcγRIII-γ |
| CD123 | DAP12 | CD4 | FcεRIβ |
| CD123 | DAP12 | CD4 | FcεRIγ |
| CD123 | DAP12 | CD4 | DAP10 |
| CD123 | DAP12 | CD4 | DAP12 |
| CD123 | DAP12 | CD4 | CD32 |
| CD123 | DAP12 | CD4 | CD79a |
| CD123 | DAP12 | CD4 | CD79b |
| CD123 | DAP12 | b2c | CD8 |
| CD123 | DAP12 | b2c | CD3ζ |
| CD123 | DAP12 | b2c | CD3δ |
| CD123 | DAP12 | b2c | CD3γ |
| CD123 | DAP12 | b2c | CD3ε |
| CD123 | DAP12 | b2c | FcγRI-γ |
| CD123 | DAP12 | b2c | FcγRIII-γ |
| CD123 | DAP12 | b2c | FcεRIβ |
| CD123 | DAP12 | b2c | FcεRIγ |
| CD123 | DAP12 | b2c | DAP10 |
| CD123 | DAP12 | b2c | DAP12 |
| CD123 | DAP12 | b2c | CD32 |
| CD123 | DAP12 | b2c | CD79a |
| CD123 | DAP12 | b2c | CD79b |
| CD123 | DAP12 | CD137/41BB | CD8 |
| CD123 | DAP12 | CD137/41BB | CD3ζ |
| CD123 | DAP12 | CD137/41BB | CD3δ |
| CD123 | DAP12 | CD137/41BB | CD3γ |
| CD123 | DAP12 | CD137/41BB | CD3ε |
| CD123 | DAP12 | CD137/41BB | FcγRI-γ |
| CD123 | DAP12 | CD137/41BB | FcγRIII-γ |
| CD123 | DAP12 | CD137/41BB | FcεRIβ |
| CD123 | DAP12 | CD137/41BB | FcεRIγ |
| CD123 | DAP12 | CD137/41BB | DAP10 |
| CD123 | DAP12 | CD137/41BB | DAP12 |
| CD123 | DAP12 | CD137/41BB | CD32 |
| CD123 | DAP12 | CD137/41BB | CD79a |
| CD123 | DAP12 | CD137/41BB | CD79b |
| CD123 | DAP12 | ICOS | CD8 |
| CD123 | DAP12 | ICOS | CD3ζ |
| CD123 | DAP12 | ICOS | CD3δ |
| CD123 | DAP12 | ICOS | CD3γ |
| CD123 | DAP12 | ICOS | CD3ε |
| CD123 | DAP12 | ICOS | FcγRI-γ |
| CD123 | DAP12 | ICOS | FcγRIII-γ |
| CD123 | DAP12 | ICOS | FcεRIβ |
| CD123 | DAP12 | ICOS | FcεRIγ |
| CD123 | DAP12 | ICOS | DAP10 |
| CD123 | DAP12 | ICOS | DAP12 |
| CD123 | DAP12 | ICOS | CD32 |
| CD123 | DAP12 | ICOS | CD79a |
| CD123 | DAP12 | ICOS | CD79b |
| CD123 | DAP12 | CD27 | CD8 |
| CD123 | DAP12 | CD27 | CD3ζ |
| CD123 | DAP12 | CD27 | CD3δ |
| CD123 | DAP12 | CD27 | CD3γ |
| CD123 | DAP12 | CD27 | CD3ε |
| CD123 | DAP12 | CD27 | FcγRI-γ |
| CD123 | DAP12 | CD27 | FcγRIII-γ |
| CD123 | DAP12 | CD27 | FcεRIβ |
| CD123 | DAP12 | CD27 | FcεRIγ |
| CD123 | DAP12 | CD27 | DAP10 |
| CD123 | DAP12 | CD27 | DAP12 |
| CD123 | DAP12 | CD27 | CD32 |
| CD123 | DAP12 | CD27 | CD79a |
| CD123 | DAP12 | CD27 | CD79b |
| CD123 | DAP12 | CD28δ | CD8 |
| CD123 | DAP12 | CD28δ | CD3ζ |
| CD123 | DAP12 | CD28δ | CD3δ |
| CD123 | DAP12 | CD28δ | CD3γ |
| CD123 | DAP12 | CD28δ | CD3ε |
| CD123 | DAP12 | CD28δ | FcγRI-γ |
| CD123 | DAP12 | CD28δ | FcγRIII-γ |
| CD123 | DAP12 | CD28δ | FcεRIβ |
| CD123 | DAP12 | CD28δ | FcεRIγ |
| CD123 | DAP12 | CD28δ | DAP10 |
| CD123 | DAP12 | CD28δ | DAP12 |
| CD123 | DAP12 | CD28δ | CD32 |
| CD123 | DAP12 | CD28δ | CD79a |
| CD123 | DAP12 | CD28δ | CD79b |
| CD123 | DAP12 | CD80 | CD8 |
| CD123 | DAP12 | CD80 | CD3ζ |
| CD123 | DAP12 | CD80 | CD3δ |
| CD123 | DAP12 | CD80 | CD3γ |
| CD123 | DAP12 | CD80 | CD3ε |
| CD123 | DAP12 | CD80 | FcγRI-γ |
| CD123 | DAP12 | CD80 | FcγRIII-γ |
| CD123 | DAP12 | CD80 | FcεRIβ |
| CD123 | DAP12 | CD80 | FcεRIγ |
| CD123 | DAP12 | CD80 | DAP10 |
| CD123 | DAP12 | CD80 | DAP12 |
| CD123 | DAP12 | CD80 | CD32 |
| CD123 | DAP12 | CD80 | CD79a |
| CD123 | DAP12 | CD80 | CD79b |
| CD123 | DAP12 | CD86 | CD8 |
| CD123 | DAP12 | CD86 | CD3ζ |
| CD123 | DAP12 | CD86 | CD3δ |
| CD123 | DAP12 | CD86 | CD3γ |
| CD123 | DAP12 | CD86 | CD3ε |
| CD123 | DAP12 | CD86 | FcγRI-γ |
| CD123 | DAP12 | CD86 | FcγRIII-γ |
| CD123 | DAP12 | CD86 | FcεRIβ |
| CD123 | DAP12 | CD86 | FcεRIγ |
| CD123 | DAP12 | CD86 | DAP10 |
| CD123 | DAP12 | CD86 | DAP12 |
| CD123 | DAP12 | CD86 | CD32 |
| CD123 | DAP12 | CD86 | CD79a |
| CD123 | DAP12 | CD86 | CD79b |
| CD123 | DAP12 | OX40 | CD8 |
| CD123 | DAP12 | OX40 | CD3ζ |
| CD123 | DAP12 | OX40 | CD3δ |
| CD123 | DAP12 | OX40 | CD3γ |
| CD123 | DAP12 | OX40 | CD3ε |
| CD123 | DAP12 | OX40 | FcγRI-γ |
| CD123 | DAP12 | OX40 | FcγRIII-γ |
| CD123 | DAP12 | OX40 | FcεRIβ |
| CD123 | DAP12 | OX40 | FcεRIγ |
| CD123 | DAP12 | OX40 | DAP10 |
| CD123 | DAP12 | OX40 | DAP12 |
| CD123 | DAP12 | OX40 | CD32 |
| CD123 | DAP12 | OX40 | CD79a |
| CD123 | DAP12 | OX40 | CD79b |
| CD123 | DAP12 | DAP10 | CD8 |
| CD123 | DAP12 | DAP10 | CD3ζ |
| CD123 | DAP12 | DAP10 | CD3δ |
| CD123 | DAP12 | DAP10 | CD3γ |
| CD123 | DAP12 | DAP10 | CD3ε |
| CD123 | DAP12 | DAP10 | FcγRI-γ |
| CD123 | DAP12 | DAP10 | FcγRIII-γ |
| CD123 | DAP12 | DAP10 | FcεRIβ |
| CD123 | DAP12 | DAP10 | FcεRIγ |
| CD123 | DAP12 | DAP10 | DAP10 |
| CD123 | DAP12 | DAP10 | DAP12 |
| CD123 | DAP12 | DAP10 | CD32 |
| CD123 | DAP12 | DAP10 | CD79a |
| CD123 | DAP12 | DAP10 | CD79b |
| CD123 | DAP12 | DAP12 | CD8 |
| CD123 | DAP12 | DAP12 | CD3ζ |
| CD123 | DAP12 | DAP12 | CD3δ |
| CD123 | DAP12 | DAP12 | CD3γ |
| CD123 | DAP12 | DAP12 | CD3ε |
| CD123 | DAP12 | DAP12 | FcγRI-γ |
| CD123 | DAP12 | DAP12 | FcγRIII-γ |
| CD123 | DAP12 | DAP12 | FcεRIβ |
| CD123 | DAP12 | DAP12 | FcεRIγ |
| CD123 | DAP12 | DAP12 | DAP10 |
| CD123 | DAP12 | DAP12 | DAP12 |
| CD123 | DAP12 | DAP12 | CD32 |
| CD123 | DAP12 | DAP12 | CD79a |
| CD123 | DAP12 | DAP12 | CD79b |
| CD123 | DAP12 | MyD88 | CD8 |

TABLE 3-continued

Third Generation CARs

| ScFv | Co-stimulatory Signal | Co-stimulatory Signal | Signal Domain |
|---|---|---|---|
| CD123 | DAP12 | MyD88 | CD3ζ |
| CD123 | DAP12 | MyD88 | CD3δ |
| CD123 | DAP12 | MyD88 | CD3γ |
| CD123 | DAP12 | MyD88 | CD3ε |
| CD123 | DAP12 | MyD88 | FcγRI-γ |
| CD123 | DAP12 | MyD88 | FcγRIII-γ |
| CD123 | DAP12 | MyD88 | FcεRIβ |
| CD123 | DAP12 | MyD88 | FcεRIγ |
| CD123 | DAP12 | MyD88 | DAP10 |
| CD123 | DAP12 | MyD88 | DAP12 |
| CD123 | DAP12 | MyD88 | CD32 |
| CD123 | DAP12 | MyD88 | CD79a |
| CD123 | DAP12 | MyD88 | CD79b |
| CD123 | DAP12 | CD7 | CD8 |
| CD123 | DAP12 | CD7 | CD3ζ |
| CD123 | DAP12 | CD7 | CD3δ |
| CD123 | DAP12 | CD7 | CD3γ |
| CD123 | DAP12 | CD7 | CD3ε |
| CD123 | DAP12 | CD7 | FcγRI-γ |
| CD123 | DAP12 | CD7 | FcγRIII-γ |
| CD123 | DAP12 | CD7 | FcεRIβ |
| CD123 | DAP12 | CD7 | FcεRIγ |
| CD123 | DAP12 | CD7 | DAP10 |
| CD123 | DAP12 | CD7 | DAP12 |
| CD123 | DAP12 | CD7 | CD32 |
| CD123 | DAP12 | CD7 | CD79a |
| CD123 | DAP12 | CD7 | CD79b |
| CD123 | DAP12 | BTNL3 | CD8 |
| CD123 | DAP12 | BTNL3 | CD3ζ |
| CD123 | DAP12 | BTNL3 | CD3δ |
| CD123 | DAP12 | BTNL3 | CD3γ |
| CD123 | DAP12 | BTNL3 | CD3ε |
| CD123 | DAP12 | BTNL3 | FcγRI-γ |
| CD123 | DAP12 | BTNL3 | FcγRIII-γ |
| CD123 | DAP12 | BTNL3 | FcεRIβ |
| CD123 | DAP12 | BTNL3 | FcεRIγ |
| CD123 | DAP12 | BTNL3 | DAP10 |
| CD123 | DAP12 | BTNL3 | DAP12 |
| CD123 | DAP12 | BTNL3 | CD32 |
| CD123 | DAP12 | BTNL3 | CD79a |
| CD123 | DAP12 | BTNL3 | CD79b |
| CD123 | DAP12 | NKG2D | CD8 |
| CD123 | DAP12 | NKG2D | CD3ζ |
| CD123 | DAP12 | NKG2D | CD3δ |
| CD123 | DAP12 | NKG2D | CD3γ |
| CD123 | DAP12 | NKG2D | CD3ε |
| CD123 | DAP12 | NKG2D | FcγRI-γ |
| CD123 | DAP12 | NKG2D | FcγRIII-γ |
| CD123 | DAP12 | NKG2D | FcεRIβ |
| CD123 | DAP12 | NKG2D | FcεRIγ |
| CD123 | DAP12 | NKG2D | DAP10 |
| CD123 | DAP12 | NKG2D | DAP12 |
| CD123 | DAP12 | NKG2D | CD32 |
| CD123 | DAP12 | NKG2D | CD79a |
| CD123 | DAP12 | NKG2D | CD79b |
| CD123 | MyD88 | CD28 | CD8 |
| CD123 | MyD88 | CD28 | CD3ζ |
| CD123 | MyD88 | CD28 | CD3δ |
| CD123 | MyD88 | CD28 | CD3γ |
| CD123 | MyD88 | CD28 | CD3ε |
| CD123 | MyD88 | CD28 | FcγRI-γ |
| CD123 | MyD88 | CD28 | FcγRIII-γ |
| CD123 | MyD88 | CD28 | FcεRIβ |
| CD123 | MyD88 | CD28 | FcεRIγ |
| CD123 | MyD88 | CD28 | DAP10 |
| CD123 | MyD88 | CD28 | DAP12 |
| CD123 | MyD88 | CD28 | CD32 |
| CD123 | MyD88 | CD28 | CD79a |
| CD123 | MyD88 | CD28 | CD79b |
| CD123 | MyD88 | CD8 | CD8 |
| CD123 | MyD88 | CD8 | CD3ζ |
| CD123 | MyD88 | CD8 | CD3δ |
| CD123 | MyD88 | CD8 | CD3γ |
| CD123 | MyD88 | CD8 | CD3ε |
| CD123 | MyD88 | CD8 | FcγRI-γ |
| CD123 | MyD88 | CD8 | FcγRIII-γ |
| CD123 | MyD88 | CD8 | FcεRIβ |
| CD123 | MyD88 | CD8 | FcεRIγ |
| CD123 | MyD88 | CD8 | DAP10 |
| CD123 | MyD88 | CD8 | DAP12 |
| CD123 | MyD88 | CD8 | CD32 |
| CD123 | MyD88 | CD8 | CD79a |
| CD123 | MyD88 | CD8 | CD79b |
| CD123 | MyD88 | CD4 | CD8 |
| CD123 | MyD88 | CD4 | CD3ζ |
| CD123 | MyD88 | CD4 | CD3δ |
| CD123 | MyD88 | CD4 | CD3γ |
| CD123 | MyD88 | CD4 | CD3ε |
| CD123 | MyD88 | CD4 | FcγRI-γ |
| CD123 | MyD88 | CD4 | FcγRIII-γ |
| CD123 | MyD88 | CD4 | FcεRIβ |
| CD123 | MyD88 | CD4 | FcεRIγ |
| CD123 | MyD88 | CD4 | DAP10 |
| CD123 | MyD88 | CD4 | DAP12 |
| CD123 | MyD88 | CD4 | CD32 |
| CD123 | MyD88 | CD4 | CD79a |
| CD123 | MyD88 | CD4 | CD79b |
| CD123 | MyD88 | b2c | CD8 |
| CD123 | MyD88 | b2c | CD3ζ |
| CD123 | MyD88 | b2c | CD3δ |
| CD123 | MyD88 | b2c | CD3γ |
| CD123 | MyD88 | b2c | CD3ε |
| CD123 | MyD88 | b2c | FcγRI-γ |
| CD123 | MyD88 | b2c | FcγRIII-γ |
| CD123 | MyD88 | b2c | FcεRIβ |
| CD123 | MyD88 | b2c | FcεRIγ |
| CD123 | MyD88 | b2c | DAP10 |
| CD123 | MyD88 | b2c | DAP12 |
| CD123 | MyD88 | b2c | CD32 |
| CD123 | MyD88 | b2c | CD79a |
| CD123 | MyD88 | b2c | CD79b |
| CD123 | MyD88 | CD137/41BB | CD8 |
| CD123 | MyD88 | CD137/41BB | CD3ζ |
| CD123 | MyD88 | CD137/41BB | CD3δ |
| CD123 | MyD88 | CD137/41BB | CD3γ |
| CD123 | MyD88 | CD137/41BB | CD3ε |
| CD123 | MyD88 | CD137/41BB | FcγRI-γ |
| CD123 | MyD88 | CD137/41BB | FcγRIII-γ |
| CD123 | MyD88 | CD137/41BB | FcεRIβ |
| CD123 | MyD88 | CD137/41BB | FcεRIγ |
| CD123 | MyD88 | CD137/41BB | DAP10 |
| CD123 | MyD88 | CD137/41BB | DAP12 |
| CD123 | MyD88 | CD137/41BB | CD32 |
| CD123 | MyD88 | CD137/41BB | CD79a |
| CD123 | MyD88 | CD137/41BB | CD79b |
| CD123 | MyD88 | ICOS | CD8 |
| CD123 | MyD88 | ICOS | CD3ζ |
| CD123 | MyD88 | ICOS | CD3δ |
| CD123 | MyD88 | ICOS | CD3γ |
| CD123 | MyD88 | ICOS | CD3ε |
| CD123 | MyD88 | ICOS | FcγRI-γ |
| CD123 | MyD88 | ICOS | FcγRIII-γ |
| CD123 | MyD88 | ICOS | FcεRIβ |
| CD123 | MyD88 | ICOS | FcεRIγ |
| CD123 | MyD88 | ICOS | DAP10 |
| CD123 | MyD88 | ICOS | DAP12 |
| CD123 | MyD88 | ICOS | CD32 |
| CD123 | MyD88 | ICOS | CD79a |
| CD123 | MyD88 | ICOS | CD79b |
| CD123 | MyD88 | CD27 | CD8 |
| CD123 | MyD88 | CD27 | CD3ζ |
| CD123 | MyD88 | CD27 | CD3δ |
| CD123 | MyD88 | CD27 | CD3γ |
| CD123 | MyD88 | CD27 | CD3ε |
| CD123 | MyD88 | CD27 | FcγRI-γ |
| CD123 | MyD88 | CD27 | FcγRIII-γ |
| CD123 | MyD88 | CD27 | FcεRIβ |
| CD123 | MyD88 | CD27 | FcεRIγ |
| CD123 | MyD88 | CD27 | DAP10 |
| CD123 | MyD88 | CD27 | DAP12 |

TABLE 3-continued

Third Generation CARs

| ScFv | Co-stimulatory Signal | Co-stimulatory Signal | Signal Domain |
|---|---|---|---|
| CD123 | MyD88 | CD27 | CD32 |
| CD123 | MyD88 | CD27 | CD79a |
| CD123 | MyD88 | CD27 | CD79b |
| CD123 | MyD88 | CD28δ | CD8 |
| CD123 | MyD88 | CD28δ | CD3ζ |
| CD123 | MyD88 | CD28δ | CD3δ |
| CD123 | MyD88 | CD28δ | CD3γ |
| CD123 | MyD88 | CD28δ | CD3ε |
| CD123 | MyD88 | CD28δ | FcγRI-γ |
| CD123 | MyD88 | CD28δ | FcγRIII-γ |
| CD123 | MyD88 | CD28δ | FcεRIβ |
| CD123 | MyD88 | CD28δ | FcεRIγ |
| CD123 | MyD88 | CD28δ | DAP10 |
| CD123 | MyD88 | CD28δ | DAP12 |
| CD123 | MyD88 | CD28δ | CD32 |
| CD123 | MyD88 | CD28δ | CD79a |
| CD123 | MyD88 | CD28δ | CD79b |
| CD123 | MyD88 | CD80 | CD8 |
| CD123 | MyD88 | CD80 | CD3ζ |
| CD123 | MyD88 | CD80 | CD3δ |
| CD123 | MyD88 | CD80 | CD3γ |
| CD123 | MyD88 | CD80 | CD3ε |
| CD123 | MyD88 | CD80 | FcγRI-γ |
| CD123 | MyD88 | CD80 | FcγRIII-γ |
| CD123 | MyD88 | CD80 | FcεRIβ |
| CD123 | MyD88 | CD80 | FcεRIγ |
| CD123 | MyD88 | CD80 | DAP10 |
| CD123 | MyD88 | CD80 | DAP12 |
| CD123 | MyD88 | CD80 | CD32 |
| CD123 | MyD88 | CD80 | CD79a |
| CD123 | MyD88 | CD80 | CD79b |
| CD123 | MyD88 | CD86 | CD8 |
| CD123 | MyD88 | CD86 | CD3ζ |
| CD123 | MyD88 | CD86 | CD3δ |
| CD123 | MyD88 | CD86 | CD3γ |
| CD123 | MyD88 | CD86 | CD3ε |
| CD123 | MyD88 | CD86 | FcγRI-γ |
| CD123 | MyD88 | CD86 | FcγRIII-γ |
| CD123 | MyD88 | CD86 | FcεRIβ |
| CD123 | MyD88 | CD86 | FcεRIγ |
| CD123 | MyD88 | CD86 | DAP10 |
| CD123 | MyD88 | CD86 | DAP12 |
| CD123 | MyD88 | CD86 | CD32 |
| CD123 | MyD88 | CD86 | CD79a |
| CD123 | MyD88 | CD86 | CD79b |
| CD123 | MyD88 | OX40 | CD8 |
| CD123 | MyD88 | OX40 | CD3ζ |
| CD123 | MyD88 | OX40 | CD3δ |
| CD123 | MyD88 | OX40 | CD3γ |
| CD123 | MyD88 | OX40 | CD3ε |
| CD123 | MyD88 | OX40 | FcγRI-γ |
| CD123 | MyD88 | OX40 | FcγRIII-γ |
| CD123 | MyD88 | OX40 | FcεRIβ |
| CD123 | MyD88 | OX40 | FcεRIγ |
| CD123 | MyD88 | OX40 | DAP10 |
| CD123 | MyD88 | OX40 | DAP12 |
| CD123 | MyD88 | OX40 | CD32 |
| CD123 | MyD88 | OX40 | CD79a |
| CD123 | MyD88 | OX40 | CD79b |
| CD123 | MyD88 | DAP10 | CD8 |
| CD123 | MyD88 | DAP10 | CD3ζ |
| CD123 | MyD88 | DAP10 | CD3δ |
| CD123 | MyD88 | DAP10 | CD3γ |
| CD123 | MyD88 | DAP10 | CD3ε |
| CD123 | MyD88 | DAP10 | FcγRI-γ |
| CD123 | MyD88 | DAP10 | FcγRIII-γ |
| CD123 | MyD88 | DAP10 | FcεRIβ |
| CD123 | MyD88 | DAP10 | FcεRIγ |
| CD123 | MyD88 | DAP10 | DAP10 |
| CD123 | MyD88 | DAP10 | DAP12 |
| CD123 | MyD88 | DAP10 | CD32 |
| CD123 | MyD88 | DAP10 | CD79a |
| CD123 | MyD88 | DAP10 | CD79b |
| CD123 | MyD88 | DAP12 | CD8 |
| CD123 | MyD88 | DAP12 | CD3ζ |
| CD123 | MyD88 | DAP12 | CD3δ |
| CD123 | MyD88 | DAP12 | CD3γ |
| CD123 | MyD88 | DAP12 | CD3ε |
| CD123 | MyD88 | DAP12 | FcγRI-γ |
| CD123 | MyD88 | DAP12 | FcγRIII-γ |
| CD123 | MyD88 | DAP12 | FcεRIβ |
| CD123 | MyD88 | DAP12 | FcεRIγ |
| CD123 | MyD88 | DAP12 | DAP10 |
| CD123 | MyD88 | DAP12 | DAP12 |
| CD123 | MyD88 | DAP12 | CD32 |
| CD123 | MyD88 | DAP12 | CD79a |
| CD123 | MyD88 | DAP12 | CD79b |
| CD123 | MyD88 | MyD88 | CD8 |
| CD123 | MyD88 | MyD88 | CD3ζ |
| CD123 | MyD88 | MyD88 | CD3δ |
| CD123 | MyD88 | MyD88 | CD3γ |
| CD123 | MyD88 | MyD88 | CD3ε |
| CD123 | MyD88 | MyD88 | FcγRI-γ |
| CD123 | MyD88 | MyD88 | FcγRIII-γ |
| CD123 | MyD88 | MyD88 | FcεRIβ |
| CD123 | MyD88 | MyD88 | FcεRIγ |
| CD123 | MyD88 | MyD88 | DAP10 |
| CD123 | MyD88 | MyD88 | DAP12 |
| CD123 | MyD88 | MyD88 | CD32 |
| CD123 | MyD88 | MyD88 | CD79a |
| CD123 | MyD88 | MyD88 | CD79b |
| CD123 | MyD88 | CD7 | CD8 |
| CD123 | MyD88 | CD7 | CD3ζ |
| CD123 | MyD88 | CD7 | CD3δ |
| CD123 | MyD88 | CD7 | CD3γ |
| CD123 | MyD88 | CD7 | CD3ε |
| CD123 | MyD88 | CD7 | FcγRI-γ |
| CD123 | MyD88 | CD7 | FcγRIII-γ |
| CD123 | MyD88 | CD7 | FcεRIβ |
| CD123 | MyD88 | CD7 | FcεRIγ |
| CD123 | MyD88 | CD7 | DAP10 |
| CD123 | MyD88 | CD7 | DAP12 |
| CD123 | MyD88 | CD7 | CD32 |
| CD123 | MyD88 | CD7 | CD79a |
| CD123 | MyD88 | CD7 | CD79b |
| CD123 | MyD88 | BTNL3 | CD8 |
| CD123 | MyD88 | BTNL3 | CD3ζ |
| CD123 | MyD88 | BTNL3 | CD3δ |
| CD123 | MyD88 | BTNL3 | CD3γ |
| CD123 | MyD88 | BTNL3 | CD3ε |
| CD123 | MyD88 | BTNL3 | FcγRI-γ |
| CD123 | MyD88 | BTNL3 | FcγRIII-γ |
| CD123 | MyD88 | BTNL3 | FcεRIβ |
| CD123 | MyD88 | BTNL3 | FcεRIγ |
| CD123 | MyD88 | BTNL3 | DAP10 |
| CD123 | MyD88 | BTNL3 | DAP12 |
| CD123 | MyD88 | BTNL3 | CD32 |
| CD123 | MyD88 | BTNL3 | CD79a |
| CD123 | MyD88 | BTNL3 | CD79b |
| CD123 | MyD88 | NKG2D | CD8 |
| CD123 | MyD88 | NKG2D | CD3ζ |
| CD123 | MyD88 | NKG2D | CD3δ |
| CD123 | MyD88 | NKG2D | CD3γ |
| CD123 | MyD88 | NKG2D | CD3ε |
| CD123 | MyD88 | NKG2D | FcγRI-γ |
| CD123 | MyD88 | NKG2D | FcγRIII-γ |
| CD123 | MyD88 | NKG2D | FcεRIβ |
| CD123 | MyD88 | NKG2D | FcεRIγ |
| CD123 | MyD88 | NKG2D | DAP10 |
| CD123 | MyD88 | NKG2D | DAP12 |
| CD123 | MyD88 | NKG2D | CD32 |
| CD123 | MyD88 | NKG2D | CD79a |
| CD123 | MyD88 | NKG2D | CD79b |
| CD123 | CD7 | CD28 | CD8 |
| CD123 | CD7 | CD28 | CD3ζ |
| CD123 | CD7 | CD28 | CD3δ |
| CD123 | CD7 | CD28 | CD3γ |
| CD123 | CD7 | CD28 | CD3ε |
| CD123 | CD7 | CD28 | FcγRI-γ |
| CD123 | CD7 | CD28 | FcγRIII-γ |

TABLE 3-continued

Third Generation CARs

| ScFv | Co-stimulatory Signal | Co-stimulatory Signal | Signal Domain |
|---|---|---|---|
| CD123 | CD7 | CD28 | FcεRIβ |
| CD123 | CD7 | CD28 | FcεRIγ |
| CD123 | CD7 | CD28 | DAP10 |
| CD123 | CD7 | CD28 | DAP12 |
| CD123 | CD7 | CD28 | CD32 |
| CD123 | CD7 | CD28 | CD79a |
| CD123 | CD7 | CD28 | CD79b |
| CD123 | CD7 | CD8 | CD8 |
| CD123 | CD7 | CD8 | CD3ζ |
| CD123 | CD7 | CD8 | CD3δ |
| CD123 | CD7 | CD8 | CD3γ |
| CD123 | CD7 | CD8 | CD3ε |
| CD123 | CD7 | CD8 | FcγRI-γ |
| CD123 | CD7 | CD8 | FcγRIII-γ |
| CD123 | CD7 | CD8 | FcεRIβ |
| CD123 | CD7 | CD8 | FcεRIγ |
| CD123 | CD7 | CD8 | DAP10 |
| CD123 | CD7 | CD8 | DAP12 |
| CD123 | CD7 | CD8 | CD32 |
| CD123 | CD7 | CD8 | CD79a |
| CD123 | CD7 | CD8 | CD79b |
| CD123 | CD7 | CD4 | CD8 |
| CD123 | CD7 | CD4 | CD3ζ |
| CD123 | CD7 | CD4 | CD3δ |
| CD123 | CD7 | CD4 | CD3γ |
| CD123 | CD7 | CD4 | CD3ε |
| CD123 | CD7 | CD4 | FcγRI-γ |
| CD123 | CD7 | CD4 | FcγRIII-γ |
| CD123 | CD7 | CD4 | FcεRIβ |
| CD123 | CD7 | CD4 | FcεRIγ |
| CD123 | CD7 | CD4 | DAP10 |
| CD123 | CD7 | CD4 | DAP12 |
| CD123 | CD7 | CD4 | CD32 |
| CD123 | CD7 | CD4 | CD79a |
| CD123 | CD7 | CD4 | CD79b |
| CD123 | CD7 | b2c | CD8 |
| CD123 | CD7 | b2c | CD3ζ |
| CD123 | CD7 | b2c | CD3δ |
| CD123 | CD7 | b2c | CD3γ |
| CD123 | CD7 | b2c | CD3ε |
| CD123 | CD7 | b2c | FcγRI-γ |
| CD123 | CD7 | b2c | FcγRIII-γ |
| CD123 | CD7 | b2c | FcεRIβ |
| CD123 | CD7 | b2c | FcεRIγ |
| CD123 | CD7 | b2c | DAP10 |
| CD123 | CD7 | b2c | DAP12 |
| CD123 | CD7 | b2c | CD32 |
| CD123 | CD7 | b2c | CD79a |
| CD123 | CD7 | b2c | CD79b |
| CD123 | CD7 | CD137/41BB | CD8 |
| CD123 | CD7 | CD137/41BB | CD3ζ |
| CD123 | CD7 | CD137/41BB | CD3δ |
| CD123 | CD7 | CD137/41BB | CD3γ |
| CD123 | CD7 | CD137/41BB | CD3ε |
| CD123 | CD7 | CD137/41BB | FcγRI-γ |
| CD123 | CD7 | CD137/41BB | FcγRIII-γ |
| CD123 | CD7 | CD137/41BB | FcεRIβ |
| CD123 | CD7 | CD137/41BB | FcεRIγ |
| CD123 | CD7 | CD137/41BB | DAP10 |
| CD123 | CD7 | CD137/41BB | DAP12 |
| CD123 | CD7 | CD137/41BB | CD32 |
| CD123 | CD7 | CD137/41BB | CD79a |
| CD123 | CD7 | CD137/41BB | CD79b |
| CD123 | CD7 | ICOS | CD8 |
| CD123 | CD7 | ICOS | CD3ζ |
| CD123 | CD7 | ICOS | CD3δ |
| CD123 | CD7 | ICOS | CD3γ |
| CD123 | CD7 | ICOS | CD3ε |
| CD123 | CD7 | ICOS | FcγRI-γ |
| CD123 | CD7 | ICOS | FcγRIII-γ |
| CD123 | CD7 | ICOS | FcεRIβ |
| CD123 | CD7 | ICOS | FcεRIγ |
| CD123 | CD7 | ICOS | DAP10 |
| CD123 | CD7 | ICOS | DAP12 |
| CD123 | CD7 | ICOS | CD32 |
| CD123 | CD7 | ICOS | CD79a |
| CD123 | CD7 | ICOS | CD79b |
| CD123 | CD7 | CD27 | CD8 |
| CD123 | CD7 | CD27 | CD3ζ |
| CD123 | CD7 | CD27 | CD3δ |
| CD123 | CD7 | CD27 | CD3γ |
| CD123 | CD7 | CD27 | CD3ε |
| CD123 | CD7 | CD27 | FcγRI-γ |
| CD123 | CD7 | CD27 | FcγRIII-γ |
| CD123 | CD7 | CD27 | FcεRIβ |
| CD123 | CD7 | CD27 | FcεRIγ |
| CD123 | CD7 | CD27 | DAP10 |
| CD123 | CD7 | CD27 | DAP12 |
| CD123 | CD7 | CD27 | CD32 |
| CD123 | CD7 | CD27 | CD79a |
| CD123 | CD7 | CD27 | CD79b |
| CD123 | CD7 | CD28δ | CD8 |
| CD123 | CD7 | CD28δ | CD3ζ |
| CD123 | CD7 | CD28δ | CD3δ |
| CD123 | CD7 | CD28δ | CD3γ |
| CD123 | CD7 | CD28δ | CD3ε |
| CD123 | CD7 | CD28δ | FcγRI-γ |
| CD123 | CD7 | CD28δ | FcγRIII-γ |
| CD123 | CD7 | CD28δ | FcεRIβ |
| CD123 | CD7 | CD28δ | FcεRIγ |
| CD123 | CD7 | CD28δ | DAP10 |
| CD123 | CD7 | CD28δ | DAP12 |
| CD123 | CD7 | CD28δ | CD32 |
| CD123 | CD7 | CD28δ | CD79a |
| CD123 | CD7 | CD28δ | CD79b |
| CD123 | CD7 | CD80 | CD8 |
| CD123 | CD7 | CD80 | CD3ζ |
| CD123 | CD7 | CD80 | CD3δ |
| CD123 | CD7 | CD80 | CD3γ |
| CD123 | CD7 | CD80 | CD3ε |
| CD123 | CD7 | CD80 | FcγRI-γ |
| CD123 | CD7 | CD80 | FcγRIII-γ |
| CD123 | CD7 | CD80 | FcεRIβ |
| CD123 | CD7 | CD80 | FcεRIγ |
| CD123 | CD7 | CD80 | DAP10 |
| CD123 | CD7 | CD80 | DAP12 |
| CD123 | CD7 | CD80 | CD32 |
| CD123 | CD7 | CD80 | CD79a |
| CD123 | CD7 | CD80 | CD79b |
| CD123 | CD7 | CD86 | CD8 |
| CD123 | CD7 | CD86 | CD3ζ |
| CD123 | CD7 | CD86 | CD3δ |
| CD123 | CD7 | CD86 | CD3γ |
| CD123 | CD7 | CD86 | CD3ε |
| CD123 | CD7 | CD86 | FcγRI-γ |
| CD123 | CD7 | CD86 | FcγRIII-γ |
| CD123 | CD7 | CD86 | FcεRIβ |
| CD123 | CD7 | CD86 | FcεRIγ |
| CD123 | CD7 | CD86 | DAP10 |
| CD123 | CD7 | CD86 | DAP12 |
| CD123 | CD7 | CD86 | CD32 |
| CD123 | CD7 | CD86 | CD79a |
| CD123 | CD7 | CD86 | CD79b |
| CD123 | CD7 | OX40 | CD8 |
| CD123 | CD7 | OX40 | CD3ζ |
| CD123 | CD7 | OX40 | CD3δ |
| CD123 | CD7 | OX40 | CD3γ |
| CD123 | CD7 | OX40 | CD3ε |
| CD123 | CD7 | OX40 | FcγRI-γ |
| CD123 | CD7 | OX40 | FcγRIII-γ |
| CD123 | CD7 | OX40 | FcεRIβ |
| CD123 | CD7 | OX40 | FcεRIγ |
| CD123 | CD7 | OX40 | DAP10 |
| CD123 | CD7 | OX40 | DAP12 |
| CD123 | CD7 | OX40 | CD32 |
| CD123 | CD7 | OX40 | CD79a |
| CD123 | CD7 | OX40 | CD79b |
| CD123 | CD7 | DAP10 | CD8 |
| CD123 | CD7 | DAP10 | CD3ζ |
| CD123 | CD7 | DAP10 | CD3δ |

TABLE 3-continued

Third Generation CARs

| ScFv | Co-stimulatory Signal | Co-stimulatory Signal | Signal Domain |
|---|---|---|---|
| CD123 | CD7 | DAP10 | CD3γ |
| CD123 | CD7 | DAP10 | CD3ε |
| CD123 | CD7 | DAP10 | FcγRI-γ |
| CD123 | CD7 | DAP10 | FcγRIII-γ |
| CD123 | CD7 | DAP10 | FcεRIβ |
| CD123 | CD7 | DAP10 | FcεRIγ |
| CD123 | CD7 | DAP10 | DAP10 |
| CD123 | CD7 | DAP10 | DAP12 |
| CD123 | CD7 | DAP10 | CD32 |
| CD123 | CD7 | DAP10 | CD79a |
| CD123 | CD7 | DAP10 | CD79b |
| CD123 | CD7 | DAP12 | CD8 |
| CD123 | CD7 | DAP12 | CD3ζ |
| CD123 | CD7 | DAP12 | CD3δ |
| CD123 | CD7 | DAP12 | CD3γ |
| CD123 | CD7 | DAP12 | CD3ε |
| CD123 | CD7 | DAP12 | FcγRI-γ |
| CD123 | CD7 | DAP12 | FcγRIII-γ |
| CD123 | CD7 | DAP12 | FcεRIβ |
| CD123 | CD7 | DAP12 | FcεRIγ |
| CD123 | CD7 | DAP12 | DAP10 |
| CD123 | CD7 | DAP12 | DAP12 |
| CD123 | CD7 | DAP12 | CD32 |
| CD123 | CD7 | DAP12 | CD79a |
| CD123 | CD7 | DAP12 | CD79b |
| CD123 | CD7 | MyD88 | CD8 |
| CD123 | CD7 | MyD88 | CD3ζ |
| CD123 | CD7 | MyD88 | CD3δ |
| CD123 | CD7 | MyD88 | CD3γ |
| CD123 | CD7 | MyD88 | CD3ε |
| CD123 | CD7 | MyD88 | FcγRI-γ |
| CD123 | CD7 | MyD88 | FcγRIII-γ |
| CD123 | CD7 | MyD88 | FcεRIβ |
| CD123 | CD7 | MyD88 | FcεRIγ |
| CD123 | CD7 | MyD88 | DAP10 |
| CD123 | CD7 | MyD88 | DAP12 |
| CD123 | CD7 | MyD88 | CD32 |
| CD123 | CD7 | MyD88 | CD79a |
| CD123 | CD7 | MyD88 | CD79b |
| CD123 | CD7 | CD7 | CD8 |
| CD123 | CD7 | CD7 | CD3ζ |
| CD123 | CD7 | CD7 | CD3δ |
| CD123 | CD7 | CD7 | CD3γ |
| CD123 | CD7 | CD7 | CD3ε |
| CD123 | CD7 | CD7 | FcγRI-γ |
| CD123 | CD7 | CD7 | FcγRIII-γ |
| CD123 | CD7 | CD7 | FcεRIβ |
| CD123 | CD7 | CD7 | FcεRIγ |
| CD123 | CD7 | CD7 | DAP10 |
| CD123 | CD7 | CD7 | DAP12 |
| CD123 | CD7 | CD7 | CD32 |
| CD123 | CD7 | CD7 | CD79a |
| CD123 | CD7 | CD7 | CD79b |
| CD123 | CD7 | BTNL3 | CD8 |
| CD123 | CD7 | BTNL3 | CD3ζ |
| CD123 | CD7 | BTNL3 | CD3δ |
| CD123 | CD7 | BTNL3 | CD3γ |
| CD123 | CD7 | BTNL3 | CD3ε |
| CD123 | CD7 | BTNL3 | FcγRI-γ |
| CD123 | CD7 | BTNL3 | FcγRIII-γ |
| CD123 | CD7 | BTNL3 | FcεRIβ |
| CD123 | CD7 | BTNL3 | FcεRIγ |
| CD123 | CD7 | BTNL3 | DAP10 |
| CD123 | CD7 | BTNL3 | DAP12 |
| CD123 | CD7 | BTNL3 | CD32 |
| CD123 | CD7 | BTNL3 | CD79a |
| CD123 | CD7 | BTNL3 | CD79b |
| CD123 | CD7 | NKG2D | CD8 |
| CD123 | CD7 | NKG2D | CD3ζ |
| CD123 | CD7 | NKG2D | CD3δ |
| CD123 | CD7 | NKG2D | CD3γ |
| CD123 | CD7 | NKG2D | CD3ε |
| CD123 | CD7 | NKG2D | FcγRI-γ |
| CD123 | CD7 | NKG2D | FcγRIII-γ |
| CD123 | CD7 | NKG2D | FcεRIβ |
| CD123 | CD7 | NKG2D | FcεRIγ |
| CD123 | CD7 | NKG2D | DAP10 |
| CD123 | CD7 | NKG2D | DAP12 |
| CD123 | CD7 | NKG2D | CD32 |
| CD123 | CD7 | NKG2D | CD79a |
| CD123 | CD7 | NKG2D | CD79b |
| CD123 | BTNL3 | CD28 | CD8 |
| CD123 | BTNL3 | CD28 | CD3ζ |
| CD123 | BTNL3 | CD28 | CD3δ |
| CD123 | BTNL3 | CD28 | CD3γ |
| CD123 | BTNL3 | CD28 | CD3ε |
| CD123 | BTNL3 | CD28 | FcγRI-γ |
| CD123 | BTNL3 | CD28 | FcγRIII-γ |
| CD123 | BTNL3 | CD28 | FcεRIβ |
| CD123 | BTNL3 | CD28 | FcεRIγ |
| CD123 | BTNL3 | CD28 | DAP10 |
| CD123 | BTNL3 | CD28 | DAP12 |
| CD123 | BTNL3 | CD28 | CD32 |
| CD123 | BTNL3 | CD28 | CD79a |
| CD123 | BTNL3 | CD28 | CD79b |
| CD123 | BTNL3 | CD8 | CD8 |
| CD123 | BTNL3 | CD8 | CD3ζ |
| CD123 | BTNL3 | CD8 | CD3δ |
| CD123 | BTNL3 | CD8 | CD3γ |
| CD123 | BTNL3 | CD8 | CD3ε |
| CD123 | BTNL3 | CD8 | FcγRI-γ |
| CD123 | BTNL3 | CD8 | FcγRIII-γ |
| CD123 | BTNL3 | CD8 | FcεRIβ |
| CD123 | BTNL3 | CD8 | FcεRIγ |
| CD123 | BTNL3 | CD8 | DAP10 |
| CD123 | BTNL3 | CD8 | DAP12 |
| CD123 | BTNL3 | CD8 | CD32 |
| CD123 | BTNL3 | CD8 | CD79a |
| CD123 | BTNL3 | CD8 | CD79b |
| CD123 | BTNL3 | CD4 | CD8 |
| CD123 | BTNL3 | CD4 | CD3ζ |
| CD123 | BTNL3 | CD4 | CD3δ |
| CD123 | BTNL3 | CD4 | CD3γ |
| CD123 | BTNL3 | CD4 | CD3ε |
| CD123 | BTNL3 | CD4 | FcγRI-γ |
| CD123 | BTNL3 | CD4 | FcγRIII-γ |
| CD123 | BTNL3 | CD4 | FcεRIβ |
| CD123 | BTNL3 | CD4 | FcεRIγ |
| CD123 | BTNL3 | CD4 | DAP10 |
| CD123 | BTNL3 | CD4 | DAP12 |
| CD123 | BTNL3 | CD4 | CD32 |
| CD123 | BTNL3 | CD4 | CD79a |
| CD123 | BTNL3 | CD4 | CD79b |
| CD123 | BTNL3 | b2c | CD8 |
| CD123 | BTNL3 | b2c | CD3ζ |
| CD123 | BTNL3 | b2c | CD3δ |
| CD123 | BTNL3 | b2c | CD3γ |
| CD123 | BTNL3 | b2c | CD3ε |
| CD123 | BTNL3 | b2c | FcγRI-γ |
| CD123 | BTNL3 | b2c | FcγRIII-γ |
| CD123 | BTNL3 | b2c | FcεRIβ |
| CD123 | BTNL3 | b2c | FcεRIγ |
| CD123 | BTNL3 | b2c | DAP10 |
| CD123 | BTNL3 | b2c | DAP12 |
| CD123 | BTNL3 | b2c | CD32 |
| CD123 | BTNL3 | b2c | CD79a |
| CD123 | BTNL3 | b2c | CD79b |
| CD123 | BTNL3 | CD137/41BB | CD8 |
| CD123 | BTNL3 | CD137/41BB | CD3ζ |
| CD123 | BTNL3 | CD137/41BB | CD3δ |
| CD123 | BTNL3 | CD137/41BB | CD3γ |
| CD123 | BTNL3 | CD137/41BB | CD3ε |
| CD123 | BTNL3 | CD137/41BB | FcγRI-γ |
| CD123 | BTNL3 | CD137/41BB | FcγRIII-γ |
| CD123 | BTNL3 | CD137/41BB | FcεRIβ |
| CD123 | BTNL3 | CD137/41BB | FcεRIγ |
| CD123 | BTNL3 | CD137/41BB | DAP10 |
| CD123 | BTNL3 | CD137/41BB | DAP12 |
| CD123 | BTNL3 | CD137/41BB | CD32 |
| CD123 | BTNL3 | CD137/41BB | CD79a |

TABLE 3-continued

Third Generation CARs

| ScFv | Co-stimulatory Signal | Co-stimulatory Signal | Signal Domain |
|---|---|---|---|
| CD123 | BTNL3 | CD137/41BB | CD79b |
| CD123 | BTNL3 | ICOS | CD8 |
| CD123 | BTNL3 | ICOS | CD3ζ |
| CD123 | BTNL3 | ICOS | CD3δ |
| CD123 | BTNL3 | ICOS | CD3γ |
| CD123 | BTNL3 | ICOS | CD3ε |
| CD123 | BTNL3 | ICOS | FcγRI-γ |
| CD123 | BTNL3 | ICOS | FcγRIII-γ |
| CD123 | BTNL3 | ICOS | FcεRIβ |
| CD123 | BTNL3 | ICOS | FcεRIγ |
| CD123 | BTNL3 | ICOS | DAP10 |
| CD123 | BTNL3 | ICOS | DAP12 |
| CD123 | BTNL3 | ICOS | CD32 |
| CD123 | BTNL3 | ICOS | CD79a |
| CD123 | BTNL3 | ICOS | CD79b |
| CD123 | BTNL3 | CD27 | CD8 |
| CD123 | BTNL3 | CD27 | CD3ζ |
| CD123 | BTNL3 | CD27 | CD3δ |
| CD123 | BTNL3 | CD27 | CD3γ |
| CD123 | BTNL3 | CD27 | CD3ε |
| CD123 | BTNL3 | CD27 | FcγRI-γ |
| CD123 | BTNL3 | CD27 | FcγRIII-γ |
| CD123 | BTNL3 | CD27 | FcεRIβ |
| CD123 | BTNL3 | CD27 | FcεRIγ |
| CD123 | BTNL3 | CD27 | DAP10 |
| CD123 | BTNL3 | CD27 | DAP12 |
| CD123 | BTNL3 | CD27 | CD32 |
| CD123 | BTNL3 | CD27 | CD79a |
| CD123 | BTNL3 | CD27 | CD79b |
| CD123 | BTNL3 | CD28δ | CD8 |
| CD123 | BTNL3 | CD28δ | CD3ζ |
| CD123 | BTNL3 | CD28δ | CD3δ |
| CD123 | BTNL3 | CD28δ | CD3γ |
| CD123 | BTNL3 | CD28δ | CD3ε |
| CD123 | BTNL3 | CD28δ | FcγRI-γ |
| CD123 | BTNL3 | CD28δ | FcγRIII-γ |
| CD123 | BTNL3 | CD28δ | FcεRIβ |
| CD123 | BTNL3 | CD28δ | FcεRIγ |
| CD123 | BTNL3 | CD28δ | DAP10 |
| CD123 | BTNL3 | CD28δ | DAP12 |
| CD123 | BTNL3 | CD28δ | CD32 |
| CD123 | BTNL3 | CD28δ | CD79a |
| CD123 | BTNL3 | CD28δ | CD79b |
| CD123 | BTNL3 | CD80 | CD8 |
| CD123 | BTNL3 | CD80 | CD3ζ |
| CD123 | BTNL3 | CD80 | CD3δ |
| CD123 | BTNL3 | CD80 | CD3γ |
| CD123 | BTNL3 | CD80 | CD3ε |
| CD123 | BTNL3 | CD80 | FcγRI-γ |
| CD123 | BTNL3 | CD80 | FcγRIII-γ |
| CD123 | BTNL3 | CD80 | FcεRIβ |
| CD123 | BTNL3 | CD80 | FcεRIγ |
| CD123 | BTNL3 | CD80 | DAP10 |
| CD123 | BTNL3 | CD80 | DAP12 |
| CD123 | BTNL3 | CD80 | CD32 |
| CD123 | BTNL3 | CD80 | CD79a |
| CD123 | BTNL3 | CD80 | CD79b |
| CD123 | BTNL3 | CD86 | CD8 |
| CD123 | BTNL3 | CD86 | CD3ζ |
| CD123 | BTNL3 | CD86 | CD3δ |
| CD123 | BTNL3 | CD86 | CD3γ |
| CD123 | BTNL3 | CD86 | CD3ε |
| CD123 | BTNL3 | CD86 | FcγRI-γ |
| CD123 | BTNL3 | CD86 | FcγRIII-γ |
| CD123 | BTNL3 | CD86 | FcεRIβ |
| CD123 | BTNL3 | CD86 | FcεRIγ |
| CD123 | BTNL3 | CD86 | DAP10 |
| CD123 | BTNL3 | CD86 | DAP12 |
| CD123 | BTNL3 | CD86 | CD32 |
| CD123 | BTNL3 | CD86 | CD79a |
| CD123 | BTNL3 | CD86 | CD79b |
| CD123 | BTNL3 | OX40 | CD8 |
| CD123 | BTNL3 | OX40 | CD3ζ |
| CD123 | BTNL3 | OX40 | CD3δ |
| CD123 | BTNL3 | OX40 | CD3γ |
| CD123 | BTNL3 | OX40 | CD3ε |
| CD123 | BTNL3 | OX40 | FcγRI-γ |
| CD123 | BTNL3 | OX40 | FcγRIII-γ |
| CD123 | BTNL3 | OX40 | FcεRIβ |
| CD123 | BTNL3 | OX40 | FcεRIγ |
| CD123 | BTNL3 | OX40 | DAP10 |
| CD123 | BTNL3 | OX40 | DAP12 |
| CD123 | BTNL3 | OX40 | CD32 |
| CD123 | BTNL3 | OX40 | CD79a |
| CD123 | BTNL3 | OX40 | CD79b |
| CD123 | BTNL3 | DAP10 | CD8 |
| CD123 | BTNL3 | DAP10 | CD3ζ |
| CD123 | BTNL3 | DAP10 | CD3δ |
| CD123 | BTNL3 | DAP10 | CD3γ |
| CD123 | BTNL3 | DAP10 | CD3ε |
| CD123 | BTNL3 | DAP10 | FcγRI-γ |
| CD123 | BTNL3 | DAP10 | FcγRIII-γ |
| CD123 | BTNL3 | DAP10 | FcεRIβ |
| CD123 | BTNL3 | DAP10 | FcεRIγ |
| CD123 | BTNL3 | DAP10 | DAP10 |
| CD123 | BTNL3 | DAP10 | DAP12 |
| CD123 | BTNL3 | DAP10 | CD32 |
| CD123 | BTNL3 | DAP10 | CD79a |
| CD123 | BTNL3 | DAP10 | CD79b |
| CD123 | BTNL3 | DAP12 | CD8 |
| CD123 | BTNL3 | DAP12 | CD3ζ |
| CD123 | BTNL3 | DAP12 | CD3δ |
| CD123 | BTNL3 | DAP12 | CD3γ |
| CD123 | BTNL3 | DAP12 | CD3ε |
| CD123 | BTNL3 | DAP12 | FcγRI-γ |
| CD123 | BTNL3 | DAP12 | FcγRIII-γ |
| CD123 | BTNL3 | DAP12 | FcεRIβ |
| CD123 | BTNL3 | DAP12 | FcεRIγ |
| CD123 | BTNL3 | DAP12 | DAP10 |
| CD123 | BTNL3 | DAP12 | DAP12 |
| CD123 | BTNL3 | DAP12 | CD32 |
| CD123 | BTNL3 | DAP12 | CD79a |
| CD123 | BTNL3 | DAP12 | CD79b |
| CD123 | BTNL3 | MyD88 | CD8 |
| CD123 | BTNL3 | MyD88 | CD3ζ |
| CD123 | BTNL3 | MyD88 | CD3δ |
| CD123 | BTNL3 | MyD88 | CD3γ |
| CD123 | BTNL3 | MyD88 | CD3ε |
| CD123 | BTNL3 | MyD88 | FcγRI-γ |
| CD123 | BTNL3 | MyD88 | FcγRIII-γ |
| CD123 | BTNL3 | MyD88 | FcεRIβ |
| CD123 | BTNL3 | MyD88 | FcεRIγ |
| CD123 | BTNL3 | MyD88 | DAP10 |
| CD123 | BTNL3 | MyD88 | DAP12 |
| CD123 | BTNL3 | MyD88 | CD32 |
| CD123 | BTNL3 | MyD88 | CD79a |
| CD123 | BTNL3 | MyD88 | CD79b |
| CD123 | BTNL3 | CD7 | CD8 |
| CD123 | BTNL3 | CD7 | CD3δ |
| CD123 | BTNL3 | CD7 | CD3γ |
| CD123 | BTNL3 | CD7 | CD3ε |
| CD123 | BTNL3 | CD7 | FcγRI-γ |
| CD123 | BTNL3 | CD7 | FcγRIII-γ |
| CD123 | BTNL3 | CD7 | FcεRIβ |
| CD123 | BTNL3 | CD7 | FcεRIγ |
| CD123 | BTNL3 | CD7 | DAP10 |
| CD123 | BTNL3 | CD7 | DAP12 |
| CD123 | BTNL3 | CD7 | CD32 |
| CD123 | BTNL3 | CD7 | CD79a |
| CD123 | BTNL3 | CD7 | CD79b |
| CD123 | BTNL3 | BTNL3 | CD8 |
| CD123 | BTNL3 | BTNL3 | CD3ζ |
| CD123 | BTNL3 | BTNL3 | CD3δ |
| CD123 | BTNL3 | BTNL3 | CD3γ |
| CD123 | BTNL3 | BTNL3 | CD3ε |
| CD123 | BTNL3 | BTNL3 | FcγRI-γ |
| CD123 | BTNL3 | BTNL3 | FcγRIII-γ |
| CD123 | BTNL3 | BTNL3 | FcεRIβ |
| CD123 | BTNL3 | BTNL3 | FcεRIγ |

TABLE 3-continued

Third Generation CARs

| ScFv | Co-stimulatory Signal | Co-stimulatory Signal | Signal Domain |
|---|---|---|---|
| CD123 | BTNL3 | BTNL3 | DAP10 |
| CD123 | BTNL3 | BTNL3 | DAP12 |
| CD123 | BTNL3 | BTNL3 | CD32 |
| CD123 | BTNL3 | BTNL3 | CD79a |
| CD123 | BTNL3 | BTNL3 | CD79b |
| CD123 | BTNL3 | NKG2D | CD8 |
| CD123 | BTNL3 | NKG2D | CD3ζ |
| CD123 | BTNL3 | NKG2D | CD3δ |
| CD123 | BTNL3 | NKG2D | CD3γ |
| CD123 | BTNL3 | NKG2D | CD3ε |
| CD123 | BTNL3 | NKG2D | FcγRI-γ |
| CD123 | BTNL3 | NKG2D | FcγRIII-γ |
| CD123 | BTNL3 | NKG2D | FcεRIβ |
| CD123 | BTNL3 | NKG2D | FcεRIγ |
| CD123 | BTNL3 | NKG2D | DAP10 |
| CD123 | BTNL3 | NKG2D | DAP12 |
| CD123 | BTNL3 | NKG2D | CD32 |
| CD123 | BTNL3 | NKG2D | CD79a |
| CD123 | BTNL3 | NKG2D | CD79b |
| CD123 | NKG2D | CD28 | CD8 |
| CD123 | NKG2D | CD28 | CD3ζ |
| CD123 | NKG2D | CD28 | CD3δ |
| CD123 | NKG2D | CD28 | CD3γ |
| CD123 | NKG2D | CD28 | CD3ε |
| CD123 | NKG2D | CD28 | FcγRI-γ |
| CD123 | NKG2D | CD28 | FcγRIII-γ |
| CD123 | NKG2D | CD28 | FcεRIβ |
| CD123 | NKG2D | CD28 | FcεRIγ |
| CD123 | NKG2D | CD28 | DAP10 |
| CD123 | NKG2D | CD28 | DAP12 |
| CD123 | NKG2D | CD28 | CD32 |
| CD123 | NKG2D | CD28 | CD79a |
| CD123 | NKG2D | CD28 | CD79b |
| CD123 | NKG2D | CD8 | CD8 |
| CD123 | NKG2D | CD8 | CD3δ |
| CD123 | NKG2D | CD8 | CD3γ |
| CD123 | NKG2D | CD8 | CD3ε |
| CD123 | NKG2D | CD8 | FcγRI-γ |
| CD123 | NKG2D | CD8 | FcγRIII-γ |
| CD123 | NKG2D | CD8 | FcεRIβ |
| CD123 | NKG2D | CD8 | FcεRIγ |
| CD123 | NKG2D | CD8 | DAP10 |
| CD123 | NKG2D | CD8 | DAP12 |
| CD123 | NKG2D | CD8 | CD32 |
| CD123 | NKG2D | CD8 | CD79a |
| CD123 | NKG2D | CD8 | CD79b |
| CD123 | NKG2D | CD4 | CD8 |
| CD123 | NKG2D | CD4 | CD3ζ |
| CD123 | NKG2D | CD4 | CD3δ |
| CD123 | NKG2D | CD4 | CD3γ |
| CD123 | NKG2D | CD4 | CD3ε |
| CD123 | NKG2D | CD4 | FcγRI-γ |
| CD123 | NKG2D | CD4 | FcγRIII-γ |
| CD123 | NKG2D | CD4 | FcεRIβ |
| CD123 | NKG2D | CD4 | FcεRIγ |
| CD123 | NKG2D | CD4 | DAP10 |
| CD123 | NKG2D | CD4 | DAP12 |
| CD123 | NKG2D | CD4 | CD32 |
| CD123 | NKG2D | CD4 | CD79a |
| CD123 | NKG2D | CD4 | CD79b |
| CD123 | NKG2D | b2c | CD8 |
| CD123 | NKG2D | b2c | CD3ζ |
| CD123 | NKG2D | b2c | CD3δ |
| CD123 | NKG2D | b2c | CD3γ |
| CD123 | NKG2D | b2c | CD3ε |
| CD123 | NKG2D | b2c | FcγRI-γ |
| CD123 | NKG2D | b2c | FcγRIII-γ |
| CD123 | NKG2D | b2c | FcεRIβ |
| CD123 | NKG2D | b2c | FcεRIγ |
| CD123 | NKG2D | b2c | DAP10 |
| CD123 | NKG2D | b2c | DAP12 |
| CD123 | NKG2D | b2c | CD32 |
| CD123 | NKG2D | b2c | CD79a |
| CD123 | NKG2D | b2c | CD79b |
| CD123 | NKG2D | CD137/41BB | CD8 |
| CD123 | NKG2D | CD137/41BB | CD3ζ |
| CD123 | NKG2D | CD137/41BB | CD3δ |
| CD123 | NKG2D | CD137/41BB | CD3γ |
| CD123 | NKG2D | CD137/41BB | CD3ε |
| CD123 | NKG2D | CD137/41BB | FcγRI-γ |
| CD123 | NKG2D | CD137/41BB | FcγRIII-γ |
| CD123 | NKG2D | CD137/41BB | FcεRIβ |
| CD123 | NKG2D | CD137/41BB | FcεRIγ |
| CD123 | NKG2D | CD137/41BB | DAP10 |
| CD123 | NKG2D | CD137/41BB | DAP12 |
| CD123 | NKG2D | CD137/41BB | CD32 |
| CD123 | NKG2D | CD137/41BB | CD79a |
| CD123 | NKG2D | CD137/41BB | CD79b |
| CD123 | NKG2D | ICOS | CD8 |
| CD123 | NKG2D | ICOS | CD3ζ |
| CD123 | NKG2D | ICOS | CD3δ |
| CD123 | NKG2D | ICOS | CD3γ |
| CD123 | NKG2D | ICOS | CD3ε |
| CD123 | NKG2D | ICOS | FcγRI-γ |
| CD123 | NKG2D | ICOS | FcγRIII-γ |
| CD123 | NKG2D | ICOS | FcεRIβ |
| CD123 | NKG2D | ICOS | FcεRIγ |
| CD123 | NKG2D | ICOS | DAP10 |
| CD123 | NKG2D | ICOS | DAP12 |
| CD123 | NKG2D | ICOS | CD32 |
| CD123 | NKG2D | ICOS | CD79a |
| CD123 | NKG2D | ICOS | CD79b |
| CD123 | NKG2D | CD27 | CD8 |
| CD123 | NKG2D | CD27 | CD3ζ |
| CD123 | NKG2D | CD27 | CD3δ |
| CD123 | NKG2D | CD27 | CD3γ |
| CD123 | NKG2D | CD27 | CD3ε |
| CD123 | NKG2D | CD27 | FcγRI-γ |
| CD123 | NKG2D | CD27 | FcγRIII-γ |
| CD123 | NKG2D | CD27 | FcεRIβ |
| CD123 | NKG2D | CD27 | FcεRIγ |
| CD123 | NKG2D | CD27 | DAP10 |
| CD123 | NKG2D | CD27 | DAP12 |
| CD123 | NKG2D | CD27 | CD32 |
| CD123 | NKG2D | CD27 | CD79a |
| CD123 | NKG2D | CD27 | CD79b |
| CD123 | NKG2D | CD28δ | CD8 |
| CD123 | NKG2D | CD28δ | CD3ζ |
| CD123 | NKG2D | CD28δ | CD3δ |
| CD123 | NKG2D | CD28δ | CD3γ |
| CD123 | NKG2D | CD28δ | CD3ε |
| CD123 | NKG2D | CD28δ | FcγRI-γ |
| CD123 | NKG2D | CD28δ | FcγRIII-γ |
| CD123 | NKG2D | CD28δ | FcεRIβ |
| CD123 | NKG2D | CD28δ | FcεRIγ |
| CD123 | NKG2D | CD28δ | DAP10 |
| CD123 | NKG2D | CD28δ | DAP12 |
| CD123 | NKG2D | CD28δ | CD32 |
| CD123 | NKG2D | CD28δ | CD79a |
| CD123 | NKG2D | CD28δ | CD79b |
| CD123 | NKG2D | CD80 | CD8 |
| CD123 | NKG2D | CD80 | CD3ζ |
| CD123 | NKG2D | CD80 | CD3δ |
| CD123 | NKG2D | CD80 | CD3γ |
| CD123 | NKG2D | CD80 | CD3ε |
| CD123 | NKG2D | CD80 | FcγRI-γ |
| CD123 | NKG2D | CD80 | FcγRIII-γ |
| CD123 | NKG2D | CD80 | FcεRIβ |
| CD123 | NKG2D | CD80 | FcεRIγ |
| CD123 | NKG2D | CD80 | DAP10 |
| CD123 | NKG2D | CD80 | DAP12 |
| CD123 | NKG2D | CD80 | CD32 |
| CD123 | NKG2D | CD80 | CD79a |
| CD123 | NKG2D | CD80 | CD79b |
| CD123 | NKG2D | CD86 | CD8 |
| CD123 | NKG2D | CD86 | CD3ζ |
| CD123 | NKG2D | CD86 | CD3δ |
| CD123 | NKG2D | CD86 | CD3γ |
| CD123 | NKG2D | CD86 | CD3ε |

TABLE 3-continued

Third Generation CARs

| ScFv | Co-stimulatory Signal | Co-stimulatory Signal | Signal Domain |
|---|---|---|---|
| CD123 | NKG2D | CD86 | FcγRI-γ |
| CD123 | NKG2D | CD86 | FcγRIII-γ |
| CD123 | NKG2D | CD86 | FcεRIβ |
| CD123 | NKG2D | CD86 | FcεRIγ |
| CD123 | NKG2D | CD86 | DAP10 |
| CD123 | NKG2D | CD86 | DAP12 |
| CD123 | NKG2D | CD86 | CD32 |
| CD123 | NKG2D | CD86 | CD79a |
| CD123 | NKG2D | CD86 | CD79b |
| CD123 | NKG2D | OX40 | CD8 |
| CD123 | NKG2D | OX40 | CD3ζ |
| CD123 | NKG2D | OX40 | CD3δ |
| CD123 | NKG2D | OX40 | CD3γ |
| CD123 | NKG2D | OX40 | CD3ε |
| CD123 | NKG2D | OX40 | FcγRI-γ |
| CD123 | NKG2D | OX40 | FcγRIII-γ |
| CD123 | NKG2D | OX40 | FcεRIβ |
| CD123 | NKG2D | OX40 | FcεRIγ |
| CD123 | NKG2D | OX40 | DAP10 |
| CD123 | NKG2D | OX40 | DAP12 |
| CD123 | NKG2D | OX40 | CD32 |
| CD123 | NKG2D | OX40 | CD79a |
| CD123 | NKG2D | OX40 | CD79b |
| CD123 | NKG2D | DAP10 | CD8 |
| CD123 | NKG2D | DAP10 | CD3ζ |
| CD123 | NKG2D | DAP10 | CD3δ |
| CD123 | NKG2D | DAP10 | CD3γ |
| CD123 | NKG2D | DAP10 | CD3ε |
| CD123 | NKG2D | DAP10 | FcγRI-γ |
| CD123 | NKG2D | DAP10 | FcγRIII-γ |
| CD123 | NKG2D | DAP10 | FcεRIβ |
| CD123 | NKG2D | DAP10 | FcεRIγ |
| CD123 | NKG2D | DAP10 | DAP10 |
| CD123 | NKG2D | DAP10 | DAP12 |
| CD123 | NKG2D | DAP10 | CD32 |
| CD123 | NKG2D | DAP10 | CD79a |
| CD123 | NKG2D | DAP10 | CD79b |
| CD123 | NKG2D | DAP12 | CD8 |
| CD123 | NKG2D | DAP12 | CD3ζ |
| CD123 | NKG2D | DAP12 | CD3δ |
| CD123 | NKG2D | DAP12 | CD3γ |
| CD123 | NKG2D | DAP12 | CD3ε |
| CD123 | NKG2D | DAP12 | FcγRI-γ |
| CD123 | NKG2D | DAP12 | FcγRIII-γ |
| CD123 | NKG2D | DAP12 | FcεRIβ |
| CD123 | NKG2D | DAP12 | FcεRIγ |
| CD123 | NKG2D | DAP12 | DAP10 |
| CD123 | NKG2D | DAP12 | DAP12 |
| CD123 | NKG2D | DAP12 | CD32 |
| CD123 | NKG2D | DAP12 | CD79a |
| CD123 | NKG2D | DAP12 | CD79b |
| CD123 | NKG2D | MyD88 | CD8 |
| CD123 | NKG2D | MyD88 | CD3ζ |
| CD123 | NKG2D | MyD88 | CD3δ |
| CD123 | NKG2D | MyD88 | CD3γ |
| CD123 | NKG2D | MyD88 | CD3ε |
| CD123 | NKG2D | MyD88 | FcγRI-γ |
| CD123 | NKG2D | MyD88 | FcγRIII-γ |
| CD123 | NKG2D | MyD88 | FcεRIβ |
| CD123 | NKG2D | MyD88 | FcεRIγ |
| CD123 | NKG2D | MyD88 | DAP10 |
| CD123 | NKG2D | MyD88 | DAP12 |
| CD123 | NKG2D | MyD88 | CD32 |
| CD123 | NKG2D | MyD88 | CD79a |
| CD123 | NKG2D | MyD88 | CD79b |
| CD123 | NKG2D | CD7 | CD8 |
| CD123 | NKG2D | CD7 | CD3ζ |
| CD123 | NKG2D | CD7 | CD3δ |
| CD123 | NKG2D | CD7 | CD3γ |
| CD123 | NKG2D | CD7 | CD3ε |
| CD123 | NKG2D | CD7 | FcγRI-γ |
| CD123 | NKG2D | CD7 | FcγRIII-γ |
| CD123 | NKG2D | CD7 | FcεRIβ |
| CD123 | NKG2D | CD7 | FcεRIγ |
| CD123 | NKG2D | CD7 | DAP10 |
| CD123 | NKG2D | CD7 | DAP12 |
| CD123 | NKG2D | CD7 | CD79a |
| CD123 | NKG2D | CD7 | CD79b |
| CD123 | NKG2D | BTNL3 | CD8 |
| CD123 | NKG2D | BTNL3 | OD3ζ |
| CD123 | NKG2D | BTNL3 | CD3δ |
| CD123 | NKG2D | BTNL3 | CD3γ |
| CD123 | NKG2D | BTNL3 | CD3ε |
| CD123 | NKG2D | BTNL3 | FcγRI-γ |
| CD123 | NKG2D | BTNL3 | FcγRIII-γ |
| CD123 | NKG2D | BTNL3 | FcεRIβ |
| CD123 | NKG2D | BTNL3 | FcεRIγ |
| CD123 | NKG2D | BTNL3 | DAP10 |
| CD123 | NKG2D | BTNL3 | DAP12 |
| CD123 | NKG2D | BTNL3 | CD32 |
| CD123 | NKG2D | BTNL3 | CD79a |
| CD123 | NKG2D | BTNL3 | CD79b |
| CD123 | NKG2D | NKG2D | CD8 |
| CD123 | NKG2D | NKG2D | OD3ζ |
| CD123 | NKG2D | NKG2D | CD3δ |
| CD123 | NKG2D | NKG2D | CD3γ |
| CD123 | NKG2D | NKG2D | CD3ε |
| CD123 | NKG2D | NKG2D | FcγRI-γ |
| CD123 | NKG2D | NKG2D | FcγRIII-γ |
| CD123 | NKG2D | NKG2D | FcεRIβ |
| CD123 | NKG2D | NKG2D | FcεRIγ |
| CD123 | NKG2D | NKG2D | DAP10 |
| CD123 | NKG2D | NKG2D | DAP12 |
| CD123 | NKG2D | NKG2D | CD32 |
| CD123 | NKG2D | NKG2D | CD79a |
| CD123 | NKG2D | NKG2D | CD79b |

TABLE 4

CARs lacking Co-Simulatory Signal (for dual CAR approach)

| ScFv | Co-stimulatory Signal | Signal Domain |
|---|---|---|
| CD123 | none | CD8 |
| CD123 | none | CD3ζ |
| CD123 | none | CD3δ |
| CD123 | none | CD3γ |
| CD123 | none | CD3ε |
| CD123 | none | FcγRI-γ |
| CD123 | none | FcγRIII-γ |
| CD123 | none | FcεRIβ |
| CD123 | none | FcεRIγ |
| CD123 | none | DAP10 |
| CD123 | none | DAP12 |
| CD123 | none | CD32 |
| CD123 | none | CD79a |
| CD123 | none | CD8 |
| CD123 | none | CD3ζ |
| CD123 | none | CD3δ |
| CD123 | none | CD3γ |
| CD123 | none | CD3ε |
| CD123 | none | FcγRI-γ |

TABLE 5

CARs lacking Signal Domain (for dual CAR approach)

| ScFv | Co-stimulatory Signal | Signal Domain |
|---|---|---|
| CD123 | CD28 | none |
| CD123 | CD8 | none |
| CD123 | CD4 | none |
| CD123 | b2c | none |
| CD123 | CD137/41BB | none |

TABLE 5-continued

CARs lacking Signal Domain (for dual CAR approach)

| ScFv | Co-stimulatory Signal | Signal Domain |
|---|---|---|
| CD123 | ICOS | none |
| CD123 | CD27 | none |
| CD123 | CD28δ | none |
| CD123 | CD80 | none |
| CD123 | CD86 | none |
| CD123 | OX40 | none |
| CD123 | DAP10 | none |
| CD123 | MyD88 | none |
| CD123 | CD7 | none |
| CD123 | DAP12 | none |
| CD123 | MyD88 | none |
| CD123 | CD7 | none |
| CD123 | BTNL3 | none |
| CD123 | NKG2D | none |

TABLE 6

Third Generation CARs lacking Signal Domain (for dual CAR approach)

| ScFv | Co-stimulatory Signal | Co-stimulatory Signal | Signal Domain |
|---|---|---|---|
| CD123 | CD28 | CD28 | none |
| CD123 | CD28 | CD8 | none |
| CD123 | CD28 | CD4 | none |
| CD123 | CD28 | b2c | none |
| CD123 | CD28 | CD137/41BB | none |
| CD123 | CD28 | ICOS | none |
| CD123 | CD28 | CD27 | none |
| CD123 | CD28 | CD28δ | none |
| CD123 | CD28 | CD80 | none |
| CD123 | CD28 | CD86 | none |
| CD123 | CD28 | OX40 | none |
| CD123 | CD28 | DAP10 | none |
| CD123 | CD28 | MyD88 | none |
| CD123 | CD28 | CD7 | none |
| CD123 | CD28 | DAP12 | none |
| CD123 | CD28 | MyD88 | none |
| CD123 | CD28 | CD7 | none |
| CD123 | CD8 | CD28 | none |
| CD123 | CD8 | CD8 | none |
| CD123 | CD8 | CD4 | none |
| CD123 | CD8 | b2c | none |
| CD123 | CD8 | CD137/41BB | none |
| CD123 | CD8 | ICOS | none |
| CD123 | CD8 | CD27 | none |
| CD123 | CD8 | CD28δ | none |
| CD123 | CD8 | CD80 | none |
| CD123 | CD8 | CD86 | none |
| CD123 | CD8 | OX40 | none |
| CD123 | CD8 | DAP10 | none |
| CD123 | CD8 | MyD88 | none |
| CD123 | CD8 | CD7 | none |
| CD123 | CD8 | DAP12 | none |
| CD123 | CD8 | MyD88 | none |
| CD123 | CD8 | CD7 | none |
| CD123 | CD4 | CD28 | none |
| CD123 | CD4 | CD8 | none |
| CD123 | CD4 | CD4 | none |
| CD123 | CD4 | b2c | none |
| CD123 | CD4 | CD137/41BB | none |
| CD123 | CD4 | ICOS | none |
| CD123 | CD4 | CD27 | none |
| CD123 | CD4 | CD28δ | none |
| CD123 | CD4 | CD80 | none |
| CD123 | CD4 | CD86 | none |
| CD123 | CD4 | OX40 | none |
| CD123 | CD4 | DAP10 | none |
| CD123 | CD4 | MyD88 | none |
| CD123 | CD4 | CD7 | none |
| CD123 | CD4 | DAP12 | none |
| CD123 | CD4 | MyD88 | none |
| CD123 | CD4 | CD7 | none |
| CD123 | b2c | CD28 | none |
| CD123 | b2c | CD8 | none |
| CD123 | b2c | CD4 | none |
| CD123 | b2c | b2c | none |
| CD123 | b2c | CD137/41BB | none |
| CD123 | b2c | ICOS | none |
| CD123 | b2c | CD27 | none |
| CD123 | b2c | CD28δ | none |
| CD123 | b2c | CD80 | none |
| CD123 | b2c | CD86 | none |
| CD123 | b2c | OX40 | none |
| CD123 | b2c | DAP10 | none |
| CD123 | b2c | MyD88 | none |
| CD123 | b2c | CD7 | none |
| CD123 | b2c | DAP12 | none |
| CD123 | b2c | MyD88 | none |
| CD123 | b2c | CD7 | none |
| CD123 | CD137/41BB | CD28 | none |
| CD123 | CD137/41BB | CD8 | none |
| CD123 | CD137/41BB | CD4 | none |
| CD123 | CD137/41BB | b2c | none |
| CD123 | CD137/41BB | CD137/41BB | none |
| CD123 | CD137/41BB | ICOS | none |
| CD123 | CD137/41BB | CD27 | none |
| CD123 | CD137/41BB | CD28δ | none |
| CD123 | CD137/41BB | CD80 | none |
| CD123 | CD137/41BB | CD86 | none |
| CD123 | CD137/41BB | OX40 | none |
| CD123 | CD137/41BB | DAP10 | none |
| CD123 | CD137/41BB | MyD88 | none |
| CD123 | CD137/41BB | CD7 | none |
| CD123 | CD137/41BB | DAP12 | none |
| CD123 | CD137/41BB | MyD88 | none |
| CD123 | CD137/41BB | CD7 | none |
| CD123 | ICOS | CD28 | none |
| CD123 | ICOS | CD8 | none |
| CD123 | ICOS | CD4 | none |
| CD123 | ICOS | b2c | none |
| CD123 | ICOS | CD137/41BB | none |
| CD123 | ICOS | ICOS | none |
| CD123 | ICOS | CD27 | none |
| CD123 | ICOS | CD28δ | none |
| CD123 | ICOS | CD80 | none |
| CD123 | ICOS | CD86 | none |
| CD123 | ICOS | OX40 | none |
| CD123 | ICOS | DAP10 | none |
| CD123 | ICOS | MyD88 | none |
| CD123 | ICOS | CD7 | none |
| CD123 | ICOS | DAP12 | none |
| CD123 | ICOS | MyD88 | none |
| CD123 | ICOS | CD7 | none |
| CD123 | ICOS | CD28 | none |
| CD123 | ICOS | CD8 | none |
| CD123 | ICOS | CD4 | none |
| CD123 | ICOS | b2c | none |
| CD123 | ICOS | CD137/41BB | none |
| CD123 | ICOS | ICOS | none |
| CD123 | ICOS | CD27 | none |
| CD123 | ICOS | CD28δ | none |
| CD123 | ICOS | CD80 | none |
| CD123 | ICOS | CD86 | none |
| CD123 | ICOS | OX40 | none |
| CD123 | ICOS | DAP10 | none |
| CD123 | ICOS | MyD88 | none |
| CD123 | ICOS | CD7 | none |
| CD123 | ICOS | DAP12 | none |
| CD123 | ICOS | MyD88 | none |
| CD123 | ICOS | CD7 | none |
| CD123 | CD27 | CD28 | none |
| CD123 | CD27 | CD8 | none |
| CD123 | CD27 | CD4 | none |
| CD123 | CD27 | b2c | none |
| CD123 | CD27 | CD137/41BB | none |
| CD123 | CD27 | ICOS | none |
| CD123 | CD27 | CD27 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD123 | CD27 | CD28δ | none |
| CD123 | CD27 | CD80 | none |
| CD123 | CD27 | CD86 | none |
| CD123 | CD27 | OX40 | none |
| CD123 | CD27 | DAP10 | none |
| CD123 | CD27 | MyD88 | none |
| CD123 | CD27 | CD7 | none |
| CD123 | CD27 | DAP12 | none |
| CD123 | CD27 | MyD88 | none |
| CD123 | CD27 | CD7 | none |
| CD123 | CD28δ | CD28 | none |
| CD123 | CD28δ | CD8 | none |
| CD123 | CD28δ | CD4 | none |
| CD123 | CD28δ | b2c | none |
| CD123 | CD28δ | CD137/41BB | none |
| CD123 | CD28δ | ICOS | none |
| CD123 | CD28δ | CD27 | none |
| CD123 | CD28δ | CD28δ | none |
| CD123 | CD28δ | CD80 | none |
| CD123 | CD28δ | CD86 | none |
| CD123 | CD28δ | OX40 | none |
| CD123 | CD28δ | DAP10 | none |
| CD123 | CD28δ | MyD88 | none |
| CD123 | CD28δ | CD7 | none |
| CD123 | CD28δ | DAP12 | none |
| CD123 | CD28δ | MyD88 | none |
| CD123 | CD28δ | CD7 | none |
| CD123 | CD80 | CD28 | none |
| CD123 | CD80 | CD8 | none |
| CD123 | CD80 | CD4 | none |
| CD123 | CD80 | b2c | none |
| CD123 | CD80 | CD137/41BB | none |
| CD123 | CD80 | ICOS | none |
| CD123 | CD80 | CD27 | none |
| CD123 | CD80 | CD28δ | none |
| CD123 | CD80 | CD80 | none |
| CD123 | CD80 | CD86 | none |
| CD123 | CD80 | OX40 | none |
| CD123 | CD80 | DAP10 | none |
| CD123 | CD80 | MyD88 | none |
| CD123 | CD80 | CD7 | none |
| CD123 | CD80 | DAP12 | none |
| CD123 | CD80 | MyD88 | none |
| CD123 | CD80 | CD7 | none |
| CD123 | CD86 | CD28 | none |
| CD123 | CD86 | CD8 | none |
| CD123 | CD86 | CD4 | none |
| CD123 | CD86 | b2c | none |
| CD123 | CD86 | CD137/41BB | none |
| CD123 | CD86 | ICOS | none |
| CD123 | CD86 | CD27 | none |
| CD123 | CD86 | CD28δ | none |
| CD123 | CD86 | CD80 | none |
| CD123 | CD86 | CD86 | none |
| CD123 | CD86 | OX40 | none |
| CD123 | CD86 | DAP10 | none |
| CD123 | CD86 | MyD88 | none |
| CD123 | CD86 | CD7 | none |
| CD123 | CD86 | DAP12 | none |
| CD123 | CD86 | MyD88 | none |
| CD123 | CD86 | CD7 | none |
| CD123 | OX40 | CD28 | none |
| CD123 | OX40 | CD8 | none |
| CD123 | OX40 | CD4 | none |
| CD123 | OX40 | b2c | none |
| CD123 | OX40 | CD137/41BB | none |
| CD123 | OX40 | ICOS | none |
| CD123 | OX40 | CD27 | none |
| CD123 | OX40 | CD28δ | none |
| CD123 | OX40 | CD80 | none |
| CD123 | OX40 | CD86 | none |
| CD123 | OX40 | OX40 | none |
| CD123 | OX40 | DAP10 | none |
| CD123 | OX40 | MyD88 | none |
| CD123 | OX40 | CD7 | none |
| CD123 | OX40 | DAP12 | none |
| CD123 | OX40 | MyD88 | none |
| CD123 | OX40 | CD7 | none |
| CD123 | DAP10 | CD28 | none |
| CD123 | DAP10 | CD8 | none |
| CD123 | DAP10 | CD4 | none |
| CD123 | DAP10 | b2c | none |
| CD123 | DAP10 | CD137/41BB | none |
| CD123 | DAP10 | ICOS | none |
| CD123 | DAP10 | CD27 | none |
| CD123 | DAP10 | CD28δ | none |
| CD123 | DAP10 | CD80 | none |
| CD123 | DAP10 | CD86 | none |
| CD123 | DAP10 | OX40 | none |
| CD123 | DAP10 | DAP10 | none |
| CD123 | DAP10 | MyD88 | none |
| CD123 | DAP10 | CD7 | none |
| CD123 | DAP10 | DAP12 | none |
| CD123 | DAP10 | MyD88 | none |
| CD123 | DAP10 | CD7 | none |
| CD123 | DAP12 | CD28 | none |
| CD123 | DAP12 | CD8 | none |
| CD123 | DAP12 | CD4 | none |
| CD123 | DAP12 | b2c | none |
| CD123 | DAP12 | CD137/41BB | none |
| CD123 | DAP12 | ICOS | none |
| CD123 | DAP12 | CD27 | none |
| CD123 | DAP12 | CD28δ | none |
| CD123 | DAP12 | CD80 | none |
| CD123 | DAP12 | CD86 | none |
| CD123 | DAP12 | OX40 | none |
| CD123 | DAP12 | DAP10 | none |
| CD123 | DAP12 | MyD88 | none |
| CD123 | DAP12 | CD7 | none |
| CD123 | DAP12 | DAP12 | none |
| CD123 | DAP12 | MyD88 | none |
| CD123 | DAP12 | CD7 | none |
| CD123 | MyD88 | CD28 | none |
| CD123 | MyD88 | CD8 | none |
| CD123 | MyD88 | CD4 | none |
| CD123 | MyD88 | b2c | none |
| CD123 | MyD88 | CD137/41BB | none |
| CD123 | MyD88 | ICOS | none |
| CD123 | MyD88 | CD27 | none |
| CD123 | MyD88 | CD28δ | none |
| CD123 | MyD88 | CD80 | none |
| CD123 | MyD88 | CD86 | none |
| CD123 | MyD88 | OX40 | none |
| CD123 | MyD88 | DAP10 | none |
| CD123 | MyD88 | MyD88 | none |
| CD123 | MyD88 | CD7 | none |
| CD123 | MyD88 | DAP12 | none |
| CD123 | MyD88 | MyD88 | none |
| CD123 | MyD88 | CD7 | none |
| CD123 | CD7 | CD28 | none |
| CD123 | CD7 | CD8 | none |
| CD123 | CD7 | CD4 | none |
| CD123 | CD7 | b2c | none |
| CD123 | CD7 | CD137/41BB | none |
| CD123 | CD7 | ICOS | none |
| CD123 | CD7 | CD27 | none |
| CD123 | CD7 | CD28δ | none |
| CD123 | CD7 | CD80 | none |
| CD123 | CD7 | CD86 | none |
| CD123 | CD7 | OX40 | none |
| CD123 | CD7 | DAP10 | none |
| CD123 | CD7 | MyD88 | none |
| CD123 | CD7 | CD7 | none |
| CD123 | CD7 | DAP12 | none |
| CD123 | CD7 | MyD88 | none |
| CD123 | CD7 | CD7 | none |
| CD123 | BTNL3 | CD28 | none |
| CD123 | BTNL3 | CD8 | none |
| CD123 | BTNL3 | CD4 | none |
| CD123 | BTNL3 | b2c | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD123 | BTNL3 | CD137/41BB | none |
| CD123 | BTNL3 | ICOS | none |
| CD123 | BTNL3 | CD27 | none |
| CD123 | BTNL3 | CD28δ | none |
| CD123 | BTNL3 | CD80 | none |
| CD123 | BTNL3 | CD86 | none |
| CD123 | BTNL3 | OX40 | none |
| CD123 | BTNL3 | DAP10 | none |
| CD123 | BTNL3 | MyD88 | none |
| CD123 | BTNL3 | CD7 | none |
| CD123 | BTNL3 | DAP12 | none |
| CD123 | BTNL3 | MyD88 | none |
| CD123 | BTNL3 | CD7 | none |
| CD123 | NKG2D | CD28 | none |
| CD123 | NKG2D | CD8 | none |
| CD123 | NKG2D | CD4 | none |
| CD123 | NKG2D | b2c | none |
| CD123 | NKG2D | CD137/41BB | none |
| CD123 | NKG2D | ICOS | none |
| CD123 | NKG2D | CD27 | none |
| CD123 | NKG2D | CD28δ | none |
| CD123 | NKG2D | CD80 | none |
| CD123 | NKG2D | CD86 | none |
| CD123 | NKG2D | OX40 | none |
| CD123 | NKG2D | DAP10 | none |
| CD123 | NKG2D | MyD88 | none |
| CD123 | NKG2D | CD7 | none |
| CD123 | NKG2D | DAP12 | none |
| CD123 | NKG2D | MyD88 | none |
| CD123 | NKG2D | CD7 | none |

In some embodiments, the anti-CD123 binding agent is single chain variable fragment (scFv) antibody. The affinity/specificity of an anti-CD123 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CD123 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target CD123 and at least one additional tumor antigen. Also disclosed are CARs designed to work only in conjunction with another CAR that binds a different antigen, such as a tumor antigen. For example, in these embodiments, the endodomain of the disclosed CAR can contain only an signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, TIM3, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6, E7, sperm protein 17, SSEA-4, tyrosinase, TARP, VVT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, TIM3, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, pl80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed CD123-specific CARs that allow expression of the CD123-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either $CD4^+$ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic $CD8^+$ T lymphocytes. In some embodiments, the T cells comprise γδ T cells, which possess a distinct T-cell receptor (TCR) having one γ chain and one δ chain instead of α and β chains.

Natural-killer (NK) cells are $CD56^+CD3^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic $CD8^+$ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter DL, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against CD123-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to CD123.

Adoptive transfer of immune effector cells expressing chimeric antigen receptors is a promising anti-cancer therapeutic. Following the collection of a patient's immune effector cells, the cells may be genetically engineered to express the disclosed CD123-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any CD123-expressing cell in a subject undergoing unregulated growth, invasion, or metastasis. Cancers that express CD123 include prostate cancer, ovarian cancer, adenocarcinoma of the lung, breast cancer, endometrial cancer, gastric cancer, colon cancer, and pancreatic cancer. CD123 has also been found on Jurkat cells. In some aspects, the cancer is a gallbladder cancer, exocrine adenocarcinoma, or apocrine adenocarcinomas.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent is a targeted agent, such as ibrutinib or idelalisib.

In some embodiments, such an additional therapeutic agent is an epigenetic modifier such as azacitdine or vidaza.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen)

when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Screen for Anti-AML Antibodies

EL4 mouse lymphoma cells that express immunogen or irrelevant antigen were screened for anti-AML antibody binding. As shown in FIG. 1, EL4-empty, EL4-CD123, and EL4-CD33 cells were incubated together in each well of a 96 well plate. In addition an anti-CD123 PE antibody and hybridoma antibody, with putative anti-C33 reactivity, was included in the culture. The antibodies and cells were co-incubated, washed, and stained with Rat anti-mouse IgG APC. Positive binding was revealed by flow cytometry as anti-CD33/APC$^+$ and anti-CD123/PE$^-$.

Figure 2:
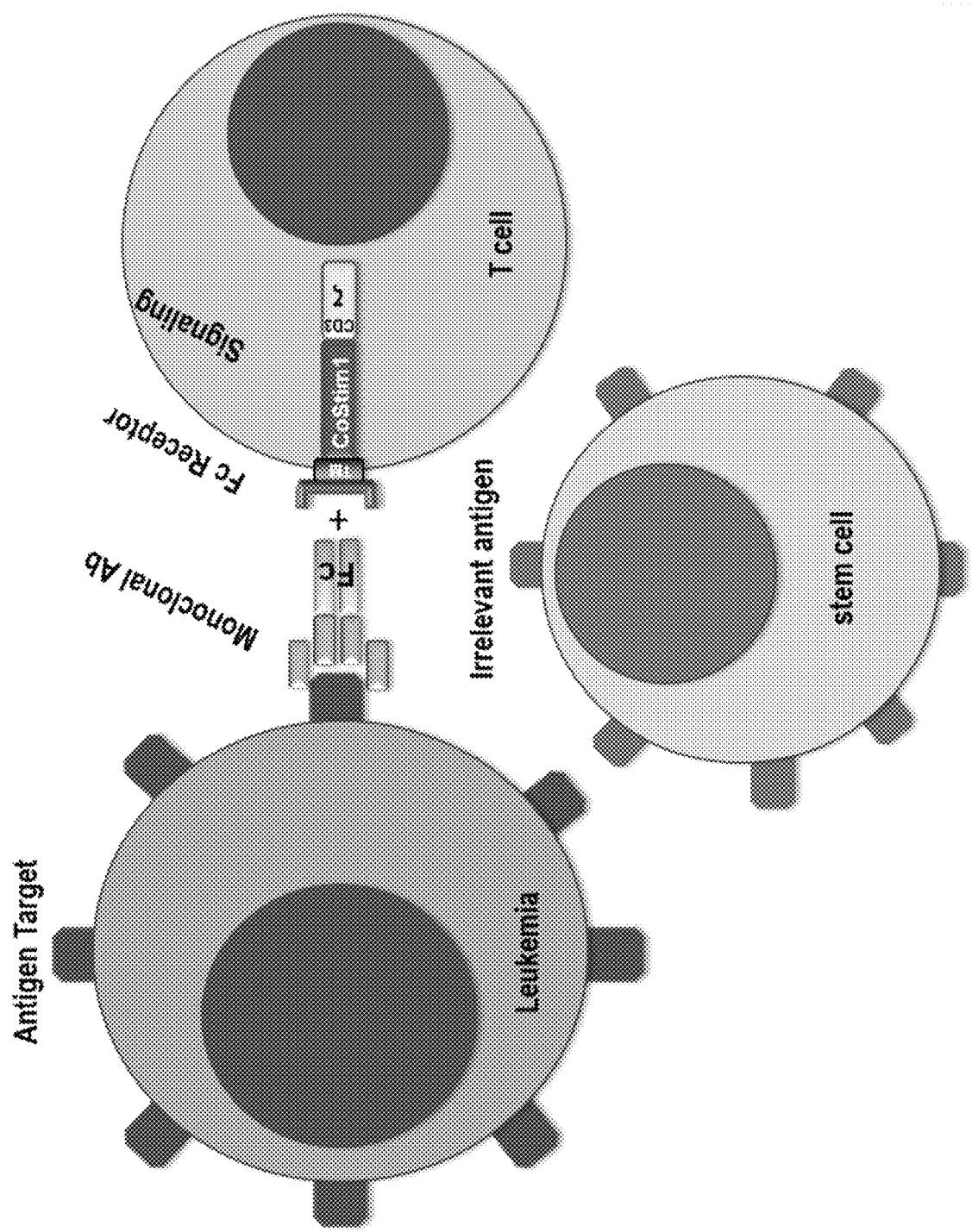
FIG. 2 illustrates secondary screening method for functional antibodies.

As illustrated in FIG. 2, chosen antibodies were subjected to a secondary, functional screening with Jurkat cells that express a CAR docking platform for antibodies and target cells. These antibodies were screened for T cell activation. 150 clones were selected based on EL4 binding. EL4 CD123 (target) and CD33 (negative control) were incubated with Jurkat mCD16 or mCD32 with its NFKB/RE GFP reporter. See Tables 5 and 6.

TABLE 5

| CD33 | 1A9 | 1B1 | 2H1 | 2H11 | 3D2 | 3E5 | 3F5 | 4E4 | 4E10 | 4F2 | 4G11 | 6A5 |
|---|---|---|---|---|---|---|---|---|---|---|---|---|
| | 7C1 | 7C12 | 7F7 | 9B12 | 9C5 | 9E10 | 9F12 | 9H6 | 10A12 | 10C11 | 10D8 | 11F12 |
| | 12B4 | 12F7 | 12F8 | 12G3 | 12G11 | 12H3 | 12H5 | 12H11 | 15A9 | 15A12 | 15E1 | 15G5 |
| | 16B5 | 17D2 | 17E7 | 17E9 | 21B12 | 22E7 | 24C5 | 32G4 | NS | L/D | CD123 | NO SUP |
| CD123 | 1A9 | 1B1 | 2H1 | 2H11 | 3D2 | 3E5 | 3F5 | 4E4 | 4E10 | 4F2 | 4G11 | 6A5 |
| | 7C1 | 7C12 | 7F7 | 9B12 | 9C5 | 9E10 | 9F12 | 9H6 | 10A12 | 10C11 | 10D8 | 11F12 |
| | 12B4 | 12F7 | 12F8 | 12G3 | 12G11 | 12H3 | 12H5 | 12H11 | 15A9 | 15A12 | 15E1 | 15G5 |
| | 16B5 | 17D2 | 17E7 | 17E9 | 21B12 | 22E7 | 24C5 | 32G4 | NS | L/D | CD123 | NO SUP |

CD33 = $1.53 \times 10^6$/ml = $30.6 \times 10^6$ total, 75% Live
CD123 = $4.28 \times 10^5$/ml = $20.1 \times 10^6$ total, 83% Live

TABLE 6

| Clone | CD123/APC+ | CD33/APC+ | Difference |
|---|---|---|---|
| 3F5 | 98.9 | 51.99 | 46.91 |
| 4E4 | 90.36 | 38.52 | 51.84 |
| 4E10 | 98.11 | 55.59 | 42.52 |
| 10C11 | 99 | 42.34 | 56.66 |
| 12H3 | 57.94 | 21 | 36.94 |
| 12H5 | 81.94 | 13.4 | 68.54 |
| 12H11 | 99.14 | 14.29 | 84.85 |

TABLE 6-continued

| Clone | CD123/APC+ | CD33/APC+ | Difference |
|---|---|---|---|
| 15A9 | 99.14 | 40.28 | 58.86 |
| 15A12 | 99.32 | 57.06 | 42.26 |
| 15G5 | 10.34 | 11.02 | −0.68 |
| 16B5 | 10.39 | 2.32 | 8.07 |
| 17E7 | 95.93 | 10.41 | 85.52 |

Figure 3:
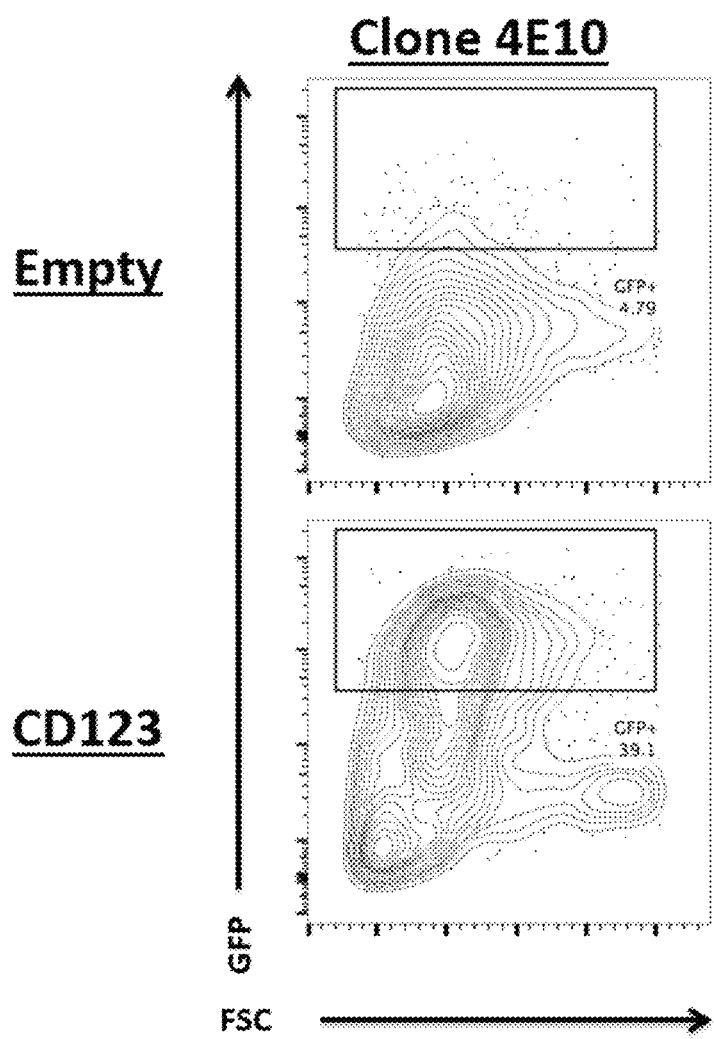
FIG. 3 shows Jurkat T cell activation measured by GFP flow cytometry for cultured EL4-CD123 or EL4-CD33 targets, hybridoma antibodies, and Jurkat cells modified to include either a CD16 or CD32 Fc receptor conjugated to 41BB and CD3zeta.
Figure 4A:
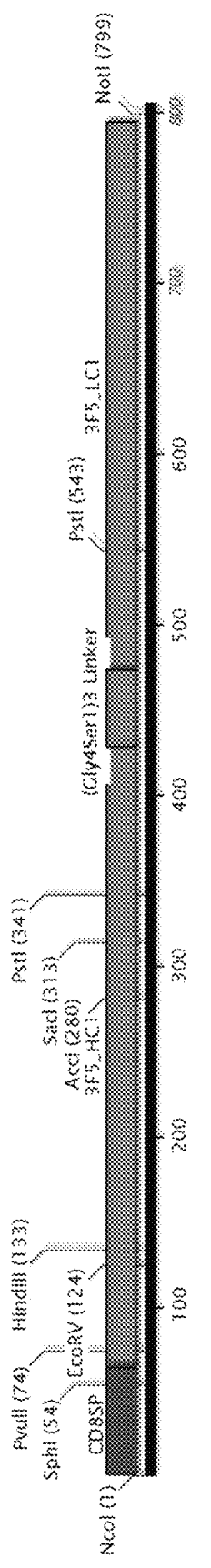
Figure 4B:
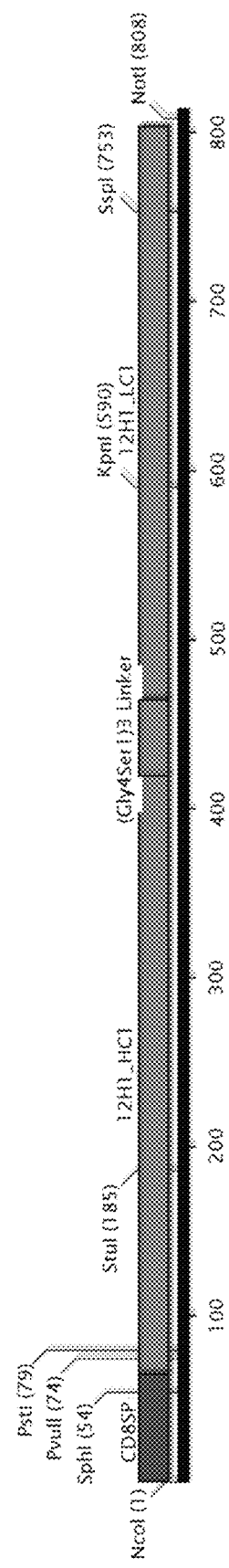
Figure 4C:
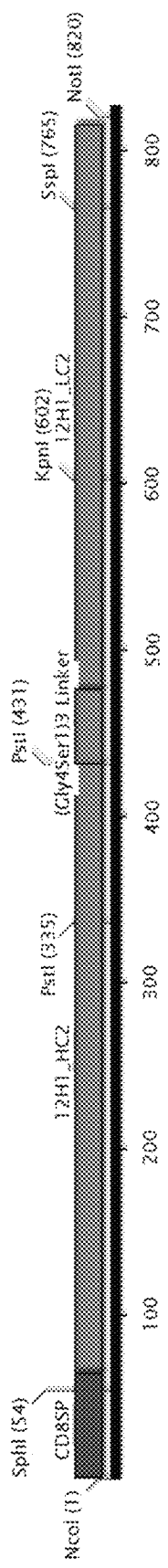
Figures 4G, 4H:
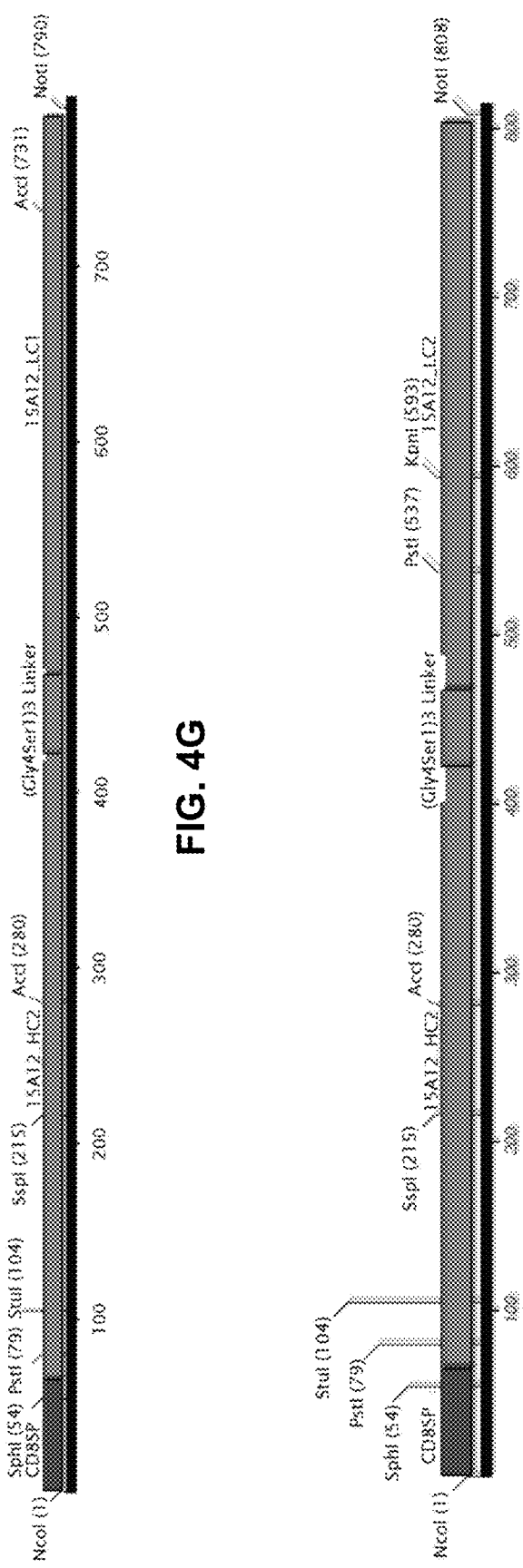

12 clones were selected for EL4-CD123 validation using CHO CD123 (target) or empty (negative control) and Jurkat mCD16-GFP or mCD32 as a reporter. $1 \times 10^4$ CHO cells were cultured into wells of a 96 well plate. Hybridoma supernatant (3G5, 4E4, etc), which included the putative anti-AML antibodies, were added to the culture media. Jurkat cells were modified to include either a CD16 or CD32 Fc receptor conjugated to human 41BB and CD3zeta. In addition, these Jurkat cells have a transgene GFP that is controlled by NFκB-responsive elements. The EL4 targets, hybridoma antibodies, and $1 \times 10^4$ Jurkat cells were incubated overnight and antibody ligation and Jurkat T cell activation was measured by GFP flow cytometry (FIG. 3).

CD123 Clones were selected after EL4 binding and Jurkat activation screening (Table 7).

TABLE 7

| Hybridoma Clone | Binding (APC+ %) | Activation (GFP+ %) |
|---|---|---|
| 27A3 | 55 | 37 |
| 33G3 | 63 | 35 |
| 36C2 | 70 | 34 |
| 6A11 | 2 | 20 |
| 35D5 | 63 | 7 |
| 38G5 | 56 | 6 |

Example 2: CD123 CARs

Figure 5:
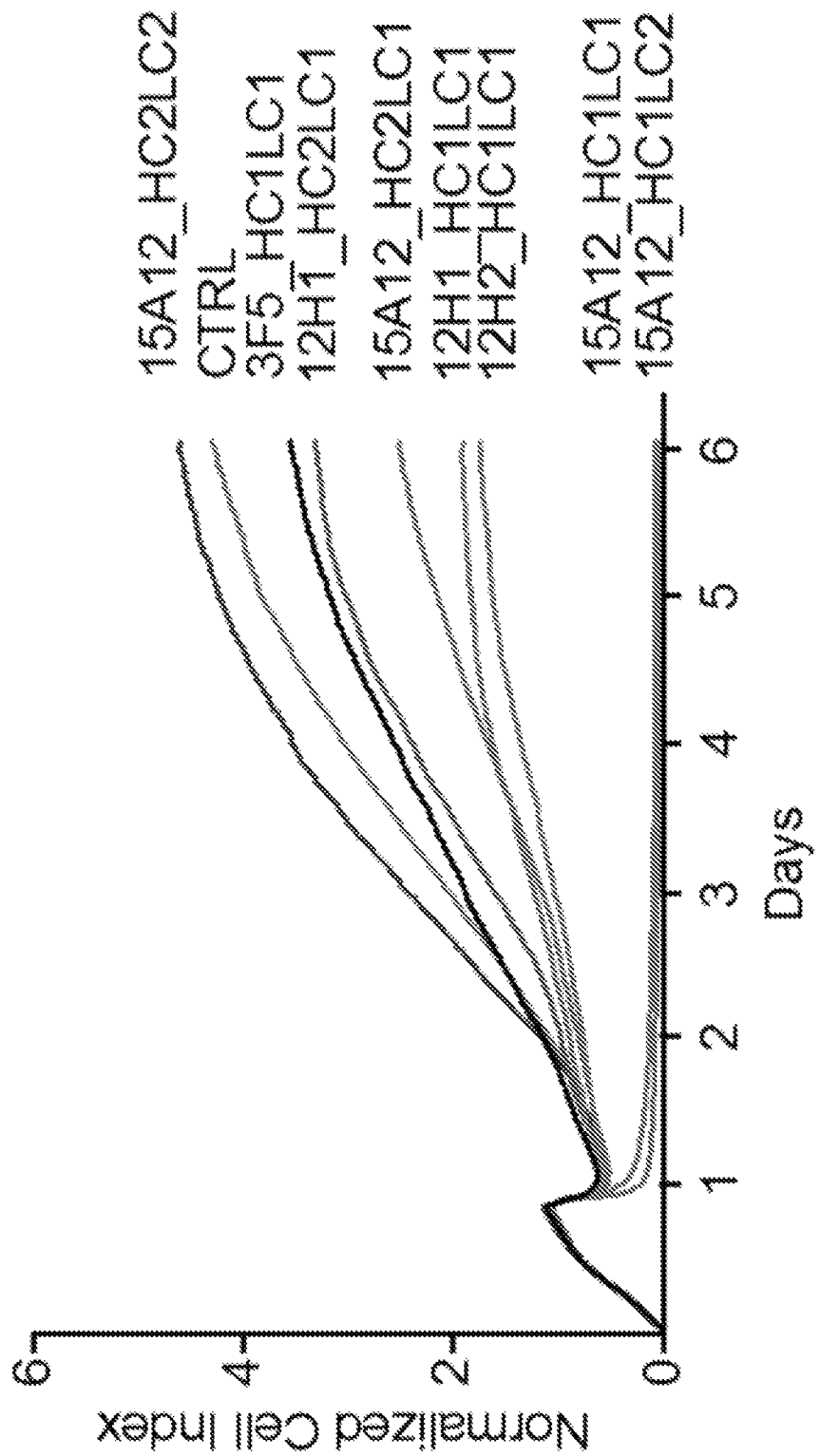
FIG. 5 is a bar graph showing effect of CD123 CARs on cytotoxicity. Various effector CD123 CARs or mock transduced T cells (CTRL) were co-cultured with target CHO-CD123 cells at a ratio of 10:1. Cell cytotoxicity (Normalized Cell Index) was analyzed via xCELLigence for a week. High Cell index indicates higher number of target cells and low cytotoxicity and low cell indicates higher cytotoxicity.
Figure 6A:
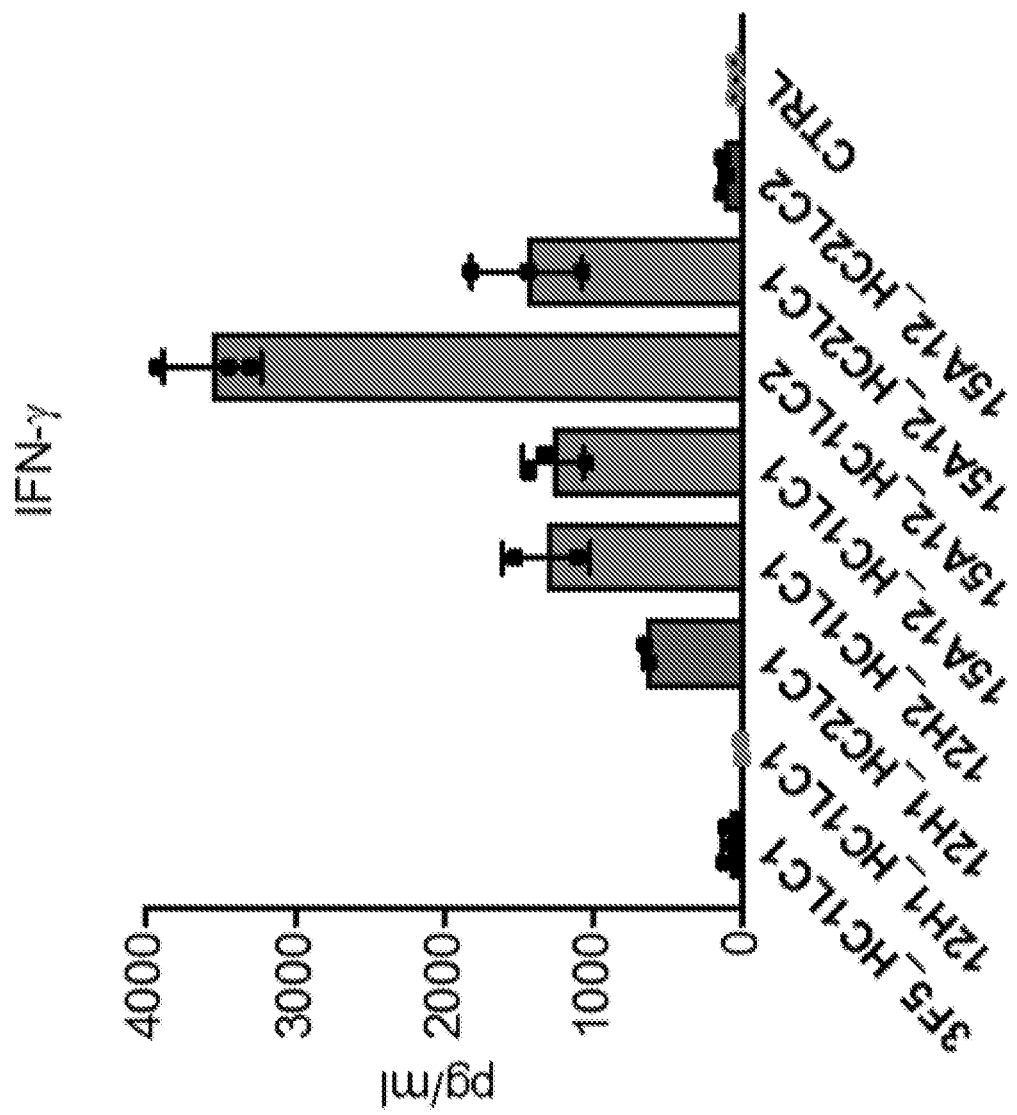
FIGS. 6A to 6C are bar graphs showing effect of CD123 CARs on cytokine release. Various Effector CD123 CARs or mock transduced T cells (CTRL) were activated with target CHO-CD123 cells at a ratio of 10:1. Cell supernatant was collected and analyzed via luminex for IFN-γ (FIG. 6A), TNF-α (FIG. 6B), and IL-6 (FIG. 6C) cytokine.
Figure 6B:
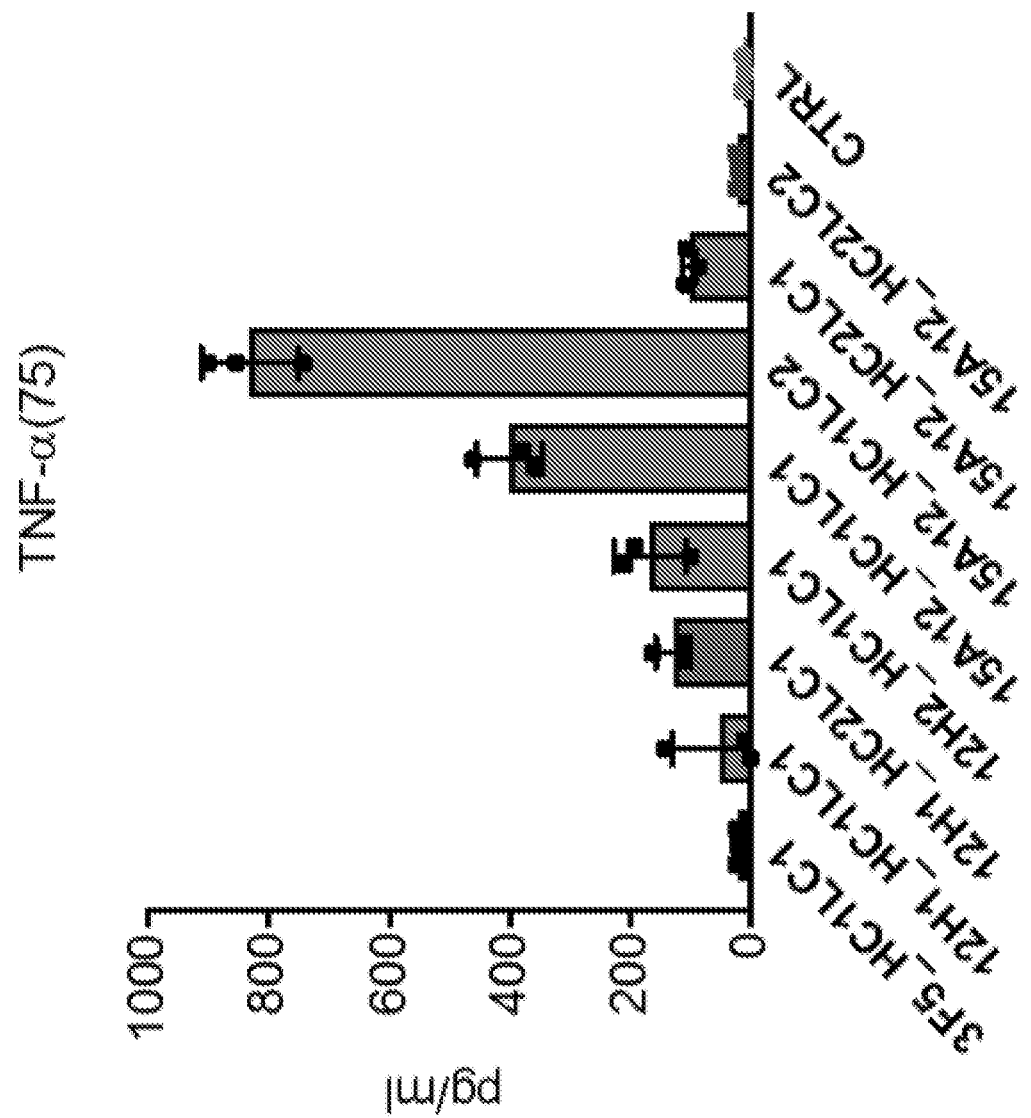
Figure 6C:
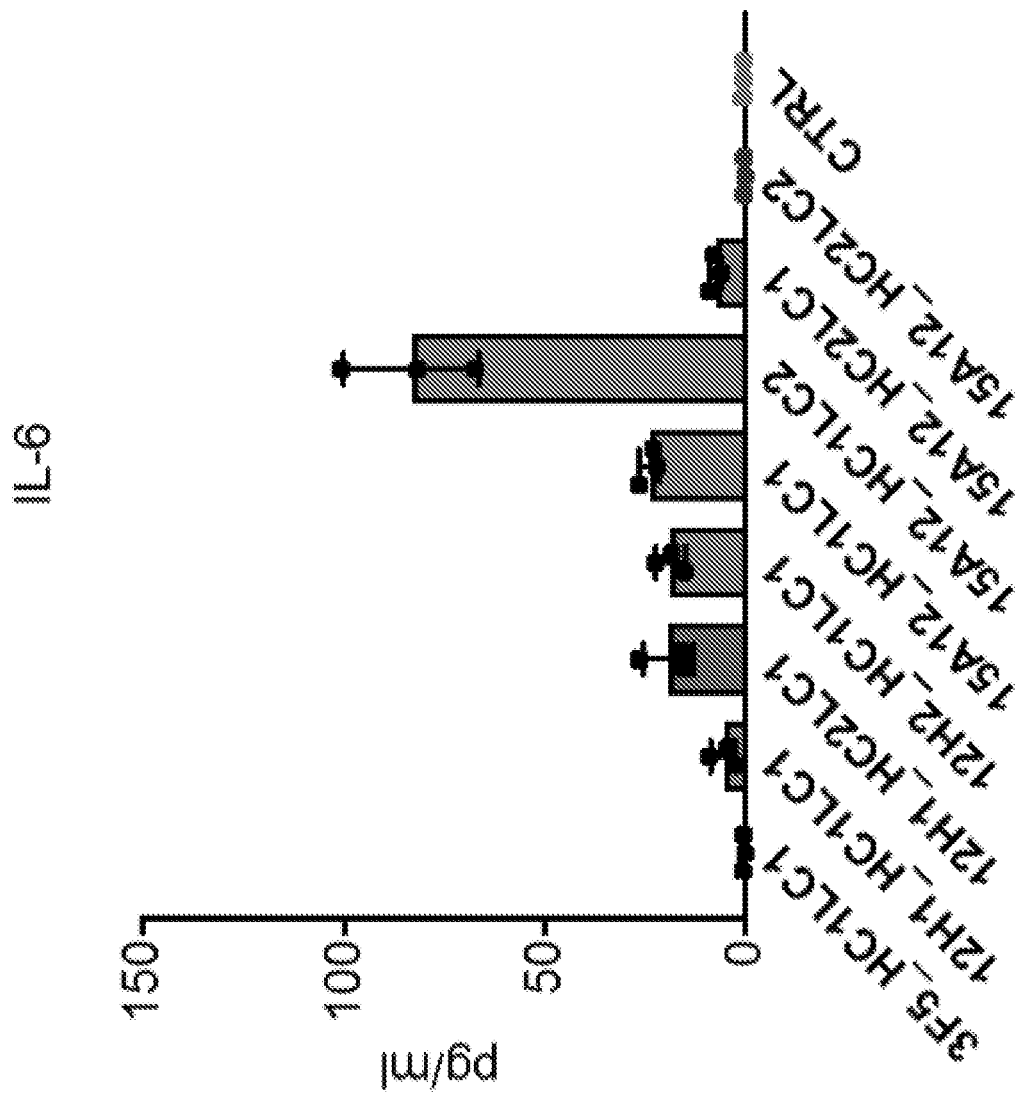
Figure 7:
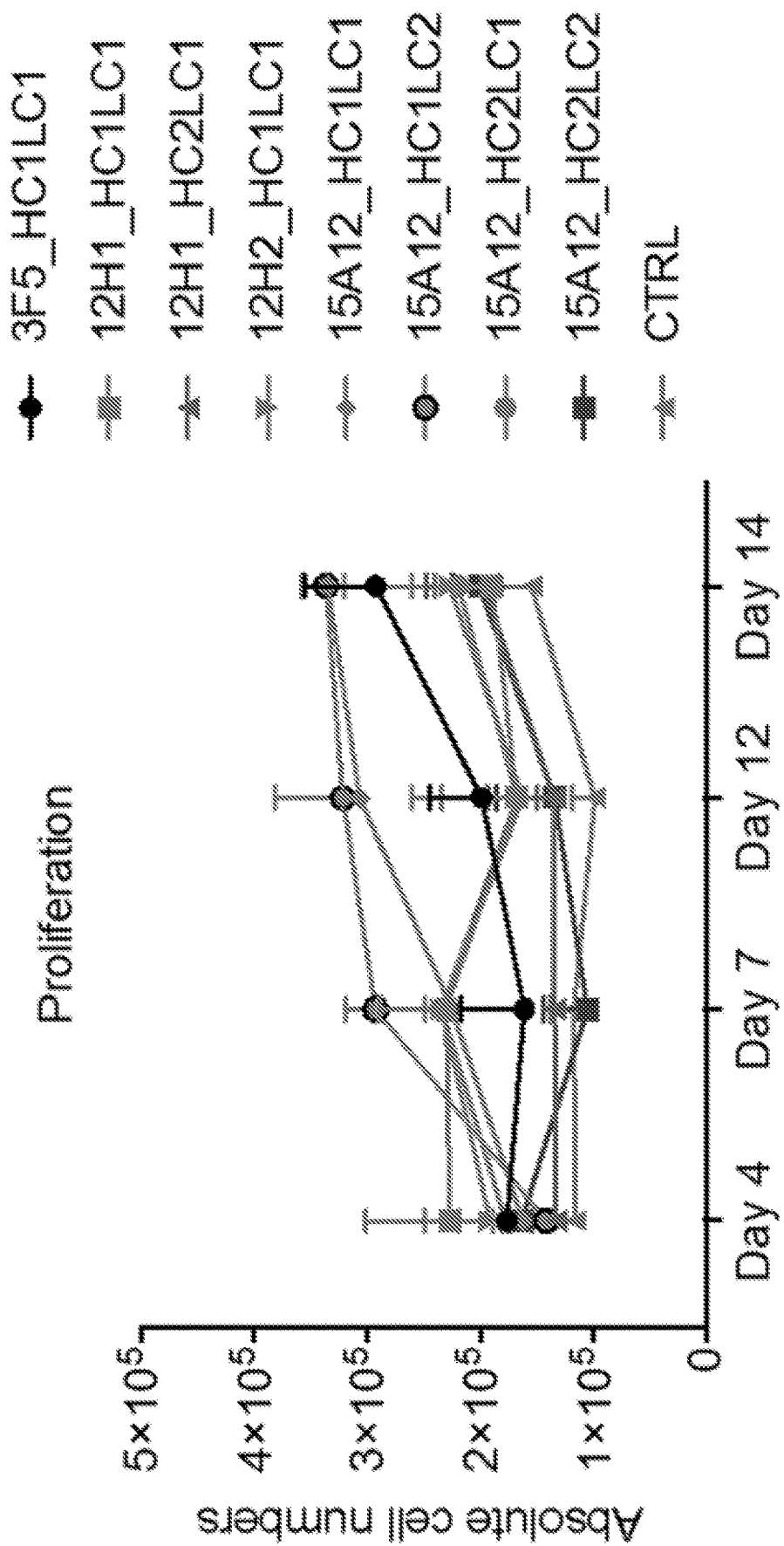
FIG. 7 is a graph showing effect of CD123 CARs on proliferation: Various Effector CD123 CARs or mock transduced T cells (CTRL) were activated with target CHO-CD123 cells at a ratio of 1:1. CART cells were counted on indicated days.
Figure 8:
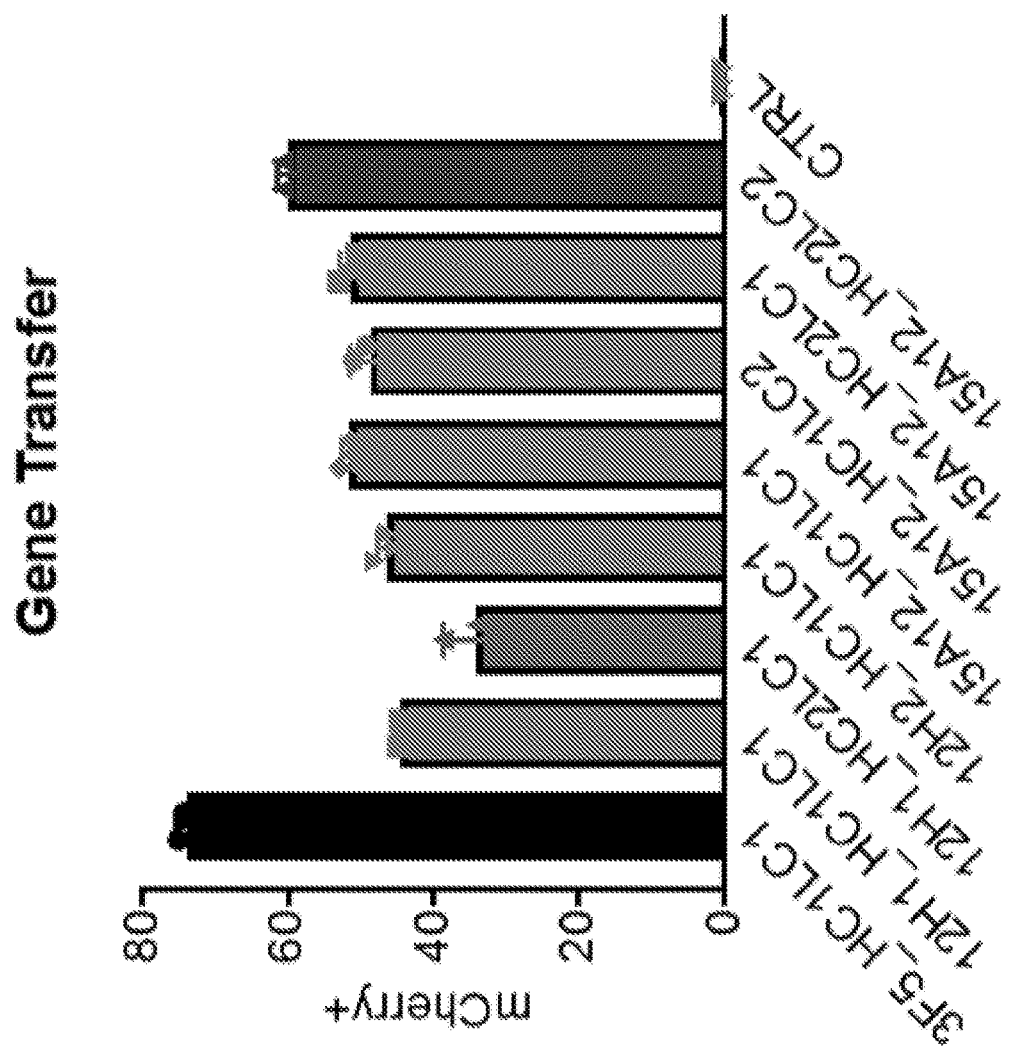
FIG. 8 is a bar graph showing gene transfer. T cells were isolated by density gradient centrifugation followed by a T-Cell isolation kit and stimulated with anti-CD3 and anti-CD28 beads in RPMI with recombinant human IL-2. Activated T cells were transduced on RetroNectin coated plates with anti-CD33 CAR retrovirus prepared from H29 and RD114 packaging cells. CD33 CAR T cells were de-beaded after approximately 7 days and evaluated for gene transfer. Mock transduced T cells (CTRL) were used as a control.

FIGS. 5 to 7 show the effects of CD123 CARs on cytotoxicity (FIG. 5), cytokine release (FIGS. 6A to 6C), and proliferation (FIG. 7) in CHO-CD123 cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a CD123 antigen binding domain, a transmembrane domain, an intracellular signaling domain, and a co-stimulatory signaling region, wherein the CD123 antigen binding domain is a single-chain variable fragment (scFv) of an antibody comprising a variable heavy ($V_H$) domain having CDR1, CDR2 and CDR3 sequences and a variable light ($V_L$) domain having CDR1, CDR2 and CDR3 sequences, and wherein (a) the CDR1 sequence of the $V_H$ domain comprises the amino acid sequence GYTFTDYN (SEQ ID NO:1), the CDR2 sequence of the $V_H$ domain comprises the amino acid sequence INPNNGGT (SEQ ID NO:2), the CDR3 sequence of the $V_H$ domain comprises the amino acid sequence ARKGYGGNYDYFDY (SEQ ID NO:3), the CDR1 sequence of the $V_L$ comprises the amino acid sequence QSIGTS (SEQ ID NO:4), the CDR2 sequence of the $V_L$ domain comprises the amino acid sequence YASx (SEQ ID NO:5), and the CDR3 sequence of the $V_L$ domain comprises the amino acid sequence QQSNSWPYT (SEQ ID NO:6); or (b) the CDR1 sequence of the $V_H$ domain comprises the amino acid sequence GFNIKDTY (SEQ ID NO:7), the CDR2 sequence of the $V_H$ domain comprises the amino acid sequence IDPANGNT (SEQ ID NO:9), the CDR3 sequence of the $V_H$ domain comprises the amino acid sequence ALYYYGGSLDY (SEQ ID NO:11), the CDR1 sequence of the $V_L$ comprises the amino acid sequence QSLLYSGNQKNY (SEQ ID NO:13), the CDR2 sequence of the $V_L$ domain comprises the amino acid sequence WASx (SEQ ID NO:14), and the CDR3 sequence of the $V_L$ domain comprises the amino acid sequence QQYYSYPRT (SEQ ID NO:15); or (c) the CDR1 sequence of the $V_H$ domain comprises the amino acid sequence GFSLSTYGMG (SEQ ID NO:8), the CDR2 sequence of the $V_H$ domain comprises the amino acid sequence IYWDDDK (SEQ ID NO:10), the CDR3 sequence of the $V_H$ domain comprises the amino acid sequence AQSLIYDGYYGFAY (SEQ ID NO:12), the CDR1 sequence of the $V_L$ comprises the amino acid sequence QSLLYSGNQKNY (SEQ ID NO:13), the CDR2 sequence of the $V_L$ domain comprises the amino acid sequence WASx (SEQ ID NO:14), and the CDR3 sequence of the $V_L$ domain comprises the amino acid sequence QQYYSYPRT (SEQ ID NO:15); or (d) the CDR1 sequence of the $V_H$ domain comprises the amino acid sequence GYTFTYYG (SEQ ID NO:16), the CDR2 sequence of the $V_H$ domain comprises the amino acid sequence INTYSGVP (SEQ ID NO:17), the CDR3 sequence of the $V_H$ domain comprises the amino acid sequence ARWIYYSDLYGMDY (SEQ ID NO:18), the CDR1 sequence of the $V_L$ comprises the amino acid sequence QSIVHSNGDTY (SEQ ID NO:19), the CDR2 sequence of the $V_L$ domain comprises the amino acid sequence KVSx (SEQ ID NO:20), and the CDR3 sequence of the $V_L$ domain comprises the amino acid sequence FQGSHVPWT (SEQ ID NO:21); or (e) the CDR1 sequence of the $V_H$ domain comprises the amino acid sequence GYTFSSYW (SEQ ID NO:22), the CDR2 sequence of the $V_H$ domain comprises the amino acid sequence INPSSGYT (SEQ ID NO:24), the CDR3 sequence of the $V_H$ domain comprises the amino acid sequence ARDGNYDHWYFDV (SEQ ID NO:26), or the CDR1 sequence of the $V_H$ domain comprises the amino acid sequence GYTLTTYL (SEQ ID NO:23), the CDR2 sequence of the $V_H$ domain comprises the amino acid sequence INPNSGSS (SEQ ID NO:25), the CDR3 sequence of the $V_H$ domain comprises the amino acid sequence AIRHYGGSLFDY (SEQ ID NO:27), and the CDR1 sequence of the $V_L$ comprises the amino acid sequence QDINSY (SEQ ID NO:28), the CDR2 sequence of the $V_L$ domain comprises the amino acid sequence RANx (SEQ ID NO:30), and the CDR3 sequence of the $V_L$ domain comprises the amino acid sequence LQYDELLT (SEQ ID NO:31), or the CDR1 sequence of the $V_L$ comprises the amino acid sequence QSLLNSRTRKNY (SEQ ID NO:29), the CDR2 sequence of the $V_L$ domain comprises the amino acid sequence RANx (SEQ ID NO:30), and the CDR3 sequence of the V_L domain comprises the amino acid sequence EQSYNLFT (SEQ ID NO:32).

2. The polypeptide of claim 1,
wherein the anti-CD123 scFv V_H domain comprises the amino acid sequence SEQ ID NO:33, and wherein the anti-CD123 scFv V_L domain comprises the amino acid sequence SEQ ID NO:39;
wherein the anti-CD123 scFv V_H domain comprises the amino acid sequence SEQ ID NO:34 or SEQ ID NO:35, and wherein the anti-CD123 scFv V_L domain comprises the amino acid sequence SEQ ID NO:40;
wherein the anti-CD123 scFv V_H domain comprises the amino acid sequence SEQ ID NO:36, and wherein the anti-CD123 scFv V_L domain comprises the amino acid sequence SEQ ID NO:41;
wherein the anti-CD123 scFv V_H domain comprises the amino acid sequence SEQ ID NO:37, or SEQ ID NO:38, and wherein the anti-CD123 scFv V_L domain comprises the amino acid sequence SEQ ID NO:42, or SEQ ID NO:43.

3. The polypeptide of claim 1, wherein the anti-CD123 scFv comprises the amino acid sequence SEQ ID NO:44, SEQ ID NO:45, SEQ ID NO:46, SEQ ID NO:47, SEQ ID NO:48, SEQ ID NO:49, SEQ ID NO:50, or SEQ ID NO:51.

4. The polypeptide of claim 1, wherein the costimulatory signaling region comprises the cytoplasmic domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

5. The polypeptide of claim 1, wherein the CAR polypeptide is defined by the formula:

SP-CD123-HG-TM-CSR-ISD; or

SP-CD123-HG-TM-ISD-CSR wherein "SP" represents a signal peptide,
wherein "CD123" represents a CD123-binding region,
wherein "HG" represents and optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

6. The polypeptide of claim 1, wherein the intracellular signaling domain comprises a CD3 zeta (CD3ζ) signaling domain.

7. The polypeptide of claim 1, wherein the polypeptide contains only an intracellular signaling domain or a co-stimulatory domain, but not both.

8. An isolated nucleic acid sequence encoding the recombinant polypeptide of claim 1.

9. A vector comprising the isolated nucleic acid sequence of claim 8.

10. A cell comprising the vector of claim 9.

11. The cell of claim 10, wherein the cell is selected from the group consisting of an αβT cell, γδT cell, a Natural Killer (NK) cells, a Natural Killer T (NKT) cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

12. The cell of claim 11, wherein the cell exhibits an anti-tumor immunity when the antigen binding domain of the CAR polypeptide binds to CD123.

13. The cell of claim 11, wherein the cell further comprise a second CAR polypeptide comprising a CD33 antigen binding domain, wherein the cell exhibits an anti-tumor immunity when both the antigen binding domain of the CAR binds to CD123 and the antigen binding domain of the second CAR binds to CD33.

14. A method of providing an anti-cancer immunity in a subject with a CD123-expressing cancer, the method comprising administering to the subject an effective amount of the cell of claim 12, thereby providing an anti-tumor immunity in the mammal.

15. The method of claim 14, wherein the immune effector cell is selected from the group consisting of a T cell, a Natural Killer (NK) cell, a cytotoxic T lymphocyte (CTL), and a regulatory T cell.

16. The method of claim 14, further comprising administering to the subject a checkpoint inhibitor.

17. The method of claim 16, wherein the checkpoint inhibitor comprises an anti-PD-1 antibody, anti-PD-L1 antibody, anti-CTLA-4 antibody, or a combination thereof.

18. The method of claim 14, wherein the cancer comprises Acute Myeloid Leukemia (AML), blastic plasmocytoid dendritic cell neoplasm, hairy cell leukemia, and Acute Lymphoblastic Leukemia.

* * * * *

SEQUENCE LISTING

```
<160> NUMBER OF SEQ ID NOS: 60

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Asp Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Asn Pro Asn Asn Gly Gly Thr
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Ala Arg Lys Gly Tyr Gly Gly Asn Tyr Asp Tyr Phe Asp Tyr
1               5                   10

<210> SEQ ID NO 4
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gln Ser Ile Gly Thr Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Tyr Ala Ser Xaa
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Ser Asn Ser Trp Pro Tyr Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gly Phe Asn Ile Lys Asp Thr Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Gly Phe Ser Leu Ser Thr Tyr Gly Met Gly
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Ile Asp Pro Ala Asn Gly Asn Thr
1               5
```

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Ile Tyr Trp Asp Asp Asp Lys
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Ala Leu Tyr Tyr Tyr Gly Gly Ser Leu Asp Tyr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Ala Gln Ser Leu Ile Tyr Asp Gly Tyr Tyr Gly Phe Ala Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Construct

<400> SEQUENCE: 13

Gln Ser Leu Leu Tyr Ser Gly Asn Gln Lys Asn Tyr
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Trp Ala Ser Xaa
1

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Gln Gln Tyr Tyr Ser Tyr Pro Arg Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Gly Tyr Thr Phe Thr Tyr Tyr Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ile Asn Thr Tyr Ser Gly Val Pro
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Ala Arg Trp Ile Tyr Tyr Ser Asp Leu Tyr Gly Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Gln Ser Ile Val His Ser Asn Gly Asp Thr Tyr
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 20

Lys Val Ser Xaa
1

<210> SEQ ID NO 21
<211> LENGTH: 9
<212> TYPE: PRT
<213> ORGANISM: Artificial Sequence
<220> FEATURE:

```
<223> OTHER INFORMATION: Synthetic Construct

<400> SEQUENCE: 21

Phe Gln Gly Ser His Val Pro Trp Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Gly Tyr Thr Phe Ser Ser Tyr Trp
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Gly Tyr Thr Leu Thr Thr Tyr Leu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Ile Asn Pro Ser Ser Gly Tyr Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Ile Asn Pro Asn Ser Gly Ser Ser
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26

Ala Arg Asp Gly Asn Tyr Asp His Trp Tyr Phe Asp Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 27

Ala Ile Arg His Tyr Gly Gly Ser Leu Phe Asp Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Gln Asp Ile Asn Ser Tyr
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Gln Ser Leu Leu Asn Ser Arg Thr Arg Lys Asn Tyr
1               5                   10

<210> SEQ ID NO 30
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Arg Ala Asn Xaa
1

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Leu Gln Tyr Asp Glu Leu Leu Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Glu Gln Ser Tyr Asn Leu Phe Thr
1               5

<210> SEQ ID NO 33
<211> LENGTH: 121
<212> TYPE: PRT
```

<213> ORGANISM: Artificial Sequence
<220> FEATURE:
<223> OTHER INFORMATION: Synthetic Construct

<400> SEQUENCE: 33

Glu Val Gln Leu Gln Gln Ser Gly Pro Glu Leu Val Lys Pro Gly Ser
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Thr Ile Asn Pro Asn Asn Gly Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Lys Gly Tyr Gly Gly Asn Tyr Asp Tyr Phe Asp Tyr Trp Gly
            100                 105                 110

Gln Gly Thr Thr Leu Thr Val Ser Ser
        115                 120

<210> SEQ ID NO 34
<211> LENGTH: 118
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Ile Tyr Ala Ser Lys Phe
        50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Leu Tyr Tyr Tyr Gly Gly Ser Leu Asp Tyr Trp Gly Gln Gly Thr
            100                 105                 110

Thr Leu Thr Val Ser Ser
        115

<210> SEQ ID NO 35
<211> LENGTH: 122
<212> TYPE: PRT
<213> ORGANISM: Artificial Sequence
<220> FEATURE:
<223> OTHER INFORMATION: Synthetic Construct

<400> SEQUENCE: 35

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
                20                  25                  30

-continued

Gly Met Gly Val Ser Trp Ile Arg Gln Pro Ser Gly Lys Gly Leu Glu
            35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Ser Leu Ile Tyr Asp Gly Tyr Tyr Gly Phe Ala Tyr Trp
                100                 105                 110

Gly Gln Gly Thr Leu Val Thr Val Ser Ala
            115                 120

<210> SEQ ID NO 36
<211> LENGTH: 121
<212> TYPE: PRT
<213> ORGANISM: Artificial Sequence
<220> FEATURE:
<223> OTHER INFORMATION: Synthetic Construct

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Tyr Tyr
            20                  25                  30

Gly Met Asn Trp Val Lys Gln Ala Pro Gly Lys Gly Leu Glu Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Val Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Ile Tyr Tyr Ser Asp Leu Tyr Gly Met Asp Tyr Trp Gly
                100                 105                 110

Gln Gly Thr Ser Val Thr Val Ser Ser
            115                 120

<210> SEQ ID NO 37
<211> LENGTH: 120
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
            20                  25                  30

Trp Met His Trp Leu Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys

```
                    85                  90                  95

Ala Arg Asp Gly Asn Tyr Asp His Trp Tyr Phe Asp Val Trp Gly Thr
                100                 105                 110

Gly Thr Thr Val Thr Val Ser Ser
            115                 120

<210> SEQ ID NO 38
<211> LENGTH: 119
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Gln Gln Pro Gly Ala Glu Leu Val Arg Pro Gly Ala
1               5                   10                  15

Ser Val Lys Met Ser Cys Lys Ala Ser Gly Tyr Thr Leu Thr Thr Tyr
                20                  25                  30

Leu Met Asp Trp Val Lys Gln Arg Leu Gly Gln Gly Phe Glu Trp Ile
            35                  40                  45

Gly Asn Ile Asn Pro Asn Ser Gly Ser Ser Asn Tyr Asn Glu Lys Phe
50                  55                  60

Lys Gly Lys Ala Lys Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Arg His Tyr Gly Gly Ser Leu Phe Asp Tyr Trp Gly Gln Gly
                100                 105                 110

Thr Thr Leu Thr Val Ser Ser
            115

<210> SEQ ID NO 39
<211> LENGTH: 107
<212> TYPE: PRT
<213> ORGANISM: Artificial Sequence
<220> FEATURE:
<223> OTHER INFORMATION: Synthetic Construct

<400> SEQUENCE: 39

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Tyr
                85                  90                  95

Thr Phe Gly Gly Gly Thr Lys Leu Glu Ile Lys
                100                 105

<210> SEQ ID NO 40
<211> LENGTH: 113
<212> TYPE: PRT
<213> ORGANISM: Artificial Sequence
<220> FEATURE:
```

<223> OTHER INFORMATION: Synthetic Construct

<400> SEQUENCE: 40

Asp Ile Val Met Ser Gln Ser Pro Ser Ser Leu Ala Val Ser Val Gly
1               5                   10                  15

Glu Arg Val Thr Met Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Arg Thr Phe Gly Gly Gly Thr Lys Leu Glu Ile
            100                 105                 110

Lys

<210> SEQ ID NO 41
<211> LENGTH: 112
<212> TYPE: PRT
<213> ORGANISM: Artificial Sequence
<220> FEATURE:
<223> OTHER INFORMATION: Synthetic Construct

<400> SEQUENCE: 41

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Trp Thr Phe Gly Gly Gly Thr Lys Leu Glu Ile Lys
            100                 105                 110

<210> SEQ ID NO 42
<211> LENGTH: 106
<212> TYPE: PRT
<213> ORGANISM: Artificial Sequence
<220> FEATURE:
<223> OTHER INFORMATION: Synthetic Construct

<400> SEQUENCE: 42

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

```
Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Leu Leu Thr
                 85                  90                  95

Phe Gly Ala Gly Thr Lys Leu Glu Leu Lys
            100                 105
```

<210> SEQ ID NO 43
<211> LENGTH: 112
<212> TYPE: PRT
<213> ORGANISM: Artificial Sequence
<220> FEATURE:
<223> OTHER INFORMATION: Synthetic Construct

<400> SEQUENCE: 43

```
Asp Ile Val Met Ser Gln Ser Pro Ser Ser Leu Ala Val Ser Ala Gly
 1               5                  10                  15

Glu Arg Val Thr Met Ser Cys Arg Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Leu Ala Val Tyr Tyr Cys Glu Gln
                 85                  90                  95

Ser Tyr Asn Leu Phe Thr Phe Gly Ser Gly Thr Lys Leu Glu Ile Lys
            100                 105                 110
```

<210> SEQ ID NO 44
<211> LENGTH: 243
<212> TYPE: PRT
<213> ORGANISM: Artificial Sequence
<220> FEATURE:
<223> OTHER INFORMATION: Synthetic Construct

<400> SEQUENCE: 44

```
Glu Val Gln Leu Gln Gln Ser Gly Pro Glu Leu Val Lys Pro Gly Ser
 1               5                  10                  15

Ser Val Lys Ile Ser Cys Lys Ala Ser Gly Tyr Thr Phe Thr Asp Tyr
                 20                  25                  30

Asn Met Asp Trp Val Lys Gln Ser His Gly Lys Ser Leu Glu Trp Ile
             35                  40                  45

Gly Thr Ile Asn Pro Asn Asn Gly Gly Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Lys Gly Tyr Gly Gly Asn Tyr Asp Tyr Phe Asp Tyr Trp Gly
            100                 105                 110

Gln Gly Thr Thr Leu Thr Val Ser Gly Gly Gly Gly Ser Gly Gly
            115                 120                 125

Gly Gly Ser Gly Gly Gly Ser Asp Ile Leu Leu Thr Gln Ser Pro
        130                 135                 140

Ala Ile Leu Ser Val Ser Pro Gly Glu Arg Val Ser Phe Ser Cys Arg
```

```
                145                 150                 155                 160
Ala Ser Gln Ser Ile Gly Thr Ser Ile His Trp Tyr Gln Gln Arg Thr
                165                 170                 175

Asn Gly Ser Pro Arg Leu Leu Ile Lys Tyr Ala Ser Glu Ser Ile Ser
            180                 185                 190

Gly Ile Pro Ser Arg Phe Ser Gly Ser Gly Ser Gly Thr Asp Phe Thr
        195                 200                 205

Leu Ser Ile Asn Ser Val Glu Ser Glu Asp Ile Ala Asp Tyr Tyr Cys
    210                 215                 220

Gln Gln Ser Asn Ser Trp Pro Tyr Thr Phe Gly Gly Gly Thr Lys Leu
225                 230                 235                 240

Glu Ile Lys

<210> SEQ ID NO 45
<211> LENGTH: 246
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Leu Tyr Tyr Tyr Gly Gly Ser Leu Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Ser Gln Ser Pro Ser Ser Leu
    130                 135                 140

Ala Val Ser Val Gly Glu Arg Val Thr Met Ser Cys Lys Ser Ser Gln
145                 150                 155                 160

Ser Leu Leu Tyr Ser Gly Asn Gln Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Lys Ala Glu Asp Leu Ala Val
    210                 215                 220

Tyr Tyr Cys Gln Gln Tyr Tyr Ser Tyr Pro Arg Thr Phe Gly Gly Gly
225                 230                 235                 240

Thr Lys Leu Glu Ile Lys
                245

<210> SEQ ID NO 46
```

<211> LENGTH: 250
<212> TYPE: PRT
<213> ORGANISM: Artificial Sequence
<220> FEATURE:
<223> OTHER INFORMATION: Synthetic Construct

<400> SEQUENCE: 46

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Ser Leu Ile Tyr Asp Gly Tyr Tyr Gly Phe Ala Tyr Trp
            100                 105                 110

Gly Gln Gly Thr Leu Val Thr Val Ser Ala Gly Gly Gly Ser Gly
        115                 120                 125

Gly Gly Gly Ser Gly Gly Gly Ser Asp Ile Val Met Ser Gln Ser
    130                 135                 140

Pro Ser Ser Leu Ala Val Ser Val Gly Glu Arg Val Thr Met Ser Cys
145                 150                 155                 160

Lys Ser Ser Gln Ser Leu Leu Tyr Ser Gly Asn Gln Lys Asn Tyr Leu
                165                 170                 175

Ala Trp Tyr Gln Gln Lys Pro Gly Gln Ser Pro Lys Leu Leu Ile Tyr
            180                 185                 190

Trp Ala Ser Thr Arg Glu Ser Gly Val Pro Asp Arg Phe Thr Gly Ser
        195                 200                 205

Gly Ser Gly Thr Asp Phe Thr Leu Thr Ile Ser Ser Val Lys Ala Glu
    210                 215                 220

Asp Leu Ala Val Tyr Tyr Cys Gln Gln Tyr Tyr Ser Tyr Pro Arg Thr
225                 230                 235                 240

Phe Gly Gly Gly Thr Lys Leu Glu Ile Lys
                245                 250
```

<210> SEQ ID NO 47
<211> LENGTH: 248
<212> TYPE: PRT
<213> ORGANISM: Artificial Sequence
<220> FEATURE:
<223> OTHER INFORMATION: Synthetic Construct

<400> SEQUENCE: 47

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Tyr Tyr
            20                  25                  30

Gly Met Asn Trp Val Lys Gln Ala Pro Gly Lys Gly Leu Glu Trp Met
        35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Thr Ser Val Ser Thr Ala Tyr
```

65                  70                  75                  80
Leu Gln Ile Asn Asn Leu Lys Asn Glu Asp Thr Ala Thr Tyr Phe Cys
                    85                  90                  95

Ala Arg Trp Ile Tyr Tyr Ser Asp Leu Tyr Gly Met Asp Tyr Trp Gly
                    100                 105                 110

Gln Gly Thr Ser Val Thr Val Ser Ser Gly Gly Gly Ser Gly Gly
                    115                 120                 125

Gly Gly Ser Gly Gly Gly Ser Asp Val Leu Met Thr Gln Ser Pro
            130                 135                 140

Leu Ser Leu Pro Val Ser Leu Gly Asp Gln Ala Ser Ile Ser Cys Arg
145                 150                 155                 160

Ser Ser Gln Ser Ile Val His Ser Asn Gly Asp Thr Tyr Leu Glu Trp
                    165                 170                 175

Tyr Leu Gln Lys Pro Gly Gln Ser Pro Lys Leu Leu Ile Tyr Lys Val
                    180                 185                 190

Ser Asn Arg Phe Ser Gly Val Pro Asp Arg Phe Ser Gly Ser Gly Ser
                    195                 200                 205

Gly Thr Asp Phe Thr Leu Lys Ile Ser Arg Val Glu Ala Glu Asp Leu
            210                 215                 220

Gly Val Tyr His Cys Phe Gln Gly Ser His Val Pro Trp Thr Phe Gly
225                 230                 235                 240

Gly Gly Thr Lys Leu Glu Ile Lys
                245

<210> SEQ ID NO 48
<211> LENGTH: 241
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
                20                  25                  30

Trp Met His Trp Leu Lys Gln Arg Pro Gly Gln Gly Leu Glu Trp Ile
            35                  40                  45

Gly Tyr Ile Asn Pro Ser Ser Gly Tyr Thr Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Asn Tyr Asp His Trp Tyr Phe Asp Val Trp Gly Thr
                100                 105                 110

Gly Thr Thr Val Thr Val Ser Ser Gly Gly Gly Gly Ser Gly Gly Gly
            115                 120                 125

Gly Ser Gly Gly Gly Gly Ser Asp Ile Lys Met Thr Gln Ser Pro Ser
        130                 135                 140

Ser Met Tyr Ala Ser Leu Gly Glu Arg Val Thr Ile Thr Cys Lys Ala
145                 150                 155                 160

Ser Gln Asp Ile Asn Ser Tyr Leu Ser Trp Phe Gln Gln Lys Pro Gly
                165                 170                 175

Lys Ser Pro Lys Thr Leu Ile Tyr Arg Ala Asn Arg Leu Val Asp Gly

-continued

```
                180                 185                 190
Val Pro Ser Arg Phe Ser Gly Ser Gly Ser Gln Asp Tyr Ser Leu
            195                 200                 205

Thr Ile Ser Ser Leu Glu Tyr Glu Asp Met Gly Ile Tyr Tyr Cys Leu
        210                 215                 220

Gln Tyr Asp Glu Leu Leu Thr Phe Gly Ala Gly Thr Lys Leu Glu Leu
225                 230                 235                 240

Lys

<210> SEQ ID NO 49
<211> LENGTH: 247
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
            20                  25                  30

Trp Met His Trp Leu Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Asn Tyr Asp His Trp Tyr Phe Asp Val Trp Gly Thr
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Val Met Ser Gln Ser Pro Ser
    130                 135                 140

Ser Leu Ala Val Ser Ala Gly Glu Arg Val Thr Met Ser Cys Arg Ser
145                 150                 155                 160

Ser Gln Ser Leu Leu Asn Ser Arg Thr Arg Lys Asn Tyr Leu Ala Trp
                165                 170                 175

Tyr Gln Gln Lys Pro Gly Gln Ser Pro Lys Leu Leu Ile Tyr Trp Ala
            180                 185                 190

Ser Thr Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Leu
    210                 215                 220

Ala Val Tyr Tyr Cys Glu Gln Ser Tyr Asn Leu Phe Thr Phe Gly Ser
225                 230                 235                 240

Gly Thr Lys Leu Glu Ile Lys
                245

<210> SEQ ID NO 50
<211> LENGTH: 240
<212> TYPE: PRT
<213> ORGANISM: Artificial Sequence
<220> FEATURE:
<223> OTHER INFORMATION: Synthetic Construct
```

```
<400> SEQUENCE: 50

Gln Val Gln Leu Gln Gln Pro Gly Ala Glu Leu Val Arg Pro Gly Ala
1               5                  10                  15

Ser Val Lys Met Ser Cys Lys Ala Ser Gly Tyr Thr Leu Thr Thr Tyr
            20                  25                  30

Leu Met Asp Trp Val Lys Gln Arg Leu Gly Gln Gly Phe Glu Trp Ile
        35                  40                  45

Gly Asn Ile Asn Pro Asn Ser Gly Ser Ser Asn Tyr Asn Glu Lys Phe
    50                  55                  60

Lys Gly Lys Ala Lys Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Arg His Tyr Gly Gly Ser Leu Phe Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Gln Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Glu Tyr Glu Asp Met Gly Ile Tyr Tyr Cys Leu Gln
    210                 215                 220

Tyr Asp Glu Leu Leu Thr Phe Gly Ala Gly Thr Lys Leu Glu Leu Lys
225                 230                 235                 240

<210> SEQ ID NO 51
<211> LENGTH: 246
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Gln Gln Pro Gly Ala Glu Leu Val Arg Pro Gly Ala
1               5                  10                  15

Ser Val Lys Met Ser Cys Lys Ala Ser Gly Tyr Thr Leu Thr Thr Tyr
            20                  25                  30

Leu Met Asp Trp Val Lys Gln Arg Leu Gly Gln Gly Phe Glu Trp Ile
        35                  40                  45

Gly Asn Ile Asn Pro Asn Ser Gly Ser Ser Asn Tyr Asn Glu Lys Phe
    50                  55                  60

Lys Gly Lys Ala Lys Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Arg His Tyr Gly Gly Ser Leu Phe Asp Tyr Trp Gly Gln Gly
            100                 105                 110

Thr Thr Leu Thr Val Ser Ser Gly Gly Gly Gly Ser Gly Gly Gly Gly
```

```
            115                 120                 125
Ser Gly Gly Gly Ser Asp Ile Val Met Ser Gln Ser Pro Ser Ser
        130                 135                 140

Leu Ala Val Ser Ala Gly Glu Arg Val Thr Met Ser Cys Arg Ser
145                 150                 155                 160

Gln Ser Leu Leu Asn Ser Arg Thr Arg Lys Asn Tyr Leu Ala Trp Tyr
                165                 170                 175

Gln Gln Lys Pro Gly Gln Ser Pro Lys Leu Leu Ile Tyr Trp Ala Ser
            180                 185                 190

Thr Arg Glu Ser Gly Val Pro Asp Arg Phe Ser Gly Ser Gly Ser Gly
                195                 200                 205

Thr Asp Phe Thr Leu Thr Ile Ser Ser Val Gln Ala Glu Asp Leu Ala
        210                 215                 220

Val Tyr Tyr Cys Glu Gln Ser Tyr Asn Leu Phe Thr Phe Gly Ser Gly
225                 230                 235                 240

Thr Lys Leu Glu Ile Lys
                245

<210> SEQ ID NO 52
<211> LENGTH: 806
<212> TYPE: DNA
<213> ORGANISM: Artificial Sequence
<220> FEATURE:
<223> OTHER INFORMATION: Synthetic Construct

<400> SEQUENCE: 52
ccatggccct cccggtaacg gctctgctgc ttccactcgc actgctcttg catgctgcca      60
gaccagaggt ccagctgcaa cagtctggac ctgagctggt gaagcctggg tcttcagtga     120
agatatcctg caaagcttct ggatacacat tcactgacta caacatggac tgggtgaagc     180
agagtcatgg aaagagcctt gagtggattg aactattaa tcctaacaat ggtggtacta     240
gctacaacca gaagttcaag ggcaaggcca cattgactgt agacaagtcc tccagcacag     300
cctacatgga gctccgcagc ctgacatctg aagactctgc agtctattac tgtgcaagaa     360
agggctatgg tggtaactac gactactttg actactgggg ccaaggcacc actctcacag     420
tctcctcagg tggaggtgga tcaggtggag gtggatctgg tggaggtgga tctgacatct     480
tgctgactca gtctccagcc atcctgtctg tgagtccagg agaaagagtc agtttctcct     540
gcagggccag tcagagcatt ggcacaagca tacactggta tcagcaaaga acaaatggtt     600
ctccaaggct tctcataaag tatgcttctg agtctatctc tgggttccct tccaggttta     660
gtggcagtgg atcagggaca gatttttactc ttagcatcaa cagtgtggag tctgaagata     720
ttgcagatta ttactgtcaa caaagtaata gctggccgta cacgttcgga ggggggacca     780
agctggaaat aaaacgggcg gccgca                                          806

<210> SEQ ID NO 53
<211> LENGTH: 804
<212> TYPE: DNA
<213> ORGANISM: Artificial Sequence
<220> FEATURE:
<223> OTHER INFORMATION: Synthetic Construct

<400> SEQUENCE: 53
atggccctcc cggtaacggc tctgctgctt ccactcgcac tgctcttgca tgctgccaga      60
ccagaggttc agctgcagca gtctggggca gagcttgtga agccaggggc ctcagtcaag     120
ttgtcctgca cagcttctgg cttcaacatt aaagacacct atatgcactg ggtgaagcag     180
```

```
aggcctgaac agggcctgga gtggattgga aggattgatc ctgcgaatgg taatactata    240
tatgcctcaa agttccaggg caaggccact ataacagcag acacatcatc caacacagcc    300
tacatgcagc tcagcagcct gacatctggg gacactgccg tctattactg tgctctttat    360
tactatggtg gtagccttga ctactggggc caaggcacca ctctcacagt ctcctcaggt    420
ggaggtggat caggtggagg tggatctggt ggaggtggat ctgacattgt gatgtcacag    480
tctccatcct ccctagctgt gtcagttgga gagagggtta ctatgagctg caagtccagt    540
cagagccttt tatatagtgg caatcaaaag aactacttgg cctggtacca gcagaaacca    600
gggcagtctc ctaaactgct gatttactgg gcatccacta gggaatctgg ggtccctgat    660
cgcttcacag gcagtggatc tgggacagat ttcactctca ccatcagcag tgtgaaggct    720
gaagacctgg cagtttatta ctgtcagcaa tattatagct atcctcggac gttcggtgga    780
ggcaccaagc tggaaatcaa acgg                                          804

<210> SEQ ID NO 54
<211> LENGTH: 816
<212> TYPE: DNA
<213> ORGANISM: Artificial Sequence
<220> FEATURE:
<223> OTHER INFORMATION: Synthetic Construct

<400> SEQUENCE: 54
atggccctcc cggtaacggc tctgctgctt ccactcgcac tgctcttgca tgctgccaga     60
ccacaggtta ctctgaaaga gtctggccct gggatattgc agccctccca gaccctcagt    120
ctgacttgtt ctttctctgg gttttcactg agcacttatg gtatgggtgt gagctggatt    180
cgtcagcctt caggaaaggg tctggagtgg ctggcacaca tttactggga tgatgacaag    240
cgctataacc catccctgaa gagccggctc acaatctcca aggatacctc caacaaccag    300
gtattcctca agatcaccag tgtggacact gcagatactg ccacatacta ctgtgctcaa    360
agcctgatct atgatggtta ctacgggttt gcctactggg gccaagggac tctggtcact    420
gtctctgcag gtggaggtgg atcaggtgga ggtggatctg gtggaggtgg atctgacatt    480
gtgatgtcac agtctccatc ctccctagct gtgtcagttg gagagagggt tactatgagc    540
tgcaagtcca gtcagagcct tttatatagt ggcaatcaaa agaactactt ggcctggtac    600
cagcagaaac agggcagtc tcctaaactg ctgatttact gggcatccac tagggaatct    660
ggggtccctg atcgcttcac aggcagtgga tctgggacag atttcactct caccatcagc    720
agtgtgaagg ctgaagacct ggcagtttat tactgtcagc aatattatag ctatcctcgg    780
acgttcggtg gaggcaccaa gctggaaatc aaacgg                             816

<210> SEQ ID NO 55
<211> LENGTH: 810
<212> TYPE: DNA
<213> ORGANISM: Artificial Sequence
<220> FEATURE:
<223> OTHER INFORMATION: Synthetic Construct

<400> SEQUENCE: 55
atggccctcc cggtaacggc tctgctgctt ccactcgcac tgctcttgca tgctgccaga     60
ccacagatcc agttggtgca atctggacct gagctgaaga agcctggaga gacagtcaag    120
atctcctgca aggcttctgg gtataccttc acatactatg gaatgaactg ggtgaagcag    180
gctccaggaa agggtttaga gtggatgggc tggataaaca cctactctgg agtgccaaca    240
```

| | |
|---|---:|
| tatgctgatg acttcaaggg acggtttgcc ttctctttgg aaacctctgt cagcactgcc | 300 |
| tatttgcaga tcaacaacct caaaaatgag gacacggcta catattttg tgcaagatgg | 360 |
| atctactata gtgacctcta tggtatggac tactggggtc aaggaacctc agtcaccgtc | 420 |
| tcctcaggtg gaggtggatc aggtggaggt ggatctggtg gaggtggatc tgatgttttg | 480 |
| atgacccaaa gtccactctc cctgcctgtc agtcttggag atcaagcctc catctcttgt | 540 |
| agatctagtc agagtattgt acatagtaat ggagacacgt atttagaatg gtatttgcag | 600 |
| aaaccaggcc agtctccaaa gctcctgatc tacaaagttt ctaaccgatt ttctggggtc | 660 |
| ccagacaggt tcagtggcag tggatcaggg acagatttca cactcaagat cagcagagtg | 720 |
| gaggctgagg atctgggagt ttatcactgc tttcaaggtt cacatgttcc gtggacgttc | 780 |
| ggtggaggca ccaagctgga atcaaacgg | 810 |

<210> SEQ ID NO 56
<211> LENGTH: 789
<212> TYPE: DNA
<213> ORGANISM: Artificial Sequence
<220> FEATURE:
<223> OTHER INFORMATION: Synthetic Construct

<400> SEQUENCE: 56

| | |
|---|---:|
| atggccctcc cggtaacggc tctgctgctt ccactcgcac tgctcttgca tgctgccaga | 60 |
| ccacaggtcc agctgcagca gtctggggct gaactggcaa aacctggggc ctcagtgaag | 120 |
| atgtcctgca aggcttctgg ctacaccttt tctagctact ggatgcactg gctaaaacag | 180 |
| aggcctggac agggtctgga gtggattgga tacattaatc ctagcagtgg ttatactaac | 240 |
| tacaatcaga gttcaagga caaggccaca ttgactgcag acaaatcctc cagcacagcc | 300 |
| tacatgcaac tgagcagcct gacatctgag gactctgcag tctattactg tgcaagagat | 360 |
| ggtaactatg accactggta cttcgatgtc tggggcacag ggaccacggt caccgtctcc | 420 |
| tcaggtggag gtggatcagg tggaggtgga tctggtggag gtggatctga catcaagatg | 480 |
| acccagtctc catcttccat gtatgcatct ctaggagaga gagtcactat cacttgcaag | 540 |
| gcgagtcagg acattaatag ctatttaagc tggttccagc agaaaccagg gaaatctcct | 600 |
| aagaccctga tctatcgtgc aaacagattg gtagatgggg tcccatcaag gttcagtggc | 660 |
| agtggatctg ggcaagatta ttctctcacc atcagcagcc tggagtatga agatatggga | 720 |
| atttattatt gtctacagta tgatgagttg ctcacgttcg gtgctgggac caagctggag | 780 |
| ctgaaacgg | 789 |

<210> SEQ ID NO 57
<211> LENGTH: 807
<212> TYPE: DNA
<213> ORGANISM: Artificial Sequence
<220> FEATURE:
<223> OTHER INFORMATION: Synthetic Construct

<400> SEQUENCE: 57

| | |
|---|---:|
| atggccctcc cggtaacggc tctgctgctt ccactcgcac tgctcttgca tgctgccaga | 60 |
| ccacaggtcc agctgcagca gtctggggct gaactggcaa aacctggggc ctcagtgaag | 120 |
| atgtcctgca aggcttctgg ctacaccttt tctagctact ggatgcactg gctaaaacag | 180 |
| aggcctggac agggtctgga gtggattgga tacattaatc ctagcagtgg ttatactaac | 240 |
| tacaatcaga gttcaagga caaggccaca ttgactgcag acaaatcctc cagcacagcc | 300 |
| tacatgcaac tgagcagcct gacatctgag gactctgcag tctattactg tgcaagagat | 360 |

| | |
|---|---|
| ggtaactatg accactggta cttcgatgtc tggggcacag ggaccacggt caccgtctcc | 420 |
| tcaggtggag gtggatcagg tggaggtgga tctggtggag gtggatctga cattgtgatg | 480 |
| tcacagtctc catcctccct ggctgtgtca gcaggagaga gggtcactat gagctgcaga | 540 |
| tccagtcaga gtctgctcaa cagtagaacc cgaaagaact acttggcttg gtaccagcag | 600 |
| aaaccagggc agtctcctaa gctgctgatc tactgggcat ccactaggga atctggggtc | 660 |
| cctgatcgct tctcaggcag tggatctggg acagatttca ctctcaccat cagcagtgtg | 720 |
| caggctgaag acctggcagt ttattactgc gagcaatctt ataatctatt cacgttcggc | 780 |
| tcggggacaa agttggaaat aaaacgg | 807 |

<210> SEQ ID NO 58
<211> LENGTH: 786
<212> TYPE: DNA
<213> ORGANISM: Artificial Sequence
<220> FEATURE:
<223> OTHER INFORMATION: Synthetic Construct

<400> SEQUENCE: 58

| | |
|---|---|
| atggccctcc cggtaacggc tctgctgctt ccactcgcac tgctcttgca tgctgccaga | 60 |
| ccacaggttc aactgcagca gcctggggct gagctggtga ggcctggggc ttcagtgaag | 120 |
| atgtcctgca aggcttctgg ctacaccctc accacctact tgatggactg ggtaaaacag | 180 |
| aggcttggac aaggctttga gtggattgga aatattaatc ctaatagtgg tagtagtaac | 240 |
| tacaatgaga agttcaaggg caaggccaag ctgactgtag acaaatcctc cagcacagcc | 300 |
| tacatgcaac tcagcagcct gacatctgag gactctgcgg tctattactg tgcaatacgg | 360 |
| cactatggtg gtagtctctt tgactactgg ggccaaggca ccactctcac agtctcctca | 420 |
| ggtggaggtg gatcaggtgg aggtggatct ggtggaggtg gatctgacat caagatgacc | 480 |
| cagtctccat cttccatgta tgcatctcta ggagagagag tcactatcac ttgcaaggcg | 540 |
| agtcaggaca ttaatagcta tttaagctgg ttccagcaga accagggaaa atctcctaag | 600 |
| accctgatct atcgtgcaaa cagattggta gatggggtcc catcaaggtt cagtggcagt | 660 |
| ggatctgggc aagattattc tctcaccatc agcagcctgg agtatgaaga tatgggaatt | 720 |
| tattattgtc tacagtatga tgagttgctc acgttcggtg ctgggaccaa gctggagctg | 780 |
| aaacgg | 786 |

<210> SEQ ID NO 59
<211> LENGTH: 804
<212> TYPE: DNA
<213> ORGANISM: Artificial Sequence
<220> FEATURE:
<223> OTHER INFORMATION: Synthetic Construct

<400> SEQUENCE: 59

| | |
|---|---|
| atggccctcc cggtaacggc tctgctgctt ccactcgcac tgctcttgca tgctgccaga | 60 |
| ccacaggttc aactgcagca gcctggggct gagctggtga ggcctggggc ttcagtgaag | 120 |
| atgtcctgca aggcttctgg ctacaccctc accacctact tgatggactg ggtaaaacag | 180 |
| aggcttggac aaggctttga gtggattgga aatattaatc ctaatagtgg tagtagtaac | 240 |
| tacaatgaga agttcaaggg caaggccaag ctgactgtag acaaatcctc cagcacagcc | 300 |
| tacatgcaac tcagcagcct gacatctgag gactctgcgg tctattactg tgcaatacgg | 360 |
| cactatggtg gtagtctctt tgactactgg ggccaaggca ccactctcac agtctcctca | 420 |

```
ggtggaggtg gatcaggtgg aggtggatct ggtggaggtg gatctgacat tgtgatgtca    480
cagtctccat cctccctggc tgtgtcagca ggagagaggg tcactatgag ctgcagatcc    540
agtcagagtc tgctcaacag tagaacccga aagaactact tggcttggta ccagcagaaa    600
ccagggcagt ctcctaagct gctgatctac tgggcatcca ctagggaatc tggggtccct    660
gatcgcttct caggcagtgg atctgggaca gatttcactc tcaccatcag cagtgtgcag    720
gctgaagacc tggcagttta ttactgcgag caatcttata atctattcac gttcggctcg    780
gggacaaagt tggaaataaa acgg                                           804

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

Gly Gly Gly Gly Ser Gly Gly Gly Gly Ser Gly Gly Gly Gly Ser
1               5                   10                  15
```